US012076412B2

(12) United States Patent
Spycher et al.

(10) Patent No.: US 12,076,412 B2
(45) Date of Patent: Sep. 3, 2024

(54) ANTIBODY-DRUG CONJUGATES THROUGH SPECIFIC LINKER OLIGOPEPTIDES

(71) Applicant: ARARIS BIOTECH AG, Au (CH)

(72) Inventors: Philipp Spycher, Au (CH); Philipp Probst, Au (CH); Isabella Attinger-Toller, Au (CH); Romain Bertrand, Au (CH); Ramona Stark, Au (CH); Dragan Grabulovski, Au (CH)

(73) Assignee: ARARIS BIOTECH AG, Au (CH)

( * ) Notice: Subject to any disclaimer, the term of this patent is extended or adjusted under 35 U.S.C. 154(b) by 0 days.

(21) Appl. No.: 18/188,991

(22) Filed: Mar. 23, 2023

(65) Prior Publication Data

US 2023/0263904 A1  Aug. 24, 2023

Related U.S. Application Data

(63) Continuation of application No. PCT/EP2021/079560, filed on Oct. 25, 2021.

(51) Int. Cl.
*A61K 47/68* (2017.01)
*A61P 35/00* (2006.01)
*C12N 9/10* (2006.01)

(52) U.S. Cl.
CPC .......... *A61K 47/6889* (2017.08); *A61P 35/00* (2018.01); *C12N 9/1044* (2013.01); *C12Y 203/02013* (2013.01)

(58) Field of Classification Search
CPC .............. A61K 47/6889; C12N 9/1044; C12Y 203/02013; C07K 2317/524
See application file for complete search history.

(56) References Cited

U.S. PATENT DOCUMENTS

| 4,137,230 | A | 1/1979 | Hashimoto et al. |
| 4,151,042 | A | 4/1979 | Higashide et al. |
| 4,248,870 | A | 2/1981 | Miyashita et al. |
| 4,260,608 | A | 4/1981 | Miyashita et al. |
| 4,265,814 | A | 5/1981 | Hashimoto et al. |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,317,821 | A | 3/1982 | Miyashita et al. |
| 4,322,348 | A | 3/1982 | Asai et al. |
| 4,331,598 | A | 5/1982 | Hasegawa et al. |
| 5,416,064 | A | 5/1995 | Chari et al. |
| 6,660,510 | B2 | 12/2003 | Lin et al. |
| 8,211,912 | B2 | 7/2012 | Roulston et al. |
| 9,427,478 | B2 | 8/2016 | Bregeon et al. |
| 9,676,721 | B2 | 6/2017 | Bair et al. |
| 9,717,803 | B2 | 8/2017 | Bregeon et al. |
| 9,764,038 | B2 | 9/2017 | Dennler et al. |
| 10,132,799 | B2 | 11/2018 | Belmant et al. |
| 10,434,180 | B2 | 10/2019 | Bregeon et al. |
| 10,639,291 | B2 | 5/2020 | Hu et al. |
| 10,675,359 | B2 | 6/2020 | Dennler et al. |
| 11,396,649 | B2 | 7/2022 | Spycher et al. |
| 2005/0256030 | A1 | 11/2005 | Feng |
| 2005/0260186 | A1 | 11/2005 | Bookbinder et al. |
| 2006/0104968 | A1 | 5/2006 | Bookbinder et al. |
| 2008/0063783 | A1 | 3/2008 | Kreij et al. |
| 2010/0143970 | A1 | 6/2010 | Yokoyama et al. |
| 2012/0270810 | A1 | 10/2012 | Preiss-Bloom et al. |
| 2014/0356385 | A1 | 12/2014 | Dennler et al. |
| 2017/0043033 | A1 | 2/2017 | Strop et al. |
| 2017/0151341 | A1 | 6/2017 | Ma et al. |

(Continued)

FOREIGN PATENT DOCUMENTS

| EP | 2287317 A2 | 2/2011 |
| EP | 2777714 A1 | 9/2014 |

(Continued)

OTHER PUBLICATIONS

Vidarsson et al. IgG subclasses and allotypes: from structure to effector functions. Frontiers in Immunol., 5, article 520, p. 1-17, 2014. (Year: 2014).*
Agard et al., "A Comparative Study of Bioorthogonal Reactions with Azides", ACS Chem. Biol., 2006, 1: 644-648.
Amant et al., "A Reactive Antibody Platform for One-Step Production of Antibody-Drug Conjugates through a Diels-Alder Reaction with Maleimide", Bioconjugate Chem, 2019, 30(9): 2340-2348.
Amant et al., "Tuning the Diels-Alder Reaction for Bioconjugation to Maleimide Drug-Linkers", Bioconjugate Chem., 2018, 29(7): 2406 2414.
Amsberry et al., "The lactonization of 2'-hydroxyhydrocinnamic acid amides: a potential prodrug for amines", J. Org. Chem., 1990, 55: 5867.
Azhdarinia et al., "Dual-Labeling Strategies for Nuclear and Fluorescence Molecular Imaging: A Review and Analysis", Mol Imaging Biol., 2011, 14(3): 261-276.

(Continued)

*Primary Examiner* — Elly-Gerald Stoica
(74) *Attorney, Agent, or Firm* — LATHROP GPM LLP; James H. Velema, Esq.

(57) ABSTRACT

The present invention relates to a method for generating an antibody-payload conjugate by means of a microbial transglutaminase (MTG). The method comprises a step of conjugating a linker comprising the structure (shown in N→C direction) $(Sp_1)$-RK-$(Sp_2)$-B-$(Sp_3)$ or $(Sp_1)$-B-$(Sp_2)$-RK-$(Sp_3)$ to a Gln residue comprised in an antibody, wherein $(Sp_1)$ is a chemical spacer or is absent; $(Sp_2)$ is a chemical spacer or is absent; $(Sp_3)$ is a chemical spacer or is absent; R is arginine or an arginine derivative or an arginine mimetic; K is lysine or a lysine derivative or a lysine mimetic; B is a linking moiety or a payload; and wherein the linker is conjugated to the Gln residue comprised in the antibody via a primary amine comprised in the side chain of the lysine residue, the lysine derivative or the lysine mimetic. Further, the invention relates to antibody-linker conjugates, antibody-drug conjugates and linker constructs comprising an RK motif.

26 Claims, 27 Drawing Sheets

Specification includes a Sequence Listing.

(56) References Cited

U.S. PATENT DOCUMENTS

| | | |
|---|---|---|
| 2018/0071402 A1 | 3/2018 | Bregeon et al. |
| 2018/0078656 A1 | 3/2018 | Steinkuhler et al. |
| 2018/0134766 A1 | 5/2018 | Larson et al. |
| 2018/0193476 A1 | 7/2018 | Dennler et al. |
| 2019/0194641 A1 | 6/2019 | Spycher et al. |
| 2021/0128743 A1 | 5/2021 | Spycher et al. |
| 2022/0133904 A1 | 5/2022 | Schibli |
| 2022/0333093 A1 | 10/2022 | Spycher et al. |
| 2023/0372525 A1 | 11/2023 | Bertrand et al. |

FOREIGN PATENT DOCUMENTS

| | | |
|---|---|---|
| JP | 2006-524037 A | 10/2006 |
| JP | 2015-209426 A | 11/2015 |
| WO | WO 1994/012520 A1 | 6/1994 |
| WO | WO 1998/006692 A1 | 2/1998 |
| WO | WO 1999/005536 A1 | 2/1999 |
| WO | WO 2002/083180 A1 | 10/2002 |
| WO | WO 2003/012068 A2 | 2/2003 |
| WO | WO 2003/087131 A2 | 10/2003 |
| WO | WO 2004/043493 A1 | 5/2004 |
| WO | WO 2008/102007 A1 | 8/2008 |
| WO | WO 2009/012268 A1 | 1/2009 |
| WO | WO 2009/099728 A1 | 8/2009 |
| WO | WO 2010/115629 A2 | 10/2010 |
| WO | WO 2010/115630 A2 | 10/2010 |
| WO | WO 2011/119484 A1 | 9/2011 |
| WO | WO 2012/041504 A1 | 4/2012 |
| WO | WO 2012/047724 A1 | 4/2012 |
| WO | WO 2012/059882 A2 | 5/2012 |
| WO | WO 2012/119787 A1 | 9/2012 |
| WO | WO 2013/040142 A2 | 3/2013 |
| WO | WO 2013/049830 A2 | 4/2013 |
| WO | WO 2013/092983 A2 | 6/2013 |
| WO | WO 2013/092998 A1 | 6/2013 |
| WO | WO 2014/135282 A1 | 9/2014 |
| WO | WO 2014/140300 A1 | 9/2014 |
| WO | WO 2014/202775 A1 | 12/2014 |
| WO | WO 2015/015448 A2 | 2/2015 |
| WO | WO 2015/054060 A1 | 4/2015 |
| WO | WO 2015/097267 A1 | 7/2015 |
| WO | WO 2015/162563 A1 | 10/2015 |
| WO | WO 2015/191883 A1 | 12/2015 |
| WO | WO 2016/030791 A1 | 3/2016 |
| WO | WO 2016/100735 A1 | 6/2016 |
| WO | WO 2016/128410 A1 | 8/2016 |
| WO | WO 2016/144608 A1 | 9/2016 |
| WO | WO 2016/207090 A2 | 12/2016 |
| WO | WO 2017/025179 A1 | 2/2017 |
| WO | WO 2017/106643 A1 | 6/2017 |
| WO | WO 2019/030223 A1 | 2/2019 |
| WO | WO 2019/057772 A1 | 3/2019 |
| WO | WO 2019/082020 A1 | 5/2019 |
| WO | WO 2020/188061 A1 | 9/2020 |

OTHER PUBLICATIONS

Balhorn et al., "Hexa-arginine enhanced uptake and residualization of selective high affinity ligands by Raji lymphoma cells", Molecular Cancer, 2009, 8(25): 1-9.
Bargh et al., "Cleavable linkers in antibody-drug conjugates", Chem Soc Rev., Aug. 12, 2019, 48(16): 4361-4374.
Baskin et al., "Copper-free click chemistry for dynamic in vivo imaging", PNAS, 2007, 104(43): 16793-16797.
Benjamin et al., "Thiolation of Q295: Site-Specific Conjugation of Hydrophobic Payloads without the Need for Genetic Engineering", Mol. Pharmaceutics, 2019, 16: 2795-2807.
Blackman et al., "The Tetrazine Ligation: Fast Bioconjugation based on Inverse-electron-demand Diels-Alder Reactivity", Journal of the American Chemical Society, 2008, 130(41): 13518-13519.
Bodero et al., "Synthesis and biological evaluation of RGD and isoDGR peptidomimetic-a-amanitin conjugates for tumor-targeting", Beilstein J. Org. Chem., 2018, 14: 407 415.
Costoplus et al., "Peptide-Cleavable Self-immolative Maytansinoid Antibody-Drug Conjugates Designed to Provide Improved Bystander Killing", ACS Med. Chem. Lett., 2019, 10(10): 1393-1399.
Dal Corso et al., "Innovative Linker Strategies for Tumor-Targeted Drug Conjugates", Chemistry, 2019, 25(65): 14740-14757.
De Young et al., "Transglutaminase Activity in Human and Rabbit Ear Comedogenesis: A Histochemical Study", Journal of Investigative Dermatology, 1984, 82(3): 275-279.
Dennler, "Microbial Transglutaminase as a Versatile Tool for Site-Specific Protein Modification", Doctoral Thesis, 2015, ETH Zürich, Dissertation No. 22512.
Dickgiesser et al., "Site-Specific Conjugation of Native Antibodies Using Engineered Microbial Transglutaminases", Bioconjug Chem., Mar. 12, 2020, 31(4): 1070-1076.
Dokter et al., "Preclinical profile of the HER2-targeting ADC SYD983/SYD985: introduction of a new duocarmycin-based linker-drug platform", Mol Cancer Ther., Nov. 2014, 13(11): 2618-2629.
Doronina et al., "Enhanced activity of monomethylauristatin F through monoclonal antibody delivery: effects of linker technology on efficacy and toxicity", Bioconjug Chem., Jan. 2006, 17(1): 114-124.
Dorywalska et al., "Site-Dependent Degradation of a Non-Cleavable Auristatin-Based Linker-Payload in Rodent Plasma and Its Effect on ADC Efficacy", PLoS One, 2015, 10(7): e0132282.
Dorywalska et al., "Molecular Basis of Valine-Citrulline-PABC Linker Instability in Site-Specific ADCs and Its Mitigation by Linker Design", Mol Cancer Ther., May 2016, 15(5): 958-970.
Dubowchik et al., "Cathepsin B-labile dipeptide linkers for lysosomal release of doxorubicin from internalizing immunoconjugates: model studies of enzymatic drug release and antigen-specific in vitro anticancer activity", Bioconjug Chem, 2002, 13(4): 855-869.
Fornera et al., "Immobilization of Peroxidase on SiO2 Surfaces with the Help of a Dendronized Polymer and the Avidin-Biotin System", Macromolecular Bioscience, Aug. 2011, 11(8): 1052-1067.
Great Britain Search Report for Great Britain Patent Application No. GB1800878.9, dated Oct. 9, 2018.
Hay et al., "A 2-nitroimidazole carbamate prodrug of 5-amino-1-(chloromethyl)-3-[(5,6,7-trimethoxyindol-2-yl)carbonyl]-1,2-dihydro-3H-benz[e]indole (amino-seco-CBI-TMI) for use with ADEPT and GDEPT", Bioorg. Med. Chem. Lett., 1999, 9(15): 2237-2242.
Higashide et al., "Ansamitocin, a group of novel maytansinoid antibiotics with antitumour properties from Nocardia", Nature, 1977, 270: 721-722.
Houghton et al., "Site-specifically labeled CA19.9-targeted immunoconjugates for the PET, NIRF, and multimodal PET/NIRF imaging of pancreatic cancer", PNAS USA, Dec. 29, 2015, 112(52): 15850-15855.
Huang et al., "Characterization of antibody-drug conjugates by mass spectrometry: advances and future trends", Drug Discover Today, 2016, 21(5): 850-855.
Huggins et al., "Site Selective Antibody-Oligonucleotide Conjugation via Microbial Transglutaminase", Molecules, Sep. 10, 2019, 24(18): 3287.
International Search Report and Written Opinion for PCT International Patent Application No. PCT/EP2014/067403, dated Oct. 25, 2017.
International Search Report and Written Opinion for PCT International Patent Application No. PCT/EP2018/075350, dated Jan. 28, 2019.
International Search Report and Written Opinion for PCT International Patent Application No. PCT/EP2020/057697, dated Jun. 16, 2020.
International Search Report and Written Opinion for PCT International Patent Application No. PCT/EP2021/075831, dated Dec. 14, 2021.
International Search Report and Written Opinion for PCT International Patent Application No. PCT/EP2021/079560, dated Feb. 8, 2022.
International Search Report and Written Opinion for PCT International Patent Application No. PCT/EP2022/079787, dated Feb. 13, 2023.

(56) References Cited

OTHER PUBLICATIONS

Jeger et al., "Site-specific and stoichiometric modification of antibodies by bacterial transglutaminase", Agnew Chem Int Ed Engl., Dec. 17, 2010, 49(51): 9995-9997.
Kato et al. "Peptide-binding assessment using mass spectrometry as a new screening method for skin sensitization", J Toxicol Sci., Feb. 2003, 28(1): 19-24.
Kawai et al., "Chemical Modification of Ansamitocins. III. Synthesis and Biological Effects of 3-Acyl Esters of Maytansinol", Chem. Pharm Bull., 1984, vol. 32(9): 3441-3451.
Kehrer et al., "Modulation of camptothecin analogs in the treatment of cancer: a review", Anticancer Drugs, 2001, 12(2): 89-105.
Khew et al., "Characterization of amine donor and acceptor sites for tissue type transglutaminase using a sequence from the C-terminus of human fibrillin-1 and the N-terminus of osteonectin", Biomaterials, Jun. 2010, 31(16): 4600-4608.
Kieliszek, "Microbial transglutaminase and its application in the food industry. A review", Folia Microbiol (Praha), 2014, 59(3): 241-250.
Kingsbury et al., "A novel peptide delivery system involving peptidase activated prodrugs as antimicrobial agents. Synthesis and biological activity of peptidyl derivatives of 5-fluorouracil", J. Med. Chem., 1984, 27(11): 1447-1451.
Kolb et al., "The growing impact of click chemistry on drug discovery", Drug Discov Today, Dec. 15, 2003, 8(24): 1128-1137.
Kontermann et al., "Bispecific antibodies", Drug Discov Today, 2015, 20(7): 838-847.
Kupchan et al., "Tumor inhibitors. 124. Structural requirements for antileukemic activity among the naturally occurring and semisynthetic maytansinoids", J. Med. Chem., 1978, 21(1): 31-37.
Lambert et al., "Antibody-Drug Conjugates for Cancer Treatment", Annu. Rev. Med., 2018, 69: 191 207.
Levengood et al., "Orthogonal Cysteine Protection Enables Homogeneous Multi-Drug Antibody-Drug Conjugates", Angewandte Chem Int Ed Engl., Jan. 16, 2017, 56(3): 733-737.
Lhospice et al., "Site-Specific Conjugation of Monomethyl Auristatin E to Anti-CD30 Antibodies Improves Their Pharmacokinetics and Therapeutic Index in Rodent Models", Mol Pharm., Jun. 2015, 12(6): 1863-1871.
Li et al., "Synthesis and Evaluation of Camptothecin Antibody-Drug Conjugates", ACS Med Chem. Lett., 2019, 10(10): 1386-1392.
Lyon et al., "Reducing hydrophobicity of homogeneous antibody-drug conjugates improves pharmacokinetics and therapeutic index", Nat Biotechnol, 2015, 33: 733-735.
MacKenzie et al., "Strain-promoted cycloadditions involving nitrones and alkynes-rapid tunable reactions for bioorthogonal labeling", Curr Opin Chem Biol., 2014, 21: 81-88.
Maude et al., "Peptide Synthesis and Self-Assembly", Peptide-Based Materials, Topics in Current Chemistry 310, Jan. 10, 2012, p. 62.
Mindt et al., "Modification of Different IgG1 Antibodies via Glutamine and Lysine using Bacterial and Human Tissue Transglutaminase", Bioconjugate Chem., 2008, 19(1): 271-278.
Nakada et al., "Novel antibody drug conjugates containing exatecan derivative-based cytotoxic payloads", Bioorg Med Chem Lett., Mar. 15, 2016, 26(6): 1542-1545.
New Zealand Search and Examination Report for New Zealand Patent Application No. 762376, dated Feb. 1, 2022.
Nicolaou et al., "Chemistry and biology of natural and designed enediynes", PNAS, 1993, 90(13): 5881-5888.
Ning et al., "Protein Modification by Strain-Promoted Alkyne-Nitrone Cycloaddition", Angewandte Chemie International Edition, 2010, 49(17): 3065-3068.
Nunes et al., "Use of a next generation maleimide in combination with THIOMAB™ antibody technology delivers a highly stable, potent and near homogeneous THIOMAB™ antibody-drug conjugate (TDC)", RSC Adv., 2017, 7: 24828-24832.
Oh et al., "Characteristics of an immobilized form of transglutaminase: A possible increase in substrate specificity by selective interaction with a protein spacer", Journ Agric Food Chem., 1993, 41(8): 1337-1342.
Park et al., "Aryl Sulfate is a Useful Motif for Conjugating and Releasing Phenolic Molecules: Sulfur Fluorine Exchange Click Chemistry Enables Discovery of Ortho-Hydroxy-Protected Aryl Sulfate Linker", Bioconjugate Chem, 2019, 30(7): 1957-1968.
Rodrigues et al., "Synthesis and p-lactamase-mediated activation of a cephalosporin-taxol prodrug", Chemistry Biology, 1995, 2: p. 223.
Roig et al., "Biotechnology and applied biology section applications of immobilized enzymes", Biochemical Education, Oct. 1987, 15(4): 198-208.
Salomon et al., "Optimizing Lysosomal Activation of Antibody-Drug Conjugates (ADCs) by Incorporation of Novel Cleavable Dipeptide Linkers", Mol Pharm., 2019, 16(12): 4817-4825.
Sletten et al., "A Bioorthogonal Quadricyclane Ligation", J Am Chem Soc, 2011, 133(44): 17570-17573.
Smith et al., "The Enediyne Antibiotics", J. Med. Chem., 1996, 39(11): 2103-2117.
Sonzini et al., "Improved Physical Stability of an Antibody-Drug Conjugate Using Host-Guest Chemistry", Bioconjug Chem., Jan. 15, 2020, 31(1): 123-129.
Spycher et al., "Dual, Site-Specific Modification of Antibodies by Using Solid-Phase Immobilized Microbial Transglutaminase", Chembiochem., Oct. 5, 2017, 18(19): 1923-1927.
Staben et al., "Targeted drug delivery through the traceless release of tertiary and heteroaryl amines from antibody-drug conjugates", Nature Chemistry, Oct. 17, 2016, 8: 1112-1119.
Stöckmann et al.,"Exploring isonitrile-based click chemistry for ligation with biomolecules", Organic & Biomolecular Chemistry, 2011, 21: 7303-7305.
Strop et al., "RN927C, a Site-Specific Trop-2 Antibody-Drug Conjugate (ADC) with Enhanced Stability, Is Highly Efficacious in Preclinical Solid Tumor Models", Molecular Cancer Therapeutics, Aug. 31, 2016, 15(11): 2698-2708.
Strop et al., "Versatility of Microbial Transglutaminase", Bioconjugate Chemistry, 2014, 25(5): 855-862.
Strop et al., "Location Matters: Site of Conjugation Modulates Stability and Pharmacokinetics of Antibody Drug Conjugates", Chemistry & Biology, Feb. 21, 2013, 20: pp. 161-167.
Su et al., "Modulating Antibody-Drug Conjugate Payload Metabolism by Conjugation Site and Linker Modification", Bioconjugate Chem., 2018, 29(4): 1155-1167.
Subedi et al., "The Structural Role of Antibody N-Glycosylation in Receptor Interactions", Structure, 2015, 23(9): 1573-1583.
Tanaka et al., "N-terminal glycine-specific protein conjugation catalyzed by microbial transglutaminase", FEBS Letters, 579(10): 2092-2096.
Tsesmetzis et al., "Nucleobase and Nucleoside Analogues: Resistance and Re-Sensitisation at the Level of Pharmacokinetics, Pharmacodynamics and Metabolism", Cancers, 2018, 10(7): 240.
Walker et al., "Cleavage behavior of calicheamicin gamma 1 and calicheamicin T", PNAS USA, 1992, 89(10): 4608-4612.
Yarema et al., "Metabolic Delivery of Ketone Groups to Sialic Acid Residues. Application to Cell Surface Glycoform Engineering", Journal of Biological Chemistry, Nov. 1998, 273(47): 31168-31179.
Yuan et al. "Tissue transglutaminase 2 inhibition promotes cell death and chemosensitivity in glioblastomas", Mol. Cancer Ther., Sep. 2005, 4(9): 1293-1302.
Zhang et al., "A Rigid, Chiral, Dendronized Polymer with a Thermally Stable, Right-Handed Helical Conformation", Chemistry A European Journal, Aug. 8, 2008, 14(23): 6924-6934.
Zhang et al., "Multifunctional Tumor-Targeting Cathepsin B-Sensitive Gemcitabine Prodrug Covalently Targets Albumin in Situ and Improves Cancer Therapy", Bioconjugate Chem., 2018, 29(6): 1852-1858.
Zhao et al., "Recent advances of antibody drug conjugates for clinical applications", Acta Pharmaceutica Sinica B, 2020, 10(9): 1589-1600.
Zheng et al., "The impact of glycosylation on monoclonal antibody conformation and stability", Mabs-Austin, 2011, 3(6): 568-576.

(56) References Cited

OTHER PUBLICATIONS

Zhou et al., "The microbial transglutaminase immobilization on carboxylated poly(N-isopropylacrylamide) for thermo-responsivity", Enzyme and Microbial Technology, 2016, vol. 87-88, pp. 44-51.
Kamiya et al., "S-peptide as a potent peptidyl linker for protein cross-linking by microbial transglutaminase from Streptomyces mobaraensis," Bioconj Chem., Mar-Apr. 2003, 14(2): 351-357.
Plagmann et al., "Transglutaminase-catalyzed covalent multimerization of Camelidae anti-human TNF single domain antibodies improves neutralizing activity," J Biotechnol., Jun. 15, 2009, 142(2): 170-178.
Takazawa et al., "Enzymatic labeling of a single chain variable fragment of an antibody with alkaline phosphatase by microbial transglutaminase," Biotechnol Bioeng., May 20, 2004, 86(4): 399-404.
European Examination Report for European Patent Application No. 17742684.8, mailed Nov. 6, 2023.
U.S. Appl. No. 16/319,502, filed Jan. 22, 2019, Philipp Rene Spycher, Site-Specific Conjugation to Antibody Lysine Residues with Solid-Phase Immobilized Microbial Transglutaminase MTG and MTG in Solution.
U.S. Pub. No. 2019/0194641, filed Jun. 27, 2019, Philipp Rene Spycher, Site-Specific Conjugation to Antibody Lysine Residues with Solid-Phase Immobilized Microbial Transglutaminase MTG and MTG in Solution.
U.S. Pat. No. 11,396,649, filed Jul. 26, 2022, Philipp Rene Spycher, Site-Specific Conjugation to Antibody Lysine Residues with Solid-Phase Immobilized Microbial Transglutaminase MTG and MTG in Solution.
U.S. Appl. No. 17/704,960, filed Mar. 25, 2022, Philipp Rene Spycher, Site-Specific Conjugation to Antibody Lysine Residues with Solid-Phase Immobilized Microbial Transglutaminase MTG and MTG in Solution.
U.S. Pub. No. 2022/0333093, filed Oct. 20, 2022, Philipp Rene Spycher, Site-Specific Conjugation to Antibody Lysine Residues with Solid-Phase Immobilized Microbial Transglutaminase MTG and MTG in Solution.
U.S. Appl. No. 18/426,675, filed Jan. 30, 2024, Philipp Rene Spycher, Site-Specific Conjugation to Antibody Lysine Residues with Solid-Phase Immobilized Microbial Transglutaminase MTG and MTG in Solution.
U.S. Appl. No. 16/648,636, filed Mar. 18, 2020, Philipp Spycher, Transglutaminase Conjugation Method and Linker.
U.S. Pub. No. 2021/0128743, filed May 6, 2021, Philipp Spycher, Transglutaminase Conjugation Method and Linker.
U.S. Appl. No. 17/435,356, filed Mar. 19, 2020, Roger Schibli, Transglutaminase Conjugation Method with a Glycine Based Linker.
U.S. Pub. No. 2022/0133904, filed May 5, 2022, Roger Schibli, Transglutaminase Conjugation Method with a Glycine Based Linker.
U.S. Appl. No. 18/177,430, filed Mar. 2, 2023, Romain Bertrand, Transglutaminase Conjugation Method with Amino Acid-Based Linkers.
U.S. Pub. No. 2023/0372525, filed Nov. 23, 2023, Romain Bertrand, Transglutaminase Conjugation Method with Amino Acid-Based Linkers.
U.S. Appl. No. 18/188,991, filed Mar. 23, 2023, Philipp Spycher, Means and Methods for Producing Antibody-Linker Conjugates.
U.S. Pub. No. 2023/0263904, filed Aug. 24, 2023, Philipp Spycher, Means and Methods for Producing Antibody-Linker Conjugates.

* cited by examiner a) BJAB b) GRANTA-519 c) WSU d) HT (CD79b negative)

ANTIBODY-DRUG CONJUGATES THROUGH SPECIFIC LINKER OLIGOPEPTIDES

RELATED APPLICATIONS

This application is a continuation of International Patent Application No. PCT/EP2021/079560, filed Oct. 25, 2021, which claims priority to European Patent Application Nos. 20020492.3, filed Oct. 25, 2020, and 20203887.3, filed Oct. 26, 2020, the entire disclosures of which are hereby incorporated herein by reference.

SEQUENCE LISTING

The instant application contains a Sequence Listing which has been submitted electronically in XML format and is hereby incorporated by reference in its entirety. Said XML file, created on Mar. 17, 2023, is named 739203_ARA9-005PCCON_ST26.xml and is 79,055 bytes in size.

The present invention relates to methods for generating an antibody-linker conjugate by means of a microbial transglutaminase. The invention further provides antibody-linker conjugates, antibody-drug-conjugates, linker constructs and pharmaceutical compositions comprising the antibody-linker conjugates or antibody-drug conjugates of the invention and uses thereof.

Antibody-drug conjugates (ADCs) are typically composed of an antibody and a small molecule drug conjugated to the antibody via a chemical linker. After decades of preclinical and clinical studies, a series of ADCs have been approved for treating specific tumor types such as brentuximab vedotin (Adcetris®) for relapsed Hodgkin's lymphoma and systemic anaplastic large cell lymphoma, gemtuzumab ozogamicin (Mylotarg®) for acute myeloid leukemia, ado-trastuzumab emtansine (Kadcyla®) for HER2-positive metastatic breast cancer, inotuzumab ozogamicin (Besponsa®) and recently polatuzumab vedotin-piiq (Polivy®) for B cell malignancies. Most recently, enfortumab vedotin (Padcev®), trastuzumab deruxtecan (Enhertu®), sacituzumab govitecan (Trodelvy®) and belantamab mafadotin (Blenrep®) have received market approval. For a review on ADCs see for example (Zhao P. et al., 2020, Acta Pharmaceutica Sinica B, 10, 1589-1600). While many ADCs have shown impressive anticancer activity, many patients do not respond to these treatments, experience severe side-effects before signs of efficacy or experience a relapse after a certain period of time, so there is still a large medical need for novel ADC formats which have favorable drug-like properties, can be produced in sufficient quantity and quality at reasonable costs to support drug development, and which are suitable as therapeutics.

A key step in the preparation of an ADC is the covalent conjugation step of a payload to the antibody. Most ADCs in current clinical development were made by conjugation to endogenous lysine or cysteine residues of the antibody, carefully controlling the average degree of modification to yield an average drug-to-antibody ratio (DAR) in the range of 3.5-4.0. This ratio was historically selected on the basis of (a) minimizing the amount of nonconjugated antibody and (b) avoiding species in the mixture with very high DAR, which may be problematic in manufacturing and formulation because of higher hydrophobicity and lower solubility (Lambert J M and Berkenbilt A., 2018, Annu. Rev. Med. 69, 191-207) and typically results in poor pharmacokinetic properties (Lyon R P, et al., 2015, Nat Biotechnol, 33, 733-735). Recently, a variety of genetic, chemical, and enzymatic methods have been developed for site-specific conjugation, which can enable DARs of 2 (or 4) while avoiding under- or overmodification of the antibody. An overview of these methodologies are given in Yamada et al. (reviewed in Kei Yamada and Yuji Ito, 2019, ChemBioChem, 20, 2729-2739).

Enzymatic conjugation has shown great interest since these conjugation reactions are typically fast, site-specific and can be done under physiological conditions. Among the available enzymes, microbial transglutaminase (MTG) from the species *Streptomyces mobaraensis* has found increasing interest as an attractive alternative to conventional chemical protein conjugation of functional moieties including antibodies. The MTG catalyzes under physiological conditions a transamidation reaction between a 'reactive' glutamine of a protein or peptide and a 'reactive' lysine residue of a protein or peptide, whereas the latter can also be a simple, low molecular weight primary amine such as a 5-aminopentyl group (Jeger S. et al., 2010, Angew. Chem. Int. Ed., 49, 9995-9997).

Jeger et al. described that conjugation of an antibody using transglutaminase as an enzyme happens at the Q295 residue, however, conjugation was only possible upon removal of the glycan moiety at the asparagine residue 297 (N297) with PNGase F, while glycosylated antibodies could not be conjugated efficiently (conjugation efficiency below 20%) (Jeger S. et al., 2010, Angew. Chem. Int. Ed., 49, 9995-9997; Mindt T. et al. 2008, Bioconj Chem, 9, 271-278).

Other approaches to generate ADCs by means of an MTG are based on the use of aglycosylated antibodies, wherein residue N297 is substituted with an amino acid residue that cannot be subject to glycosylation. However substitution of N297 against another amino acid may lead to unwanted effects, as it may affect the overall stability of the entire Fc domain (Subedi G P and Barb A W., 2015, Structure, 23, 1573-1583), and the efficacy of the entire conjugate. As a consequence that can lead to increased antibody aggregation and a decreased solubility that particularly becomes important for hydrophobic payloads. Further, the glycan that is present at N297 has important immunomodulatory effects, as it triggers effector functions such as antibody dependent cellular cytotoxicity (ADCC) and the like. These immunomodulatory effects would get lost upon deglycosylation or any of the other approaches discussed above to obtain an aglycosylated antibody. Further, any sequence modification of an established antibody can also lead to regulatory problems, which is problematic because often times an accepted and clinically validated antibody is used as a starting point for ADC conjugation.

Recently, Spycher et al. disclosed a transglutaminase-based conjugation approach which does not require prior deglycosylation of the antibody for payload conjugation (Spycher et al., WO 2019/057772). The possibility to conjugate native, glycosylated antibodies offers significant advantages under manufacturing aspects: an enzymatic deglycosylation step is undesired under good manufacturing process (GMP) aspects, because it has to be made sure that the both the deglycosylation enzyme (e.g., PNGase F) as well as the cleaved glycan are removed from the reaction mixture. Furthermore, no genetic engineering of the antibody for payload attachment is necessary, so that sequence insertions which may increase immunogenicity and decrease the overall stability of the antibody can be avoided.

In view of the foregoing, there is still a need in the art for improved methods for generating ADCs with a high conjugation efficiency.

Further, there is a need in the art for novel ADCs with improved efficacy and/or pharmacokinetic properties as well as highly defined drug-to-antibody ratios.

SUMMARY OF THE INVENTION

The present invention is characterized in the herein provided embodiments and claims. In particular, the present invention relates, inter alia, to the following embodiments:

1. A method for producing an antibody-linker conjugate by means of a microbial transglutaminase (MTG), the method comprising a step of conjugating a linker comprising the structure (shown in N→C direction)

(Sp$_1$)-RK-(Sp$_2$)-B-(Sp$_3$) or (Sp$_1$)-B-(Sp$_2$)-RK-(Sp$_3$)

to a Gln residue comprised in an antibody, wherein
- (Sp$_1$) is a chemical spacer or is absent;
- (Sp$_2$) is a chemical spacer or is absent;
- (Sp$_3$) is a chemical spacer or is absent;
- R is arginine or an arginine derivative or an arginine mimetic;
- K is lysine or a lysine derivative or a lysine mimetic;
- B is a linking moiety or a payload;
and wherein the linker is conjugated to the Gln residue comprised in the antibody via a primary amine comprised in the side chain of the lysine residue, the lysine derivative or the lysine mimetic.

2. The method according to embodiment 1, wherein the chemical spacers (Sp$_1$), (Sp$_2$) and (Sp$_3$) each independently comprise between 0 and 12 amino acid residues.

3. The method according to embodiment 1 or 2, wherein the linker comprises not more than 25, 20, 15, 14, 13, 12, 11, 10, 9, 8, 7, 6, 5, 4 amino acid residues.

4. The method according to any one of embodiments 1 to 3, wherein the net charge of the linker is neutral or positive.

5. The method according to any one of embodiments 1 to 4, wherein the linker comprises no negatively-charged amino acid residues.

6. The method according to any one of embodiments 1 to 5, wherein the linker comprises the amino acid sequence RKAA (SEQ ID NO:1), RKA (SEQ ID NO:2), ARK (SEQ ID NO:3) or RKR (SEQ ID NO:4).

7. The method according to any one of embodiments 1 to 6, wherein the linker comprises the amino acid sequence RKAA (SEQ ID NO:1), RKA (SEQ ID NO:2) or ARK (SEQ ID NO:3).

8. The method according to any one of embodiments 1 to 7, wherein the linker comprises the amino acid sequence RKAA (SEQ ID NO:1).

9. The method according to any one of embodiments 1 to 8, wherein B is a linking moiety.

10. The method according to embodiment 9, wherein the linking moiety B comprises
- a bioorthogonal marker group, or
- a non-bio-orthogonal entity for crosslinking.

11. The method according to embodiment 10, wherein the bioorthogonal marker group or the non-bio-orthogonal entity for crosslinking consists of or comprises at least one molecule or moiety selected from the group consisting of:
- —N—N≡N, or —N$_3$;
- Lys(N$_3$);
- a tetrazine;
- an alkyne;
- a strained cyclooctyne;
- BCN;
- a strained alkene;
- a photoreactive group;
- an aldehyde;
- an acyltrifluoroborate;
- a protein degradation agent ('PROTAC');
- a cyclopentadiene/spirolocyclopentadiene;
- a thio-selective electrophile;
- —SH; and
- cysteine.

12. The method according to any one of embodiments 9 to 11, the method comprising a further step of conjugating one or more payloads to the linking moiety B.

13. The method according to embodiment 12, wherein the one or more payload is conjugated to the linking moiety B via a click-reaction.

14. The method according to any one of embodiments 1 to 8, wherein B is a payload.

15. The method according to any one of embodiments 12 to 14, wherein the payload comprises at least one of:
- a toxin;
- a cytokine;
- a growth factor;
- a radionuclide;
- a hormone;
- an anti-viral agent;
- an anti-bacterial agent;
- a fluorescent dye;
- an immunoregulatory/immunostimulatory agent;
- a half-life increasing moiety;
- a solubility increasing moiety;
- a polymer-toxin conjugate;
- a nucleic acid;
- a biotin or streptavidin moiety;
- a vitamin;
- a protein degradation agent ('PROTAC');
- a target binding moiety; and/or
- an anti-inflammatory agent.

16. The method according to embodiment 15, wherein the toxin is at least one selected from the group consisting of
- a pyrrolobenzodiazepine (e.g., PBD);
- an auristatin (e.g., MMAE, MMAF);
- a maytansinoid (e.g., maytansine, DM1, DM4, DM21);
- a duocarmycin;
- a nicotinamide phosphoribosyltransferase (NAMPT) inhibitor;
- a tubulysin;
- an enediyne (e.g., calicheamicin);
- an anthracycline derivative (PNU) (e.g., doxorubicin);
- a pyrrole-based kinesin spindle protein (KSP) inhibitor;
- a cryptophycin;
- a drug efflux pump inhibitor;
- a sandramycin;
- an amanitin (e.g., α-amanitin); and
- a camptothecin (e.g., exatecans, deruxtecans).

17. The method according to any one of embodiments 14 to 16, wherein the chemical spacer (Sp$_2$) comprises a self-immolative moiety.

18. The method according to embodiment 17, wherein the self-immolative moiety is directly attached to the payload B.

19. The method according to embodiment 17 or 18, wherein the self-immolative moiety comprises a p-aminobenzyl carbamoyl (PABC) moiety.

20. The method according to any one of embodiments 1 to 19, wherein the antibody is an IgG antibody, in particular an IgG1 antibody.

21. The method according to embodiment 20, wherein the Gln residue to which the linker is conjugated is comprised in an Fc domain of the antibody, in particular wherein the Gln residue to which the linker is conjugated is Gln residue Q295 (EU numbering) of the $C_H2$ domain of an IgG antibody.

22. The method according to embodiment 20, wherein the Gln residue to which the linker is conjugated has been introduced into the heavy or light chain of the antibody by molecular engineering.

23. The method according to embodiment 22, wherein the Gln residue that has been introduced into the heavy or light chain of the antibody by molecular engineering is N297Q (EU numbering) of the $C_H2$ domain of an aglycosylated IgG antibody.

24. The method according to embodiment 22, wherein the Gln residue that has been introduced into the heavy or light chain of the antibody by molecular engineering is comprised in a peptide that has been (a) integrated into the heavy or light chain of the antibody or (b) fused to the N- or C-terminal end of the heavy or light chain of the antibody.

25. The method according to embodiment 24, wherein the peptide comprising the Gln residue has been fused to the C-terminal end of the heavy chain of the antibody.

26. The method according to any one of embodiments 20 to 22 or 24 to 25, wherein the IgG antibody is a glycosylated IgG antibody, in particular wherein the IgG antibody is glycosylated at residue N297 (EU numbering) of the $C_H2$ domain.

27. The method according to any one of embodiments 1 to 26, wherein the antibody is selected from the group consisting of: Brentuximab, Trastuzumab, Gemtuzumab, Inotuzumab, Avelumab, Cetuximab, Rituximab, Daratumumab, Pertuzumab, Vedolizumab, Ocrelizumab, Tocilizumab, Ustekinumab, Golimumab, Obinutuzumab, Sacituzumab, Belantamab, Polatuzumab and Enfortumab.

28. The method according to any one of embodiments 1 to 27, wherein the antibody is selected from the group consisting of: Brentuximab, Gemtuzumab, Trastuzumab, Inotuzumab, Polatuzumab, Enfortumab, Sacituzumab and Belantamab.

29. The method according to any one of embodiments 1 to 28, wherein the antibody is Polatuzumab or Trastuzumab or Enfortumab.

30. The method according to any one of embodiments 1 to 29, wherein the linker is conjugated to the γ-carboxamide group of the Gln residue comprised in the antibody.

31. The method according to any one of embodiments 1 to 30, wherein the linker is suitable for conjugation to a glycosylated antibody with a conjugation efficiency of at least 20%, 30%, 40%, 50%, 60%, 70%, 75%, 80%, 85%, 90% or 95%.

32. The method according to any one of embodiments 1 to 31, wherein the microbial transglutaminase is derived from a *Streptomyces* species, in particular *Streptomyces mobaraensis*.

33. An antibody-linker conjugate which has been produced with a method according to any one of embodiments 1 to 32.

34. An antibody-linker conjugate comprising:
a) an antibody; and
b) a linker comprising the structure:

($Sp_1$)-RK-($Sp_2$)-B-($Sp_3$) or ($Sp_1$)-B-($Sp_2$)-RK-($Sp_3$); wherein ($Sp_1$) is a chemical spacer or is absent;
($Sp_2$) is a chemical spacer or is absent;
($Sp_3$) is a chemical spacer or is absent;

R is arginine or an arginine derivative or an arginine mimetic;
K is lysine or a lysine derivative or a lysine mimetic;
B is a linking moiety or a payload;
wherein the linker is conjugated to the antibody via an isopeptide bond formed between a γ-carboxamide group of a glutamine residue comprised in the antibody and a primary amine comprised in the side chain of the lysine residue, the lysine derivative or the lysine mimetic comprised in the RK motif comprised in the linker.

35. The antibody-linker conjugate according to embodiment 34, wherein the chemical spacers ($Sp_1$), ($Sp_2$) and ($Sp_3$) each independently comprise between 0 and 12 amino acid residues.

36. The antibody-linker conjugate according to embodiment 34 or 35, wherein the linker comprises not more than 25, 20, 15, 14, 13, 12, 11, 10, 9, 8, 7, 6, 5, 4 amino acid residues.

37. The antibody-linker conjugate according to any one of embodiments 34 to 36, wherein the net charge of the linker is neutral or positive.

38. The antibody-linker conjugate according to any one of embodiments 34 to 37, wherein the linker comprises no negatively-charged amino acid residues.

39. The antibody-linker conjugate according to any one of embodiments 34 to 38, wherein the linker comprises an amino acid sequence selected from the group consisting of: RKAA (SEQ ID NO:1), RKA (SEQ ID NO:2), ARK (SEQ ID NO:3) and RKR (SEQ ID NO:4).

40. The antibody-linker conjugate according to any one of embodiments 34 to 39, wherein the linker comprises an amino acid sequence selected from the group consisting of: RKAA (SEQ ID NO:1), RKA (SEQ ID NO:2) and ARK (SEQ ID NO:3).

41. The antibody-linker conjugate according to any one of embodiments 34 to 40, wherein the linker comprises the amino acid sequence RKAA (SEQ ID NO:1).

42. The antibody-linker conjugate according to any one of embodiments 34 to 41, wherein B is a linking moiety.

43. The antibody-linker conjugate according to embodiment 42, wherein the linking moiety B comprises
a bioorthogonal marker group, or
a non-bio-orthogonal entity for crosslinking.

44. The antibody-linker conjugate according to embodiment 43, wherein the bioorthogonal marker group or the non-bio-orthogonal entity for crosslinking consists of or comprises at least one molecule or moiety selected from the group consisting of:
—N—N≡N, or —$N_3$;
Lys($N_3$);
a tetrazine;
an alkyne;
a strained cyclooctyne;
BCN;
a strained alkene;
a photoreactive group;
an aldehyde;
an acyltrifluoroborate;
a protein degradation agent ('PROTAC');
a cyclopentadiene/spirolocyclopentadiene;
a thio-selective electrophile;
—SH; and
cysteine.

45. The antibody-linker conjugate according to any one of embodiments 42 to 44, wherein one or more payloads have conjugated to the linking moiety B.

46. The antibody-linker conjugate according to embodiment 45, wherein one or more payloads have been conjugated to the linking moiety B via a click-reaction.

47. The antibody-linker conjugate according to any one of embodiments 34 to 41, wherein B is a payload.

48. The antibody-linker conjugate according to any one of embodiments 45 to 47, wherein the payload comprises at least one of:
- a toxin;
- a cytokine;
- a growth factor;
- a radionuclide;
- a hormone;
- an anti-viral agent;
- an anti-bacterial agent;
- a fluorescent dye;
- an immunoregulatory/immunostimulatory agent;
- a half-life increasing moiety;
- a solubility increasing moiety;
- a polymer-toxin conjugate;
- a nucleic acid;
- a biotin or streptavidin moiety;
- a vitamin;
- a protein degradation agent ('PROTAC');
- a target binding moiety; and/or
- an anti-inflammatory agent.

49. The antibody-linker conjugate according to embodiment 48, wherein the toxin is at least one selected from the group consisting of
- a pyrrolobenzodiazepine (e.g., PBD);
- an auristatin (e.g., MMAE, MMAF);
- a maytansinoid (e.g., maytansine, DM1, DM4, DM21);
- a duocarmycin;
- a nicotinamide phosphoribosyltransferase (NAMPT) inhibitor;
- a tubulysin;
- an enediyne (e.g., calicheamicin);
- an anthracycline derivative (PNU) (e.g., doxorubicin);
- a pyrrole-based kinesin spindle protein (KSP) inhibitor;
- a cryptophycin;
- a drug efflux pump inhibitor;
- a sandramycin;
- an amanitin (e.g., α-amanitin); and
- a camptothecin (e.g., exatecans, deruxtecans).

50. The antibody-linker conjugate according to any one of embodiments 47 to 49, wherein the chemical spacer ($Sp_2$) comprises a self-immolative moiety.

51. The antibody-linker conjugate according to embodiment 50, wherein the self-immolative moiety is directly attached to the payload B.

52. The antibody-linker conjugate according to embodiment 50 or 51, wherein the self-immolative moiety comprises a p-aminobenzyl carbamoyl (PABC) moiety.

53. The antibody-linker conjugate according to any one of embodiments 34 to 52, wherein the antibody is an IgG antibody, in particular an IgG1 antibody.

54. The antibody-linker conjugate according to embodiment 53, wherein the Gln residue to which the linker is conjugated is comprised in an Fc domain of the antibody, in particular wherein the Gln residue to which the linker is conjugated is Gln residue Q295 (EU numbering) of the $C_H2$ domain of an IgG antibody.

55. The antibody-linker conjugate according to embodiment 53, wherein the Gln residue to which the linker is conjugated has been introduced into the heavy or light chain of the antibody by molecular engineering.

56. The antibody-linker conjugate according to embodiment 55, wherein the Gln residue that has been introduced into the heavy or light chain of the antibody by molecular engineering is N297Q (EU numbering) of the $C_H2$ domain of an aglycosylated IgG antibody.

57. The antibody-linker conjugate according to embodiment 55, wherein the Gln residue that has been introduced into the heavy or light chain of the antibody by molecular engineering is comprised in a peptide that has been (a) integrated into the heavy or light chain of the antibody or (b) fused to the N- or C-terminal end of the heavy or light chain of the antibody.

58. The antibody-linker conjugate according to embodiment 57, wherein the peptide comprising the Gln residue has been fused to the C-terminal end of the heavy chain of the antibody.

59. The antibody-linker conjugate according to any one of embodiments 53 to 55 or 57 to 58, wherein the IgG antibody is a glycosylated IgG antibody, in particular wherein the IgG antibody is glycosylated at residue N297 (EU numbering) of the $C_H2$ domain.

60. The antibody-linker conjugate according to any one of embodiments 34 to 59, wherein the antibody is selected from the group consisting of: Brentuximab, Trastuzumab, Gemtuzumab, Inotuzumab, Avelumab, Cetuximab, Rituximab, Daratumumab, Pertuzumab, Vedolizumab, Ocrelizumab, Tocilizumab, Ustekinumab, Golimumab, Obinutuzumab, Sacituzumab, Belantamab, Polatuzumab and Enfortumab.

61. The antibody-linker conjugate according to any one of embodiments 34 to 60, wherein the antibody is selected from the group consisting of: Brentuximab, Gemtuzumab, Trastuzumab, Inotuzumab, Polatuzumab, Enfortumab, Sacituzumab and Belantamab.

62. The antibody-linker conjugate according to any one of embodiments 34 to 61, wherein the antibody is Polatuzumab or Trastuzumab or Enfortumab.

63. An antibody-drug conjugate comprising:
a) an IgG antibody; and
b) a linker comprising a drug moiety B, wherein the drug moiety B is covalently linked to an amino acid sequence selected from the group consisting of: RKAA (SEQ ID NO:1), RKA (SEQ ID NO:2), ARK (SEQ ID NO:3) or RKR (SEQ ID NO:4);
wherein the linker is conjugated to the IgG antibody via an isopeptide bond formed between the γ-carboxamide group of glutamine residue Q295 (EU numbering) of the $C_H2$ domain of the antibody and the primary amine comprised in the side chain of the lysine residue comprised in the linker.

64. The antibody-drug conjugate according to embodiment 63, wherein the drug moiety B is linked to the N- or C-terminus of the amino acid sequence comprised in the linker via a self-immolative moiety.

65. The antibody-drug conjugate according to embodiment 64, wherein the self-immolative moiety comprises a p-aminobenzyl carbamoyl (PABC) moiety.

66. The antibody-drug conjugate according to any one of embodiments 63 to 65, wherein the IgG antibody is a glycosylated IgG antibody, in particular wherein the IgG antibody is glycosylated at residue N297 (EU numbering) of the $C_H2$ domain.

67. The antibody-drug conjugate according to any one of embodiments 63 to 66, wherein the IgG antibody is an IgG1 antibody.

68. The antibody-drug conjugate according to any one of embodiments 63 to 67, wherein the IgG antibody is Polatuzumab or an antibody comprising a heavy chain as set forth in SEQ ID NO:5 and a light chain as set forth in SEQ ID NO:6.

69. The antibody-drug conjugate according to any one of embodiments 63 to 67, wherein the IgG antibody is Trastuzumab or an antibody comprising a heavy chain as set forth in SEQ ID NO:7 and a light chain as set forth in SEQ ID NO:8.

70. The antibody-drug conjugate according to any one of embodiments 63 to 67, wherein the IgG antibody is Enfortumab or an antibody comprising a heavy chain as set forth in SEQ ID NO:9 and a light chain as set forth in SEQ ID NO:10 or 11.

71. The antibody-drug conjugate according to any one of embodiments 63 to 70, wherein the drug is a toxin selected from the group consisting of:
- a pyrrolobenzodiazepine (e.g., PBD);
- an auristatin (e.g., MMAE, MMAF);
- a maytansinoid (e.g., maytansine, DM1, DM4, DM21);
- a duocarmycin;
- a nicotinamide phosphoribosyltransferase (NAMPT) inhibitor;
- a tubulysin;
- an enediyne (e.g. calicheamicin);
- an anthracycline derivative (PNU) (e.g., doxorubicin);
- a pyrrole-based kinesin spindle protein (KSP) inhibitor;
- a cryptophycin;
- a drug efflux pump inhibitor;
- a sandramycin;
- an amanitin (e.g., α-amanitin); and
- a camptothecin (e.g., exatecans, deruxtecans).

72. The antibody-drug conjugate according to any one of embodiments 63 to 71, wherein the linker has the structure RKAA-PABC-B, in particular wherein B is an auristatin or a maytansinoid, in particular wherein the auristatin is MMAE and wherein the maytansinoid is DM1 or maytansine.

73. The antibody-drug conjugate according to any one of embodiments 63 to 71, wherein the linker has the structure RKA-PABC-B, in particular wherein B is an auristatin or a maytansinoid, in particular wherein the auristatin is MMAE and wherein the maytansinoid is DM1 or maytansine.

74. The antibody-drug conjugate according to any one of embodiments 63 to 71, wherein the linker has the structure ARK-PABC-B, in particular wherein B is an auristatin or a maytansinoid, in particular wherein the auristatin is MMAE and wherein the maytansinoid is DM1 or maytansine.

75. The antibody-drug conjugate according to any one of embodiments 63 to 71, wherein the linker has the structure RKR-PABC-B, in particular wherein B is an auristatin or a maytansinoid, in particular wherein the auristatin is MMAE and wherein the maytansinoid is DM1 or maytansine.

76. A linker construct comprising the structure:

$(Sp_1)$-RK-$(Sp_2)$-B-$(Sp_3)$ or $(Sp_1)$-B-$(Sp_2)$-RK-$(Sp_3)$; wherein $(Sp_1)$ is a chemical spacer or is absent;
$(Sp_2)$ is a chemical spacer or is absent;
$(Sp_3)$ is a chemical spacer or is absent;
R is arginine or an arginine derivative or an arginine mimetic;
K is lysine or a lysine derivative or a lysine mimetic;
B is a linking moiety or a payload.

77. The linker construct according to embodiment 76, wherein the chemical spacers $(Sp_1)$, $(Sp_2)$ and $(Sp_3)$ each independently comprise between 0 and 12 amino acid residues.

78. The linker construct according to embodiment 76 or 77, wherein the linker comprises not more than 25, 20, 15, 14, 13, 12, 11, 10, 9, 8, 7, 6, 5, 4 amino acid residues.

79. The linker construct according to any one of embodiments 76 to 78, wherein the net charge of the linker is neutral or positive.

80. The linker construct according to any one of embodiments 76 to 79, wherein the linker comprises no negatively-charged amino acid residues.

81. The linker construct according to any one of embodiments 76 to 80, wherein the linker comprises the amino acid sequence RKAA (SEQ ID NO:1), RKA (SEQ ID NO:2), ARK (SEQ ID NO:3) or RKR (SEQ ID NO:4).

82. The linker construct according to any one of embodiments 76 to 81, wherein B is a linking moiety.

83. The linker construct according to embodiment 82, wherein the linking moiety B comprises
- a bioorthogonal marker group, or
- a non-bio-orthogonal entity for crosslinking.

84. The linker construct according to embodiment 83, wherein the bioorthogonal marker group or the non-bio-orthogonal entity for crosslinking consists of or comprises at least one molecule or moiety selected from the group consisting of:
- —N—N≡N, or —$N_3$;
- Lys($N_3$);
- a tetrazine;
- an alkyne;
- a strained cyclooctyne;
- BCN;
- a strained alkene;
- a photoreactive group;
- an aldehyde;
- an acyltrifluoroborate;
- a protein degradation agent ('PROTAC');
- a cyclopentadiene/spirolocyclopentadiene;
- a thio-selective electrophile;
- —SH; and
- cysteine.

85. The linker construct according to any one of embodiments 76 to 84, wherein the linker construct consists of or comprises the structure RKAA-B, in particular wherein B is Lys($N_3$) or cysteine.

86. The linker construct according to any one of embodiments 76 to 84, wherein the linker construct consists of or comprises the structure RKA-B, in particular wherein B is Lys($N_3$) or cysteine.

87. The linker construct according to any one of embodiments 76 to 84, wherein the linker construct consists of or comprises the structure ARK-B, in particular wherein B is Lys($N_3$) or cysteine.

88. The linker construct according to any one of embodiments 76 to 84, wherein the linker construct consists of or comprises the structure B-RKR, in particular wherein B is Lys($N_3$) or cysteine.

89. The linker construct according to any one of embodiments 76 to 81, wherein B is a payload.

90. The linker construct according to embodiment 89, wherein the payload comprises at least one of:
- a toxin;
- a cytokine;
- a growth factor;
- a radionuclide;

a hormone;
an anti-viral agent;
an anti-bacterial agent;
a fluorescent dye;
an immunoregulatory/immunostimulatory agent;
a half-life increasing moiety;
a solubility increasing moiety;
a polymer-toxin conjugate;
a nucleic acid;
a biotin or streptavidin moiety;
a vitamin;
a protein degradation agent ('PROTAC');
a target binding moiety; and/or
an anti-inflammatory agent.

91. The linker construct according to embodiment 90, wherein the toxin is at least one selected from the group consisting of
a pyrrolobenzodiazepine (e.g., PBD);
an auristatin (e.g., MMAE, MMAF);
a maytansinoid (e.g., maytansine, DM1, DM4, DM21);
a duocarmycin;
a nicotinamide phosphoribosyltransferase (NAMPT) inhibitor;
a tubulysin;
an enediyne (e.g. calicheamicin);
an anthracycline derivative (PNU) (e.g., doxorubicin);
a pyrrole-based kinesin spindle protein (KSP) inhibitor;
a cryptophycin;
a drug efflux pump inhibitor;
a sandramycin;
an amanitin (e.g., α-amanitin); and
a camptothecin (e.g., exatecans, deruxtecans).

92. The linker construct according to any one of embodiments 89 to 91, wherein the chemical spacer ($Sp_2$) comprises a self-immolative moiety.

93. The linker construct according to embodiment 92, wherein the self-immolative moiety is directly attached to the payload B.

94. The linker construct according to embodiment 92 or 93, wherein the self-immolative moiety comprises a p-aminobenzyl carbamoyl (PABC) moiety.

95. The linker construct according to any one of embodiments 89 to 94, wherein the linker construct consists of or comprises the structure RKAA-PABC-B, in particular wherein B is an auristatin or a maytansinoid, in particular wherein the auristatin is MMAE and wherein the maytansinoid is DM1 or maytansine.

96. The linker construct according to any one of embodiments 89 to 94, wherein the linker construct consists of or comprises the structure RKA-PABC-B, in particular wherein B is an auristatin or a maytansinoid, in particular wherein the auristatin is MMAE and wherein the maytansinoid is DM1 or maytansine.

97. The linker construct according to any one of embodiments 89 to 94, wherein the linker construct consists of or comprises the structure ARK-PABC-B, in particular wherein B is an auristatin or a maytansinoid, in particular wherein the auristatin is MMAE and wherein the maytansinoid is DM1 or maytansine.

98. The linker construct according to any one of embodiments 89 to 94, wherein the linker construct consists of or comprises the structure B-PABC-RKR, in particular wherein B is an auristatin or a maytansinoid, in particular wherein the auristatin is MMAE and wherein the maytansinoid is DM1 or maytansine.

99. Use of a linker construct according to any one of embodiments 76 to 98 in the production of an antibody-linker conjugate by means of a microbial transglutaminase.

100. The use according to embodiment 99, wherein the antibody is an IgG antibody, in particular an IgG1 antibody.

101. The use according to embodiment 65 or 66, wherein the antibody is Polatuzumab or Trastuzumab or Enfortumab.

102. A pharmaceutical composition comprising
a) the antibody-linker conjugate according to any one of embodiments 33 to 62, in particular wherein the antibody-linker conjugate comprises at least one payload; or
b) the antibody drug-conjugate according to any one of embodiments 63 to 75; and
the pharmaceutical composition comprising at least one pharmaceutically acceptable ingredient.

103. The pharmaceutical composition according to embodiment 102 comprising at least one additional therapeutically active agent.

104. The antibody-linker conjugate according to any one of embodiments 33 to 62, in particular wherein the antibody-linker conjugate comprises at least one payload, the antibody-drug conjugate according to any one of embodiments 63 to 75, or the pharmaceutical composition according to embodiment 102 or 103 for use in therapy and/or diagnostics.

105. The antibody-linker conjugate according to any one of embodiments 33 to 62, in particular wherein the antibody-linker conjugate comprises at least one payload, the antibody-drug conjugate according to any one of embodiments 63 to 75, or the pharmaceutical composition according to embodiment 102 or 103 for use in the treatment of a patient suffering from,
being at risk of developing, and/or
being diagnosed for
a neoplastic disease, a neurological disease, an autoimmune disease, an inflammatory disease or an infectious disease.

106. The antibody-linker conjugate, the antibody-drug conjugate or the pharmaceutical composition for use according to embodiment 105, wherein the antibody-linker conjugate or the antibody-drug conjugate comprised in the pharmaceutical composition comprises Polatuzumab and wherein the neoplastic disease is a B-cell associated cancer.

107. The antibody-linker conjugate, the antibody-drug conjugate or the pharmaceutical composition for use according to embodiment 106, wherein the B-cell associated cancer is non-Hodgkin lymphoma, in particular wherein the B-cell associated cancer is diffuse large B-cell lymphoma.

108. The antibody-linker conjugate, the antibody-drug conjugate or the pharmaceutical composition for use according to embodiment 106 or 107, wherein the antibody-linker conjugate, the antibody-drug conjugate or the pharmaceutical composition is administered in combination with bendamustine and/or rituximab.

109. The antibody-linker conjugate, the antibody-drug conjugate or the pharmaceutical composition for use according to embodiment 105, wherein the antibody-linker conjugate or the antibody-drug conjugate comprised in the pharmaceutical composition comprises Trastuzumab and wherein the neoplastic disease is a HER2-positive cancer, in particular HER2-positive breast, gastric, ovarian or lung cancer.

110. The antibody-linker conjugate, the antibody-drug conjugate or the pharmaceutical composition for use according to embodiment 109, wherein the antibody-linker conjugate, the antibody-drug conjugate or the pharmaceutical composition is administered in combination with lapatinib, capecitabine and/or a taxane.

111. The antibody-linker conjugate, the antibody-drug conjugate or the pharmaceutical composition for use according to embodiment 105, wherein the antibody-linker conjugate or the antibody-drug conjugate comprised in the pharmaceutical composition comprises Enfortumab or an Enfortumab variant and wherein the neoplastic disease is a Nectin-4 positive cancer, in particular Nectin-4 positive pancreatic cancer, lung cancer, bladder cancer or breast cancer.

112. The antibody-linker conjugate, the antibody-drug conjugate or the pharmaceutical composition for use according to embodiment 111, wherein the antibody-linker conjugate, the antibody-drug conjugate or the pharmaceutical composition is administered in combination with a cisplatin-based chemotherapeutic agent and/or Pembrolizumab.

113. Use of the antibody-linker conjugate according to any one of embodiments 33 to 62, in particular wherein the antibody-linker conjugate comprises at least one payload, the antibody-drug conjugate according to any one of embodiments 63 to 75, or the pharmaceutical composition according to embodiment 102 or 103 for the manufacture of a medicament for the treatment of a patient
  suffering from,
  being at risk of developing, and/or
  being diagnosed for
  a neoplastic disease, neurological disease, an autoimmune disease, an inflammatory disease or an infectious disease.

114. A method of treating or preventing a neoplastic disease, said method comprising administering to a patient in need thereof the antibody-linker conjugate according to any one of embodiments 33 to 62, in particular wherein the antibody-linker conjugate comprises at least one payload, the antibody-drug conjugate according to any one of embodiments 63 to 75, or the pharmaceutical composition according to embodiment 102 or 103.

Accordingly, in one embodiment, the invention relates to a method for producing an antibody-linker conjugate by means of a microbial transglutaminase (MTG), the method comprising a step of conjugating a linker comprising the structure (shown in N→C direction)

$(Sp_1)$-RK-$(Sp_2)$-B-$(Sp_3)$ or $(Sp_1)$-B-$(Sp_2)$-RK-$(Sp_3)$ to a Gln residue comprised in an antibody, wherein
  $(Sp_1)$ is a chemical spacer or is absent;
  $(Sp_2)$ is a chemical spacer or is absent;
  $(Sp_3)$ is a chemical spacer or is absent;
  R is arginine or an arginine derivative or an arginine mimetic;
  K is lysine or a lysine derivative or a lysine mimetic;
  B is a linking moiety or a payload;
  and wherein the linker is conjugated to the Gln residue comprised in the antibody via a primary amine comprised in the side chain of the lysine residue, the lysine derivative or the lysine mimetic.

That is, the invention is based, at least in part, on the surprising finding that linkers comprising the peptide motif RK (arginyl-lysyl) can be conjugated to glycosylated antibodies with high efficiency. In the patent application WO 2019/057772 it was demonstrated that peptide-based linkers can be efficiently conjugated to a glutamine-residue of a glycosylated antibody via a lysine residue in the linker. However, now it was surprisingly shown that the extended motif RK provides further improved conjugation efficiency.

The inventors have shown that lysine-comprising linkers without the RK motif result in conjugation efficiencies ranging from 27 to 77%, when being directly attached to a drug molecule (see Table 4). Linkers comprising an RK motif, as provided herein, were conjugated to glycosylated antibodies with efficiencies of at least 82% and, in certain instances, up to 100% (see Tables 3 and 5). Thus, linkers comprising an RK motif are particularly preferred over other lysine-based linkers for MTG-based conjugation to glycosylated antibodies, in particular when a payload is directly conjugated to a glycosylated antibody in a one-step reaction.

It is preferred within the present invention, that the linker comprises the structure $(Sp_1)$-RK-$(Sp_2)$-B-$(Sp_3)$ or $(Sp_1)$-B-$(Sp_2)$-RK-$(Sp_3)$, wherein the linker is conjugated to a glutamine residue in an antibody via a primary amine comprised in the residue K comprised in the RK motif of the linker. In certain embodiment, the residue K is a lysine residue. However, in certain embodiments, the residue K may also be a lysine mimetic or a lysine derivative, provided that the lysine mimetic or lysine derivative comprises a primary amine in its amino acid side chain.

Thus, in certain embodiments, the residue K may be a lysine mimetic. The term "lysine mimetic", as used herein, refers to a compound that has a structure that is different from lysine, but that has similar characteristics as lysine and may thus be used to replace lysine in a peptide or protein without significantly altering the function and/or structure of said peptide or protein. In certain embodiments, a lysine mimetic may differ from lysine in the length or composition of the aliphatic chain that connects the primary amine and the α-carbon atom. Thus, in certain embodiments, the lysine mimetic may be ornithine or 2,7-diaminoheptanoic acid. In certain embodiments, the lysine mimetic may be a beta-amino acid, such as beta-homolysine.

In certain embodiments, the residue K may be a lysine derivative. The term "lysine derivative", as used herein, refers to a lysine or lysine mimetic, wherein one or more functional groups comprised in the lysine or lysine mimetic is (are) modified or substituted. Within the present invention, it is preferred that the amino group in the side chain of the lysine derivative is unmodified, such that is available for conjugation to a glutamine residue in a protein. In embodiments, where the residue K is located in the C-terminal position of the linker, K may be a lysine derivative wherein the α-carboxyl group is modified or substituted. In certain embodiments the α-carboxyl group of the lysine mimetic may be amidated.

The linker further comprises the residue R, which, in conjunction with the residue K, forms the RK motif of the linker. In certain embodiments, the residue R is an arginine residue. However, in certain embodiments, the residue R may also be an arginine mimetic or an arginine derivative.

Thus, in certain embodiments, the residue R may be an arginine mimetic. The term "arginine mimetic", as used herein, refers to a compound that has a structure that is different from arginine, but that has similar characteristics as arginine and may thus be used to replace arginine in a peptide or protein without significantly altering the function and/or structure of said peptide or protein. An arginine mimetic may differ from arginine in length or composition of the aliphatic chain that connects the guanidino group and the α-carbon atom. Alternatively, or in addition, arginine mimetics may differ from arginine in the guanidino group itself. That is, the arginine mimetic may comprise a functional group with similar physicochemical properties as the guanidino group. In certain embodiments, the arginine mimetic may be homoarginine, 2-amino-3-guanidino-propionic acid, β-ureidoalanine or citrulline.

In certain embodiments, the residue R may be an arginine derivative. The term "arginine derivative", as used herein, refers to an arginine or arginine mimetic, wherein one or more functional groups comprised in the arginine or arginine mimetic is (are) modified or substituted. An arginine derivative may be arginine or an arginine mimetic, wherein the guanidino group is substituted or modified. In certain embodiments, the arginine derivative may be o-methylarginine. In embodiments, where the residue R is located in the N-terminal position of the linker, R may be an arginine derivative wherein the α-amino group is modified or substituted. In certain embodiments the α-amino group of the arginine mimetic may be acetylated.

It is to be understood that the RK motif preferably consists of the amino-acids arginine and lysine. However, the arginine or lysine residue, or both, may be replaced by a mimetic or derivative as disclosed above. In certain embodiments, the RK motif may consist of the amino acids arginine and ornithine. In certain embodiments, the RK motif may consist of the amino acids arginine and 2,7-diaminoheptanoic. In certain embodiments, the RK motif may consist of the amino acids homoarginine and lysine. In certain embodiments, the RK motif may consist of the amino acids 2-amino-3-guanidino-propionic and lysine. In certain embodiments, the RK motif may consist of the amino acids homoarginine and ornithine. In certain embodiments, the RK motif may consist of the amino acids homoarginine and 2,7-diaminoheptanoic. In certain embodiments, the RK motif may consist of the amino acids 2-amino-3-guanidino-propionic and ornithine. In certain embodiments, the RK motif may consist of the amino acids 2-amino-3-guanidino-propionic and 2,7-diaminoheptanoic.

Within the present invention, the RK motif is embedded in the structure $(Sp_1)$-RK-$(Sp_2)$-B-$(Sp_3)$ or $(Sp_1)$-B-$(Sp_2)$-RK-$(Sp_3)$. That is, the linker may comprise one or more chemical spacers (Sp). The term "chemical spacer" as used herein describes a chemical moiety that is covalently attached to a chemical residue of the linker and/or interposed between two chemical residues of the linker.

In a particular embodiment, the invention relates to the method according to the invention, wherein the chemical spacers $(Sp_1)$, $(Sp_2)$ and $(Sp_3)$ each independently comprise between 0 and 12 amino acid residues.

That is, in certain embodiments, the chemical spacers $(Sp_1)$, $(Sp_2)$ and/or $(Sp_3)$ may be present or absent. In embodiments where $(Sp_1)$, $(Sp_2)$ and/or $(Sp_3)$ are present, $(Sp_1)$, $(Sp_2)$ and/or $(Sp_3)$ may comprise one or more amino acid residues. In such embodiments, each of $(Sp_1)$, $(Sp_2)$ and/or $(Sp_3)$ may comprise between 0 and 12 amino acid residues. It has to be noted that the chemical spacers $(Sp_1)$, $(Sp_2)$ and/or $(Sp_3)$ may also comprise non-amino acid residues, which is disclosed in more detail below.

An "amino acid residue" comprised in the chemical spacer $(Sp_1)$, $(Sp_2)$ and/or $(Sp_3)$ may be an amino acid, an amino acid mimetic or an amino acid derivative. It is to be understood, that the term amino acid encompasses not only α-amino acids, but also other amino acids such as β-, γ- or δ-amino acids. An α-amino acid residue may be present in the chemical spacer $(Sp_1)$, $(Sp_2)$ and/or $(Sp_3)$ in its L- or D-form. In embodiments, where $(Sp_1)$, $(Sp_2)$ and/or $(Sp_3)$ comprises a chiral β-, γ- or δ-amino acid, the chiral β-, γ- or δ-amino acid may be present in its S- or R-form. Thus, in its broadest sense, the term "amino acid residue", as used herein, may refer to any organic compound that contains an amino group (—$NH_2$) and a carboxyl group (—COOH).

Thus, whenever an "amino acid" or an "amino acid residue" is referred to throughout this disclosure, it is to be understood that the term amino acid residue may also encompass amino acid mimetics or derivatives.

Further, it is to be understood that the term amino acid residue is not limited to the known set of proteinogenic amino acids, namely alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine and valine, but also encompasses non-canonical and non-natural amino acids. A "non-canonical amino acid", as used herein, may be any amino acid that is not part of the set of proteinogenic amino acids, but that can be obtained from a natural source. However, it has to be noted that some non-canonical amino acids may also be found in naturally occurring peptides and/or proteins.

A "non-natural amino acid" or "synthetic amino acid", as used herein, may be any molecule that falls under the general definition of an amino acid, i.e., that comprises an amino group and a carboxyl group, but that is not found in nature. Thus, non-natural amino acids are preferably obtained by chemical synthesis. It is to be understood that the differentiation between a non-canonical amino acid and a non-natural amino acid may be uncertain in some instances. For example, an amino acid that is defined as a non-natural amino acid may be, at a later time point, identified in nature and thus reclassified as a non-canonical amino acid.

Examples of non-canonical or non-natural amino acids may be, without limitation, D-amino acids (such as D-alanine, D-arginine, D-methionine), homo-amino acids (such as homoserine, homoarginine, homocysteine, α-aminoadipic acid), N-methylated amino acids (such as sarcosine, N-Me-leucine), α-methyl amino acids (such as α-methylhistidine, α-aminoisobutyric acid), β-amino acids (such as β-alanine, D-3-aminoisobutyric acid, L-β-homoalanine), γ-amino acids (such as γ-aminobutyric acid), alanine mimetics or derivatives (such as β-cyclopropylalanine, phenylglycine, dehydro-alanine, β-cyanoalanine, β-(3-pyridyl)-alanine, β-(1,2,4-triazol-1-yl)-alanine, β-(1-piperazinyl)-alanine), phenylalanine mimetics or derivatives (such as 4-iodophenylalanine, pentafluoro-phenylalanine, naphthylalanine, 4-Aminophenylalanine), arginine mimetics or derivatives (such as β-ureidoalanine, ω-methylarginine), lysine mimetics or derivatives (such as (3-(3-methyl-3H-diazirine-3-yl)propamino)carbonyl-1-lysine, Nε,Nε,Nε-trimethyllysine), histidine mimetics or derivatives (such as 2,5-di-iodohistidine, 1-methylhistidine), tyrosine mimetics or derivatives (such as 3-aminotyrosine, thyronine, 3,5-dinitrotyrosine, 3-hydroxy-methyl-tyrosine, O-phospho-L-tyrosine), tryptophan mimetics or derivatives (such as 5-hydroxy-tryptophan, 1-methyltryptophan), serine mimetics or derivatives (such as β-(2-thienyl)-serine, β-(3,4-dihydroxyphenyl)-serine, O-phosphoserine), threonine mimetics or derivatives (such as allo-threonine, O-phosphothreonine), proline mimetics or derivatives (such as Hydroxyproline, 3,4-dehydro-proline, pyroglutamic acid, thiaproline, cis-octahydroindole-2-carboxylic acid), leucine and isoleucine mimetics or derivatives (such as allo-isoleucine, norleucine, 4,5-dehydroleucine, (4S)-4-hydroxy-L-isoleucine), valine mimetics or derivatives (such as norvaline, γ-hydroxyvaline), citrulline mimetics or derivatives (such as thiocitrulline, homocitrulline), cysteine mimetics or derivatives (such as penicillamine, selenocysteine, buthionine-sulfoximine), methionine mimetics or derivatives (such as S-methylmethionine, L-methionine sulfone, L-methionine sulfoxide, L-methionine sulfo-ximine, selenomethionine), aspartic acid mimetics or derivatives (such as DL-threo-β-hydroxyaspartic acid, L-aspartic acid β-methyl ester), glutamic acid mimetics or derivatives (such as γ-methyleneglutamic acid, γ-carboxyglutamic acid, γ-hydroxyglutamic acid, L-glutamic acid 5-methyl ester, L-2-aminoheptanedioic acid), asparagine mimetics or derivatives (such as L-threo-3-hydroxyasparagine, N,N-dimethyl-L-asparagine, L-2-amino-2-carboxyethanesulfonamide, 5-diazo-4-oxo-L-norvaline), glutamine mimetics or derivatives (such as 4-F-(2S, 4R)-fluoroglutamine, γ-glutamylmethylamide, theanine, L-glutamic acid γ-monohydroxamate), amino acids comprising a cyclic moiety (such as 4-aminopiperidine-4-carboxylic acid, azetidine-2-carboxylic acid, pipecolic acid, 1-aminocyclopentanecarboxylic acid, spinacine), or amino acids comprising a bio-orthogonal moiety (such as propargylglycine, α-allylglycine, L-azido-homoalanine, p-benzoyl-1-phenylalanine, p-2-fluoroacetyl-1-phenylalanine, (S)-2-amino-3-(4-(6-methyl-1,2,4,5-tetrazin-3-yl) phenyl) propanoic acid).

Besides the alpha-amino acids described above, the chemical spacers $(Sp_1)$, $(Sp_2)$ and/or $(Sp_3)$ may comprise one or more β-, γ-, δ- or ε-amino acids. Thus, in certain embodiments, the linker may be a peptidomimetic. The peptidomimetic may not exclusively contain classical peptide bonds that are formed between two α-amino acids but may additionally or instead comprise one or more amide bonds that are formed between an alpha amino acid and a β-, γ-, δ- or ε-amino acid, or between two β-, γ-, δ- or ε-amino acids, respectively. Accordingly, in any instance of the present invention where the linker is described as a peptide, it is to be understood that the linker may also be a peptidomimetic and thus not exclusively consist of α-amino acids, but may instead comprise one or more β-, γ-, δ- or ε-amino acids or molecules that are not classified as an amino acid. Examples of β-, γ-, δ- or ε-amino acids that may be comprised in the linker of the present invention include, but are not limited to, β-alanine, γ-aminobutyric acid, 4-amino-3-hydroxy-5-phenylpentanoic acid, 4-amino-3-hydroxy-6-methylheptanoic acid, 6-aminohexanoic acid and statine.

Furthermore, the chemical spacers $(Sp_1)$, $(Sp_2)$ and/or $(Sp_3)$ may comprise amino acid derivatives and/or amino acid mimetics. In embodiments where $(Sp_1)$, $(Sp_2)$ and/or $(Sp_3)$ comprise one or more amino acid derivatives, it is preferred that the amino acid derivatives have free amino and carboxyl groups, such that they can undergo the formation of peptide or isopeptide bonds. In embodiments where $(Sp_1)$, $(Sp_2)$ and/or $(Sp_3)$ comprise one or more amino acid mimetics, the amino acid mimetics may have free amino and carboxyl groups, such that they can undergo the formation of peptide or isopeptide bonds. However, in certain embodiments, amino acid mimetics or derivatives may have a substituted amino group that does not prevent the formation of a peptide bond. Examples of such amino acid mimetics or derivatives may be N-methylated amino acids such as sarcosine or N-Me-leucine.

In embodiments where an amino acid residue comprised in $(Sp_1)$ or $(Sp_3)$ is a terminal amino acid residue, the terminal amino acid residue may comprise a modified, protected or substituted N-terminal amino group or C-terminal carboxyl group.

Further, the amino acid mimetic or derivative may be an amino acid comprising a derivatized amino group, such as mimetics or derivatives of proline or other cyclic amino acids such as azetidine-2-carboxylic acid, pipecolic acid or spinacine. Further, an amino acid mimetic may also comprise other functional groups that replace the amino and/or carboxyl groups of a standard amino acid, which allows the amino acid mimetic to undergo the formation of alternative bonds with adjacent amino acids, amino acid derivatives and/or amino acid mimetics and to form a peptidomimetic.

The term "amino acid mimetic", as used herein, refers to a compound that has a structure that is different from a particular amino acid, but that functions in a manner similar to said particular amino acid and may thus be used to replace said particular amino acid. An amino acid mimetic is said to function in a similar manner as a particular amino acid, if it fulfils, at least to some extent, similar structural and/or functional features as the amino acid it mimics. The term "amino acid derivative" refers to an amino acid as defined herein, wherein one or more functional group(s) comprised in the amino acid is (are) modified or substituted. An amino acid derivative may preferably be a derivative of a proteinogenic or non-canonical amino acid. Any functional group of an amino acid derivative may be substituted or modified.

In embodiments where the linker comprises one or more terminal amino acid residue(s), the terminal amino acid residue may be protected. For example, in embodiments where $(Sp_1)$ comprises an N-terminal amino acid residue, the N-terminal amino group may be protected. For example, in certain embodiments, the N-terminal amino acid residue comprised in the spacer $(Sp_1)$ may be acetylated. In other embodiments, the R residue comprised in the RK motif may be the N-terminal amino acid of the linker. In such embodiments, the N-terminal amino group of the arginine, the arginine mimetic or the arginine derivative may be protected, for example by acetylation. In certain embodiments, the linking moiety B or the payload B may be an amino acid or based on an amino acid. In such embodiments, the N-terminal amino group of the amino acid-based payload or linking moiety B may be protected, for example by acetylation.

Likewise, in embodiments where $(Sp_3)$ comprises a C-terminal amino acid residue, the C-terminal carboxyl group may be protected. For example, in certain embodiments, the C-terminal amino acid residue in the spacer $(Sp_3)$ may be amidated. In other embodiments, the K residue comprised in the RK motif may be the C-terminal amino acid of the linker. In such embodiments, the C-terminal carboxyl group of the lysine, the lysine mimetic or the lysine derivative may be protected, for example by amidation. In certain embodiments, the linking moiety B or the payload B may be an amino acid or based on an amino acid. In such embodiments, the C-terminal carboxyl group of the amino acid-based payload or linking moiety B may be protected, for example by amidation.

In certain embodiments, each of the chemical spacers $(Sp_1)$, $(Sp_2)$ and/or $(Sp_3)$ may comprise 0 to 12 amino acid residues, including amino acid derivatives and amino acid mimetics. That is, in certain embodiments, $(Sp_1)$ may comprise 0, 1, 2, 3, 4, 5, 6, 7, 8, 9, 10, 11 or 12 amino acid residues, $(Sp_2)$ may comprise 0, 1, 2, 3, 4, 5, 6, 7, 8, 9, 10, 11 or 12 amino acid residues and $(Sp_3)$ may comprise 0, 1, 2, 3, 4, 5, 6, 7, 8, 9, 10, 11 or 12 amino acid residues.

In a particular embodiment, the invention relates to the method according to the invention, wherein the linker comprises not more than 25, 20, 15, 14, 13, 12, 11, 10, 9, 8, 7, 6, 5, 4 amino acid residues.

That is, in certain embodiments, the linker may comprise 25, 24, 23, 22, 21, 20, 19, 18, 17, 16, 15, 14, 13, 12, 11, 10, 9, 8, 7, 6, 5, 4, 3 or 2 amino acid residues, including amino acid mimetics and amino acid derivative. It is to be understood that the amino acid residues comprised in the linker, including amino acid mimetics and amino acid derivatives, are preferably amino acid residues comprised in the RK motif, in the chemical spacers ($Sp_1$), ($Sp_2$) and/or ($Sp_3$) and, in certain embodiments, also in B, when B is an amino acid-based linking moiety or payload. In embodiments where the linker only comprises two amino acid residues, the two amino acid residues are comprised in the RK motif. In such embodiments, ($Sp_1$), ($Sp_2$) and/or ($Sp_3$) are either absent or do not comprise any amino acids, amino acid mimetics or amino acid derivatives.

In certain embodiments, the linker may comprise between 2 and 25 amino acid residues, including amino acid mimetics and amino acid derivatives. In other embodiments, the linker may comprise between 2 and 20 amino acid residues, including amino acid mimetics and amino acid derivatives. In other embodiments, the linker may comprise between 2 and 15 amino acid residues, including amino acid mimetics and amino acid derivatives. In other embodiments, the linker may comprise between 2 and 10 amino acid residues, including amino acid mimetics and amino acid derivatives. In other embodiments, the linker may comprise between 3 and 10 amino acid residues, including amino acid mimetics and amino acid derivatives. In other embodiments, the linker may comprise between 3 and 8 amino acid residues, including amino acid mimetics and amino acid derivatives. In other embodiments, the linker may comprise between 3 and 6 amino acid residues, including amino acid mimetics and amino acid derivatives.

In a particular embodiment, the invention relates to the method according to the invention, wherein the net charge of the linker is neutral or positive.

In certain embodiments, the linker is a peptide linker (or a peptidomimetic as disclosed herein). That is, the chemical spacers ($Sp_1$), ($Sp_2$) and/or ($Sp_3$), if present, consist exclusively of amino acids, amino acid mimetics or amino acid derivatives. The net charge of a peptide is usually calculated at neutral pH (7.0). In the simplest approach, the net charge is determined by adding the number of positively charged amino acid residues (Arg and Lys and optionally His) and the number of negatively charged ones (Asp and Glu) and calculate the difference of the two groups. In cases where the linker comprises non-canonical amino acids or amino acid derivatives in which a charged functional group is modified or substituted, the skilled person is aware of methods to determine the charge of the non-canonical amino acid or amino acid derivative at neutral pH.

In certain embodiments, the payload or linking moiety B or any non-amino acid moiety comprised in ($Sp_1$), ($Sp_2$) and/or ($Sp_3$) may also contribute to the net charge of the linker. However, the skilled person is aware of methods to calculate the net charge of the entire linker, including any non-amino acid moieties, preferably at neutral pH (7.0).

In certain embodiments, the net charge of a linker is calculated solely based on the amino acid residues comprised in the linker, including amino acid mimetics and amino acid derivatives. Thus, in a particular embodiment, the invention relates to the method according to the invention, wherein the net charge of the amino acid residues comprised in the linker is neutral or positive.

In a particular embodiment, the invention relates to the method according to the invention, wherein the linker comprises no negatively-charged amino acid residues.

That is, the linker may be free of negatively charged amino acid residues, including amino acid mimetics and amino acid derivatives. A negatively charged amino acid residue is an amino acid, amino acid mimetic or amino acid derivative which carries a negative charge at neutral pH (7.0). Negatively charged canonical amino acids are glutamic acid and aspartic acid. However, negatively charged non-canonical amino acids, amino acid mimetics and amino acid derivatives are known in the art.

In a particular embodiment, the invention relates to the method according to the invention, wherein the linker comprises at least one positively-charged amino acid residue outside of the RK motif. That is, ($Sp_1$), ($Sp_2$) and/or ($Sp_3$) comprise at least one positively-charged amino acid. In certain embodiments, ($Sp_1$), ($Sp_2$) and/or ($Sp_3$) comprise at least one histidine residue.

Besides or instead of amino acid residues, including amino acid mimetics and derivatives, the chemical spacers ($Sp_1$), ($Sp_2$) and/or ($Sp_3$) may comprise or consist of non-amino acid moieties.

That is, in certain embodiments, the chemical spacers ($Sp_1$), ($Sp_2$) and/or ($Sp_3$) may not exclusively consist of amino acids, amino acid mimetics or amino acid derivatives. That is, the chemical spacers ($Sp_1$), ($Sp_2$) and/or ($Sp_3$) may comprise non-amino acid components or may exclusively consist of non-amino acid components. In certain embodiments, the chemical spacers ($Sp_1$), ($Sp_2$) and/or ($Sp_3$) may comprise amino acid and non-amino acid components.

For example, but without limitation, each of the chemical spacers ($Sp_1$), ($Sp_2$) and/or ($Sp_3$) may comprise a carbon comprising framework of 1 to 200 atoms, optionally a carbon comprising framework of at least 10 atoms, e.g. 10 to 100 atoms or 20 to 100 atoms, substituted at one or more atoms, optionally wherein the carbon comprising framework is a linear hydrocarbon or comprises a cyclic group, a symmetrically or asymmetrically branched hydrocarbon, monosaccharide, disaccharide, linear or branched oligosaccharide (asymmetrically branched or symmetrically branched), other natural linear or branched oligomers (asymmetrically branched or symmetrically branched), or more generally any dimer, trimer, or higher oligomer (linear, asymmetrically branched or symmetrically branched) resulting from any chain-growth or step-growth polymerization process.

($Sp_1$), ($Sp_2$) and/or ($Sp_3$) may be any straight, branched and/or cyclic $C_{2-30}$ alkyl, $C_{2-30}$ alkenyl, $C_{2-30}$ alkynyl, $C_{2-30}$ heteroalkyl, $C_{2-30}$ heteroalkenyl, $C_{2-30}$ heteroalkynyl, optionally wherein one or more homocyclic aromatic compound radical or heterocyclic compound radical may be inserted; notably, any straight or branched $C_{2-5}$ alkyl, $C_{5-10}$ alkyl, $C_{11-20}$ alkyl, —O—$C_{1-5}$ alkyl, —O—$C_{5-10}$ alkyl, —O—$C_{11-20}$ alkyl, or $(CH_2-CH_2-O-)_{1-24}$ or $(CH_2)_{x1}-(CH_2-O-CH_2)_{1-24}-(CH_2)_{x2}-$ group, wherein x1 and x2 are independently an integer selected among the range of 0 to 20, an amino acid, an oligopeptide, glycan, sulfate, phosphate, or carboxylate. In some embodiments, ($Sp_1$), ($Sp_2$) and/or ($Sp_3$) may comprise a $C_{2-6}$ alkyl group.

In certain embodiments, the chemical spacers ($Sp_1$), ($Sp_2$) and/or ($Sp_3$) may comprise one or more polyethylene glycol (PEG) moieties or comparable condensation polymers, such as poly(carboxybetaine methacrylate) (pCBMA), polyoxazoline, polyglycerol, polyvinylpyrrolidone or poly(hydroxyethylmethacrylate) (pHEMA). Polyethylene glycol (PEG) is a polyether compound with many applications from industrial manufacturing to medicine. PEG is also known as polyethylene oxide (PEO) or polyoxyethylene (POE), depending on its molecular weight. The structure of PEG is commonly expressed as H—(O—$CH_2$—$CH_2$)$_n$—OH. The skilled person is aware of methods to functionalize condensation polymers such that they can be coupled to an amino acid residue or a payload.

It has been shown by the inventors that linkers comprising a PEG moiety can be conjugated to a glycosylated antibody as efficiently as comparable linkers without a PEG moiety. For example, the linkers ARK-PEG$_2$-PABC-MMAE (FIG. 14) and ARK-PEG$_2$-(NH)—(CH$_3$)—S—C4-maytansine (FIG. 15) were conjugated to glycosylated Polatuzumab with an efficiency of 92 and 90%, respectively (compared to 94% for ARK-PABC-MMAE). In another example, the linkers ARK-PEG$_2$-PABC-MMAE (FIG. 14) and ARK-PEG$_2$-(NH)—(CH$_3$)—S—C4-maytansine (FIG. 15) were conjugated to glycosylated Trastuzumab with an efficiency of 99% (compared to 100% for ARK-PABC-MMAE).

Thus, in a particular embodiment, the invention relates to the method according to the invention, wherein the linker comprises one or more PEG moieties. In certain embodiments, a PEG moiety may be comprised in the chemical spacers (Sp$_1$), (Sp$_2$) and/or (Sp$_3$). In certain embodiments, each PEG moiety comprised in a linker may comprise between 2 and 20 ethylene glycol monomers, between 2 and 15 ethylene glycol monomers, between 2 and 10 ethylene glycol monomers or between 2 and 5 ethylene glycol monomers. In certain embodiments, a PEG moiety is comprised in (Sp$_2$) to directly connect a linking moiety or a payload to the RK motif. In certain embodiments, a PEG moiety is comprised in (Sp$_2$) to connect a linking moiety or a payload to an amino acid residue comprised in (Sp$_2$). In certain embodiments, a PEG moiety is comprised in (Sp$_2$) to connect the RK motif to a self-immolative moiety, which is in turn connected to a payload. In certain embodiments, a PEG moiety is comprised in (Sp$_2$) to connect an amino acid residue comprised in (Sp$_2$) with a self-immolative moiety, which is in turn connected to a payload.

In certain embodiments, the chemical spacers (Sp$_1$), (Sp$_2$) and/or (Sp$_3$) may comprise a dextran. The term "dextran" as used herein refers to a complex, branched glucan composed of chains of varying lengths, which may have weights of ranging from 3 to 2000 kDa. The straight chain typically consists of alpha-1,6 glycosidic linkages between glucose molecules, while branches begin from alpha-1,3 linkages. Dextran may be synthesized from sucrose, e.g. by lactic acid bacteria. In the context of the present invention dextran to be used as carrier may preferably have a molecular weight of about 15 to 1500 kDa.

In certain embodiments, the chemical spacers (Sp$_1$), (Sp$_2$) and/or (Sp$_3$) may comprise an oligonucleotide. The term "oligonucleotide" as used herein refers to an oligomer or polymer of either ribonucleic acid (RNA) or deoxyribonucleic acid (DNA), as well as non-naturally occurring oligonucleotides. Due to higher stability, an oligonucleotide is preferably a polymer of DNA.

In certain embodiments, the chemical spacers (Sp$_1$), (Sp$_2$) and/or (Sp$_3$), if present, consist exclusively of amino acid residues, including amino acid mimetics and derivatives, and PEG moieties. In certain embodiments, the chemical spacers (Sp$_1$), (Sp$_2$) and/or (Sp$_3$), if present, consist exclusively of amino acid residues, including amino acid mimetics and derivatives. In certain embodiments, all amino acid residues comprised in the chemical spacers (Sp$_1$), (Sp$_2$) and/or (Sp$_3$) are α-L-amino acids. That is, in certain embodiments, the linker, excluding the payload or linking moiety B, consists exclusively of amino acid residues. In certain embodiments, the linker, excluding the payload or linking moiety B, consists exclusively of α-L-amino acid residues. Such peptide-based linkers may comprise a protection group at the N- and/or C-terminus. That is, the N-terminal amino group may be acetylated and/or the C-terminal carboxyl group may be amidated.

It has to be noted that the chemical spacers (Sp$_1$), (Sp$_2$) and/or (Sp$_3$) may have identical structures. However, it is preferred that each of the chemical spacers (Sp$_1$), (Sp$_2$) and/or (Sp$_3$) has a different structure and/or that not all of the chemical spacers (Sp$_1$), (Sp$_2$) and/or (Sp$_3$) are present at the same time. That is, in certain embodiments, only one or two of the chemical spacers (Sp$_1$), (Sp$_2$) and/or (Sp$_3$) may be present in a linker.

In certain embodiments, the RK motif may be directly connected to one or more small hydrophobic amino acid residue. For example, in certain embodiments, the RK motif may be directly connected to one or more alanine residues.

That is, in a particular embodiment, the invention relates to the method according to the invention, wherein the linker comprises the amino acid sequence RKAA (SEQ ID NO:1), RKA (SEQ ID NO:2), ARK (SEQ ID NO:3), RKR (SEQ ID NO:4) or RK-Val-Cit (SEQ ID NO:54). It is to be understood that the RK motif that is used for conjugating the linker to a glutamine residue of an antibody may be comprised in the amino acid sequences RKAA, RKA, ARK, RKR or RK-Val-Cit.

In a particular embodiment, the invention relates to the method according to the invention, wherein the linker comprises the amino acid sequence RKAA (SEQ ID NO:1), RKA (SEQ ID NO:2) or ARK (SEQ ID NO:3).

In a particular embodiment, the invention relates to the method according to the invention, wherein the linker comprises the amino acid sequence RKAA (SEQ ID NO:1).

In a particular embodiment, the invention relates to the method according to the invention, wherein the linker comprises the amino acid sequence RK-Val-Cit (SEQ ID NO:54).

Within the present invention, it is preferred that the linker is conjugated to the antibody via a primary amine comprised in the side chain of the residue K comprised in the RK motif. Thus, it is preferred that the chemical spacers (Sp$_1$), (Sp$_2$) and/or (Sp$_3$) do not comprise additional lysine residues, lysine mimetics or lysine derivatives that could serve as additional amine donors in the transglutaminase-based conjugation reaction. In other embodiments, any free N-terminal amino group comprised in a linker may be substituted, e.g., acetylated, such that it cannot serve as substrate for a microbial transglutaminase.

The linker according to the invention further comprises at least one linking moiety or payload B. The linker according to the invention may be used to directly conjugate a payload to an antibody in a one-step conjugation process. In other embodiments, a linker comprising one or more linking moiety may be conjugated to an antibody in a first step and one or more payloads may then be linked to the antibody-linker conjugate in a second step. The following Table 1 clarifies the two terms as used herein:

TABLE 1

| One- and two step conjugation | | |
|---|---|---|
| Linker peptide (exemplary) | Process type | Steps |
| (Sp$_1$)-RK-(Sp$_2$)-payload-(Sp$_3$) or | One-step conjugation | step 1: conjugation of linker comprising the payload to |

TABLE 1-continued

One- and two step conjugation

| Linker peptide (exemplary) | Process type | Steps |
|---|---|---|
| $(Sp_1)$-payload-$(Sp_2)$-RK-$(Sp_3)$ | | Gln residue in antibody |
| $(Sp_1)$-RK-$(Sp_2)$-linking moiety-$(Sp_3)$ or $(Sp_1)$-linking moiety-$(Sp_2)$-RK-$(Sp_3)$ | Two-step conjugation | step 1: conjugation of linker comprising the linking moiety to Gln residue in antibody step 2: conjugation of a payload to linking moiety |

In certain embodiments, the linker may comprise one or more linking moieties B. Thus, in a particular embodiment, the invention relates to the method according to the invention, wherein B is a linking moiety.

A "linking moiety" as used herein generally refers to an at least bi-functional molecule. Within the present invention, a linking moiety comprises a first functional group that allows coupling of the linking moiety to the linker of the invention and a second functional group that can be used for coupling an additional molecule to the linker before or after the linker has been conjugated to an antibody. In certain embodiments, the linking moiety of the invention is an amino acid, an amino acid mimetic or an amino acid derivative. In such embodiments, the linking moiety is preferably connected to the linker via its amino group, while the functional group comprised in the amino acid side chain can be used for coupling an additional molecule to the linker. Alternatively, the linking moiety may be connected to the linker via its carboxyl group, while the functional group comprised in the amino acid side chain can be used for coupling an additional molecule to the linker.

In a particular embodiment, the invention relates to the method according to the invention, wherein the linking moiety B comprises
 a bioorthogonal marker group, or
 a non-bio-orthogonal entity for crosslinking.

The term "bioorthogonal marker group" has been established by Sletten and Bertozzi (A Bioorthogonal Quadricyclane Ligation. J Am Chem Soc 2011, 133 (44), 17570-17573) to designate reactive groups that can lead to chemical reactions to occur inside of living systems without interfering with native biochemical processes. A "non-bioorthogonal entity for crosslinking" may be any molecule that comprises or consists of a first functional group, wherein the first functional group can be chemically or enzymatically crosslinked to a payload comprising a compatible second functional group. Even in cases where the crosslinking reaction is a non-bio-orthogonal reaction, it is preferred that the reaction does not introduce additional modifications to the antibody other than the crosslinking of the payload to the linker. In view of the above, the linking moiety B may either consist of the "bioorthogonal marker group" or the "non-bio-orthogonal entity" or may comprise the "bioorthogonal marker group" or the "non-bio-orthogonal entity". For example, in case of the linking moiety $Lys(N_3)$, both the entire $Lys(N_3)$ and the azide group alone may be seen as a bioorthogonal marker group within the present invention. $Lys(N_3)$ refers to 6-azido-L-lysine, which may also be abbreviated $K(N_3)$.

In a particular embodiment, the invention relates to the method according to the invention, wherein the bioorthogonal marker group or the non-bio-orthogonal entity for crosslinking consists of or comprises at least one molecule or moiety selected from the group consisting of:
 —N—N≡N, or —$N_3$;
 $Lys(N_3)$;
 a tetrazine;
 an alkyne;
 a strained cyclooctyne;
 BCN;
 a strained alkene;
 a photoreactive group;
 an aldehyde;
 an acyltrifluoroborate;
 a protein degradation agent ('PROTAC');
 a cyclopentadiene/spirolocyclopentadiene;
 a thio-selective electrophile;
 —SH; and
 cysteine.

The bioorthogonal marker group or the non-bio-orthogonal entity for crosslinking comprised in the linker may, for example, engage in any of the binding reactions shown in Table 2:

TABLE 2

| binding partner 1 | binding partner 2 | reaction type |
|---|---|---|
| —N—N≡N | cyclooctyne derivatives (e.g. DIFO, BCN, DIBAC, DIBO, ADIBO/DBCO) | SPAAC |
| —N—N≡N | Alkyne | CuAAC |
| —N—N≡N | Triarylphosphines | Staudinger ligation |
| tetrazine | Cyclopropene Norborene Trans-cyclooctene Cyclooctyne (BCN) | tetrazine ligation |
| —SH, e.g., of a Cys residue | Maleimide | Thiol-Maleimide conjugation |
| Amine | N-hydroxysuccinimid | |

TABLE 2-continued

| binding partner 1 | binding partner 2 | reaction type |
|---|---|---|
| —O— carbamoylhydroxylamines | Acyltrifluoroborates | KAT-ligation (potassium acyl-trifluoroborate) |
| $R_x$—S—S—$R_y$ | $R_z$—SH + reducing agent (e.g. TCEP, DTT) | Direct disulfide bioconjugation |
| —CHO (aldehyde) | HIPS-probe | Hydrazino-iso-Pictet-Spengler (HIPS) |
| —CHO (aldehyde) | N-pyrrolyl alanine derivative | pyrrolyl alanine Pictet-Spengler (PAPS) |
| —CHO (aldehyde) | $R_1$—N—N—$R_2$<br>HO—N—$R_1$<br>H2N—CHR$_1$—CH2—SH | Hydrazone-ligation<br>Oxime-ligation<br>Thiazolidine-Ligation |
| maleimide | —SH, e.g., of a Cys residue | Thiol-Maleimide conjugation |
| maleimide | | Thiol-cylcopentadiene conjugation (Diels-Alder Reaction) |
| Biotin | Streptavidin | Biotin-streptavidin interaction |

The linking moiety B may either be or comprise what is called "binding partner 1" or "binding partner 2" in Table 2.

In certain embodiments, the linking moiety B may be a cysteine, a cysteine mimetic or a cysteine derivative with a free sulfhydryl group.

The free sulfhydryl group of such Cys residue (or mimetic or derivative) may be conjugated to a payload construct comprising a thio-selective electrophile, such as maleimide. Toxin constructs comprising a maleimide moiety have frequently been used, and also approved by medical authorities, like Adcetris. Thus, toxin constructs comprising an MMAE toxin may be coupled to a free sulfhydryl group of a Cys residue in the linker of the invention.

It has to be noted that also other thio-selective electrophiles such as 3-arylpropionitrile (APN) or phosphonamidate may be used instead of maleimide in the method of the invention.

Providing a Cys-residue in the linker according to the present invention does therefore have the advantage to allow using off-the-shelf-toxin-maleimide constructs to create antibody-payload conjugates, or, more generally, to be able to fully exploit the advantages of Cys-maleimide binding chemistry. At the same time, off-the-shelf antibodies can be used, which do not have to be deglycosylated. In specific embodiments, the Cys residue may be C-terminal or intra-chain in the amino acid-based linker.

In another embodiment, the linking moiety B may comprise an azide group. The skilled person is aware of molecules comprising an azide group which may be incorporated into a linker according to the invention, such as 6-azido-lysine (Lys($N_3$)) or 4-azido-homoalanine (Xaa ($N_3$)). Linking moieties comprising an azide group may be used as substrates in various bio-orthogonal reactions, such as strain-promoted azide-alkyne cycloaddition (SPAAC), copper-catalyzed azide-alkyne cycloaddition (CuAAC) or Staudinger ligation. For example, in certain embodiments, payloads comprising a cyclooctyne derivative, such as DBCO, DIBO, BCN or BARAC may be coupled to a linker comprising an azide group by SPAAC.

In yet another embodiment, the linking moiety B may comprise a tetrazine group. The skilled person is aware of tetrazine-comprising molecules which may be incorporated into a linker according to the invention, preferably amino acid derivatives comprising a tetrazine group. Linking moieties comprising a tetrazine may be used as substrates in a bio-orthogonal tetrazine ligation. For example, in certain embodiments, payloads comprising a cyclopropene, a norborene, a norborene derivative or a cyclooctyne group, such as bicyclo[6.1.0]nonyne (BCN), may be coupled to a linker comprising a tetrazine group.

In certain embodiments, the linking moiety B may comprise a cyclic diene, such as a cyclopentadiene derivative. Potential cyclopentadienes derivatives that can be linked to a maleimide-comprising payload molecule have been described by Amant et al., Tuning the Diels-Alder Reaction for Bioconjugation to Maleimide Drug-Linkers; Bioconjugate Chem. 2018, 29, 7, 2406-2414 and Amant et al., A Reactive Antibody Platform for One-Step Production of Antibody-Drug Conjugates through a Diels-Alder Reaction with Maleimide; Bioconjugate Chem. 2019, 30, 9, 2340-2348.

In certain embodiments, the linking moiety B may comprise a photoreactive group. The term "photoreactive group", as used herein, refers to a chemical group that responds to an applied external energy source in order to undergo active species generation, resulting in covalent bonding to an adjacent chemical structure (e.g., an abstractable hydrogen). Examples of photoreactive groups are, without limitation, aryl azides, such as phenyl azide, o-hydroxyphenyl azide, m-hydroxyphenylazide, tetrafluorophenyl azide, o-nitrophenyl azide, m-nitrophenyl azide, or azido-methylcoumarin, diazirine, psoralen or benzophenon.

In a particular embodiment, the invention relates to the method according to the invention, the method comprising a further step of conjugating one or more payloads to the linking moiety B.

Instead of directly conjugating a linker comprising one or more payloads to an antibody in a one-step process, the invention, in certain embodiments, refers to a two-step process, wherein a linker comprising at least one linking moiety B is conjugated to an antibody in a first step and one or more payloads may be subsequently coupled to the linking moiety B in a second step.

The term "payload", as used herein, represents any naturally occurring or synthetically generated molecule, including small-molecular weight molecules or chemical entities that can chemically be synthesized, and larger molecules or biological entities that need to be produced by fermentation of host cells or may also be synthesized chemically and that confer a novel functionality to an antibody. It is to be understood that the payload may comprise further structures or functional groups that allow coupling of the payload to a linking moiety comprised in a linker or to other parts of the linker, such as the chemical spacers ($Sp_1$) and/or ($Sp_3$) or the RK motif.

In a two-step conjugation process, a payload may be linked to a linking moiety by any suitable method known in the art. Preferably, the payload may be linked to any of the bioorthogonal marker groups or non-bio-orthogonal entities for crosslinking that have been disclosed herein. That is, the payload preferably comprises a functional group that is compatible with a bioorthogonal marker group or non-bio-orthogonal entities for crosslinking comprised in the at least one linking moiety B.

Several bioorthogonal reactions that may be used for linking a payload to a bioorthogonal marker group comprised in a linking moiety B are known in the art. For example, a number of chemical ligation strategies have been developed that fulfill the requirements of bio-orthogonality, including the 1,3-dipolar cycloaddition between azides and cyclooctynes (also termed copper-free click chemistry, Baskin et al ("Copper-free click chemistry for dynamic in vivo imaging". Proceedings of the National Academy of Sciences. 104 (43): 16793-7)), between nitrones and cyclooctynes (Ning et al ("Protein Modification by Strain-Promoted Alkyne-Nitrone Cycloaddition". Angewandte Chemie International Edition. 49 (17): 3065)), oxime/hydrazone formation from aldehydes and ketones (Yarema, et al ("Metabolic Delivery of Ketone Groups to Sialic Acid Residues. Application To Cell Surface Glycoform Engineering". Journal of Biological Chemistry. 273 (47): 31168-79)), the tetrazine ligation (Blackman et al ("The Tetrazine Ligation: Fast Bioconjugation based on Inverse-electron-demand Diels-Alder Reactivity". Journal of the American Chemical Society. 130 (41): 13518-9)), the isonitrile-based click reaction (Stockmann et al ("Exploring isonitrile-based click chemistry for ligation with biomolecules". Organic & Biomolecular Chemistry. 9 (21): 7303)), and most recently, the quadricyclane ligation (Sletten & Bertozzi (JACS, A Bioorthogonal Quadricyclane Ligation. J Am Chem Soc 2011, 133 (44), 17570-17573)), Copper(I)-catalyzed azide-alkyne cycloaddition (CuAAC, Kolb & Sharpless ("The growing impact of click chemistry on drug discovery". Drug Discov Today. 8 (24): 1128-1137)), Strain-promoted azide-alkyne cycloaddition (SPAAC, Agard et al ("A Comparative Study of Bioorthogonal Reactions with Azides". ACS Chem. Biol. 1: 644-648)), or Strain-promoted alkyne-nitrone cycloaddition (SPANC, MacKenzie et al ("Strain-promoted cycloadditions involving nitrones and alkynes—rapid tunable reactions for bioorthogonal labeling". Curr Opin Chem Biol. 21: 81-8)). All these documents are incorporated by reference herein to provide sufficient enabling disclosure, and avoid lengthy repetitions.

It is to be understood that the payload is preferably coupled to the bio-orthogonal marker group or the non-bio-orthogonal entity for crosslinking comprised in the linker according to the invention after said linker has been conjugated to a Gln residue of an antibody by means of a microbial transglutaminase. However, the invention also encompasses antibody-linker conjugates wherein one or more payloads have been coupled to a linker comprising at least one linking moiety B in a first step and wherein the resulting linker-payload construct is conjugated to the antibody by a microbial transglutaminase in a second step.

In a particular embodiment, the invention relates to the method according to the invention, wherein the one or more payload is conjugated to the linking moiety B via a click-reaction.

That is, one or more payloads may be linked to a linking moiety B in a click-reaction, in particular any of the click reaction disclosed herein.

In a particularly preferred embodiment, at least one payload may be conjugated to the linking moiety B comprised in a linker via a thiol-maleimide conjugation. That is, in certain embodiments, the payload may comprise a maleimide group and the linking moiety B may be a molecule comprising a thiol group, such as, without limitation, a cysteine residue or a cysteine mimetic such as homocysteine. However, B may also be a non-amino acid molecule comprising a free thiol group. In another embodiment, the payload may comprise a free thiol group and the linking moiety B may comprise a maleimide group.

In another particularly preferred embodiment, at least one payload may be conjugated to the linking moiety B comprised in a linker via strain-promoted azide-alkyne cycloaddition (SPAAC). That is, in certain embodiments, the payload may comprise an alkyne group, such as, without limitation, a cycloocyne group, and the linking moiety B may be a molecule comprising an azide group, such as, without limitation, the lysine derivative Lys(N$_3$) disclosed herein. However, B may also be non-amino acid molecules comprising a free azide group. In another embodiment, the payload may comprise an alkyne group, such as a cyclooctyne group and the linking moiety B may comprise an azide group.

Besides a click reaction between the linking moiety in the linker and a functional group in the payload, the payload may be covalently bound to the linking moiety by any enzymatic or non-enzymatic reaction known in the art.

It is preferred that a payload is linked to a linking moiety via a covalent bond. However, in certain embodiments, a payload may be linked to a linking moiety via a strong non-covalent bond. That is, in certain embodiments, the linking moiety B may comprise a biotin moiety, such as, without limitation, the lysine derivative biocytin. In such embodiments, a payload comprising a streptavidin moiety may be linked to the linker comprising a biotin moiety.

In a particular embodiment, the invention relates to the method according to the invention, wherein B is a payload.

In certain embodiments, the payload may already be part of the linker such that the payload can be conjugated to the antibody in a one-step process. In such embodiments, the linker is preferably coupled to the linker by chemical synthesis. The payload is preferably coupled to a chemical spacer comprised in the linker or directly to the RK motif. In embodiments where the payload is coupled to an amino acid residue, including amino acid mimetics and derivatives, the payload may be coupled to the C-terminal carboxyl group or the N-terminal amino group of an amino acid residue. Alternatively, the payload may be coupled to a functional group comprised in the side chain of an amino acid residue. The skilled person is aware of methods to functionalize a payload such that it can be coupled to a carboxyl group, an amino group or an amino acid side chain.

Further, the skilled person is aware of methods to couple a payload to an amino acid-based linker by chemical synthesis. For example, an amine-comprising payload, or a thiol-comprising payload (for e.g. maytansine analogs), or a hydroxyl-containing payload (for e.g. SN-38 analogs) may be attached to the C-terminus of an amino acid-based linker by chemical synthesis. However, the skilled person is aware of further reactions and reactive groups that may be utilized for coupling a payload to the N-terminus, C-terminus or the side chain of an amino acid or amino acid derivative by chemical synthesis. Typical reactions that may be used to couple a payload to an amino acid-based linker by chemical synthesis include, without limitation: peptide coupling, activated ester coupling (NHS ester, PFP ester), click reaction (CuAAC, SPAAC), Michael addition (thiol maleimide conjugation). The coupling of payloads to peptides has been extensively described in the prior art, for example by Costoplus et al. (Peptide-Cleavable Self-immolative Maytansinoid Antibody-Drug Conjugates Designed To Provide Improved Bystander Killing. ACS Med Chem Lett. 2019 Sep. 27; 10(10):1393-1399), Sonzini et al. (Improved Physical Stability of an Antibody-Drug Conjugate Using Host-Guest Chemistry. Bioconjug Chem. 2020 Jan. 15; 31(1): 123-129), Bodero et al. (Synthesis and biological evaluation of RGD and isoDGR peptidomimetic-α-amanitin conjugates for tumor-targeting. Beilstein J. Org. Chem. 2018, 14, 407-415), Nunes et al. (Use of a next generation maleimide in combination with THIOMAB™ antibody technology delivers a highly stable, potent and near homogeneous THIOMAB™ antibody-drug conjugate (TDC). RSC Adv., 2017, 7, 24828-24832), Doronina et al. (Enhanced activity of monomethylauristatin F through monoclonal antibody delivery: effects of linker technology on efficacy and toxicity. Bioconjug Chem. 2006 January-February; 17(1):114-24), Nakada et al. (Novel antibody drug conjugates containing exatecan derivative-based cytotoxic payloads. Bioorg Med Chem Lett. 2016 Mar. 15; 26(6):1542-1545) and Dickgiesser et al. (Site-Specific Conjugation of Native Antibodies Using Engineered Microbial Transglutaminases. Bioconjug Chem. 2020 Mar. 12. doi: 10.1021/acs.bioconjchem.0c00061).

It is to be understood that the payload may be coupled to the N-terminal or to the C-terminal end of a peptide-based or a peptide-comprising linker according to the invention. In certain embodiments, a payload may be coupled directly to the N-terminal amino group or the C-terminal carboxyl group of a peptide or an amino acid residue (see for example FIG. 22).

The skilled person is aware of reactive groups that are suitable for coupling a payload to an amino acid residue. For example, an amine-comprising payload may be coupled to the C-terminal carboxyl group of an amino acid residue via an amide bond (FIG. 22). Alternatively, a payload comprising a thiol group or and hydroxyl group may be coupled to the C-terminal carboxyl group of an amino acid via a thioester or an ester bond, respectively. A payload comprising a carboxylic acid group may be coupled to the N-terminal amino group of an amino acid residue via an amide bond.

In certain embodiments, a payload may be coupled indirectly to the N- or C-terminal end of a peptide or amino acid residue comprised in the linker according to the invention. The skilled person is aware of linker molecules that may be used to couple a payload to the N-terminal amino group or the C-terminal carboxyl group of an amino acid residue comprised in the linker according to the invention.

In certain embodiments, a payload comprising a hydroxyl group may be coupled to the N-terminus of an amino acid residue via a linker molecule. For example, payloads comprising a hydroxyl group may be coupled to an N-terminal amino group via a carbamate linker molecule (FIG. 24).

In certain embodiments, a payload comprising a thiol group may be coupled to the N-terminus of an amino acid residue via a linker molecule. For example, payloads comprising a thiol group may be coupled to an N-terminal amino group via a thiocarbamate linker molecule (FIG. 28). Alternatively, payloads comprising a thiol group may be coupled to an N-terminal amino group via an alkyl linker molecule comprising a carboxyl group and a thiol group. In certain embodiments the alkyl linker molecule may be a 3-mercaptopropionic acid linker molecule, wherein the payload forms a di-sulfur bond with the thiol group comprised in the 3-mercaptopropionic acid linker molecule (FIG. 29).

In certain embodiments, a payload comprising an amide group may be coupled to the N-terminus of an amino acid residue via a linker molecule. For example, payloads comprising an amine group may be coupled to an N-terminal amino group via a dicarboxylic acid linker molecule, wherein the dicarboxylic acid linker forms an amide bond with the payload and the amino group of the N-terminal amino acid residue. Examples of dicarboxylic acids that may be used as linker molecules in the present invention are, without limitation, succinic acid or pimelic acid (see FIGS. 9 and 30)

Alternative linker molecules for indirectly coupling payloads to the N-terminus of an amino acid residue comprised in the linker according to the invention or linker molecules that are suitable for indirectly coupling payloads to the C-terminus of an amino acid residue comprised in the linker according to the invention have been described in the art and are encompassed by the present invention.

In a particular embodiment, the invention relates to the method according to the invention, wherein the payload comprises at least one of:
 a toxin;
 a cytokine;
 a growth factor;
 a radionuclide;
 a hormone;
 an anti-viral agent;
 an anti-bacterial agent;
 a fluorescent dye;
 an immunoregulatory/immunostimulatory agent;
 a half-life increasing moiety;
 a solubility increasing moiety;
 a polymer-toxin conjugate;
 a nucleic acid;
 a biotin or streptavidin moiety;
 a vitamin;
 a protein degradation agent ('PROTAC');
 a target binding moiety; and/or
 an anti-inflammatory agent.

Any one of the payloads disclosed herein may either be directly coupled to a linker for use in the one-step conjugation process disclosed herein or may be linked to a linking moiety comprised in an antibody-linker conjugate that has been generated as part of the two-step process disclosed herein.

In certain embodiments, the payload may be a cytokine. The term "cytokine," as used herein, means any secreted polypeptide that affects the functions of other cells, and that modulates interactions between cells in the immune or inflammatory response. Cytokines include, but are not limited to monokines, lymphokines, and chemokines regardless of which cells produce them. For instance, a monokine is generally referred to as being produced and secreted by a monocyte, however, many other cells produce monokines, such as natural killer cells, fibroblasts, basophils, neutrophils, endothelial cells, brain astrocytes, bone marrow stromal cells, epidermal keratinocytes, and B-lymphocytes. Lymphokines are generally referred to as being produced by lymphocyte cells. Examples of cytokines include, but are not limited to, interleukin-1 (IL-1), interleukin-6 (IL-6), Tumor Necrosis Factor alpha (TNFα), and Tumor Necrosis Factor beta (TNFβ).

In certain embodiments, the payload may be an anti-inflammatory agent. As used herein, the term "anti-inflammatory agent" means those agent classes whose main mode of action and use is in the area of treating inflammation and also any other agent from another therapeutic class that possesses useful anti-inflammatory effects. Such anti-inflammatory agents include, but are not limited to non-steroidal anti-inflammatory drugs (NSAIDs), disease modifying anti-rheumatic drugs (DMARDs), macrolide antibiotics and statins. Preferably, the NSAIDs include, but are not limited to, salicylates (e.g. aspirin), arylpropionic acids (e.g. ibuprofen), anthranilic acids (e.g. mefenamic acid), pyrazoles (e.g. phenylbutazone), cyclic acetic acids (indomethicin) and oxicams (e.g. piroxicam). Preferably, anti-inflammatory agents for use in the methods of the present invention include sulindac, diclofenac, tenoxicam, ketorolac, naproxen, nabunetone, diflunasal, ketoprofen, arlypropionic acids, tenidap, hydroxychloroquine, sulfasalazine, celecoxib, rofecoxib, meloxicam, etoricoxib, valdecoxib, methotrexate, etanercept, infliximab, adalimumab, atorvastatin, fluvastatin, lovastatin, pravastatin, simvastatin, clarithromycin, azithromycin, roxithromycin, erythromycin, ibuprofen, dexibuprofen, flurbiprofen, fenoprofen, fenbufen, benoxaprofen, dexketoprofen, tolfenamic acid, nimesulide and oxaprozin.

In certain embodiments, the anti-inflammatory agent may be an anti-inflammatory cytokine, which, when conjugated to a target specific antibody, can ameliorate inflammations caused, e.g., by autoimmune diseases. Cytokines with anti-inflammatory activities may be, without limitation, IL-1RA, IL-4, IL-6, IL-10, IL-11, IL-13 or TGF-β.

In certain embodiments, the payload may be a growth factor. The term "growth factor" as used herein refers to a naturally occurring substance capable of stimulating cellular growth, proliferation, cellular differentiation, and/or cellular maturation. Growth factors exist in the form of either proteins or steroid hormones. Growth factors are important for regulating a variety of cellular processes. Growth factors typically act as signaling molecules between cells. However, their ability to promote cellular growth, proliferation, cellular differentiation, and cellular maturation varies between growth factors. A non-limiting list of examples of growth factors includes: basic fibroblast growth factor, adrenomedullin, angiopoietin, autocrine motility factor, bone morphogenetic proteins, brain-derived neurotrophic factor, epidermal growth factor, epithelial growth factor, fibroblast growth factor, glial cell line-derived neurotrophic factor, granulocyte colony-stimulating factor, granulocyte macrophage colony-stimulating factor, growth differentiation factor-9, hepatocyte growth factor, hepatoma-derived growth factor, insulin growth factor, insulin-like growth factor, migration-stimulating factor, myostatin, nerve growth factor, and other neurotrophins, platelet-derived growth factor, transforming growth factor alpha, transforming growth factor beta, tumor-necrosis-factor-alpha, vascular endothelial growth factor, placental growth factor, fetal bovine somatotrophin, and cytokines (e.g. IL-1-cofactor for IL-3 and IL-6, IL-2-t-cell growth factor, IL-3, IL-4, IL-5, IL-6, and IL-7).

In certain embodiments, the payload may be a hormone. The term "hormone", as used herein, refers to a chemical released by a cell or a gland in one part of the body that sends out messages that affect cells in other parts of the organism. Examples of hormones that are useful in the present invention are, without limitation, melatonin (MT), serotonin (5-HT), thyroxine (T4), triiodothyronine (T3), epinephrine or adrenaline (EPI), norepinephrine or noradrenaline (NRE), dopamine (DPM or DA), antimullerian hormone or mullerian inhibiting hormone (AMH), adiponectin (Acrp30), adrenocorticotropic hormone or corticotrophin (ACTH), angiotensinogen and angiotensin (AGT), antidiuretic hormone or vasopressin (ADH), atrial natriuretic peptide or atriopeptin (ANP), calcitonin (CT), cholecystokinin (CCK), corticotrophin-releasing hormone (CRH), erythropoietin (EPO), follicle-stimulating hormone (FSH), gastrin (GRP), ghrelin, glucagon (GCG), gonadotrophin-releasing hormone (GnRH), growth hormone-releasing hormone (GHRH), human chorionic gonadotrophin (hCG), human placental lactogen (HPL), growth hormone (GH or hGH), inhibin, insulin (INS), insulin-like growth factor or somatomedin (IGF), leptin (LEP), luteinizing hormone (LH), melanocyte stimulating hormone (MSH or α-MSH), orexin, oxytocin (OXT), parathyroid hormone (PTH), prolactin (PRL), relaxin (RLN), secretin (SCT), somatostatin (SRIF), thrombopoietin (TPO), thyroid-stimulating hormone or thyrotropin (TSH), thyrotropin-releasing hormone (TRH), cortisol, aldosterone, testosterone, dehydroepiandrosterone (DHEA), androstenedione, dihydrotestosterone (DHT), estrone, estriol (E3), progesterone, calcitriol, calcidiol, prostaglandins (PG), leukotrienes (LT), prostacyclin (PGI2), thromboxane (TXA2), prolactin releasing hormone (PRH), lipotropin (PRH), brain natriuretic peptide (BNP), neuropeptide Y (NPY), histamine, endothelin, pancreatic polypeptide, renin and enkephalin.

In certain embodiments, the payload may be an antiviral agent. The term "antiviral agent" as used herein means an agent (compound or biological) that is effective to inhibit the formation and/or replication of a virus in a mammal. This includes agents that interfere with either host or viral mechanisms necessary for the formation and/or replication of a virus in a mammal. Antiviral agents include, for example, ribavirin, amantadine, VX-497 (merimepodib, Vertex Pharmaceuticals), VX-498 (Vertex Pharmaceuticals), Levovirin, Viramidine, Ceplene (maxamine), XTL-001 and XTL-002 (XTL Biopharmaceuticals).

In certain embodiments, the payload may be an antibacterial agent. The term "antibacterial agent" as used herein refers to any substance, compound, a combination of substances, or a combination of compounds capable of: (i) inhibiting, reducing or preventing growth of bacteria; (ii) inhibiting or reducing ability of a bacteria to produce infection in a subject; or (iii) inhibiting or reducing ability of bacteria to multiply or remain infective in the environment. The term "antibacterial agent" also refers to compounds capable of decreasing infectivity or virulence of bacteria.

In certain embodiments, the payload may be an immunoregulatory agent. The term "immunoregulatory agent" as used herein for combination therapy refers to substances that act to suppress, mask, or enhance the immune system of the host. Examples of immunomodulatory agents include, but are not limited to, proteinaceous agents such as cytokines, peptide mimetics, and antibodies (e.g., human, humanized, chimeric, monoclonal, polyclonal, Fvs, ScFvs, Fab or F(ab)2 fragments or epitope binding fragments), nucleic acid molecules (e.g., antisense nucleic acid molecules, iRNA and triple helices), small molecules, organic compounds, and inorganic compounds. In particular, immunomodulatory agents include, but are not limited to, methothrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators.

In certain embodiments, the immunoregulatory agent may be an immunostimulatory agent. The term "immunostimulatory agent" as used herein preferably refers to any substance or substance that can trigger an immune response (e.g., an immune response against a particular pathogen). Immune cell activating compounds include Toll-like receptor (TLR) agonists. Such agonists include pathogen associated molecular patterns (PAMPs), e.g., an infection-mimicking composition such as a bacterially-derived immunomodulator (a.k.a., danger signal) and damage associated molecular pattern (DAMPs), e.g. a composition mimicking a stressed or damaged cell. TLR agonists include nucleic acid or lipid compositions (e.g., monophosphoryl lipid A (MPLA)). In one example, the TLR agonist comprises a TLR9 agonist such as a cytosine-guanosine oligonucleotide (CpG-ODN), a poly(ethylenimine)(PEI)-condensed oligonucleotide (ODN) such as PEI-CpG-ODN, or double stranded deoxyribonucleic acid (DNA). In another example, the TLR agonist comprises a TLR3 agonist such as polyinosine-polycytidylic acid (poly (I:C)), PEI-poly (I:C), polyadenylic-polyuridylic acid (poly (A:U)), PEI-poly (A:U), or double stranded ribonucleic acid (RNA). Other exemplary vaccine immunostimulatory compounds include lipopolysaccharide (LPS), chemokines/cytokines, fungal beta-glucans (such as lentinan), imiquimod, CRX-527, and OM-174.

In certain embodiments, the payload may be a half-life increasing moiety or a solubility increasing moiety. Half-life increasing moieties are, for example, PEG-moieties (polyethylenglycol moieties; PEGylation), other polymer moieties, PAS moieties (oliogopeptides comprising Proline, Alanine and Serine; PASylation), or Serum albumin binders. Solubility increasing moieties are, for example PEG-moieties (PEGylation) or PAS moieties (PASylation).

In certain embodiments, the payload may be a polymer-toxin conjugate. Polymer-toxin conjugates are polymers that are capable of carrying many payload molecules. Such conjugates are sometimes also called fleximers, as e.g. marketed by Mersana therapeutics. A polymer-toxin conjugate may comprise any of the toxins disclosed herein.

In certain embodiments, the payload may be a nucleotide. One example of a nucleic acid payload is MCT-485, which is a very small non-coding double stranded RNA which has oncolytic and immune activating properties, developed by MultiCell Technologies, Inc.

In certain embodiments, the payload may be a fluorescent dye. The term "fluorescent dye" as used herein refers to a dye that absorbs light at a first wavelength and emits at second wavelength that is longer than the first wavelength. In certain embodiment, the fluorescent dye is a near-infrared fluorescent dye, which emits light at a wavelength between 650 and 900 nm. In this region, tissue autofluorescence is lower, and less fluorescence extinction enhances deep tissue penetration with minimal background interference. Accordingly, near-infrared fluorescent imaging may be used to make tissues that are bound by the antibody-payload conjugate of the invention visible during surgery. "Near-infrared fluorescent dyes" are known in the art and commercially available. In certain embodiments, the near-infrared fluorescent dye may be IRDye 800CW, Cy7, Cy7.5, NIR CF750/770/790, DyLight 800 or Alexa Fluor 750.

In certain embodiments, the payload may comprise a radionuclide. The term "radionuclide", as used herein, relates to medically useful radionuclides, including, for example, positively charged ions of radiometals such as Y, In, Tb, Ac, Cu, Lu, Tc, Re, Co, Fe and the like, such as $^{99}$Y, $^{111}$In, $^{67}$Cu, $^{77}$Lu, $^{99}$Tc, $^{161}$Tb, $^{225}$Ac and the like. The radionuclide may be comprised in a chelating agent such as DOTA or NODA-GA. Further, the radionuclide may be a therapeutic radionuclide or a radionuclide that can be used as contrast agent in imaging techniques as discussed below. Radionuclides or molecules comprising radionuclides are known in the art and commercially available.

In certain embodiments, the payload may be a vitamin. The vitamin may be selected from the group consisting of folates, including folic acid, folacin, and vitamin B9.

In a particular embodiment, the invention relates to the method according to the invention, wherein the toxin is at least one selected from the group consisting of
a pyrrolobenzodiazepine (e.g., PBD);
an auristatin (e.g., MMAE, MMAF);
a maytansinoid (e.g., maytansine, DM1, DM4, DM21);
a duocarmycin;
a nicotinamide phosphoribosyltransferase (NAMPT) inhibitor;
a tubulysin;
an enediyne (e.g., calicheamicin);
an anthracycline derivative (PNU) (e.g., doxorubicin);
a pyrrole-based kinesin spindle protein (KSP) inhibitor;
a cryptophycin;
a drug efflux pump inhibitor;
a sandramycin;
an amanitin (e.g., α-amanitin); and
a camptothecin (e.g., exatecans, deruxtecans).

That is, the antibody-linker conjugates produced with the method of the invention preferably comprise a toxin payload. The term "toxin" as used herein relates to any compound produced by living cells or organisms and poisonous to a cell or organism. Toxins, thus can be, e.g. small molecules, peptides, or proteins. Specific examples are neurotoxins, necrotoxins, hemotoxins and cytotoxins. In certain embodiments, the toxin is toxin that is used in the treatment of neoplastic diseases. That is, the toxin may be conjugated to an antibody with the method of the invention and delivered to or into a malignant cell due to the target specificity of the antibody.

In certain embodiments, the toxin may be an auristatin. As used herein, the term "auristatin" refers to a family of anti-mitotic agents. Auristatin derivatives are also included within the definition of the term "auristatin". Examples of auristatin include, but are not limited to, synthetic analogues of auristatin E (AE), monomethyl auristatin E (MMAE), monomethyl auristatin F (MMAF) and dolastatin.

In certain embodiments, the toxin may be a maytansinoid. In the context of the present invention, the term "maytansinoid" refers to a class of highly cytotoxic drugs originally isolated from the African shrub *Maytenus ovatus* and further maytansinol (Maytansinol) and C-3 ester of natural maytansinol (U.S. Pat. No. 4,151,042); C-3 ester analog of synthetic maytansinol (Kupchan et al., J. Med. Chem. 21: 31-37, 1978; Higashide et al., Nature 270: 721-722, 1977; Kawai et al., Chem. Farm. Bull. 32: 3441-3451; and U.S. Pat. No. 5,416,064); C-3 esters of simple carboxylic acids (U.S. Pat. Nos. 4,248,870; 4,265,814; 4,308,268; 4,308,269; 4,309,428; 4,317,821; 4,322,348; and 4,331,598); and C-3 esters with derivatives of N-methyl-L-alanine (U.S. Pat. Nos. 4,137,230; 4,260,608; and Kawai et al., Chem. Pharm Bull. 12: 3441, 1984). Exemplary maytansinoids that may be used in the method of the invention or that may be comprised in the antibody-payload conjugate of the invention are maytansine, DM1, DM3, DM4 and/or DM21.

In certain embodiments, the toxin may be a duocarmycin. Suitable duocarmycins may be e.g. duocarmycin A, duocarmycin BI, duocarmycin B2, duocarmycin Cl, duocarmycin C2, duocarmycin D, duocarmycin SA, duocarmycin MA, and CC-1065. The term "duocarmycin" should be understood as referring also to synthetic analogs of duocarmycins, such as adozelesin, bizelesin, carzelesin, KW-2189 and CBI-TMI.

In certain embodiments, the toxin may be a NAMPT inhibitor. As used herein, the terms "NAMPT inhibitor" and "nicotinamide phosphoribosyl transferase inhibitor" refer to an inhibitor that reduces the activity of NAMPT. The term "NAMPT inhibitor" may also include prodrugs of a NAMPT inhibitor. Examples of NAMPT inhibitors include, without limitation, FK866 (also referred to as APO866), GPP 78 hydrochloride, ST 118804, STF31, pyridyl cyanoguanidine (also referred to as CH—828), GMX-1778, and P7C3. Additional NAMPT inhibitors are known in the art and may be suitable for use in the compositions and methods described herein. See, e.g., PCT Publication WO 2015/054060, U.S. Pat. Nos. 8,211,912, and 9,676,721, which are incorporated by reference herein in their entireties. In some embodiments, the NAMPT inhibitor is FK866. In some embodiments, the NAMPT inhibitor is GMX-1778.

In certain embodiments, the toxin may be a tubulysin. Tubulysins are cytotoxic peptides, which include 9 members (A-I). Tubulysin A has potential application as an anticancer agent. It arrests cells in the G2/M phase. Tubulysin A inhibits polymerization more efficiently than vinblastine and induces depolymerization of isolated microtubules. Tubulysin A has potent cytostatic effects on various tumor cell lines with IC50 in the picomolar range. Other tubulysins that may be used in the method of the invention may be tubulysin E.

In certain embodiments, the toxin may be an enediyne. The term "enediyne," as used herein, refers to a class of bacterial natural products characterized by either nine- and ten-membered rings containing two triple bonds separated by a double bond (see, e.g., K. C. Nicolaou; A. L. Smith; E. W. Yue (1993). "Chemistry and biology of natural and designed enediynes". PNAS 90 (13): 5881-5888; the entire contents of which are incorporated herein by reference). Some enediynes are capable of undergoing Bergman cyclization, and the resulting diradical, a 1,4-dehydrobenzene derivative, is capable of abstracting hydrogen atoms from the sugar backbone of DNA which results in DNA strand cleavage (see, e.g., S. Walker; R. Landovitz; W. D. Ding; G. A. Ellestad; D. Kahne (1992). "Cleavage behavior of calicheamicin gamma 1 and calicheamicin T". Proc Natl Acad Sci U.S.A. 89 (10): 4608-12; the entire contents of which are incorporated herein by reference). Their reactivity with DNA confers an antibiotic character to many enediynes, and some enediynes are clinically investigated as anticancer antibiotics. Nonlimiting examples of enediynes are dynemicin, neocarzinostatin, calicheamicin, esperamicin (see, e.g., Adrian L. Smith and K. C. Bicolaou, "The Enediyne Antibiotics" J. Med. Chem., 1996, 39 (11), pp 2103-2117; and Donald Borders, "Enediyne antibiotics as antitumor agents," Informa Healthcare; 1st edition (Nov. 23, 1994, ISBN-10: 0824789385; the entire contents of which are incorporated herein by reference). In a particular embodiment, the toxin may be calicheamicin.

In certain embodiments, the toxin may be a doxorubicin. "Doxorubicin" as used herein refers to members of the family of Anthracyclines derived from *Streptomyces* bacterium *Streptomyces peucetius* var. *caesius*, and includes doxorubicin, daunorubicin, epirubicin and idarubicin.

In certain embodiments, the toxin may be a kinesin spindle protein inhibitor. The term "kinesin spindle protein inhibitor" refers to a compound that inhibits the kinesin spindle protein, which involves in the assembly of the bipolar spindle during cell division. Kinesin spindle protein inhibitors are being investigated for the treatment of cancer. Examples of kinesin spindle protein inhibitor include ispinesib. Further, the term "kinesin spindle protein inhibitor" includes SB715992 or SB743921 from GlaxoSmithKline and pentamidine/chlorpromarine from CombinatoRx.

In certain embodiments, the toxin may a cryptophycin as described in US20180078656A1, which is incorporated by reference.

In certain embodiments, the toxin may be sandramycin. Sandramycin is a depsipeptide that has first been isolated from *Nocardioides* sp. (ATCC 39419) and has been shown to have cytotoxic and anti-tumor activity.

In certain embodiments, the toxin may be an amatoxin. Amatoxins (including alpha-amanitin, beta-amanitin and amanitin) are cyclic peptides composed of 8 amino acids. They can be isolated from *Amanita phalloides* mushrooms or prepared from the building blocks by synthesis. Amatoxins inhibit specifically the DNA-dependent RNA polymerase II of mammalian cells, and by this transcription and protein biosynthesis of the cells affected. Inhibition of transcription in a cell causes stop of growth and proliferation. Though not covalently bound, the complex between amanitin and RNA-polymerase II is very tight (KD=3 nM). Dissociation of amanitin from the enzyme is a very slow process what makes recovery of an affected cell unlikely. When in a cell the inhibition of transcription will last too long, the cell undergoes programmed cell death (apoptosis). In one preferred embodiment, term "Amatoxin" as used herein refers to an alpha-amanitin or variant thereof as described e.g. in WO2010/115630, WO2010/115629, WO2012/119787, WO2012/041504, and WO2014/135282.

In certain embodiments, the toxin may be a camptothecin. The term "camptothecin" as used herein is intended to mean a camptothecin or camptothecin derivative that functions as a topoisomerase I inhibitor. Exemplary camptothecins include, for example, topotecan, exatecan, deruxtecan, irinotecan, DX-8951f, SN38, BN 80915, lurtotecan, 9-nitrocamptothecin and aminocamptothesin. A variety of camptothecins have been described, including camptothecins used to treat human cancer patients. Several camptothecins are described, for example, in Kehrer et al., Anticancer Drugs, 12(2): 89-105, (2001) or Li et al., *ACS Med. Chem. Lett.* 2019, 10, 10, 1386-1392).

The toxin, in the sense of the present invention may also be an inhibitor of a drug efflux transporter. Antibody-payload conjugates comprising a toxin and an inhibitor of a drug efflux transporter may have the advantage that, when internalized into a cell, the inhibitor of the drug efflux transporter prevents efflux of the toxin out of the cell. Within the present invention, the drug efflux transporter may be P-glycoprotein. Some common pharmacological inhibitors of P-glycoprotein include: amiodarone, clarithromycin, ciclosporin, colchicine, diltiazem, erythromycin, felodipine, ketoconazole, lansoprazole, omeprazole and other proton-pump inhibitors, nifedipine, paroxetine, reserpine, saquinavir, sertraline, quinidine, tamoxifen, verapamil, and duloxetine. Elacridar and CP 100356 are other common P-gp inhibitors. Zosuquidar and tariquidar were also developed with this in mind. Lastly, valspodar and reversan are other examples of such agents.

It is to be understood that the payload B as defined herein is not to exclusively to be understood as the actual payload as such but rather as a payload molecule. A payload molecule, as used herein, may comprise additional structures, for example to facilitate coupling of a payload to a linking moiety B or to the RK motif or the chemical spacers via chemical synthesis.

That is, in certain embodiments, the actual payload may be comprised in a payload molecule that is linked to the linker of the invention. A payload molecule may have the structure:

X-(spacer)-payload, wherein payload represents the actual payload, e.g., one of the compounds disclosed herein, X represents a reactive group that is suitable for attaching the payload molecule to a compatible functional group in a linking moiety (two-step process) or in a chemical spacer or RK motif of a linker (one-step process), and wherein (spacer) represents a chemical spacer that spatially separates the actual payload from the reactive group X. However, it is to be understood that in certain embodiments, the reactive group X may be part of the spacer or the actual payload. For example, the spacer may comprise a peptide or an amino acid residue, wherein the reactive group X may be the amino group of the N-terminal amino acid residue comprised in the spacer. In other embodiments, the spacer may be absent. In embodiments, where the spacer is absent, the functional group may be comprised in the actual payload. In certain embodiments, a spacer may be used to attach a functional group of interest, i.e., a functional group that is compatible with a functional group comprised in a linking moiety, to the actual payload. In certain embodiments, the reactive group X may be a maleimide group or a cyclooctyne group such as, without limitation, a DBCO or BCN group.

In a particular embodiment, the invention relates to the method according to the invention, wherein the chemical spacer ($Sp_2$) comprises a self-immolative moiety.

That is, the linker may comprise a self-immolative moiety to facilitate the release of the payload in the target cell or tissue. The self-immolative moiety may be comprised in any part of the linker. However, the self-immolative moiety is preferably comprised in the chemical spacer ($Sp_2$) which separates the payload from the RK motif. Alternatively, the self-immolative moiety may be comprised in the (spacer) that is comprised in the payload molecule as defined above.

As used herein, the term "self-immolative moiety" refers to an at least bifunctional molecule that can be included in a linker and degrades spontaneously after an initial reaction has taken place and thereby releases the payload. The initial reaction may be the hydrolysis of a covalent bond between the self-immolative moiety and an amino acid residue. In certain embodiments, the covalent bond between the self-immolative moiety and an amino acid residue may be an amide bond formed between the α-carboxyl group of the amino acid and an amine group comprised in the self-immolative moiety and the initial reaction may be catalyzed by a peptidase or a protease. However, other chemistries are encompassed by this invention.

In a particular embodiment, the invention relates to the method according to the invention, wherein the self-immolative moiety is directly attached to the payload B.

More preferably, the self-immolative moiety is directly attached to the payload B, such that the payload is released upon degradation of the self-immolative moiety. In certain embodiments, the self-immolative moiety is located between the payload and the RK motif comprised in the linker. That is, the self-immolative moiety may be coupled to the N-terminus of the residue R or to the C-terminus of the residue K. Alternatively, the self-immolative moiety may be located between the payload and an amino acid residue comprised in the chemical spacer ($Sp_2$), preferably at the N- or C-terminus of said amino acid residue. Further, the self-immolative moiety may be located between the payload and a non-amino acid residue comprised in the chemical spacer ($Sp_2$) by any method known in the art.

It is to be understood that the choice of the self-immolative moiety depends, amongst others on the functional groups that are available in a payload molecule.

In a particular embodiment, the invention relates to the method according to the invention, wherein the self-immolative moiety comprises a p-aminobenzyl carbamoyl (PABC) moiety.

That is, in certain embodiments, a linker may comprise the self-immolative moiety p-aminobenzyl carbamoyl (PABC). PABC comprises a free amine group which is suitable for coupling to the C-terminus of an amino acid residue or peptide and a carbamoyl group via which it can be coupled to a payload, in particular an amine-comprising payload. However, the skilled person is aware of methods to functionalize a payload such that it comprises an amine group. The self-immolative moiety PABC is preferably located between the payload and an amino acid residue comprised in the linker. The amino acid residue is preferably the residue K comprised in the RK motif or an amino acid comprised in the chemical spacer ($Sp_2$). In certain embodiments, the self-immolative moiety PABC is located between the payload and an alanine residue comprised in the chemical spacer ($Sp_2$). In certain embodiments, the self-immolative moiety may be located between a payload and a peptidase cleavage site. In certain embodiments, the self-immolative moiety may be located between a payload and a cathepsin cleavage site. That is, the self-immolative moiety may be located between a payload and a motif that is known to be cleavable by a cathepsin.

The term "cathepsin", as used herein, refers to a family of proteases. The term cathepsin comprises cathepsin A, cathepsin B, cathepsin C, cathepsin D, cathepsin E, cathepsin F, cathepsin G, cathepsin H, cathepsin K, cathepsin L1, cathepsin L2, cathepsin O, cathepsin S, cathepsin W and cathepsin Z. In a particular embodiment, the cleavable moiety may be a motif that is specifically hydrolyzed by cathepsin B, such as valine-alanine, valine-citrulline or alanine-alanine. Further motifs that can be specifically hydrolyzed by a peptidase have been disclosed by Salomon et al., Optimizing Lysosomal Activation of Antibody-Drug Conjugates (ADCs) by Incorporation of Novel Cleavable Dipeptide Linkers, Mol Pharm. 2019, 16(12), p. 4817-4825.

One typical dipeptide structure used in ADC linkers is the valine-citrulline motif, as e.g. provided in Brentuximab Vedotin, and discussed in Dubowchik and Firestone; Cathepsin B-labile dipeptide linkers for lysosomal release of doxorubicin from internalizing immunoconjugates: model studies of enzymatic drug release and antigen-specific in vitro anticancer activity; Bioconjug Chem; 2002; 13(4); p. 855-69. This linker can be cleaved by cathepsin B to release the actual payload at the site of disease. The same applies to the valine-alanine motif, which is for example provided in SGN-CD33A.

Thus, in certain embodiments, the linker may comprise the structure ($Sp_1$)-RK-($Sp_2$)-Val-Cit-(self-immolative moiety)-Payload. In certain embodiments, the linker may comprise the structure ($Sp_1$)-RK-($Sp_2$)-Val-Cit-Payload. In certain embodiments, the linker may comprise the structure ($Sp_1$)-RK-($Sp_2$)-Val-Cit-PABC-Payload.

In certain embodiments, the linker may comprise the structure RK-Val-Cit (Seq ID NO:54). In certain embodiments, the linker may comprise or consist of the structure RK-Val-Cit-(self-immolative moiety)-Payload. In certain embodiments, the linker may comprise or consist of the structure RK-Val-Cit-PABC-Payload. In certain embodiments, the linker may comprise or consist of the structure RK-Val-Cit-PABC-MMAE. In certain embodiments, the linker may comprise or consist of the structure RK-Val-Cit-PABC-maytansine.

It has to be noted that the peptide cleavage site may also be a motif that is cleavable by other peptidases such as Caspase 3, Legumain or Neutrophil elastase or as described by Dal Corso et al., Innovative Linker Strategies for Tumor-Targeted Drug Conjugates; Chemistry; 25(65); p. 14740-14757.

However, it has to be noted that cells comprise a wide range of cellular peptidases and that also other, less conserved amino acid motifs may be efficiently cleaved by a peptidase. Thus, in certain embodiments, the linker may comprise the structure ($Sp_1$)-RK-($Sp_2$)-PABC-Payload, wherein ($Sp_2$) is absent or consists of amino acid residues.

In certain embodiments, the linker may comprise the structure ($Sp_1$)-RK-($Sp_2$)-PABC-Payload, wherein ($Sp_2$) comprises a PEG moiety between the PABC moiety and the most C-terminal amino acid residue comprised in ($Sp_2$) or in the RK motif.

In certain embodiments, linkers comprising the self-immolative moiety PABC are coupled to an amine-comprising payload, in particular payloads comprising a primary or a secondary amine. In certain embodiments, the amine-comprising payload is an ausristatin, such as MMAE. In certain embodiments, the amine-comprising payload is a maytansinoid, such as maytansine.

It has to be noted that the payload may be coupled to self-immolative PABC moiety via an additional linker molecule. For example, an amine-comprising payload may be coupled to the PABC moiety via a p-nitrophenol (PNP) group. Further linker molecules that allow coupling of payloads comprising other reactive groups than amine to a PABC moiety have been disclosed by Su et al., Bioconjugate Chem. 2018, 29, 4, 1155-1167; and Dokter et al., Mol Cancer Ther. 2014 November; 13(11):2618-29. For example, payloads comprising an alcohol or phenol group may be coupled to PABC via an ethylene diamine (EDA) linker (see FIGS. 18 and 19).

In a particular embodiment, the invention relates to the method according to the invention, wherein the self-immolative moiety comprises a methyl amine group. It has been demonstrated previously that methyl amine groups can be used as self-immolative moieties in peptide based linkers of ADCs (Costoplus et al., *ACS Med. Chem. Lett.* 2019, 10, 10, 1393-1399 and Li et al., *ACS Med. Chem. Lett.* 2019, 10, 10, 1386-1392).

In particular, the self-immolative moiety comprising a methyl amine group may be coupled to the C-terminal end of an amino acid residue via an amide bond formed between the α-carboxyl group of the amino acid residue and the amine comprised in the methyl amine group. The amino acid residue may be an amino acid residue comprised in ($Sp_2$) or the residue K comprised in the RK motif. The methyl group comprised in the methyl amine group may be coupled to the payload by an ether or thioether bond. Thus, a methyl amine group may be preferably used as a self-immolative group when the payload comprises a hydroxyl or thiol group. In certain embodiments, the hydroxyl-comprising payload may be camptothecin, such as the exatecan derivative Dxd or an anthracycline, such as PNU-159682. In certain embodiments the thiol-comprising payload may be a maytansinoid such as DM1, DM4 or DM21.

A linker comprising a methyl amine group may comprise the molecular structure C—(NH)—(CH$_3$)—O—C or C—(NH)—(CH$_3$)—S—C. An exemplary linker comprising a methyl amine group is shown in FIGS. 15, 17 and 21.

It is to be understood that PABC and self-immolative moieties comprising a methyl amine group are preferably used to couple payloads to the C-terminal carboxyl group of an amino acid residue.

Other self-immolative moieties that may be used to couple payloads to the C-terminal carboxyl group of an amino acid residue comprise p-aminobenzyl ethanol (PABE) linkers for the coupling of phenol-comprising payloads to the C-terminal carboxyl group of an amino acid residue (Zhang et al., *Bioconjugate Chem.* 2018, 29, 6, 1852-1858) or para-methyl aniline (PMA) linkers for the coupling of payloads comprising a tertiary amine or a heteroaryl moiety to the C-terminal carboxyl group of an amino acid residue (Staben et al., *Nature Chemistry volume* 8, pages 1112-1119 (2016)) (see FIGS. 20 and 23, respectively). Non-limiting examples of payloads comprising a phenol group are duocarmycin GA or the pyrrolobenzodiazepine PBD. A non-limiting example of a payload comprising a tertiary amine is duocarmycin GA.

However, payloads may also be coupled to the N-terminal amino group via a self-immolative moiety. For example, payloads may be coupled to the N-terminal amino group of an amino acid residue via a self-immolative moiety comprising an ortho-hydroxy-protected aryl sulfate. For example, an ortho-hydroxy-protected aryl sulfate (OHPAS) may be used to couple a phenolic payload, such as PBD, to the N-terminal amino group of an amino acid residue (see FIG. 27). The OHPAS moiety preferably comprises a carboxyl group via which it can be coupled directly to the N-terminal amino group of an amino acid residue. Alternatively, the OHPAS moiety may be coupled to the N-terminal amino group of an amino acid residue via a functionalized PEG linker, for example, without limitation, a functionalized (PEG)$_2$ linker. Preferably, the PEG linker is functionalized on one end with an amino group to allow coupling to the carboxyl group comprised in the OHPAS moiety and with a carboxyl group on the other side to allow coupling to the N-terminal amino group of an amino acid residue (Park et al., *Bioconjugate Chem.* 2019, 30, 7, 1957-1968) (see FIG. 26).

Alternatively or in addition, a linker molecule may be located between the sulfate group of OHPAS and the payload to allow coupling of non-phenolic payloads to OHPAS. For example, a para-hydroxy benzyl (PHB) linker molecule may be used to allow coupling of payloads comprising a primary or secondary amine to an OHPAS moiety through the formation of a carbamate (see FIGS. 31 and 32). Payloads comprising a tertiary amine may be coupled to an OHPAS comprising linker through the formation of a quaternary ammonium (see FIGS. 33 and 34). Further, a para-hydroxy benzyl ethylenediamine (PHB-EDA) linker molecule may be used to couple a hydroxyl-comprising payload to an OHPAS moiety through the formation of a carbamate (Park et al., *Bioconjugate Chem.* 2019, 30, 7, 1957-1968) (see FIG. 25)

In certain embodiments, the payload may be coupled to an amino acid residue comprised in the linker via a cleavable moiety. A "cleavable moiety", as used herein, is a chemical unit that can be separated from the actual payload by enzymatic or non-enzymatic hydrolysis. In certain embodiments, a cleavable moiety may be an amino acid motif that is hydrolyzable by a peptidase or protease.

In other embodiments, the cleavable moiety comprised in the linker may be a carbohydrate moiety. In such embodiments, the cleavable moiety may be a moiety that is cleavable by a glucosidase. Thus, in certain embodiments, the cleavable moiety may be a moiety that is cleavable by a beta-glucuronidase or a beta-galactosidase.

In other embodiments, the cleavable moiety comprised in the linker may be a phosphate moiety. In such embodiments, the cleavable moiety may be a moiety that is cleavable by a phosphatase. Thus, in certain embodiments, the cleavable moiety may be a moiety that is cleavable by a beta lysosomal acid pyrophosphatase or an acid phosphatase.

Examples for further cleavable moieties that may be used for the release of payloads from a linker molecule have been described by Bargh et al., Cleavable linkers in antibody-drug conjugates; Chem Soc Rev. 2019 Aug. 12; 48(16):4361-4374. In certain embodiments, the linker may comprise the structure (cleavable moiety)-(self-immolative moiety)-payload. In such an embodiment, the self-immolative moiety may degrade upon cleavage of the cleavable moiety and release the payload.

In a particular embodiment, the invention relates to the method according to the invention, wherein the linker is any one of the linkers shown in FIG. 1, FIG. 2, FIG. 3, FIG. 8, FIG. 9, FIG. 14, FIG. 15, FIG. 17, FIG. 18, FIG. 19, FIG. 20, FIG. 21, FIG. 22, FIG. 23, FIG. 24, FIG. 25, FIG. 26, FIG. 27, FIG. 28, FIG. 29, FIG. 30, FIG. 31, FIG. 32, FIG. 33 or FIG. 34.

In certain embodiments, the linker may comprise two or more linking moieties and/or payloads B. That is, in certain embodiments, the linker may comprise the structure

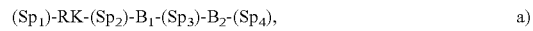
(Sp$_1$)-RK-(Sp$_2$)-B$_1$-(Sp$_3$)-B$_2$-(Sp$_4$),     a)

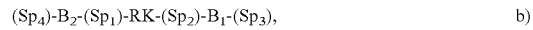
(Sp$_4$)-B$_2$-(Sp$_1$)-RK-(Sp$_2$)-B$_1$-(Sp$_3$),     b)

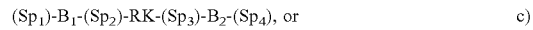
(Sp$_1$)-B$_1$-(Sp$_2$)-RK-(Sp$_3$)-B$_2$-(Sp$_4$), or     c)

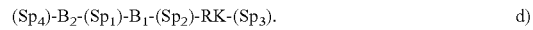
(Sp$_4$)-B$_2$-(Sp$_1$)-B$_1$-(Sp$_2$)-RK-(Sp$_3$).     d)

In such embodiments, the chemical spacers (Sp$_1$), (Sp$_2$), (Sp$_3$) and the RK motif may have the same characteristics as defined above. Further, the moieties B$_1$ and B$_2$ may be any one of the linking moieties and/or payloads defined above. Further, the chemical spacer (Sp$_4$) may have the same characteristics as the chemical spacers (Sp$_1$), (Sp$_2$) or (Sp$_3$) or may be absent.

Thus, in a particular embodiment, the invention relates to the method according to the invention, wherein the linker comprises a second linking moiety or payload B$_2$, in particular wherein B$_2$ is connected to the linker via the chemical spacer (Sp$_1$) or (Sp$_3$).

That is, the payload or linking moiety B$_2$ may be connected to the chemical spacer (Sp$_1$) or (Sp$_3$) or directly to the payload or linking moiety B$_1$. The payload or linking moiety B$_2$ may comprise any functional group that is suitable for coupling B$_2$ to a functional group comprised in (Sp$_1$), (Sp$_3$) or B$_1$.

In certain embodiments, the payload or linking moiety B$_2$ may comprise an amino group with which B$_2$ is connected to (Sp$_3$) or B$_1$. That is, B$_2$ may be connected to a carboxyl group comprised in (Sp$_3$) or B$_1$ via said amino group. In certain embodiments, the carboxyl group comprised in (Sp$_3$) may be a carboxyl group comprised in the C-terminal amino acid residue of the chemical spacer (Sp$_3$). In certain embodiments, the carboxyl group comprised in B$_1$ may be the α-carboxyl group of an amino acid-based payload or linking moiety. In certain embodiments, $B_2$ may be coupled to a carboxyl group comprised in $(Sp_3)$ or $B_1$ via a linker molecule. In certain embodiments, the linker molecule may comprise a self-immolative moiety.

In certain embodiments, the payload or linking moiety $B_2$ may comprise a carboxyl group with which $B_2$ is connected to $(Sp_1)$ or $B_1$. That is, $B_2$ may be connected to an amine group comprised in $(Sp_1)$ or $B_1$ via said carboxyl group. In certain embodiments, the amine group comprised in $(Sp_1)$ may be an amine group comprised in the N-terminal amino acid residue of the chemical spacer $(Sp_1)$. In certain embodiments, the amine group comprised in $B_1$ may be the α-amino group of an amino acid-based payload or linking moiety. In certain embodiments, $B_2$ may be coupled to an amine group comprised in $(Sp_1)$ or $B_1$ via a linker molecule. In certain embodiments, the linker molecule may comprise a self-immolative moiety.

However, it has to be noted that $B_2$ may also comprise other functional groups than an amine or a carboxyl group. In such embodiments, $B_2$ may be coupled to $(Sp_1)$, $(Sp_3)$ or $B_1$ by any method known in the art, either directly, or via a linker or self-immolative group.

In certain embodiments, the payload or linking moiety $B_2$ may be coupled to an amino acid side chain comprised in $(Sp_1)$ or $(Sp_3)$. That is, $B_2$ may be connected to a functional group of an amino acid side chain comprised in $(Sp_1)$ or $(Sp_3)$ via a compatible functional group.

In certain embodiments, $(Sp_1)$, $(Sp_2)$, $(Sp_3)$ and the RK motif consist exclusively of amino acids, amino acid mimetics and/or amino acid derivatives. In certain embodiments, also $B_1$ and/or $B_2$ comprise an amino acid backbone. In such embodiments, the linker may be a linear peptide or peptidomimetic. In embodiments where $B_1$ is an amino acid, an amino acid mimetic or an amino acid derivative, the linker may have the structure $(Sp_1)$-RK-$(Sp_2)$-$B_1$, wherein $(Sp_1)$-RK-$(Sp_2)$-$B_1$ is a linear peptide or peptidomimetic. In embodiments where $B_1$ is an amino acid, an amino acid mimetic or an amino acid derivative, the linker may have the structure $(Sp_1)$-RK-$(Sp_2)$-$B_1$-$(Sp_3)$, wherein $(Sp_1)$-RK-$(Sp_2)$-$B_1$-$(Sp_3)$ is a linear peptide or peptidomimetic. In embodiments where $B_1$ is an amino acid, an amino acid mimetic or an amino acid derivative, the linker may have the structure RK-$(Sp_2)$-$B_1$-$(Sp_3)$, wherein RK-$(Sp_2)$-$B_1$-$(Sp_3)$ is a linear peptide or peptidomimetic. In embodiments where $B_1$ is an amino acid, an amino acid mimetic or an amino acid derivative, the linker may have the structure RK-$(Sp_2)$-$B_1$, wherein RK-$(Sp_2)$-$B_1$ is a linear peptide or peptidomimetic. In embodiments where $B_1$ is an amino acid, an amino acid mimetic or an amino acid derivative, the linker may have the structure RK-$B_1$-$(Sp_3)$, wherein RK—$B_1$-$(Sp_3)$ is a linear peptide or peptidomimetic. In embodiments where $B_1$ is an amino acid, an amino acid mimetic or an amino acid derivative, the linker may have the structure RK-$B_1$, wherein RK—$B_1$ is a linear peptide or peptidomimetic.

In embodiments where $B_1$ and $B_2$ are amino acids, amino acid mimetics or amino acid derivatives, the linker may have the structure $(Sp_1)$-RK-$(Sp_2)$-$B_1$-$(Sp_3)$-$B_2$-$(Sp_4)$, wherein $(Sp_1)$-RK-$(Sp_2)$-$B_1$-$(Sp_3)$-$B_2$-$(Sp_4)$ is a linear peptide or peptidomimetic. In other embodiments where $B_1$ and $B_2$ are amino acids, amino acid mimetics or amino acid derivatives, the linker may have the structure $(Sp_4)$-$B_2$-$(Sp_1)$-RK-$(Sp_2)$-$B_1$-$(Sp_3)$, wherein $(Sp_4)$-$B_2$-$(Sp_1)$-RK-$(Sp_2)$-$B_1$-$(Sp_3)$ is a linear peptide or peptidomimetic. In other embodiments where $B_1$ and $B_2$ are amino acids, amino acid mimetics or amino acid derivatives, the linker may have the structure $(Sp_4)$-$B_2$-$(Sp_1)$-$B_1$-$(Sp_2)$-RK-$(Sp_3)$, wherein $(Sp_4)$-$B_2$-$(Sp_1)$-$B_1$-$(Sp_2)$-RK-$(Sp_3)$ is a linear peptide or peptidomimetic.

In embodiments where $B_1$ is not an amino acid, an amino acid mimetic or an amino acid derivative, the linker may have the structure $(Sp_1)$-RK-$(Sp_2)$-$B_1$-$(Sp_3)$, wherein $(Sp_1)$-RK-$(Sp_2)$ is a linear peptide or peptidomimetic and $B_1$ is connected to the C-terminal carboxyl group comprised in $(Sp_2)$. In embodiments where $B_1$ is not an amino acid, an amino acid mimetic or an amino acid derivative, the linker may have the structure $(Sp_1)$-$B_1$-$(Sp_2)$-RK-$(Sp_3)$, wherein $(Sp_2)$-RK-$(Sp_3)$ is a linear peptide or peptidomimetic and $B_1$ is connected to the N-terminal amino group comprised in $(Sp_2)$. However, it has to be noted that $B_1$ does not necessarily have to be coupled to the peptide or peptidomimetic directly. Instead, $B_1$ may be coupled to the peptide or peptidomimetic via a linker molecule and/or a self-immolative moiety.

In embodiments where $B_1$ is an amino acid, an amino acid mimetic or an amino acid derivative and $B_2$ is not an amino acid, an amino acid mimetic or an amino acid derivative, the linker may have the structure (Sp)-RK-$(Sp_2)$-$B_1$-$(Sp_3)$-$B_2$-$(Sp_4)$, $(Sp_4)$-$B_2$-$(Sp_1)$-RK-$(Sp_2)$-$B_1$-$(Sp_3)$, $(Sp_1)$-$B_1$-$(Sp_2)$-RK-$(Sp_3)$-$B_2$-$(Sp_4)$ or $(Sp_4)$-$B_2$-$(Sp_1)$-$B_1$-$(Sp_2)$-RK-$(Sp_3)$, wherein $(Sp_1)$-RK-$(Sp_2)$-$B_1$-$(Sp_3)$ or $(Sp_1)$-$B_1$-$(Sp_2)$-RK-$(Sp_3)$ is a linear peptide or peptidomimetic and $B_2$ is coupled to the C-terminal carboxyl group comprised in $(Sp_3)$, $B_1$ or RK or to the N-terminal amino group of $(Sp_1)$, $B_1$ or RK.

In such embodiments, an antibody-payload conjugate may be generated with, for example, an antibody to payload ratio of 2 or 4, for example with one or two payloads conjugated to each Q295 residue.

In a particular embodiment, the invention relates to the method according to the invention, wherein $B_1$ and $B_2$ are identical or differ from one another.

That is, the payload or linking moieties $B_1$ and $B_2$ may be identical, i.e., have the same chemical structure, or may be structurally different. In certain embodiments, $B_1$ and $B_2$ are both payloads or are both linking moieties. In embodiments where $B_1$ and $B_2$ are both payloads, the payloads $B_1$ and $B_2$ may be identical or different payloads. In embodiments where $B_1$ and $B_2$ are both linking moieties, the linking moieties $B_1$ and $B_2$ may be identical or different linking moieties. In certain embodiments, $B_1$ may be a linking moiety and $B_2$ may be a payload or vice versa.

It is to be understood that not all payloads or linking moieties can function as intrachain payloads or linking moieties in position $B_1$, for example, because they do not have the functional groups to form covalent bonds with $(Sp_2)$ or RK on one side, and $(Sp_3)$, $(Sp_1)$ or $B_2$ on the other side. Thus, it is preferred that in embodiments where $B_1$ is an intrachain payload or linking moiety, $B_1$ is a divalent or polyvalent molecule. For example, $B_1$ may be an amino acid, an amino acid mimetic or an amino acid derivative. In such embodiments, $B_1$ may be coupled via its amino group to the C-terminal carboxyl group of $(Sp_2)$ or RK and via its carboxyl group with the N-terminal amino group of $(Sp_3)$ or $B_2$. Alternatively, $B_1$ may be coupled via its carboxyl group to the N-terminal amino group of $(Sp_2)$ or RK and via its amino group with the C-terminal carboxyl group of $(Sp_1)$ or $B_2$.

In certain embodiments, the linker may comprise two linking moieties $B_1$ and $B_2$.

That is, in certain embodiments, the invention encompasses linkers comprising two bio-orthogonal marker groups and/or non-bio-orthogonal entities. For example, a linker according to the invention may comprise an azide-comprising linking moiety, such as Lys($N_3$) or Xaa($N_3$), and a sulfhydryl-comprising linking moiety, such as cysteine. In certain embodiments, the linker according to the invention may comprise an azide-comprising linking moiety, such as Lys($N_3$) or Xaa($N_3$), and a tetrazine-comprising linking moiety, such as a tetrazine-modified amino acid. In certain embodiments, the linker according to the invention may comprise a sulfhydryl-comprising linking moiety, such as cysteine, and a tetrazine-comprising linking moiety, such as a tetrazine-modified amino acid. Linkers comprising two different bio-orthogonal marker groups and/or non-bio-orthogonal entities have the advantage that they can accept two distinct payloads and thus result in antibody-payload conjugates comprising more than one payload.

In such way, an antibody payload ratio of 2+2 may be obtained. Using a second payload may allow for the development of a completely new class of antibody payload conjugates that go beyond current therapeutic approaches with respect to efficacy and potency.

Such embodiments may allow, inter alia, to target two different structures in a cell, like, e.g., the DNA and microtubule. Because some cancers can be resistant to one drug, like e.g., a mirobutule toxin, the DNA-toxin can still kill the cancer cells.

According to another embodiment, two drugs may be used that are only fully potent when they are released at the same time and in the same tissue. This may lead to reduced off-target toxicity in case the antibody is partially degraded in healthy tissues or one drug is pre-maturely lost.

Furthermore, dual-labeled probes may be used for non-invasive imaging and therapy or intra/post-operative imaging/surgery. In such embodiments, a tumor patient may be selected by means of the non-invasive imaging. Then, the tumor may be removed surgically using the other imaging agent (e.g., a fluorescent dye), which helps the surgeon or robot to identify all cancerous tissue during a surgery.

In certain embodiments, one of $B_1$ and $B_2$ may be a linking moiety comprising a thiol group, such as cysteine, and the other one of $B_1$ and $B_2$ may be a linking moiety comprising an azide moiety, such as Lys($N_3$). In such embodiments, two distinct payloads may be coupled to a linker, one via a thiol-maleimide conjugation and the other one via a SPAAC reaction.

In certain embodiments, the linker may comprise two payloads. Linkers comprising only payloads but no linking moieties may be conjugated to an antibody in a one-step process.

It is to be understood that in embodiments where $B_1$ and $B_2$ are both payloads, $B_1$ and $B_2$ may be identical or may be different in structure. In certain embodiments, linkers comprising one or more payloads may be synthesized chemically. Alternatively, one or more payloads may be coupled to a linking moiety comprised in the linker by any of the methods disclosed herein before the linker is conjugated to an antibody.

In certain embodiments, the linkers of the invention may allow to conjugate two different payloads to the residue Q295 of the $C_H2$ domain of an antibody. Using a second payload allows for the development of a completely new class of antibody-payload conjugates that go beyond current therapeutic approaches with respect to efficacy and potency. Also new application fields are envisioned, for example, dual-type imaging for imaging and therapy or intra-/post-operative surgery (cf. Azhdarinia A. et al., Dual-Labeling Strategies for Nuclear and Fluorescence Molecular Imaging: A Review and Analysis. Mol Imaging Biol. 2012 June; 14(3): 261-276). For example, dual-labeled antibodies encompassing a molecular imaging agent for preoperative positron emission tomography (PET) and a near-infrared fluorescent (NIRF)-dye for guided delineation of surgical margins could greatly enhance the diagnosis, staging, and resection of cancer (cf. Houghton J L. et al., Site-specifically labeled CA19.9-targeted immunoconjugates for the PET, NIRF, and multimodal PET/NIRF imaging of pancreatic cancer. Proc Natl Acad Sci USA. 2015 Dec. 29; 112(52): 15850-5). PET and NIRF optical imaging offer complementary clinical applications, enabling the non-invasive whole-body imaging to localize disease and identification of tumor margins during surgery, respectively. However, the generation of such dual-labeled probes up to date has been difficult due to a lack of suitable site-specific methods; attaching two different probes by chemical means results in an almost impossible analysis and reproducibility due to the random conjugation of the probes.

Furthermore, in a study of Levengood M. et al., (Orthogonal Cysteine Protection Enables Homogeneous Multi-Drug Antibody-Drug Conjugates. Angewandte Chemie, Volume 56, Issue 3, Jan. 16, 2017) a dual-drug labeled antibody, having attached two different auristatin toxins (having differing physiochemical properties and exerting complementary anti-cancer activities) imparted activity in cell line and xenograft models that were refractory to ADCs comprised of the individual auristatin components. This suggests that dual-labeled ADCs enable to address cancer heterogeneity and resistance more effectively than the single, conventional ADCs alone. Since one resistance mechanism towards ADCs include the active pumping-out of the cytotoxic moiety from the cancer cell, another dual-drug application may include the additional and simultaneous delivery of a drug that specifically blocks the efflux mechanism of the cytotoxic drug. Such a dual-labeled ADC could thus help to overcome cancer resistance to the ADC more effectively than conventional ADCs.

The term "antibody" herein is used in the broadest sense and specifically covers monoclonal antibodies, polyclonal antibodies, multispecific antibodies (e.g., bispecific antibodies) formed from at least two intact antibodies, and antibody fragments so long as they exhibit the desired biological activity. The terms "antibody" and "antibodies" broadly encompass naturally-occurring forms of antibodies (e.g., IgG, IgA, IgM, IgE).

The antibody is preferably a monoclonal antibody. The antibody can be of human origin, but likewise from mouse, rat, goat, donkey, hamster, or rabbit. In case the conjugate is for therapy, a murine or rabbit antibody may optionally be chimerized or humanized.

Fragments or recombinant variants of antibodies comprising the $C_H2$ domain may be, for example,
  antibody formats comprising mere heavy chain domains (shark antibodies/IgNAR ($V_H$—$C_H1$-$C_H2$-$C_H3$-$C_H4$-$C_H5$)$_2$ or camelid antibodies/hcIgG ($V_H$—$C_H2$-$C_H3$)$_2$)
  scFv-Fc (VH-VL-CH2-CH3)2
  Fc fusion peptides, comprising an Fc domain and one or more receptor domains.

The antibody may also be bispecific (e.g., DVD-IgG, crossMab, appended IgG-HC fusion) or biparatopic. See Brinkmann and Kontermann; Bispecific antibodies; Drug Discov Today; 2015; 20(7); p. 838-47, for an overview.

In a particular embodiment, the invention relates to the method according to the invention, wherein the antibody is an IgG antibody, in particular an IgG1 antibody.

By "IgG" as used herein is meant a polypeptide belonging to the class of antibodies that are substantially encoded by a recognized immunoglobulin gamma gene. In humans, IgG comprises the subclasses or isotypes IgG1, IgG2, IgG3, and IgG4. In mice, IgG comprises IgG1, IgG2a, IgG2b, IgG3. Full-length IgGs consist of two identical pairs of two immunoglobulin chains, each pair having one light and one heavy chain, each light chain comprising immunoglobulin domains VL and CL, and each heavy chain comprising immunoglobulin domains VH, Cγ1 (also called CH1), Cγ2 (also called CH2), and Oγ3 (also called CH3). In the context of human IgG1, "CH1" refers to positions 118-215, CH2 domain refers to positions 231-340 and CH3 domain refers to positions 341-447 according to the EU index as in Kabat. IgG1 also comprises a hinge domain which refers to positions 216-230 in the case of IgG1.

The antibody used in the method of the invention or the antibody-payload conjugate of the invention may be or comprise any antibody, preferably any IgG type antibody. For example, the antibody may be, without limitation, Brentuximab, Trastuzumab, Gemtuzumab, Inotuzumab, Avelumab, Cetuximab, Rituximab, Daratumumab, Pertuzumab, Vedolizumab, Ocrelizumab, Tocilizumab, Ustekinumab, Golimumab, Obinutuzumab, Sacituzumab, Belantamab, Polatuzumab and Enfortumab.

Thus, in a particular embodiment, the invention relates to the method according to the invention, wherein the antibody is selected from the group consisting of: Brentuximab, Trastuzumab, Gemtuzumab, Inotuzumab, Avelumab, Cetuximab, Rituximab, Daratumumab, Pertuzumab, Vedolizumab, Ocrelizumab, Tocilizumab, Ustekinumab, Golimumab, Obinutuzumab, Sacituzumab, Belantamab, Polatuzumab and Enfortumab.

In a preferred embodiment, the invention relates to the method according to the invention, wherein the antibody is selected from the group consisting of: Brentuximab, Gemtuzumab, Trastuzumab, Inotuzumab, Polatuzumab, Enfortumab, Sacituzumab and Belantamab.

In a more preferred embodiment, the invention relates to the method according to the invention, wherein the antibody is Polatuzumab or Trastuzumab or Enfortumab.

That is, in a particular embodiment, the invention relates to an antibody-linker conjugate, wherein the antibody is Polatuzumab and wherein the linker is any one of the linkers disclosed herein.

In another embodiment, the invention relates to an antibody-linker conjugate, wherein the antibody is Trastuzumab and wherein the linker is any one of the linkers disclosed herein.

In another embodiment, the invention relates to an antibody-linker conjugate, wherein the antibody is Enfortumab and wherein the linker is any one of the linkers disclosed herein.

The antibody for use in the method according to the invention may be a glycosylated antibody, a deglycosylated antibody or an aglycosylated antibody.

That is, in certain embodiments, the antibody may be an IgG antibody that is glycosylated, preferably at residue N297. Thus, in a particular embodiment, the invention relates to the method according to the invention, wherein the IgG antibody is a glycosylated IgG antibody, in particular wherein the IgG antibody is glycosylated at residue N297 (EU numbering) of the $C_H2$ domain.

As discussed herein, IgG antibodies that are glycosylated at residue N297 have several advantages over non-glycosylated antibodies.

However, the antibody may also be a deglycosylated antibody, preferably wherein the glycan at residue N297 has been cleaved off with the enzyme PNGase F. Further, the antibody may be an aglycosylated antibody, preferably wherein residue N297 has been replaced with a non-asparagine residue. Methods for deglycosylating antibodies and for generating aglycosylated antibodies are known in the art.

In certain embodiments, the linker of the invention may be conjugated to an endogenous Gln residue in the Fc domain of an antibody or to a Gln residue that has been introduced into the antibody by means of molecular engineering.

Thus, in a particular embodiment, the invention relates to the method according to the invention, wherein the Gln residue to which the linker is conjugated is comprised in an Fc domain of the antibody, in particular wherein the Gln residue to which the linker is conjugated is Gln residue Q295 (EU numbering) of the $C_H2$ domain of an IgG antibody.

The linkers of the invention may be conjugated to any Gln residue in the Fc domain of an antibody that can serve as a substrate for a microbial transglutaminase. Typically, the term Fc domain as used herein refers to the last two constant region immunoglobulin domains of IgA, IgD and IgG ($C_H2$ and $C_H3$) and the last three constant region domains of IgE, IgY and IgM ($C_H2$, $C_H3$ and $C_H4$). That is, the linker according to the invention may be conjugated to the $C_H2$, $C_H3$ and, where applicable, $C_H4$ domains of the antibody.

In certain embodiments, the endogenous Gln residue may be Gln residue Q295 (EU numbering) of the CH2 domain of an IgG antibody. Thus, in a particular embodiment, the invention relates to the method according to the invention, wherein the Gln residue in the Fc domain of the antibody is Gln residue Q295 (EU numbering) of the CH2 domain of an IgG antibody.

It is important to understand that Q295 is an extremely conserved amino acid residue in IgG type antibodies. It is conserved in human IgG1, 2, 3, 4, as well as in rabbit and rat antibodies amongst others. Hence, being able to use Q295 is a considerable advantage for making therapeutic antibody-payload conjugates, or diagnostic conjugates where the antibody is often of non-human origin. The method according to the invention does hence provide an extremely versatile and broadly applicable tool. Even though residue Q295 is extremely conserved among IgG type antibodies, some IgG type antibodies do not possess this residue, such as mouse and rat IgG2a antibodies. Thus, it is to be understood that the antibody used in the method of the present invention is preferably an IgG type antibody comprising residue Q295 (EU numbering) of the $C_H2$ domain.

Further, it has been shown that engineered conjugates using Q295 for payload attachment demonstrate good pharmacokinetics and efficacy (Lhospice et al., Site-Specific Conjugation of Monomethyl Auristatin E to Anti-Cd30 Antibodies Improves Their Pharmacokinetics and Therapeutic Index in Rodent Models, Mol Pharm; 2015; 12(6), p. 1863-1871), and are capable of carrying even unstable toxins prone for degradation (Dorywalska et al.; Site-Dependent Degradation of a Non-Cleavable Auristatin-Based Linker-Payload in Rodent Plasma and Its Effect on ADC Efficacy. PLoS ONE; 2015; 10(7): e0132282). It is thus expected that similar effects will be seen with this site-specific method since the same residue is modified, but of glycosylated antibodies. Glycosylation may further contribute to overall ADC stability, removal of the glycan moieties as with the mentioned approaches has been shown to result in less-stable antibodies (Zheng et al.; The impact of glycosylation on monoclonal antibody conformation and stability. Mabs-Austin; 2011, 3(6), p. 568-576).

In the literature discussing the conjugation of linkers to a $C_H2$ Gln residue by means of a transglutaminase, the focus has been on small, low-molecular weight substrates. However, in the prior art literature, to accomplish such conjugation, a deglycosylation step in position N297, or the use of an aglycosylated antibody, is always described as necessary (WO 2015/015448; WO 2017/025179; WO 2013/092998).

Quite surprisingly, and against all expectations, however, site-specific conjugation to Q295 of glycosylated antibodies is indeed efficiently possible by using the above discussed linker structure. In particular, coupling of linkers comprising toxin molecules was achieved with a conjugation efficiency greater than 80%.

Even though Q295 is very close to N297, which is, in its native state, glycosylated, the method according to the invention, using the specified linker, still allows the conjugation of the linker or payload thereto.

As shown, the method according to the invention does not require an upfront enzymatic deglycosylation of N297, nor the use of an aglycosylated antibody, nor a substitution of N297 against another amino acid, nor the introduction of a T299A mutation to prevent glycosylation.

These two points provide significant advantages under manufacturing aspects. An enzymatic deglycosylation step is undesired under GMP aspects, because it has to be made sure that the both the deglycosylation enzyme (e.g., PNGase F) as well as the cleaved glycan have to be removed from the medium.

Furthermore, no genetic engineering of the antibody for payload attachment is necessary, so that sequence insertions which may increase immunogenicity and decrease the overall stability of the antibody can be avoided.

The substitution of N297 against another amino acid has unwanted effects, too, because it may affect the overall stability of the entire Fc domain (Subedi et al, The Structural Role of Antibody N-Glycosylation in Receptor Interactions. Structure 2015, 23 (9), 1573-1583), and the efficacy of the entire conjugate as a consequence that can lead to increased antibody aggregation and a decreased solubility (Zheng et al.; The impact of glycosylation on monoclonal antibody conformation and stability. Mabs-Austin 2011, 3 (6), 568-576) that particularly gets important for hydrophobic payloads such as PBDs. Further, the glycan that is present at N297 has important immunomodulatory effects, as it triggers antibody dependent cellular cytotoxicity (ADCC) and the like. These immunomodulatory effects would get lost upon deglycosylation or any of the other approaches discussed above to obtain an aglycosylated antibody. Further, any sequence modification of an established antibody can also lead to regulatory problems, which is problematic because often times an accepted and clinically validated antibody is used as a starting point for ADC conjugation.

Hence, the method according to the invention allows to easily and without disadvantages make stoichiometrically well-defined ADCs with site specific payload binding.

In view of the above, it is stated that the method of the present invention is preferably used for the conjugation of an IgG antibody at residue Q295 (EU numbering) of the $C_H2$ domain of the antibody, wherein the antibody is glycosylated at residue N297 (EU numbering) of the $C_H2$ domain. However, it is expressly stated that the method of the invention also encompasses the conjugation of deglycosylated or aglycosylated antibodies at residue Q295 or any other suitable Gln residue of the antibody, wherein the Gln residue may be an endogenous Gln residue or a Gln residue that has been introduced by molecular engineering.

Thus, in a particular embodiment, the invention relates to the method according to the invention, wherein the Gln residue to which the linker is conjugated has been introduced into the heavy or light chain of the antibody by molecular engineering.

The term "molecular engineering," as used herein, refers to the use of molecular biology methods to manipulate nucleic acid sequences. Within the present invention, molecular engineering may be used to introduce Gln residues into the heavy or light chain of an antibody. In general, two different strategies to introduce Gln residues into the heavy or light chain of an antibody are envisioned within the present invention. First, single residues of the heavy or light chain of an antibody may be substituted with a Gln residue. Second, Gln-containing peptide tags consisting of two or more amino acid residues may be integrated into the heavy or light chain of an antibody. For that, the peptide tag may either be integrated into an internal position of the heavy or light chain, that is, between two existing amino acid residues of the heavy or light chain or by replacing them, or the peptide tag may be fused (appended) to the N- or C-terminal end of the heavy or light chain of the antibody.

For example, an amino residue of the heavy or light chain of an antibody may be substituted with a Gln residue, provided that the resulting antibody can be conjugated with the linkers of the invention by a microbial transglutaminase. In certain embodiments, the antibody is an antibody wherein amino acid residue N297 (EU numbering) of the $C_H2$ domain of an IgG antibody is substituted, in particular wherein the substitution is an N297Q substitution. Antibodies comprising an N297Q mutation may be conjugated to more than one linker per heavy chain of the antibody. For example, antibodies comprising an N297Q mutation may be conjugated to four linkers, wherein one linker is conjugated to residue Q295 of the first heavy chain of the antibody, one linker is conjugated to residue N297Q of the first heavy chain of the antibody, one linker is conjugated to residue Q295 of the second heavy chain of the antibody and one linker is conjugated to residue N297Q of the second heavy chain of the antibody. The skilled person is aware that replacement of residue N297 of an IgG antibody with a Gln residue results in an aglycosylated antibody.

Thus, in a particular embodiment, the invention relates to the method according to the invention, wherein the Gln residue that has been introduced into the heavy or light chain of the antibody by molecular engineering is N297Q (EU numbering) of the $C_H2$ domain of an aglycosylated IgG antibody.

In a particular embodiment, the invention relates to the method according to the invention, wherein the Gln residue that has been introduced into the heavy or light chain of the antibody by molecular engineering is comprised in a peptide that has been (a) integrated into the heavy or light chain of the antibody or (b) fused to the N- or C-terminal end of the heavy or light chain of the antibody.

Instead of substituting single amino acid residues of an antibody, peptide tags comprising a Gln residue that is accessible for a transglutaminase may be introduced into the heavy or light chain of the antibody. Such peptide tags may be fused to the N- or C-terminus of the heavy or light chain of the antibody. Alternatively, peptide tags may be inserted into the heavy or light chain of an antibody at a suitable position. Preferably, peptide tags comprising a transglutaminase-accessible Gln residue are fused to the C-terminus of the heavy chain of the antibody. Even more preferably, the peptide tags comprising a transglutaminase-accessible Gln residue are fused to the C-terminus of the heavy chain of an IgG antibody. Several peptide tags that may be fused to the C-terminus of the heavy chain of an antibody and serve as substrate for a microbial transglutaminase are described in WO 2012/059882 and WO 2016/144608.

Thus, in a particular embodiment, the invention relates to the method according to the invention, wherein the peptide comprising the Gln residue has been fused to the C-terminal end of the heavy chain of the antibody.

Exemplary peptide tags that may be introduced into the heavy or light chain of an antibody, in particular fused to the C-terminus of the heavy chain of the antibody, are

LLQGG, (SEQ ID NO: 16)

LLQG, (SEQ ID NO: 17)

LSLSQG, (SEQ ID NO: 18)

GGGLLQGG, (SEQ ID NO: 19)

GLLQG, (SEQ ID NO: 20)

LLQ, (SEQ ID NO: 21)

GSPLAQSHGG, (SEQ ID NO: 22)

GLLQGGG, (SEQ ID NO: 23)

GLLQGG, (SEQ ID NO: 24)

GLLQ, (SEQ ID NO: 25)

LLQLLQGA, (SEQ ID NO: 26)

LLQGA, (SEQ ID NO: 27)

LLQYQGA, (SEQ ID NO: 28)

LLQGSG, (SEQ ID NO: 29)

LLQYQG, (SEQ ID NO: 30)

LLQLLQG, (SEQ ID NO: 31)

SLLQG, (SEQ ID NO: 32)

LLQLQ, (SEQ ID NO: 33)

LLQLLQ, (SEQ ID NO: 34)

LLQGR, (SEQ ID NO: 35)

EEQYASTY, (SEQ ID NO: 36)

EEQYQSTY, (SEQ ID NO: 37)

EEQYNSTY, (SEQ ID NO: 38)

EEQYQS, (SEQ ID NO: 39)

EEQYQST, (SEQ ID NO: 40)

EQYQSTY, (SEQ ID NO: 41)

QYQS, (SEQ ID NO: 42)

QYQSTY, (SEQ ID NO: 43)

YRYRQ, (SEQ ID NO: 44)

DYALQ, (SEQ ID NO: 45)

FGLQRPY, (SEQ ID NO: 46)

EQKLISEEDL, (SEQ ID NO: 47)

LQR, (SEQ ID NO: 48)

and

YQR. (SEQ ID NO: 49)

The skilled person is aware of methods to substitute amino acid residues of antibodies or to introduce peptide tags into antibodies, for example by methods of molecular cloning as described in Sambrook, Joseph. (2001). Molecular cloning: a laboratory manual. Cold Spring Harbor, N.Y.: Cold Spring Harbor Laboratory Press.

In general, the skilled person is aware of methods to determine at which position of an antibody a linker is conjugated. For example, the conjugation site may be determined by proteolytic digestion of the antibody-payload conjugate and LC-MS analysis of the resulting fragments. For example, samples may be deglycosylated with GlyciNATOR (Genovis) according to the instruction manual and subsequently digested with trypsin gold (mass spectrometry grade, Promega), respectively. Therefore, 1 μg of protein may be incubated with 50 ng trypsin at 37° C. overnight. LC-MS analysis may be performed using a nanoAcquity HPLC system coupled to a Synapt-G2 mass spectrometer (Waters). For that, 100 ng peptide solution may be loaded onto an Acquity UPLC Symmetry C18 trap column (Waters, part no. 186006527) and trapped with 5 μL/min flow rate at 1% buffer A (Water, 0.1% formic acid) and 99% buffer B (acetonitrile, 0.1% formic acid) for 3 min. Peptides may then be eluted with a linear gradient from 3% to 65% Buffer B within 25 min. Data may be acquired in resolution mode with positive polarity and in a mass range from 50 to 2000 m/z. Other instrument settings may be as follows: capillary voltage 3.2 kV, sampling cone 40 V, extraction cone 4.0 V, source temperature 130° C., cone gas 35 L/h, nano flow gas 0.1 bar, and purge gas 150 L/h. The mass spectrometer may be calibrated with [Glu1]-Fibrinopeptide.

Further, the skilled person is aware of methods to determine the drug-to-antibody (DAR) ratio or payload-to-antibody ratio of an antibody-payload construct. For example, the DAR may be determined by hydrophobic interaction chromatography (HIC) or LC-MS.

For hydrophobic interaction chromatography (HIC), samples may be adjusted to 0.5 M ammonium sulfate and assessed via a MAB PAK HIC Butyl column (5 µm, 4.6×100 mm, Thermo Scientific) using a full gradient from A (1.5 M ammonium sulfate, 25 mM Tris HCl, pH 7.5) to B (20% isopropanol, 25 mM Tris HCl, pH 7.5) over 20 min at 1 mL/min and 30° C. Typically, 40 µg sample may be used and signals may be recorded at 280 nm. Relative HIC retention times (HIC-RRT) may be calculated by dividing the absolute retention time of the ADC DAR 2 species by the retention time of the respective unconjugated mAb.

For LC-MS DAR determination, ADCs may be diluted with $NH_4HCO_3$ to a final concentration of 0.025 mg/mL. Subsequently, 40 µL of this solution may be reduced with 1 µL TCEP (500 mM) for 5 min at room temperature and then alkylated by adding 10 µL chloroacetamide (200 mM), followed by overnight incubation at 37° C. in the dark. For reversed phase chromatography, a Dionex U3000 system in combination with the software Chromeleon may be used. The system may be equipped with a RP-1000 column (1000 Å, 5 µm, 1.0×100 mm, Sepax) heated to 70° C., and an UV-detector set to a wavelength of 214 nm. Solvent A may consist of water with 0.1% formic acid and solvent B may comprise 85% acetonitrile with 0.1% formic acid. The reduced and alkylated sample may be loaded onto the column and separated by a gradient from 30-55% solvent B over the course of 14 min. The liquid chromatography system may be coupled to a Synapt-G2 mass spectrometer for identification of the DAR species. The capillary voltage of the mass spectrometer may be set to 3 kV, the sampling cone to 30 V and the extraction cone may add up to a value of 5 V. The source temperature may be set to 150° C., the desolvation temperature to 500° C., the cone gas to 20 l/h, the desolvation gas to 600 l/h, and the acquisition may be made in positive mode in a mass range from 600-5000 Da with 1 s scan time. The instrument may be calibrated with sodium iodide. Deconvolution of the spectra may be performed with the MaxEnt1 algorithm of MassLynx until convergence. After assignment of the DAR species to the chromatographic peaks, the DAR may be calculated based on the integrated peak areas of the reversed phase chromatogram.

In a particular embodiment, the invention relates to the method according to the invention, wherein the linker is conjugated to the γ-carboxamide group of the Gln residue comprised in the antibody.

That is, the linker according to the invention is preferably conjugated to the amide group in the side chain of a Gln residue comprised in the antibody, preferably any one of the Gln residues disclosed herein, more preferably Gln residue Q295 (EU numbering).

In a particular embodiment, the invention relates to the method according to the invention, wherein the linker is suitable for conjugation to a glycosylated antibody with a conjugation efficiency of at least 20%, 30%, 40%, 50%, 60%, 70%, 75%, 80%, 85%, 90% or 95%.

That is, in certain embodiments, the linker may be a linker that can be conjugated to a glycosylated antibody with an efficiency of at least 20%, 30%, 40%, 50%, 60%, 70%, 75%, 80%, 85%, 90% or 95%. In a preferred embodiment, the linker may be a linker that can be conjugated to a glycosylated antibody with an efficiency of at least 70%. In another preferred embodiment, the linker may be a linker that can be conjugated to a glycosylated antibody with an efficiency of at least 75%. In another preferred embodiment, the linker may be a linker that can be conjugated to a glycosylated antibody with an efficiency of at least 80%. In another preferred embodiment, the linker may be a linker that can be conjugated to a glycosylated antibody with an efficiency of at least 85%. In another preferred embodiment, the linker may be a linker that can be conjugated to a glycosylated antibody with an efficiency of at least 90%. In another preferred embodiment, the linker may be a linker that can be conjugated to a glycosylated antibody with an efficiency of at least 95%. Preferably, the glycosylated antibody is a glycosylated IgG antibody, more preferably an IgG antibody that is glycosylated at residue N297 (EU numbering).

The skilled person is aware of methods to determine the conjugation efficiency of an antibody with a specific linker. For example, the conjugation efficiency may be determined as described herein. That is, an antibody, in particular an IgG1 antibody, may be incubated at a concentration of 1-5 mg/mL with 5-20 eq molar equivalents of a linker and 3-6 U of a microbial transglutaminase per mg of antibody in a suitable buffer for 20-48 hours at 37° C. or as described in Example 1. After the incubation period, the conjugation efficiency may be determined by LC-MS analysis under reducing conditions. The microbial transglutaminase may be an MTG from *Streptomyces mobaraensis* that is available from Zedira (Germany). A suitable buffer may be a Tris, MOPS, HEPES, PBS or BisTris buffer. However, it is to be understood that the choice of the buffer system may vary and depend to a large extent on the chemical properties of the linker. However, the skilled person is capable of identifying the optimal buffer conditions based on the disclosure of the present invention. Alternatively, the conjugation efficiency may be determined as described in Spycher et al. (Dual, Site-Specific Modification of Antibodies by Using Solid-Phase Immobilized Microbial Transglutaminase, ChemBioChem 2019 18(19):1923-1927) and analyzed as in Benjamin et al. (Thiolation of Q295: Site-Specific Conjugation of Hydrophobic Payloads without the Need for Genetic Engineering, Mol. Pharmaceutics 2019, 16: 2795-2807).

In certain embodiments, antibodies may be conjugated as described in Example 1. That is, 5 mg/ml of native, glycosylated monoclonal antibody may be incubated for 24 hours at 37° C. in 50 mM Tris pH 7.6 comprising microbial transglutaminase (MTG, Zedira) at a concentration of 5 U/mg antibody and 5 molar equivalents of the indicated linker-payload in a rotating thermomixer.

In a particular embodiment, the invention relates to the method according to the invention, wherein the microbial transglutaminase is derived from a *Streptomyces* species, in particular *Streptomyces mobaraensis*.

That is, the microbial transglutaminase used in the method of the invention may be derived from a *Streptomyces* species, in particular from *Streptomyces mobaraensis*, preferentially with a sequence identity of 80% to the native enzyme. Accordingly, the MTG may be a native enzyme or may be an engineered variant of a native enzyme.

One such microbial transglutaminase is commercially available from Zedira (Germany). It is recombinantly produced in *E. coli*. *Streptomyces mobaraensis* transglutaminase has an amino acid sequence as disclosed in SEQ ID NO:12. *S. mobaraensis* MTG variants with other amino acid sequences have been reported and are also encompassed by this invention (SEQ ID NO:13 and 14).

In another embodiment, a microbial transglutaminase from *Streptomyces ladakanum* (formerly known as *Streptoverticillium ladakanum*) may be used. *Streptomyces ladakanum* transglutaminase (U.S. Pat. No. 6,660,510 B2) has an amino acid sequence as disclosed in SEQ ID NO:15.

Both of the above transglutaminases may be sequence modified. In several embodiments, transglutaminases may be used which have 80%, 85%, 90% or 95% or more sequence identity with any one of SEQ ID NO:12-15.

Another suitable microbial transglutaminase is commercially from Ajinomoto, called ACTIVA TG. In comparison to the transglutaminase from Zedira, ACTIVA TG lacks 4 N-terminal amino acids, but has similar activity.

Further microbial transglutaminases which may be used in the context of the present invention are disclosed in Kieliszek and Misiewicz (Folia Microbiol (Praha). 2014; 59(3): 241-250), WO 2015/191883 A1, WO 2008/102007 A1 and US 2010/0143970, the content of which is fully incorporated herein by reference.

In certain embodiments, a mutant variant of a microbial transglutaminase may be used for the conjugation of a linker to an antibody. That is, the microbial transglutaminase that is used in the method of the present invention may be a variant of *S. mobaraensis* transgluatminase as set forth in SEQ ID NOs: 12 or 13. In certain embodiments, the recombinant *S. morabaensis* transglutaminase as set forth in SEQ ID NO:12 may comprise the mutation G254D. In certain embodiments, the recombinant *S. morabaensis* transglutaminase as set forth in SEQ ID NO:12 may comprise the mutations G254D and E304D. In certain embodiments, the recombinant *S. morabaensis* transglutaminase as set forth in SEQ ID NO:12 may comprise the mutations D8E and G254D. In certain embodiments, the recombinant *S. morabaensis* transglutaminase as set forth in SEQ ID NO:12 may comprise the mutations E124A and G254D. In certain embodiments, the recombinant *S. morabaensis* transglutaminase as set forth in SEQ ID NO:12 may comprise the mutations A216D and G254D. In certain embodiments, the recombinant *S. morabaensis* transglutaminase as set forth in SEQ ID NO:12 may comprise the mutations G254D and K331T.

Microbial transglutaminase may be added to the conjugation reaction at any concentration that allows efficient conjugation of an antibody with a linker. In certain embodiments, the concentration of microbial transglutaminase in a conjugation reaction may depend on the amount of antibody used in the same reaction. For example, a microbial transglutaminase may be added to the conjugation reaction at a concentration of less than 100 U/mg antibody, 90 U/mg antibody, 80 U/mg antibody, 70 U/mg antibody, 60 U/mg antibody, 50 U/mg antibody, 40 U/mg antibody, 30 U/mg antibody, 20 U/mg antibody 10 U/mg antibody or 6 U/mg antibody. In certain embodiments a microbial transglutaminase may be added to the conjugation reaction at a concentration of 1, 3, 5 or 6 U/mg antibody.

That is, in certain embodiments, a microbial transglutaminase may be added to the conjugation reaction at a concentration ranging from 1-20 U/mg antibody, preferably 1-10 U/mg antibody, more preferably 1-7.5 U/mg antibody, even more preferably 2-6 U/mg antibody, even more preferably 2-4 U/mg antibody, most preferably 3 U/mg antibody.

The method according to the invention comprises the use of a microbial transglutaminase. However, it is to be noted that an equivalent reaction may be carried out by an enzyme comprising transglutaminase activity that is of a non-microbial origin. Accordingly, also the antibody-linker conjugates according to the invention may be generated with an enzyme comprising transglutaminase activity that is of a non-microbial origin.

The antibody may be added to the conjugation reaction in any concentration. However, it is preferred that the antibody is added to the conjugation reaction at a concertation ranging from 0.1-20 mg/ml. That is, in a particular embodiment, the invention relates to the method according to the invention, wherein the antibody is added to the conjugation reaction at a concentration of 0.1-20 mg/mL, preferably 0.25-15 mg/mL, more preferably 0.5-12.5 mg/mL, even more preferably 1-10 mg/mL, even more preferably 2-7.5 mg/mL, most preferably about 5 mg/mL.

Alternatively, the antibody may be added to the conjugation reaction at a concertation ranging from 1-20 mg/ml, preferably from 2.5-20 mg/mL, more preferably from 5-20 mg/mL, most preferably from 5-17 mg/mL.

To obtain efficient conjugation, it is preferred that the linker is added to the antibody in molar excess. That is, in certain embodiments, the antibody is mixed with at least 2, 5, 10, 20, 30, 40, 50, 60, 70, 80, 90 or 100 molar equivalents of a linker.

That is, in a particular embodiment, the invention relates to the method according to the invention, wherein the antibody is contacted with 2-100 molar equivalents of linker, preferably 2-80 molar equivalents of linker, more preferably 2-70 molar equivalents of linker, even more preferably 2-60 molar equivalents of linker, even more preferably 2-50 molar equivalents of linker, even more preferably 2-40 molar equivalents of linker, even more preferably 2-30 molar equivalents of linker, even more preferably 2 to 25 molar equivalents of linker, even more preferably 2-20 molar equivalents of linker, even more preferably 2-15 molar equivalents of linker, most preferably 2-10 molar equivalents of linker.

Alternatively, the antibody may be contacted with 2.5-100 molar equivalents of linker, preferably 2.5-80 molar equivalents of linker, more preferably 2.5-70 molar equivalents of linker, even more preferably 2.5-60 molar equivalents of linker, even more preferably 2.5-50 molar equivalents of linker, even more preferably 2.5-40 molar equivalents of linker, even more preferably 2.5-30 molar equivalents of linker, even more preferably 2.5-20 molar equivalents of linker, even more preferably 2.5-15 molar equivalents of linker, even more preferably 2.5-10 molar equivalents of linker, most preferably 2.5-8 molar equivalents of linker.

Alternatively, the antibody may be contacted with 5-100 molar equivalents of linker, preferably 5-80 molar equivalents of linker, more preferably 5-70 molar equivalents of linker, even more preferably 5-60 molar equivalents of linker, even more preferably 5-50 molar equivalents of linker, even more preferably 5-40 molar equivalents of linker, even more preferably 5-30 molar equivalents of linker, even more preferably 5-20 molar equivalents of linker, even more preferably 5-15 molar equivalents of linker, most preferably 5-10 molar equivalents of linker.

The method according to the invention is preferably carried out at a pH ranging from 6 to 9. Thus, in a preferred embodiment, the invention relates to a method according to the invention, wherein the conjugation of the linker to the antibody is achieved at a pH ranging from 6 to 8.5, more preferably at a pH ranging from 6.5 to 8, even more preferably at a pH ranging from 7 to 8. In a most preferred embodiment, the invention relates to a method according to the invention, wherein the conjugation of the linker to the antibody is achieved at pH 7.6.

The method of the invention may be carried out in any buffer that is suitable for the conjugation of the payload to the linker. Buffers that are suitable for the method of the invention include, without limitation, Tris, MOPS, HEPES, PBS or BisTris buffer. The concentration of the buffer depends, amongst others, on the concentration of the antibody and/or the linker and may range from 10-1000 mM, 10-500 mM, 10-400 mM, 10 to 250 mM, 10 to 150 mM or 10 to 100 mM. Further, the buffer may comprise any salt concentration that is suitable for carrying out the method of the invention. For example, the buffer used in the method of the invention may have a salt concentration ≤150 mM, ≤140 mM, ≤130 mM, ≤120 mM, ≤110 mM, ≤100 mM, ≤90 mM, ≤80 mM, ≤70 mM, ≤60 mM, ≤50 mM, ≤40 mM, ≤30 mM, ≤20 mM or ≤10 mM or no salts. In a particular embodiment, the method of the invention is carried out in 50 mM Tris (pH 7.6), preferably without salts.

It has to be noted that the optimal reaction conditions (e.g. pH, buffer, salt concentration) may vary between payloads and to some degree depend on the physicochemical properties of the linkers and/or payloads. However, no undue experimentation is required by the skilled person to identify reaction conditions that are suitable for carrying out the method of the invention.

It is to be understood that the application encompasses any combination of the above-disclosed linker, antibody MTG and/or buffer concentrations.

In a preferred embodiment, the invention relates to a method for producing an antibody-linker conjugate by means of a microbial transglutaminase (MTG), the method comprising a step of conjugating a linker comprising the structure (shown in N→C direction)

$$(Sp_1)\text{-RK-}(Sp_2)\text{-B-}(Sp_3) \text{ or } (Sp_1)\text{-B-}(Sp_2)\text{-RK-}(Sp_3)$$

to a Gln residue comprised in an antibody, wherein
- ($Sp_1$) is a chemical spacer or is absent;
- ($Sp_2$) is a chemical spacer or is absent;
- ($Sp_3$) is a chemical spacer or is absent;
- R is arginine or an arginine derivative or an arginine mimetic;
- K is lysine or a lysine derivative or a lysine mimetic;
- B is a linking moiety or a payload;
- wherein the linker is conjugated to the Gln residue comprised in the antibody via a primary amine comprised in the side chain of the lysine residue, the lysine derivative or the lysine mimetic; and
- wherein the antibody is contacted with 2-80 molar equivalents of the linker; and/or wherein the microbial transglutaminase is added to the conjugation reaction at a concentration ranging from 1-20 U/mg antibody and, optionally, wherein the antibody is added to the conjugation reaction at a concentration ranging from 0.1-20 mg/mL.

In a more preferred embodiment, the invention relates to a method for producing an antibody-linker conjugate by means of a microbial transglutaminase (MTG), the method comprising a step of conjugating a linker comprising the structure (shown in N→C direction)

$$(Sp_1)\text{-RK-}(Sp_2)\text{-B-}(Sp_3) \text{ or } (Sp_1)\text{-B-}(Sp_2)\text{-RK-}(Sp_3)$$

to a Gln residue comprised in an antibody, wherein
- ($Sp_1$) is a chemical spacer or is absent;
- ($Sp_2$) is a chemical spacer or is absent;
- ($Sp_3$) is a chemical spacer or is absent;
- R is arginine or an arginine derivative or an arginine mimetic;
- K is lysine or a lysine derivative or a lysine mimetic;
- B is a linking moiety or a payload;
- wherein the linker is conjugated to the Gln residue comprised in the antibody via a primary amine comprised in the side chain of the lysine residue, the lysine derivative or the lysine mimetic; and
- wherein the antibody is contacted with 2-50 molar equivalents of the linker; and/or wherein the microbial transglutaminase is added to the conjugation reaction at a concentration ranging from 1-10 U/mg antibody and, optionally, wherein the antibody is added to the conjugation reaction at a concentration ranging from 1-20 mg/mL.

In an even more preferred embodiment, the invention relates to a method for producing an antibody-linker conjugate by means of a microbial transglutaminase (MTG), the method comprising a step of conjugating a linker comprising the structure (shown in N→C direction)

$$(Sp_1)\text{-RK-}(Sp_2)\text{-B-}(Sp_3) \text{ or } (Sp_1)\text{-B-}(Sp_2)\text{-RK-}(Sp_3)$$

to a Gln residue comprised in an antibody, wherein
- ($Sp_1$) is a chemical spacer or is absent;
- ($Sp_2$) is a chemical spacer or is absent;
- ($Sp_3$) is a chemical spacer or is absent;
- R is arginine or an arginine derivative or an arginine mimetic;
- K is lysine or a lysine derivative or a lysine mimetic;
- B is a linking moiety or a payload;
- wherein the linker is conjugated to the Gln residue comprised in the antibody via a primary amine comprised in the side chain of the lysine residue, the lysine derivative or the lysine mimetic; and
- wherein the antibody is contacted with 2-30 molar equivalents of the linker; and/or wherein the microbial transglutaminase is added to the conjugation reaction at a concentration ranging from 2-10 U/mg antibody and, optionally, wherein the antibody is added to the conjugation reaction at a concentration ranging from 5-20 mg/mL.

In an even more preferred embodiment, the invention relates to a method for producing an antibody-linker conjugate by means of a microbial transglutaminase (MTG), the method comprising a step of conjugating a linker comprising the structure (shown in N→C direction)

$$(Sp_1)\text{-RK-}(Sp_2)\text{-B-}(Sp_3) \text{ or } (Sp_1)\text{-B-}(Sp_2)\text{-RK-}(Sp_3)$$

to a Gln residue comprised in an antibody, wherein
- ($Sp_1$) is a chemical spacer or is absent;
- ($Sp_2$) is a chemical spacer or is absent;
- ($Sp_3$) is a chemical spacer or is absent;
- R is arginine or an arginine derivative or an arginine mimetic;
- K is lysine or a lysine derivative or a lysine mimetic;
- B is a linking moiety or a payload;
- wherein the linker is conjugated to the Gln residue comprised in the antibody via a primary amine comprised in the side chain of the lysine residue, the lysine derivative or the lysine mimetic; and
- wherein the antibody is contacted with about 2-20 molar equivalents of the linker; and/or wherein the microbial transglutaminase is added to the conjugation reaction at a concentration ranging from 2-10 U/mg antibody and, optionally, wherein the antibody is added to the conjugation reaction at a concentration ranging from 5-20 mg/mL.

In an even more preferred embodiment, the invention relates to a method for producing an antibody-linker conjugate by means of a microbial transglutaminase (MTG), the method comprising a step of conjugating a linker comprising the structure (shown in N→C direction)

$$(Sp_1)\text{-RK-}(Sp_2)\text{-B-}(Sp_3) \text{ or } (Sp_1)\text{-B-}(Sp_2)\text{-RK-}(Sp_3)$$

to a Gln residue comprised in an antibody, wherein
- ($Sp_1$) is a chemical spacer or is absent;
- ($Sp_2$) is a chemical spacer or is absent;
- ($Sp_3$) is a chemical spacer or is absent;

R is arginine or an arginine derivative or an arginine mimetic;
K is lysine or a lysine derivative or a lysine mimetic;
B is a linking moiety or a payload;
wherein the linker is conjugated to the Gln residue comprised in the antibody via a primary amine comprised in the side chain of the lysine residue, the lysine derivative or the lysine mimetic; and
wherein the antibody is contacted with about 2.5-15 molar equivalents of the linker; and/or wherein the microbial transglutaminase is added to the conjugation reaction at a concentration ranging from 2-10 U/mg antibody and, optionally, wherein the antibody is added to the conjugation reaction at a concentration ranging from 5-20 mg/mL.

In a most preferred embodiment, the invention relates to a method for producing an antibody-linker conjugate by means of a microbial transglutaminase (MTG), the method comprising a step of conjugating a linker comprising the structure (shown in N→C direction)

(Sp$_1$)-RK-(Sp$_2$)-B-(Sp$_3$) or (Sp$_1$)-B-(Sp$_2$)-RK-(Sp$_3$)

to a Gln residue comprised in an antibody, wherein
(Sp$_1$) is a chemical spacer or is absent;
(Sp$_2$) is a chemical spacer or is absent;
(Sp$_3$) is a chemical spacer or is absent;
R is arginine or an arginine derivative or an arginine mimetic;
K is lysine or a lysine derivative or a lysine mimetic;
B is a linking moiety or a payload;
wherein the linker is conjugated to the Gln residue comprised in the antibody via a primary amine comprised in the side chain of the lysine residue, the lysine derivative or the lysine mimetic; and
wherein the antibody is contacted with about 2.5-10 molar equivalents of the linker; and/or wherein the microbial transglutaminase is added to the conjugation reaction at a concentration ranging from 2-10 U/mg antibody and, optionally, wherein the antibody is added to the conjugation reaction at a concentration ranging from 5-20 mg/mL.

In a particular embodiment, the invention relates to an antibody-linker conjugate which has been produced with a method according to the invention.

That is, the invention relates to an antibody-linker conjugate which has been generated with any of the aforementioned steps.

In a particular embodiment, the invention relates to an antibody-linker conjugate comprising:
a) an antibody; and
b) a linker comprising the structure:

(Sp$_1$)-RK-(Sp$_2$)-B-(Sp$_3$) or (Sp$_1$)-B-(Sp$_2$)-RK-(Sp$_3$); wherein (Sp$_1$) is a chemical spacer or is absent;
(Sp$_2$) is a chemical spacer or is absent;
(Sp$_3$) is a chemical spacer or is absent;
R is arginine or an arginine derivative or an arginine mimetic;
K is lysine or a lysine derivative or a lysine mimetic;
B is a linking moiety or a payload;
wherein the linker is conjugated to the antibody via an isopeptide bond formed between a γ-carboxamide group of a glutamine residue comprised in the antibody and a primary amine comprised in the side chain of the lysine residue, the lysine derivative or the lysine mimetic comprised in the RK motif comprised in the linker.

That is, the invention further relates to antibody-linker conjugates that have been generated with the method of the invention. In particular, the invention refers to antibodies that have been conjugated at a glutamine residue comprised in the heavy or light chain of the antibody with any one of the linkers disclosed herein for the method of the invention. That is, all linkers that have been disclosed above for the method of the invention may be comprised in the antibody-linker construct of the invention. Preferably, the linker of the invention is conjugated to the glutamine residue in the antibody via an amide bond that is formed between the amide side chain of the glutamine residue comprised in the antibody and a primary amine comprised in the residue K comprised in the RK motif of the linker. In certain embodiments, the primary amine comprised in the residue K is the amine group comprised in the side chain of a lysine residue, a lysine mimetic or a lysine derivative, as disclosed herein. In certain embodiments, K is a lysine residue and the primary amine via which the linker is conjugated to the antibody is the ε

The chemical spacer comprised in the antibody-linker construct disclosed herein may be any one of the RK-comprising linkers disclosed herein. That is, the linker may be a linker comprising a single linking moiety or payload B or may be a linker comprising two or more linking moieties and/or payloads B$_1$, B$_2$ and so forth.

In a particular embodiment, the invention relates to the antibody-linker conjugate according to the invention, wherein the chemical spacers (Sp$_1$), (Sp$_2$) and (Sp$_3$) each independently comprise between 0 and 12 amino acid residues.

In a particular embodiment, the invention relates to the antibody-linker conjugate according to the invention, wherein the linker comprises not more than 25, 20, 15, 14, 13, 12, 11, 10, 9, 8, 7, 6, 5, 4 amino acid residues.

In a particular embodiment, the invention relates to the antibody-linker conjugate according to the invention, wherein the net charge of the linker is neutral or positive.

In a particular embodiment, the invention relates to the antibody-linker conjugate according to the invention, wherein the linker comprises no negatively-charged amino acid residues.

In a particular embodiment, the invention relates to the antibody-linker conjugate according to the invention, wherein the linker comprises an amino acid sequence selected from the group consisting of: RKAA (SEQ ID NO:1), RKA (SEQ ID NO:2), ARK (SEQ ID NO:3) and RKR (SEQ ID NO:4).

In a particular embodiment, the invention relates to the antibody-linker conjugate according to the invention, wherein the linker comprises an amino acid sequence selected from the group consisting of: RKAA (SEQ ID NO:1), RKA (SEQ ID NO:2) and ARK (SEQ ID NO:3).

In a particular embodiment, the invention relates to the antibody-linker conjugate according to the invention, wherein the linker comprises the amino acid sequence RKAA (SEQ ID NO:1).

In a particular embodiment, the invention relates to the antibody-linker conjugate according to the invention, wherein the linker comprises the amino acid sequence RK-Val-Cit (SEQ ID NO:54).

In a particular embodiment, the invention relates to the antibody-linker conjugate according to the invention, wherein B is a linking moiety.

In a particular embodiment, the invention relates to the antibody-linker conjugate according to the invention, wherein the linking moiety B comprises
a bioorthogonal marker group, or
a non-bio-orthogonal entity for crosslinking.

In a particular embodiment, the invention relates to the antibody-linker conjugate according to the invention, wherein the bioorthogonal marker group or the non-bio-orthogonal entity for crosslinking consists of or comprises at least one molecule or moiety selected from the group consisting of:
—N—N≡N, or —$N_3$;
Lys($N_3$);
a tetrazine;
an alkyne;
a strained cyclooctyne;
BCN;
a strained alkene;
a photoreactive group;
an aldehyde;
an acyltrifluoroborate;
a protein degradation agent ('PROTAC');
a cyclopentadiene/spirolocyclopentadiene;
a thio-selective electrophile;
—SH; and
cysteine.

That is, the antibody-linker conjugate according to the invention may be an antibody that is conjugated to a linker comprising one or more linking moieties. Such antibody-linker conjugates may be later on customized with one or more payloads, in particular with payloads that can are suitable for coupling to the one or more linking moieties.

In a particular embodiment, the invention relates to the antibody-linker conjugate according to the invention, wherein one or more payloads have been conjugated to the linking moiety B.

In a particular embodiment, the invention relates to the antibody-linker conjugate according to the invention, wherein the one or more payloads have been conjugated to the linking moiety B via a click-reaction.

That is, the antibody-linker conjugates according to the invention may be antibody-payload conjugates that have been produced in a two-step process as disclosed herein.

In a particular embodiment, the invention relates to the antibody-linker conjugate according to the invention, wherein B is a payload.

In a particular embodiment, the invention relates to the antibody-linker conjugate according to the invention, wherein the payload comprises at least one of:
a toxin;
a cytokine;
a growth factor;
a radionuclide;
a hormone;
an anti-viral agent;
an anti-bacterial agent;
a fluorescent dye;
an immunoregulatory/immunostimulatory agent;
a half-life increasing moiety;
a solubility increasing moiety;
a polymer-toxin conjugate;
a nucleic acid;
a biotin or streptavidin moiety;
a vitamin;
a protein degradation agent ('PROTAC');
a target binding moiety; and/or
an anti-inflammatory agent.

In a particular embodiment, the invention relates to the antibody-linker conjugate according to the invention, wherein the toxin is at least one selected from the group consisting of
a pyrrolobenzodiazepine (e.g., PBD);
an auristatin (e.g., MMAE, MMAF);
a maytansinoid (e.g., maytansine, DM1, DM4, DM21);
a duocarmycin;
a nicotinamide phosphoribosyltransferase (NAMPT) inhibitor;
a tubulysin;
an enediyne (e.g., calicheamicin);
an anthracycline derivative (PNU) (e.g., doxorubicin);
a pyrrole-based kinesin spindle protein (KSP) inhibitor;
a cryptophycin;
a drug efflux pump inhibitor;
a sandramycin;
an amanitin (e.g., α-amanitin); and
a camptothecin (e.g., exatecans, deruxtecans).

In a particular embodiment, the invention relates to the antibody-linker conjugate according to the invention, wherein the chemical spacer ($Sp_2$) comprises a self-immolative moiety.

In a particular embodiment, the invention relates to the antibody-linker conjugate according to the invention, wherein the self-immolative moiety is directly attached to the payload B.

In a particular embodiment, the invention relates to the antibody-linker conjugate according to the invention, wherein the self-immolative moiety comprises a p-aminobenzyl carbamoyl (PABC) moiety.

That is, the antibody-linker conjugates according to the invention may be antibody-payload conjugates that have been produced in a one-step process as disclosed herein.

The antibody comprised in the antibody-linker conjugate according to the invention may be any one of the antibodies, in particular any one of the IgG type antibodies, disclosed herein for the method according to the invention. That is, the antibody comprised in the antibody-linker conjugate according to the invention may comprise the same glycosylation pattern, mutations and/or modifications as the antibodies disclosed herein for the method according to the invention.

In a particular embodiment, the invention relates to the antibody-payload conjugate according to the invention, wherein the linker is any one of the linkers shown in FIG. 1, FIG. 2, FIG. 3, FIG. 8, FIG. 9, FIG. 14, FIG. 15, FIG. 17, FIG. 18, FIG. 19, FIG. 20, FIG. 21, FIG. 22, FIG. 23, FIG. 24, FIG. 25, FIG. 26, FIG. 27, FIG. 28, FIG. 29, FIG. 30, FIG. 31, FIG. 32, FIG. 33 or FIG. 34.

In a particular embodiment, the invention relates to the antibody-linker conjugate according to the invention, wherein the antibody is an IgG antibody, in particular an IgG1 antibody.

In a particular embodiment, the invention relates to the antibody-linker conjugate according to the invention, wherein the Gln residue to which the linker is conjugated is comprised in an Fc domain of the antibody, in particular wherein the Gln residue to which the linker is conjugated is Gln residue Q295 (EU numbering) of the $C_H2$ domain of an IgG antibody.

In a particular embodiment, the invention relates to the antibody-linker conjugate according to the invention, wherein the Gln residue to which the linker is conjugated has been introduced into the heavy or light chain of the antibody by molecular engineering.

In a particular embodiment, the invention relates to the antibody-linker conjugate according to the invention, wherein the Gln residue that has been introduced into the heavy or light chain of the antibody by molecular engineering is N297Q (EU numbering) of the $C_H2$ domain of an aglycosylated IgG antibody.

In a particular embodiment, the invention relates to the antibody-linker conjugate according to the invention, wherein the Gln residue that has been introduced into the heavy or light chain of the antibody by molecular engineering is comprised in a peptide that has been (a) integrated into the heavy or light chain of the antibody or (b) fused to the N- or C-terminal end of the heavy or light chain of the antibody.

In a particular embodiment, the invention relates to the antibody-linker conjugate according to the invention, wherein the peptide comprising the Gln residue has been fused to the C-terminal end of the heavy chain of the antibody.

In a particular embodiment, the invention relates to the antibody-linker conjugate according to the invention, wherein the IgG antibody is a glycosylated IgG antibody, in particular wherein the IgG antibody is glycosylated at residue N297 (EU numbering) of the $C_H2$ domain.

In a particular embodiment, the invention relates to the antibody-linker conjugate according to the invention, wherein the antibody is selected from the group consisting of: Brentuximab, Trastuzumab, Gemtuzumab, Inotuzumab, Avelumab, Cetuximab, Rituximab, Daratumumab, Pertuzumab, Vedolizumab, Ocrelizumab, Tocilizumab, Ustekinumab, Golimumab, Obinutuzumab, Sacituzumab, Belantamab, Polatuzumab and Enfortumab.

In a particular embodiment, the invention relates to the antibody-linker conjugate according to the invention, wherein the antibody is selected from the group consisting of: Brentuximab, Gemtuzumab, Trastuzumab, Inotuzumab, Polatuzumab, Enfortumab, Sacituzumab and Belantamab.

In a particular embodiment, the invention relates to the antibody-linker conjugate according to the invention, wherein the antibody is Polatuzumab or Trastuzumab or Enfortumab.

In certain embodiments, the invention relates to an antibody-drug conjugate. That is, the antibody may be conjugated to a linker according to the invention, wherein the linker comprises one or more toxins.

Thus, in a particular embodiment, the invention relates to an antibody-drug conjugate comprising:
a) an IgG antibody; and
b) a linker comprising a drug moiety B, wherein the drug moiety B is covalently linked to an amino acid sequence selected from the group consisting of: RKAA (SEQ ID NO:1), RKA (SEQ ID NO:2), ARK (SEQ ID NO:3) or RKR (SEQ ID NO:4);
   wherein the linker is conjugated to the IgG antibody via an isopeptide bond formed between the γ-carboxamide group of glutamine residue Q295 (EU numbering) of the $C_H2$ domain of the antibody and the primary amine comprised in the side chain of the lysine residue comprised in the linker.

In certain embodiments, the invention relates to an antibody-drug conjugate comprising:
a) an IgG antibody; and
b) a linker comprising a drug moiety B, wherein the drug moiety B is covalently linked to an amino acid sequence comprising or consisting of the sequence RK-Val-Cit (SEQ ID NO:54);
   wherein the linker is conjugated to the IgG antibody via an isopeptide bond formed between the γ-carboxamide group of glutamine residue Q295 (EU numbering) of the $C_H2$ domain of the antibody and the primary amine comprised in the side chain of the lysine residue comprised in the linker.

That is, in certain embodiments, the linker may comprise any one of the sequences RKAA (SEQ ID NO:1), RKA (SEQ ID NO:2), ARK (SEQ ID NO:3), RKR (SEQ ID NO:4) or RK-Val-Cit (SEQ ID NO:54), wherein the linker is conjugated to a glutamine residue in the antibody via a primary amine comprised in the residue K. It is to be understood that the drug moiety B does not have to be directly linked to the structure RKAA (SEQ ID NO:1), RKA (SEQ ID NO:2), ARK (SEQ ID NO:3), RKR (SEQ ID NO:4) or RK-Val-Cit (SEQ ID NO:54). Instead the drug moiety B may be indirectly linked to the structure RKAA (SEQ ID NO:1), RKA (SEQ ID NO:2), ARK (SEQ ID NO:3), RKR (SEQ ID NO:4) or RK-Val-Cit (SEQ ID NO:54). For example, the linker may comprise further chemical structures located between the drug moiety B and the structure RKAA (SEQ ID NO:1), RKA (SEQ ID NO:2), ARK (SEQ ID NO:3), RKR (SEQ ID NO:4) or RK-Val-Cit (SEQ ID NO:54). Such chemical structures may be any of the structures that have been disclosed herein for the chemical spacers ($Sp_1$), ($Sp_2$) or ($Sp_3$). In certain embodiments, the linker may comprise one or more amino acid residues located between the drug moiety B and the structure RKAA (SEQ ID NO:1), RKA (SEQ ID NO:2), ARK (SEQ ID NO:3), RKR (SEQ ID NO:4) or RK-Val-Cit (SEQ ID NO:54). In certain embodiments, the linker may comprise one or more PEG moieties located between the drug moiety B and the structure RKAA (SEQ ID NO:1), RKA (SEQ ID NO:2), ARK (SEQ ID NO:3), RKR (SEQ ID NO:4) or RK-Val-Cit (SEQ ID NO:54). In certain embodiments, the linker may comprise a cleavable and/or self-immolative moiety located between the drug moiety B and the structure RKAA (SEQ ID NO:1), RKA (SEQ ID NO:2), ARK (SEQ ID NO:3), RKR (SEQ ID NO:4) or RK-Val-Cit (SEQ ID NO:54).

That is, in a particular embodiment, the invention relates to the antibody-drug conjugate according to the invention, wherein the drug moiety B is linked to the N- or C-terminus of the amino acid sequence comprised in the linker via a self-immolative moiety.

In a particular embodiment, the invention relates to the antibody-drug conjugate according to the invention, wherein the self-immolative moiety comprises a p-aminobenzyl carbamoyl (PABC) moiety.

That is, the self-immolative moiety comprised in the linker according to the invention may be any one of the self-immolative moieties that have been disclosed herein. In certain embodiments, the self-immolative moiety may be PABC or a methyl amine group as disclosed herein.

In a particular embodiment, the invention relates to the antibody-drug conjugate according to the invention, wherein the IgG antibody is a glycosylated IgG antibody, in particular wherein the IgG antibody is glycosylated at residue N297 (EU numbering) of the $C_H2$ domain.

In a particular embodiment, the invention relates to the antibody-drug conjugate according to the invention, wherein the IgG antibody is an IgG1 antibody.

That is, the antibody is preferably an IgG antibody, in particular an IgG1 antibody, in particular wherein the IgG or IgG1 antibody is glycosylated at residue N297 (EU numbering).

The antibody-drug conjugate may comprise one or more of the toxins disclosed herein. Thus, in a particular embodiment, the invention relates to the antibody-drug conjugate according to the invention, wherein the drug is a toxin selected from the group consisting of:
- a pyrrolobenzodiazepine (e.g., PBD);
- an auristatin (e.g., MMAE, MMAF);
- a maytansinoid (e.g., maytansine, DM1, DM4, DM21);
- a duocarmycin;
- a nicotinamide phosphoribosyltransferase (NAMPT) inhibitor;
- a tubulysin;
- an enediyne (e.g. calicheamicin);
- an anthracycline derivative (PNU) (e.g., doxorubicin);
- a pyrrole-based kinesin spindle protein (KSP) inhibitor;
- a cryptophycin;
- a drug efflux pump inhibitor;
- a sandramycin;
- an amanitin (e.g., α-amanitin); and
- a camptothecin (e.g., exatecans, deruxtecans).

It is to be understood that the toxin may be directly coupled to the linker by chemical synthesis. However, in other embodiments, a toxin may also be linked to a linking moiety comprised in a linker in a two-step process.

In a particular embodiment, the invention relates to the antibody-drug conjugate according to the invention, wherein the linker comprises or consists of the structure RKAA-B or RKAA-(linker molecule)-B.

That is, the payload B may be coupled directly to the C-terminus of the alanine residue or may be coupled to the C-terminus of the alanine residue via a linker molecule. It is to be understood that the choice of the linker molecule depends to a large extent on the functional groups that are available in the payload B. Linker molecules that are suitable for coupling payloads with different functional groups to a peptide have been disclosed herein. The linker molecule may be a cleavable or non-cleavable linker molecule. In particular, the linker molecule may comprise a self-immolative moiety, in particular any one of the self-immolative moieties disclosed herein. Thus, in a particular embodiment, the invention relates to the antibody-drug conjugate according to the invention, wherein the linker comprises or consists of the structure RKAA-(self-immolative moiety)-B.

Alternatively, the payload may be coupled to the N-terminus of the arginine residue either directly or via a linker molecule, for example via any one of the linker molecules disclosed herein. That is, in a particular embodiment, the invention relates to the antibody-drug conjugate according to the invention, wherein the linker comprises or consists of the structure B-RKAA or B-(linker molecule)-RKAA. In a particular embodiment, the invention relates to the antibody-drug conjugate according to the invention, wherein the linker comprises or consists of the structure B-(self-immolative moiety)-RKAA. In certain embodiments, the self-immolative moiety comprised in the structure B-(self-immolative moiety)-RKAA may be a self-immolative moiety comprising an ortho-hydroxy-protected aryl sulfate (OH-PAS) moiety as disclosed herein.

In a particular embodiment, the invention relates to the antibody-drug conjugate according to the invention, wherein the linker has the structure RKAA-PABC-B, in particular wherein B is an auristatin or a maytansinoid, in particular wherein the auristatin is MMAE and wherein the maytansinoid is DM1 or maytansine.

In certain embodiments the linker may have the structure RKAA-PABC-B. That is, the linker may comprise the linear peptide RKAA, wherein the carboxyl-group of the C-terminal alanine residue is coupled to the amino group comprised in PABC via an amide bond. The toxin B may be attached to PABC through the formation of a carbamate. It is to be understood that not all toxins comprise the functional groups to allow formation of a carbamate with PABC. Thus, a toxin may be connected to PABC via a linker.

In certain embodiments, the toxin may be a toxin comprising a primary or secondary amine. In certain embodiments, the toxin may be MMAE or maytansine.

In certain embodiments, the linker may have a protected N-terminal end. In certain embodiments, the N-terminal end may be acetylated. In certain embodiments, the linker is the linker shown in FIG. 1 or FIG. 8.

In certain embodiments, the linker may have the structure RKAA-PABC-MMAE. In certain embodiments, the linker may have the structure RKAA-(PEG)$_n$-PABC-MMAE, wherein n is an integer between 2 and 20. In certain embodiments, the linker may have the structure RKAA-(PEG)$_2$-PABC-MMAE. In certain embodiments, the linker may have the structure RKAA-MMAE. In certain embodiments, the linker may have the structure RKAA-Val-Cit-PABC-MMAE. In certain embodiments, the linker may comprise an additional linker between the PABC moiety and MMAE. In certain embodiments, the additional linker may be a p-nitrophenol (PNP) group.

It has to be noted that the linker may comprise other self-immolative moieties than PABC. That is, the linker may have the structure RKAA-(self-immolative moiety)-toxin. The skilled person is aware of other self-immolative moieties that may be used within the present invention. Further, the skilled person is aware of toxins that may be coupled to a self-immolative moiety, optionally via an additional linker.

In certain embodiments, the toxin may be a toxin comprising a hydroxyl group and the linker may comprise a self-immolative methyl amine group. That is, the linker may have the structure RKAA-(NH)—(CH$_3$)—O-toxin. In certain embodiments, the hydroxyl-comprising toxin may be a camptothecin, such as exatecan or an exatecan derivative, in particular the exatecan derivative Dxd, or an anthracycline, such as PNU-159682.

In certain embodiments, the toxin may be a toxin comprising a thiol group and the linker may comprise a self-immolative methyl amine group. That is, the linker may have the structure RKAA-(NH)—(CH$_3$)—S-toxin. In certain embodiments, the thiol-comprising toxin may be a maytansinoid, such as DM1 or a thiol-comprising derivative thereof.

In a particular embodiment, the invention relates to the antibody-drug conjugate according to the invention, wherein the linker comprises or consists of the structure RKA-B or RKA-(linker molecule)-B.

That is, the payload B may be coupled directly to the C-terminus of the alanine residue or may be coupled to the C-terminus of the alanine residue via a linker molecule. It is to be understood that the choice of the linker molecule depends to a large extent on the functional groups that are available in the payload B. Linker molecules that are suitable for coupling payloads with different functional groups to a peptide have been disclosed herein. The linker molecule may be a cleavable or non-cleavable linker molecule. In particular, the linker molecule may comprise a self-immolative moiety, in particular any one of the self-immolative moieties disclosed herein. Thus, in a particular embodiment, the invention relates to the antibody-drug conjugate according to the invention, wherein the linker comprises or consists of the structure RKA-(self-immolative moiety)-B.

Alternatively, the payload may be coupled to the N-terminus of the arginine residue either directly or via a linker molecule, for example via any one of the linker molecules disclosed herein. That is, in a particular embodiment, the invention relates to the antibody-drug conjugate according to the invention, wherein the linker comprises or consists of the structure B-RKA or B-(linker molecule)-RKA. In a particular embodiment, the invention relates to the antibody-drug conjugate according to the invention, wherein the linker comprises or consists of the structure B-(self-immolative moiety)-RKA. In certain embodiments, the self-immolative moiety comprised in the structure B-(self-immolative moiety)-RKA may be a self-immolative moiety comprising an ortho-hydroxy-protected aryl sulfate (OH-PAS) moiety as disclosed herein.

In a particular embodiment, the invention relates to the antibody-drug conjugate according to the invention, wherein the linker has the structure RKA-PABC-B, in particular wherein B is an auristatin or a maytansinoid, in particular wherein the auristatin is MMAE and wherein the maytansinoid is DM1 or maytansine.

In certain embodiments the linker may have the structure RKA-PABC-B. That is, the linker may comprise the linear peptide RKA, wherein the carboxyl-group of the C-terminal alanine residue is coupled to the amino group comprised in PABC via an amide bond. The toxin B may be attached to PABC through the formation of a carbamate. It is to be understood that not all toxins comprise the functional groups to allow formation of a carbamate with PABC. Thus, a toxin may be connected to PABC via a linker.

In certain embodiments, the toxin may be a toxin comprising a primary or secondary amine. In certain embodiments, the toxin may be MMAE or maytansine.

In certain embodiments, the linker may have a protected N-terminal end. In certain embodiments, the N-terminal end may be acetylated. In certain embodiments, the linker is the linker shown in FIG. 2.

In certain embodiments, the linker may have the structure RKA-PABC-MMAE. In certain embodiments, the linker may have the structure RKA-(PEG)$_n$-PABC-MMAE, wherein n is an integer between 2 and 20. In certain embodiments, the linker may have the structure RKA-(PEG)$_2$-PABC-MMAE. In certain embodiments, the linker may have the structure RKA-MMAE. In certain embodiments, the linker may have the structure RKA-Val-Cit-PABC-MMAE. In certain embodiments, the linker may comprise an additional linker between the PABC moiety and MMAE. In certain embodiments, the additional linker may be a p-nitrophenol (PNP) group.

It has to be noted that the linker may comprise other self-immolative moieties than PABC. That is, the linker may have the structure RKA-(self-immolative moiety)-toxin. The skilled person is aware of other self-immolative moieties that may be used within the present invention. Further, the skilled person is aware of toxins that may be coupled to a self-immolative moiety, optionally via an additional linker.

In certain embodiments, the toxin may be a toxin comprising a hydroxyl group and the linker may comprise a self-immolative methyl amine group. That is, the linker may have the structure RKA-(NH)—(CH$_3$)—O-toxin. In certain embodiments, the hydroxyl-comprising toxin may be a camptothecin, such as exatecan or an exatecan derivative, in particular the exatecan derivative Dxd, or an anthracycline, such as PNU-159682.

In certain embodiments, the toxin may be a toxin comprising a thiol group and the linker may comprise a self-immolative methyl amine group. That is, the linker may have the structure RKA-(NH)—(CH$_3$)—S-toxin. In certain embodiments, the thiol-comprising toxin may be a maytansinoid, such as DM1 or a thiol-comprising derivative thereof.

In a particular embodiment, the invention relates to the antibody-drug conjugate according to the invention, wherein the linker comprises or consists of the structure ARK-B or ARK-(linker molecule)-B.

That is, the payload B may be coupled directly to the C-terminus of the lysine residue or may be coupled to the C-terminus of the lysine residue via a linker molecule. It is to be understood that the choice of the linker molecule depends to a large extent on the functional groups that are available in the payload B. Linker molecules that are suitable for coupling payloads with different functional groups to a peptide have been disclosed herein. The linker molecule may be a cleavable or non-cleavable linker molecule. In particular, the linker molecule may comprise a self-immolative moiety, in particular any one of the self-immolative moieties disclosed herein. Thus, in a particular embodiment, the invention relates to the antibody-drug conjugate according to the invention, wherein the linker comprises or consists of the structure ARK-(self-immolative moiety)-B.

Alternatively, the payload may be coupled to the N-terminus of the alanine residue either directly or via a linker molecule, for example via any one of the linker molecules disclosed herein. That is, in a particular embodiment, the invention relates to the antibody-drug conjugate according to the invention, wherein the linker comprises or consists of the structure B-ARK or B-(linker molecule)-ARK. In a particular embodiment, the invention relates to the antibody-drug conjugate according to the invention, wherein the linker comprises or consists of the structure B-(self-immolative moiety)-ARK. In certain embodiments, the self-immolative moiety comprised in the structure B-(self-immolative moiety)-ARK may be a self-immolative moiety comprising an ortho-hydroxy-protected aryl sulfate (OH-PAS) moiety as disclosed herein.

In a particular embodiment, the invention relates to the antibody-drug conjugate according to the invention, wherein the linker has the structure ARK-PABC-B, in particular wherein B is an auristatin or a maytansinoid, in particular wherein the auristatin is MMAE and wherein the maytansinoid is DM1 or maytansine.

In certain embodiments the linker may have the structure ARK-PABC-B. That is, the linker may comprise the linear peptide ARK, wherein the carboxyl-group of the C-terminal lysine residue is coupled to the amino group comprised in PABC via an amide bond. The toxin B may be attached to PABC through the formation of a carbamate. It is to be understood that not all toxins comprise the functional groups to allow formation of a carbamate with PABC. Thus, a toxin may be connected to PABC via a linker.

In certain embodiments, the toxin may be a toxin comprising a primary or secondary amine. In certain embodiments, the toxin may be MMAE or maytansine.

In certain embodiments, the linker may have a protected N-terminal end. In certain embodiments, the N-terminal end may be acetylated. In certain embodiments, the linker is the linker shown in FIG. 3.

In certain embodiments, the linker may have the structure ARK-PABC-MMAE. In certain embodiments, the linker may have the structure ARK-(PEG)$_n$-PABC-MMAE, wherein n is an integer between 2 and 20. In certain embodiments, the linker may have the structure ARK-(PEG)$_2$-PABC-MMAE (see FIG. 14). In certain embodiments, the linker may have the structure ARK-MMAE. In certain embodiments, the linker may have the structure ARK-Val-Cit-PABC-MMAE. In certain embodiments, the linker may comprise an additional linker between the PABC moiety and MMAE. In certain embodiments, the additional linker may be a p-nitrophenol (PNP) group.

It has to be noted that the linker may comprise other self-immolative moieties than PABC. That is, the linker may have the structure ARK-(self-immolative moiety)-toxin. The skilled person is aware of other self-immolative moieties that may be used within the present invention. Further, the skilled person is aware of toxins that may be coupled to a self-immolative moiety, optionally via an additional linker.

In certain embodiments, the toxin may be a toxin comprising a hydroxyl group and the linker may comprise a self-immolative methyl amine group. That is, the linker may have the structure ARK-(NH)—(CH$_3$)—O-toxin. In certain embodiments, the hydroxyl-comprising toxin may be a camptothecin, such as exatecan or an exatecan derivative, in particular the exatecan derivative Dxd, or an anthracycline, such as PNU-159682.

In certain embodiments, the toxin may be a toxin comprising a thiol group and the linker may comprise a self-immolative methyl amine group. That is, the linker may have the structure ARK-(NH)—(CH$_3$)—S-toxin (analogous to FIG. 15). In certain embodiments, the thiol-comprising toxin may be a maytansinoid, such as DM1 or a thiol-comprising derivative thereof.

In certain embodiments, the linker is the linker shown in FIG. 14 or FIG. 15

In a particular embodiment, the invention relates to the antibody-drug conjugate according to the invention, wherein the linker comprises or consists of the structure RKR—B or RKR-(linker molecule)-B.

That is, the payload B may be coupled directly to the C-terminus of the arginine residue or may be coupled to the C-terminus of the arginine residue via a linker molecule. It is to be understood that the choice of the linker molecule depends to a large extent on the functional groups that are available in the payload B. Linker molecules that are suitable for coupling payloads with different functional groups to a peptide have been disclosed herein. The linker molecule may be a cleavable or non-cleavable linker molecule. In particular, the linker molecule may comprise a self-immolative moiety, in particular any one of the self-immolative moieties disclosed herein. Thus, in a particular embodiment, the invention relates to the antibody-drug conjugate according to the invention, wherein the linker comprises or consists of the structure RKR-(self-immolative moiety)-B.

Alternatively, the payload may be coupled to the N-terminus of the arginine residue either directly or via a linker molecule, for example via any one of the linker molecules disclosed herein. That is, in a particular embodiment, the invention relates to the antibody-drug conjugate according to the invention, wherein the linker comprises or consists of the structure B—RKR or B-(linker molecule)-RKR. In certain embodiments, the linker may be a dicarboxylic acid linker (see FIG. 9). In a particular embodiment, the invention relates to the antibody-drug conjugate according to the invention, wherein the linker comprises or consists of the structure B-(self-immolative moiety)-RKR. In certain embodiments, the self-immolative moiety comprised in the structure B-(self-immolative moiety)-RKR may be a self-immolative moiety comprising an ortho-hydroxy-protected aryl sulfate (OHPAS) moiety as disclosed herein.

In a particular embodiment, the invention relates to the antibody-drug conjugate according to the invention, wherein the linker has the structure RKR-PABC-B, in particular wherein B is an auristatin or a maytansinoid, in particular wherein the auristatin is MMAE and wherein the maytansinoid is DM1 or maytansine.

In certain embodiments the linker may have the structure RKR-PABC-B. That is, the linker may comprise the linear peptide RKR, wherein the carboxyl-group of the C-terminal arginine residue is coupled to the amino group comprised in PABC via an amide bond. The toxin B may be attached to PABC through the formation of a carbamate. It is to be understood that not all toxins comprise the functional groups to allow formation of a carbamate with PABC. Thus, a toxin may be connected to PABC via a linker.

In certain embodiments, the toxin may be a toxin comprising a primary or secondary amine. In certain embodiments, the toxin may be MMAE or maytansine.

In certain embodiments, the linker may have a protected N-terminal end. In certain embodiments, the N-terminal end may be acetylated.

In certain embodiments, the linker may have the structure RKR-PABC-MMAE. In certain embodiments, the linker may have the structure RKR-(PEG)$_n$-PABC-MMAE, wherein n is an integer between 2 and 20. In certain embodiments, the linker may have the structure RKR-(PEG)$_2$-PABC-MMAE. In certain embodiments, the linker may have the structure RKR-MMAE. In certain embodiments, the linker may have the structure RKR-Val-Cit-PABC-MMAE. In certain embodiments, the linker may comprise an additional linker between the PABC moiety and MMAE. In certain embodiments, the additional linker may be a p-nitrophenol (PNP) group.

It has to be noted that the linker may comprise other self-immolative moieties than PABC. That is, the linker may have the structure RKR-(self-immolative moiety)-toxin. The skilled person is aware of other self-immolative moieties that may be used within the present invention. Further, the skilled person is aware of toxins that may be coupled to a self-immolative moiety, optionally via an additional linker.

In certain embodiments, the toxin may be a toxin comprising a hydroxyl group and the linker may comprise a self-immolative methyl amine group. That is, the linker may have the structure RKR-(NH)—(CH$_3$)—O-toxin. In certain embodiments, the hydroxyl-comprising toxin may be a camptothecin, such as exatecan or an exatecan derivative, in particular the exatecan derivative Dxd, or an anthracycline, such as PNU-159682.

In certain embodiments, the toxin may be a toxin comprising a thiol group and the linker may comprise a self-immolative methyl amine group. That is, the linker may have the structure RKR-(NH)—(CH$_3$)—S-toxin (analogous to FIG. 15). In certain embodiments, the thiol-comprising toxin may be a maytansinoid, such as DM1 or a thiol-comprising derivative thereof.

In a particular embodiment, the invention relates to the antibody-drug conjugate according to the invention, wherein the linker comprises or consists of the structure RK-Val-Cit-B or RK-Val-Cit-(linker molecule)-B.

That is, the payload B may be coupled directly to the C-terminus of the citrulline residue or may be coupled to the C-terminus of the citrulline residue via a linker molecule. It is to be understood that the choice of the linker molecule depends to a large extent on the functional groups that are available in the payload B. Linker molecules that are suitable for coupling payloads with different functional groups to a peptide have been disclosed herein. The linker molecule may be a cleavable or non-cleavable linker molecule. In particular, the linker molecule may comprise a self-immolative moiety, in particular any one of the self-immolative moieties disclosed herein. Thus, in a particular embodiment, the invention relates to the antibody-drug conjugate according to the invention, wherein the linker comprises or consists of the structure RK-Val-Cit-(self-immolative moiety)-B.

In a particular embodiment, the invention relates to the antibody-drug conjugate according to the invention, wherein the linker has the structure RK-Val-Cit-PABC-B, in particular wherein B is an auristatin or a maytansinoid, in particular wherein the auristatin is MMAE and wherein the maytansinoid is DM1 or maytansine.

In certain embodiments the linker may have the structure RK-Val-Cit-PABC-B. That is, the linker may comprise the linear peptide RK-Val-Cit, wherein the carboxyl-group of the C-terminal citrulline residue is coupled to the amino group comprised in PABC via an amide bond. The toxin B may be attached to PABC through the formation of a carbamate. It is to be understood that not all toxins comprise the functional groups to allow formation of a carbamate with PABC. Thus, a toxin may be connected to PABC via a linker.

In certain embodiments, the toxin may be a toxin comprising a primary or secondary amine. In certain embodiments, the toxin may be MMAE or maytansine.

In certain embodiments, the linker may have a protected N-terminal end. In certain embodiments, the N-terminal end may be acetylated.

In certain embodiments, the linker may have the structure RK-Val-Cit-PABC-MMAE. In certain embodiments, the linker may have the structure RK-(PEG)$_n$-Val-Cit-PABC-MMAE, wherein n is an integer between 2 and 20. In certain embodiments, the linker may have the structure RK-(PEG)$_2$-Val-Cit-PABC-MMAE. In certain embodiments, the linker may have the structure RK-Val-Cit-MMAE. In certain embodiments, the linker may comprise an additional linker between the PABC moiety and MMAE. In certain embodiments, the additional linker may be a p-nitrophenol (PNP) group.

It has to be noted that the linker may comprise other self-immolative moieties than PABC. That is, the linker may have the structure RK-Val-Cit-(self-immolative moiety)-toxin. The skilled person is aware of other self-immolative moieties that may be used within the present invention. Further, the skilled person is aware of toxins that may be coupled to a self-immolative moiety, optionally via an additional linker.

In certain embodiments, the toxin may be a toxin comprising a hydroxyl group and the linker may comprise a self-immolative methyl amine group. That is, the linker may have the structure RK-Val-Cit-(NH)—(CH$_3$)—O-toxin. In certain embodiments, the hydroxyl-comprising toxin may be a camptothecin, such as exatecan or an exatecan derivative, in particular the exatecan derivative Dxd, or an anthracycline, such as PNU-159682.

In certain embodiments, the toxin may be a toxin comprising a thiol group and the linker may comprise a self-immolative methyl amine group. That is, the linker may have the structure RK-Val-Cit-(NH)—(CH$_3$)—S-toxin. In certain embodiments, the thiol-comprising toxin may be a maytansinoid, such as DM1 or a thiol-comprising derivative thereof.

In a particular embodiment, the invention relates to an antibody-linker conjugate or an antibody drug-conjugate comprising the antibody Polatuzumab or, alternatively, an anti-CD79b antibody.

That is, in a particular embodiment, the invention relates to an antibody-linker conjugate comprising:

a) Polatuzumab or an anti-CD79b antibody; and
b) a linker comprising the structure:

(Sp$_1$)-RK-(Sp$_2$)-B-(Sp$_3$) or (Sp$_1$)-B-(Sp$_2$)-RK-(Sp$_3$); wherein (Sp$_1$) is a chemical spacer or is absent;
(Sp$_2$) is a chemical spacer or is absent;
(Sp$_3$) is a chemical spacer or is absent;
R is arginine or an arginine derivative or an arginine mimetic;
K is lysine or a lysine derivative or a lysine mimetic;
B is a linking moiety or a payload;
wherein the linker is conjugated to Polatuzumab or the anti-CD79b antibody, via an isopeptide bond formed between a γ-carboxamide group of a glutamine residue comprised in Polatuzumab or the anti-CD79b antibody, and a primary amine comprised in the side chain of the lysine residue, the lysine derivative or the lysine mimetic comprised in the RK motif comprised in the linker.

In a particular embodiment, the invention relates to the antibody-payload conjugate comprising Polatuzumab or the anti-CD79b antibody, wherein the linker is any one of the linkers shown in FIG. 1, FIG. 2, FIG. 3, FIG. 8, FIG. 9, FIG. 14, FIG. 15, FIG. 17, FIG. 18, FIG. 19, FIG. 20, FIG. 21, FIG. 22, FIG. 23, FIG. 24, FIG. 25, FIG. 26, FIG. 27, FIG. 28, FIG. 29, FIG. 30, FIG. 31, FIG. 32, FIG. 33 or FIG. 34.

Polatuzumab is commercially available as the antibody-drug conjugate Polatuzumab vedotin and marketed under the name Polivy. Polatuzumab vedotin comprises the anti-CD79b antibody Polatuzumab and the linker maleimido-caproyl-L-valine-L-citrulline-PABC-MMAE (mc-vc-PABC-MMAE), which is commonly known as vedotin. The mc-vc-PABC-MMAE linker of Polatuzumab vedotin is conjugated to free cysteine residues comprised in the antibody. The antibody Polatuzumab has been disclosed in WO 2009/012268, which is incorporated herein by reference in its entirety. Further, cysteine-engineered variants of Polatuzumab have been disclosed in WO 2009/099728, which is also incorporated herein by reference in its entirety.

It has been shown by the inventors that a Polatuzumab conjugate comprising the linker according to the invention has a longer half life in plasma compared to the commercially available conjugate Polatuzumab vedotin. Thus, antibody-linker conjugates that have been conjugated to a linker according to the invention by means of a microbial transglutaminase are surprisingly more stable than antibodies that have been produced with other techniques, for example by conjugation of maleimide-comprising linkers to cysteine residues of the antibody. Thus, antibody-linker conjugates according to the invention are more likely to reach their target cell or tissue without prematurely losing their payload.

In certain embodiments, the antibody is Polatuzumab comprising a heavy chain as set forth in SEQ ID NO:5 and a light chain as set forth in SEQ ID NO:6. However, the invention also encompasses variants of Polatuzumab wherein the heavy and/or light chain comprise at least 80%, at least 85%, at least 90%, at least 95% sequence identity with SEQ ID NO:5 and/or SEQ ID NO:6, respectively. In particular, the antibody may comprise any of the sequence variations that have been disclosed in WO 2009/012268 or WO 2009/099728.

It is preferred herein that Polatuzumab, or an anti-CD79b antibody, is present in the antibody-linker conjugate in glycosylated form. That is, Polatuzumab, or the anti-CD79b antibody, is preferably glycosylated at residue N297 (EU numbering). However, Polatuzumab, or the anti-CD79b antibody, may also be de-glycosylated as described herein.

Polatuzumab, or an anti-CD79b antibody, may be conjugated to any one of the linkers that have been disclosed herein, in particular for the method according to the invention. Preferably, the linker is conjugated in an MTG-catalyzed manner to the glutamine residue Q295 (EU numbering) of the antibody. However, the linker may also be conjugated to an engineered glutamine residue, such as N297Q (EU numbering) and/or to any one of the glutamine-comprising tags that have been disclosed herein.

The linker that is conjugated to Polatuzumab, or to the anti-CD79b antibody, may comprise a single linking moiety or payload B or may comprise multiple linking moieties and/or payloads $B_1$, $B_2$ and so forth.

That is, in certain embodiments, the linker comprised in a Polatuzumab-linker conjugate may comprise one or more linking moieties B. Such Polatuzumab-linker conjugates may be subsequently functionalized with a suitable payload in a two-step process as disclosed herein.

In certain embodiments, the linker comprised in a Polatuzumab-payload conjugate may comprise one or more payloads B. Such Polatuzumab-payload conjugates may have been obtained in a two-step process, wherein a linker comprising a linking moiety has been conjugated to Polatuzumab in a first step and a payload has been linked to the linking moiety in a second step. Alternatively, Polatuzumab-payload conjugates may have been obtained in a one-step process, wherein a linker comprising a payload is directly conjugated to Polatuzumab.

In certain embodiments, the invention relates to an antibody-drug conjugate comprising Polatuzumab or an anti-CD79B antibody. That is, the linker comprised in the antibody-drug conjugate may comprise one or more toxins as described herein.

In certain embodiments, an antibody-drug conjugate comprising Polatuzumab, or an anti-CD79b antibody, may comprises a linker comprising the amino acid sequence RKAA (SEQ ID NO:1), RKA (SEQ ID NO:2), ARK (SEQ ID NO:3), RKR (SEQ ID NO:4) or RK-Val-Cit (SEQ ID NO:54).

That is, in a particular embodiment, the invention relates to an antibody-drug conjugate comprising:
a) Polatuzumab or an anti-CD79b antibody; and
b) a linker comprising a drug moiety B, wherein the drug moiety B is covalently linked to an amino acid sequence selected from the group consisting of: RKAA (SEQ ID NO:1), RKA (SEQ ID NO:2), ARK (SEQ ID NO:3), RKR (SEQ ID NO:4) or RK-Val-Cit (SEQ ID NO:54);
wherein the linker is conjugated to Polatuzumab or the anti-CD79b antibody via an isopeptide bond formed between the γ-carboxamide group of glutamine residue Q295 (EU numbering) of the $C_H2$ domain of the antibody and the primary amine comprised in the side chain of the lysine residue comprised in the linker.

Preferably, the antibody is Polatuzumab comprising a heavy chain as set forth in SEQ ID NO:5 and a light chain as set forth in SEQ ID NO:6. Thus, in a particular embodiment, the invention relates to the antibody-drug conjugate according to the invention, wherein the IgG antibody is Polatuzumab or an antibody comprising a heavy chain as set forth in SEQ ID NO:5 and a light chain as set forth in SEQ ID NO:6.

In certain embodiments, the linker that is conjugated to Polatuzumab, or to an anti-CD79b antibody, may comprise the structure RKAA (SEQ ID NO:1), RKA (SEQ ID NO:2), ARK (SEQ ID NO:3), RKR (SEQ ID NO:4) or RK-Val-Cit (SEQ ID NO:54). In certain embodiments, a linker comprising the structure RKAA (SEQ ID NO:1), RKA (SEQ ID NO:2), ARK (SEQ ID NO:3), RKR (SEQ ID NO:4) or RK-Val-Cit (SEQ ID NO:54) may be conjugated to residue Q295 of Polatuzumab, or of an anti-CD79b antibody, via a primary amine comprised in the residue K.

In certain embodiments, Polatuzumab, or the anti-CD79b antibody, may be conjugated to the linker RKAA-B as disclosed herein, wherein B is preferably a toxin. In certain embodiments, Polatuzumab, or the anti-CD79b antibody, may be conjugated to the linker RKAA-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Polatuzumab, or the anti-CD79b antibody, may be conjugated to the linker RKAA-PABC-B. In certain embodiments, Polatuzumab, or the anti-CD79b antibody, may be conjugated to the linker RKAA-PABC-MMAE (see FIG. 1). In certain embodiments, Polatuzumab, or the anti-CD79b antibody, may be conjugated to the linker RKAA-PABC-maytansine (see FIG. 8). In certain embodiments, Polatuzumab, or the anti-CD79b antibody, may be conjugated to the linker RKAA-MMAE. In certain embodiments, Polatuzumab, or the anti-CD79b antibody, may be conjugated to the linker RKAA-PABC-PNP-MMAE. In certain embodiments, Polatuzumab, or the anti-CD79b antibody, may be conjugated to the linker RKAA-(NH)—($CH_3$)—O—B, wherein O is the oxygen atom of an ether bond and B is a hydroxyl-comprising toxin. In certain embodiments, Polatuzumab, or the anti-CD79b antibody, may be conjugated to the linker RKAA-(NH)—($CH_3$)—O-camptothecin. In certain embodiments, Polatuzumab, or the anti-CD79b antibody, may be conjugated to the linker RKAA-(NH)—($CH_3$)—S—B, wherein S is the sulfur atom of an thioether bond and B is a thiol-comprising toxin. In certain embodiments, Polatuzumab, or the anti-CD79b antibody, may be conjugated to the linker RKAA-(NH)—($CH_3$)—S-DM1.

In certain embodiments, Polatuzumab, or the anti-CD79b antibody, may be conjugated to the linker B-RKAA as disclosed herein, wherein B is preferably a toxin. In certain embodiments, Polatuzumab, or the anti-CD79b antibody, may be conjugated to the linker B-(self-immolative moiety)-RKAA as disclosed herein, wherein B is preferably a toxin. The self-immolative moiety may be any self-immolative moiety known in the art and/or disclosed herein that is suitable for coupling a payload to the N-terminus of a peptide. In certain embodiments, the self immolative moiety may be a self-immolative moiety comprising an ortho-hydroxy-protected aryl sulfate (OHPAS) moiety. In certain embodiments, an amine comprising payload B may be coupled to the N-terminal arginine moiety via a dicarboxylic acid linker, analogous to FIG. 9.

In certain embodiments, Polatuzumab, or the anti-CD79b antibody, may be conjugated to the linker RKA-B as disclosed herein, wherein B is preferably a toxin. In certain embodiments, Polatuzumab, or the anti-CD79b antibody, may be conjugated to the linker RKA-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Polatuzumab, or the anti-CD79b antibody, may be conjugated to the linker RKA-PABC-B. In certain embodiments, Polatuzumab, or the anti-CD79b antibody, may be conjugated to the linker RKA-PABC-MMAE (see FIG. 2). In certain embodiments, Polatuzumab, or the anti-CD79b antibody, may be conjugated to the linker RKA-PABC-maytansine. In certain embodiments, Polatuzumab, or the anti-CD79b antibody, may be conjugated to the linker RKA-MMAE. In certain embodiments, Polatuzumab, or the anti-CD79b antibody, may be conjugated to the linker RKA-PABC-PNP-MMAE. In certain embodiments, Polatuzumab, or the anti-CD79b antibody, may be conjugated to the linker RKA-(NH)—(CH$_3$)—O—B, wherein O is the oxygen atom of an ether bond and B is a hydroxyl-comprising toxin. In certain embodiments, Polatuzumab, or the anti-CD79b antibody, may be conjugated to the linker RKA-(NH)—(CH$_3$)—O-camptothecin. In certain embodiments, Polatuzumab, or the anti-CD79b antibody, may be conjugated to the linker RKA-(NH)—(CH$_3$)—S—B, wherein S is the sulfur atom of an thioether bond and B is a thiol-comprising toxin. In certain embodiments, Polatuzumab, or the anti-CD79b antibody, may be conjugated to the linker RKA-(NH)—(CH$_3$)—S-DM1.

In certain embodiments, Polatuzumab, or the anti-CD79b antibody, may be conjugated to the linker B-RKA as disclosed herein, wherein B is preferably a toxin. In certain embodiments, Polatuzumab, or the anti-CD79b antibody, may be conjugated to the linker B-(self-immolative moiety)-RKA as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety. In certain embodiments, an amine comprising payload B may be coupled to the N-terminal arginine moiety via a dicarboxylic acid linker, analogous to FIG. 9.

In certain embodiments, Polatuzumab, or the anti-CD79b antibody, may be conjugated to the linker ARK-B as disclosed herein, wherein B is preferably a toxin. In certain embodiments, Polatuzumab, or the anti-CD79b antibody, may be conjugated to the linker ARK-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Polatuzumab, or the anti-CD79b antibody, may be conjugated to the linker ARK-PABC-B. In certain embodiments, Polatuzumab, or the anti-CD79b antibody, may be conjugated to the linker ARK-PABC-MMAE (see FIG. 3). In certain embodiments, Polatuzumab, or the anti-CD79b antibody, may be conjugated to the linker ARK-PABC-maytansine. In certain embodiments, Polatuzumab, or the anti-CD79b antibody, may be conjugated to the linker ARK-MMAE. In certain embodiments, Polatuzumab, or the anti-CD79b antibody, may be conjugated to the linker ARK-PABC-PNP-MMAE. In certain embodiments, Polatuzumab, or the anti-CD79b antibody, may be conjugated to the linker ARK-(NH)—(CH$_3$)—O—B, wherein O is the oxygen atom of an ether bond and B is a hydroxyl-comprising toxin. In certain embodiments, Polatuzumab, or the anti-CD79b antibody, may be conjugated to the linker ARK-(NH)—(CH$_3$)—O-camptothecin. In certain embodiments, Polatuzumab, or the anti-CD79b antibody, may be conjugated to the linker ARK-(NH)—(CH$_3$)—S—B, wherein S is the sulfur atom of an thioether bond and S is a thiol-comprising toxin. In certain embodiments, Polatuzumab, or the anti-CD79b antibody, may be conjugated to the linker ARK-(NH)—(CH$_3$)—S-DM1.

In certain embodiments, Polatuzumab, or the anti-CD79b antibody, may be conjugated to the linker B-ARK as disclosed herein, wherein B is preferably a toxin. In certain embodiments, Polatuzumab, or the anti-CD79b antibody, may be conjugated to the linker B-(self-immolative moiety)-ARK as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety.

In certain embodiments, Polatuzumab, or the anti-CD79b antibody, may be conjugated to the linker RKR-B as disclosed herein, wherein B is preferably a toxin. In certain embodiments, Polatuzumab, or the anti-CD79b antibody, may be conjugated to the linker RKR-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Polatuzumab, or the anti-CD79b antibody, may be conjugated to the linker RKR-PABC-B. In certain embodiments, Polatuzumab, or the anti-CD79b antibody, may be conjugated to the linker RKR-PABC-MMAE. In certain embodiments, Polatuzumab, or the anti-CD79b antibody, may be conjugated to the linker RKR-PABC-maytansine. In certain embodiments, Polatuzumab, or the anti-CD79b antibody, may be conjugated to the linker RKR-MMAE. In certain embodiments, Polatuzumab, or the anti-CD79b antibody, may be conjugated to the linker RKR-PABC-PNP-MMAE. In certain embodiments, Polatuzumab, or the anti-CD79b antibody, may be conjugated to the linker RKR-(NH)—(CH$_3$)—O—B, wherein O is the oxygen atom of an ether bond and B is a hydroxyl-comprising toxin. In certain embodiments, Polatuzumab, or the anti-CD79b antibody, may be conjugated to the linker RKR-(NH)—(CH$_3$)—O-camptothecin. In certain embodiments, Polatuzumab, or the anti-CD79b antibody, may be conjugated to the linker RKR-(NH)—(CH$_3$)—S—B, wherein S is the sulfur atom of an thioether bond and S is a thiol-comprising toxin. In certain embodiments, Polatuzumab, or the anti-CD79b antibody, may be conjugated to the linker RKR-(NH)—(CH$_3$)—S-DM1.

In certain embodiments, Polatuzumab, or the anti-CD79b antibody, may be conjugated to the linker B—RKR as disclosed herein, wherein B is preferably a toxin. In certain embodiments, Polatuzumab, or the anti-CD79b antibody, may be conjugated to the linker B-(self-immolative moiety)-RKR as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety. In certain embodiments, an amine comprising payload B may be coupled to the N-terminal arginine moiety via a dicarboxylic acid linker, as exemplified in FIG. 9.

In certain embodiments, Polatuzumab, or the anti-CD79b antibody, may be conjugated to the linker RK-Val-Cit-B as disclosed herein, wherein B is preferably a toxin. In certain embodiments, Polatuzumab, or the anti-CD79b antibody, may be conjugated to the linker RK-Val-Cit-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Polatuzumab, or the anti-CD79b antibody, may be conjugated to the linker RK-Val-Cit-PABC-B. In certain embodiments, Polatuzumab, or the anti-CD79b antibody, may be conjugated to the linker RK-Val-Cit-PABC-MMAE. In certain embodiments, Polatuzumab, or the anti-CD79b antibody, may be conjugated to the linker RK-Val-Cit-PABC-maytansine. In certain embodiments, Polatuzumab, or the anti-CD79b antibody, may be conjugated to the linker RK-Val-Cit-MMAE. In certain embodiments, Polatuzumab, or the anti-CD79b antibody, may be conjugated to the linker RK-Val-Cit-PABC-PNP-MMAE. In certain embodiments, Polatuzumab, or the anti-CD79b antibody, may be conjugated to the linker RK-Val-Cit-(NH)—(CH$_3$)—O—B, wherein O is the oxygen atom of an ether bond and B is a hydroxyl-comprising toxin. In certain embodiments, Polatuzumab, or the anti-CD79b antibody, may be conjugated to the linker RK-Val-Cit-(NH)—(CH$_3$)—O-camptothecin. In certain embodiments, Polatuzumab, or the anti-CD79b antibody, may be conjugated to the linker RK-Val-Cit-(NH)—(CH$_3$)—S—B, wherein S is the sulfur atom of an thioether bond and B is a thiol-comprising toxin. In certain embodiments, Polatuzumab, or the anti-CD79b antibody, may be conjugated to the linker RK-Val-Cit-(NH)—(CH$_3$)—S-DM1.

In a particular embodiment, the invention relates to an antibody-linker conjugate or an antibody drug-conjugate comprising the antibody Trastuzumab or, alternatively, an anti-HER2/neu antibody.

That is, in a particular embodiment, the invention relates to an antibody-linker conjugate comprising:
a) Trastuzumab or an anti-HER2/neu antibody; and
b) a linker comprising the structure:

(Sp$_1$)-RK-(Sp$_2$)-B-(Sp$_3$) or (Sp$_1$)-B-(Sp$_2$)-RK-(Sp$_3$); wherein (Sp$_1$) is a chemical spacer or is absent;
(Sp$_2$) is a chemical spacer or is absent;
(Sp$_3$) is a chemical spacer or is absent;
R is arginine or an arginine derivative or an arginine mimetic;
K is lysine or a lysine derivative or a lysine mimetic;
B is a linking moiety or a payload;
wherein the linker is conjugated to Trastuzumab, or the anti-HER2/neu antibody, via an isopeptide bond formed between a γ-carboxamide group of a glutamine residue comprised in Trastuzumab, or the anti-HER2/neu antibody, and a primary amine comprised in the side chain of the lysine residue, the lysine derivative or the lysine mimetic comprised in the RK motif comprised in the linker.

In a particular embodiment, the invention relates to the antibody-payload conjugate comprising Trastuzumab or the anti-HER2/neu antibody, wherein the linker is any one of the linkers shown in FIG. 1, FIG. 2, FIG. 3, FIG. 8, FIG. 9, FIG. 14, FIG. 15, FIG. 17, FIG. 18, FIG. 19, FIG. 20, FIG. 21, FIG. 22, FIG. 23, FIG. 24, FIG. 25, FIG. 26, FIG. 27, FIG. 28, FIG. 29, FIG. 30, FIG. 31, FIG. 32, FIG. 33 or FIG. 34.

Trastuzumab is commercially available as the antibody-drug conjugate Trastuzumab emtasine and marketed under the name Kadcyla. Trastuzumab emtasine comprises the anti-HER2/neu antibody Trastuzumab and the toxin DM1, which is coupled to Trastuzumab via an N-succinimidyl-4-(N-maleimidomethyl)-cyclohexane-1-carboxylate (SMCC) linker. The linker-DM1 construct can be conjugated to up to eight different lysine residues comprised in the antibody, resulting in antibodies with varying drug-to-antibody ratios. Preferably, Trastuzumab comprises a heavy chain as set forth in SEQ ID NO:7 and a light chain as set forth in SEQ ID NO8. However, the invention also encompasses variants of Trastuzumab wherein the heavy and/or light chain comprise at least 80%, at least 85%, at least 90%, at least 95% sequence identity with SEQ ID NO:7 and/or SEQ ID NO:8, respectively. In certain embodiments, the antibody may be an anti-HER2/neu antibody, for example as disclosed in, without limitation, WO 1998/006692, WO 1999/905536, WO 2003/087131, which are incorporated herein by reference in their entirety.

It is preferred herein that Trastuzumab, or an anti-HER2/neu antibody, is present in the antibody-linker conjugate in glycosylated form. That is, Trastuzumab, or the anti-HER2/neu antibody, is preferably glycosylated at residue N297 (EU numbering). However, Trastuzumab, or the anti-HER2/neu antibody, may also be de-glycosylated as described herein.

Trastuzumab, or an anti-HER2/neu antibody, may be conjugated to any one of the linkers that have been disclosed herein, in particular for the method according to the invention. Preferably, the linker is conjugated in an MTG-catalyzed manner to the glutamine residue Q295 (EU numbering) of the antibody. However, the linker may also be conjugated to an engineered glutamine residue, such as N297Q (EU numbering) and/or to any one of the glutamine-comprising tags that have been disclosed herein.

The linker that is conjugated to Trastuzumab, or to the anti-HER2/neu antibody, may comprise a single linking moiety or payload B or may comprise multiple linking moieties and/or payloads B$_1$, B$_2$ and so forth.

That is, in certain embodiments, the linker comprised in a Trastuzumab-linker conjugate may comprise one or more linking moieties B. Such Trastuzumab-linker conjugates may be subsequently functionalized with a suitable payload in a two-step process as disclosed herein.

In certain embodiments, the linker comprised in a Trastuzumab-payload conjugate may comprise one or more payloads B. Such Trastuzumab-payload conjugates may have been obtained in a two-step process, wherein a linker comprising a linking moiety has been conjugated to Trastuzumab in a first step and a payload has been linked to the linking moiety in a second step. Alternatively, Trastuzumab-payload conjugates may have been obtained in a one-step process, wherein a linker comprising a payload is directly conjugated to Trastuzumab.

In certain embodiments, the invention relates to an antibody-drug conjugate comprising Trastuzumab, or an anti-HER2/neu antibody. That is, the linker comprised in the antibody-drug conjugate may comprise one or more toxins as described herein.

In certain embodiments, an antibody-drug conjugate comprising Trastuzumab, or an anti-HER2/neu antibody, may comprises a linker comprising the amino acid sequence RKAA (SEQ ID NO:1), RKA (SEQ ID NO:2), ARK (SEQ ID NO:3), RKR (SEQ ID NO:4) or RK-Val-Cit (SEQ ID NO:54).

That is, in a particular embodiment, the invention relates to an antibody-drug conjugate comprising:
a) Trastuzumab, or an anti-HER2/neu antibody; and
b) a linker comprising a drug moiety B, wherein the drug moiety B is covalently linked to an amino acid sequence selected from the group consisting of: RKAA (SEQ ID NO:1), RKA (SEQ ID NO:2), ARK (SEQ ID NO:3), RKR (SEQ ID NO:4) or RK-Val-Cit (SEQ ID NO:54);
wherein the linker is conjugated to Trastuzumab, or the anti-HER2/neu antibody via an isopeptide bond formed between the γ-carboxamide group of glutamine residue Q295 (EU numbering) of the $C_H2$ domain of the antibody and the primary amine comprised in the side chain of the lysine residue comprised in the linker.

Preferably, the antibody is Trastuzumab comprising a heavy chain as set forth in SEQ ID NO:7 and a light chain as set forth in SEQ ID NO:8. Thus, in a particular embodiment, the invention relates to the antibody-drug conjugate according to the invention, wherein the IgG antibody is Trastuzumab or an antibody comprising a heavy chain as set forth in SEQ ID NO:7 and a light chain as set forth in SEQ ID NO:8.

In certain embodiments, the linker that is conjugated to Trastuzumab, or to an anti-HER2/neu antibody, may comprise the structure RKAA (SEQ ID NO:1), RKA (SEQ ID NO:2), ARK (SEQ ID NO:3), RKR (SEQ ID NO:4) or RK-Val-Cit (SEQ ID NO:54). In certain embodiments, a linker comprising the structure RKAA (SEQ ID NO:1), RKA (SEQ ID NO:2), ARK (SEQ ID NO:3), RKR (SEQ ID NO:4) or RK-Val-Cit (SEQ ID NO:54) may be conjugated to residue Q295 of Trastuzumab, or of an anti-HER2/neu antibody, via a primary amine comprised in the residue K.

In certain embodiments, Trastuzumab, or the anti-HER2/neu antibody, may be conjugated to the linker RKAA-B as disclosed herein, wherein B is preferably a toxin. In certain embodiments, Trastuzumab, or the anti-HER2/neu antibody, may be conjugated to the linker RKAA-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Trastuzumab, or the anti-HER2/neu antibody, may be conjugated to the linker RKAA-PABC-B. In certain embodiments, Trastuzumab, or the anti-HER2/neu antibody, may be conjugated to the linker RKAA-PABC-MMAE (see FIG. 1). In certain embodiments, Trastuzumab, or the anti-HER2/neu antibody, may be conjugated to the linker RKAA-PABC-maytansine (see FIG. 8). In certain embodiments, Trastuzumab, or the anti-HER2/neu antibody, may be conjugated to the linker RKAA-MMAE. In certain embodiments, Trastuzumab, or the anti-HER2/neu antibody, may be conjugated to the linker RKAA-PABC-PNP-MMAE. In certain embodiments, Trastuzumab, or the anti-HER2/neu antibody, may be conjugated to the linker RKAA-(NH)—(CH$_3$)—O—B, wherein O is the oxygen atom of an ether bond and B is a hydroxyl-comprising toxin. In certain embodiments, Trastuzumab, or the anti-HER2/neu antibody, may be conjugated to the linker RKAA-(NH)—(CH$_3$)—O-camptothecin. In certain embodiments, Trastuzumab, or the anti-HER2/neu antibody, may be conjugated to the linker RKAA-(NH)—(CH$_3$)—S—B, wherein S is the sulfur atom of an thioether bond and B is a thiol-comprising toxin. In certain embodiments, Trastuzumab, or the anti-HER2/neu antibody, may be conjugated to the linker RKAA-(NH)—(CH$_3$)—S-DM1.

In certain embodiments, Trastuzumab, or the anti-HER2/neu antibody, may be conjugated to the linker B-RKAA as disclosed herein, wherein B is preferably a toxin. In certain embodiments, Trastuzumab, or the anti-HER2/neu antibody, may be conjugated to the linker B-(self-immolative moiety)-RKAA as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety. In certain embodiments, an amine comprising payload B may be coupled to the N-terminal arginine moiety via a dicarboxylic acid linker, analogous to FIG. 9.

In certain embodiments, Trastuzumab, or the anti-HER2/neu antibody, may be conjugated to the linker RKA-B as disclosed herein, wherein B is preferably a toxin. In certain embodiments, Trastuzumab, or the anti-HER2/neu antibody, may be conjugated to the linker RKA-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Trastuzumab, or the anti-HER2/neu antibody, may be conjugated to the linker RKA-PABC-B. In certain embodiments, Trastuzumab, or the anti-HER2/neu antibody, may be conjugated to the linker RKA-PABC-MMAE (see FIG. 2). In certain embodiments, Trastuzumab, or the anti-HER2/neu antibody, may be conjugated to the linker RKA-PABC-maytansine. In certain embodiments, Trastuzumab, or the anti-HER2/neu antibody, may be conjugated to the linker RKA-MMAE. In certain embodiments, Trastuzumab, or the anti-HER2/neu antibody, may be conjugated to the linker RKA-PABC-PNP-MMAE. In certain embodiments, Trastuzumab, or the anti-HER2/neu antibody, may be conjugated to the linker RKA-(NH)—(CH$_3$)—O—B, wherein O is the oxygen atom of an ether bond and B is a hydroxyl-comprising toxin. In certain embodiments, Trastuzumab, or the anti-HER2/neu antibody, may be conjugated to the linker RKA-(NH)—(CH$_3$)—O-camptothecin. In certain embodiments, Trastuzumab, or the anti-HER2/neu antibody, may be conjugated to the linker RKA-(NH)—(CH$_3$)—S—B, wherein S is the sulfur atom of an thioether bond and B is a thiol-comprising toxin. In certain embodiments, Trastuzumab, or the anti-HER2/neu antibody, may be conjugated to the linker RKA-(NH)—(CH$_3$)—S-DM1.

In certain embodiments, Trastuzumab, or the anti-HER2/neu antibody, may be conjugated to the linker B-RKA as disclosed herein, wherein B is preferably a toxin. In certain embodiments, Trastuzumab, or the anti-HER2/neu antibody, may be conjugated to the linker B-(self-immolative moiety)-RKA as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety. In certain embodiments, an amine comprising payload B may be coupled to the N-terminal arginine moiety via a dicarboxylic acid linker, analogous to FIG. 9.

In certain embodiments, Trastuzumab, or the anti-HER2/neu antibody, may be conjugated to the linker ARK-B as disclosed herein, wherein B is preferably a toxin. In certain embodiments, Trastuzumab, or the anti-HER2/neu antibody, may be conjugated to the linker ARK-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Trastuzumab, or the anti-HER2/neu antibody, may be conjugated to the linker ARK-PABC-B. In certain embodiments, Trastuzumab, or the anti-HER2/neu antibody, may be conjugated to the linker ARK-PABC-MMAE (see FIG. 3). In certain embodiments, Trastuzumab, or the anti-HER2/neu antibody, may be conjugated to the linker ARK-PABC-maytansine. In certain embodiments, Trastuzumab, or the anti-HER2/neu antibody, may be conjugated to the linker ARK-MMAE. In certain embodiments, Trastuzumab, or the anti-HER2/neu antibody, may be conjugated to the linker ARK-PABC-PNP-MMAE. In certain embodiments, Trastuzumab, or the anti-HER2/neu antibody, may be conjugated to the linker ARK-(NH)—(CH$_3$)—O—B, wherein O is the oxygen atom of an ether bond and B is a hydroxyl-comprising toxin. In certain embodiments, Trastuzumab, or the anti-HER2/neu antibody, may be conjugated to the linker ARK-(NH)—(CH$_3$)—O-camptothecin. In certain embodiments, Trastuzumab, or the anti-HER2/neu antibody, may be conjugated to the linker ARK-(NH)—(CH$_3$)—S—B, wherein S is the sulfur atom of an thioether bond and S is a hydroxyl-comprising toxin. In certain embodiments, Trastuzumab, or the anti-HER2/neu antibody, may be conjugated to the linker ARK-(NH)—(CH$_3$)—S-DM1.

In certain embodiments, Trastuzumab, or the anti-HER2/neu antibody, may be conjugated to the linker B-ARK as disclosed herein, wherein B is preferably a toxin. In certain embodiments, Trastuzumab, or the anti-HER2/neu antibody, may be conjugated to the linker B-(self-immolative moiety)-ARK as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety.

In certain embodiments, Trastuzumab, or the anti-HER2/neu antibody, may be conjugated to the linker RKR-B as disclosed herein, wherein B is preferably a toxin. In certain embodiments, Trastuzumab, or the anti-HER2/neu antibody, may be conjugated to the linker RKR-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self immolative moiety may be PABC or a methyl-amine comprising group.

In certain embodiments, Trastuzumab, or the anti-HER2/neu antibody, may be conjugated to the linker RKR-PABC-B. In certain embodiments, Trastuzumab, or the anti-HER2/neu antibody, may be conjugated to the linker RKR-PABC-MMAE. In certain embodiments, Trastuzumab, or the anti-HER2/neu antibody, may be conjugated to the linker RKR-PABC-maytansine. In certain embodiments, Trastuzumab, or the anti-HER2/neu antibody, may be conjugated to the linker RKR-MMAE. In certain embodiments, Trastuzumab, or the anti-HER2/neu antibody, may be conjugated to the linker RKR-PABC-PNP-MMAE. In certain embodiments, Trastuzumab, or the anti-HER2/neu antibody, may be conjugated to the linker RKR-(NH)—(CH$_3$)—O—B, wherein O is the oxygen atom of an ether bond and B is a hydroxyl-comprising toxin. In certain embodiments, Trastuzumab, or the anti-HER2/neu antibody, may be conjugated to the linker RKR-(NH)—(CH$_3$)—O-camptothecin. In certain embodiments, Trastuzumab, or the anti-HER2/neu antibody, may be conjugated to the linker RKR-(NH)—(CH$_3$)—S—B, wherein S is the sulfur atom of an thioether bond and S is a thiol-comprising toxin. In certain embodiments, Trastuzumab, or the anti-HER2/neu antibody, may be conjugated to the linker RKR-(NH)—(CH$_3$)—S-DM1.

In certain embodiments, Trastuzumab, or the anti-HER2/neu antibody, may be conjugated to the linker B—RKR as disclosed herein, wherein B is preferably a toxin. In certain embodiments, Trastuzumab, or the anti-HER2/neu antibody, may be conjugated to the linker B-(self-immolative moiety)-RKR as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety. In certain embodiments, an amine comprising payload B may be coupled to the N-terminal arginine moiety via a dicarboxylic acid linker, as exemplified in FIG. 9.

In certain embodiments, Trastuzumab, or the anti-HER2/neu antibody, may be conjugated to the linker RK-Val-Cit-B as disclosed herein, wherein B is preferably a toxin. In certain embodiments, Trastuzumab, or the anti-HER2/neu antibody, may be conjugated to the linker RK-Val-Cit-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Trastuzumab, or the anti-HER2/neu antibody, may be conjugated to the linker RK-Val-Cit-PABC-B. In certain embodiments, Trastuzumab, or the anti-HER2/neu antibody, may be conjugated to the linker RK-Val-Cit-PABC-MMAE. In certain embodiments, Trastuzumab, or the anti-HER2/neu antibody, may be conjugated to the linker RK-Val-Cit-PABC-maytansine. In certain embodiments, Trastuzumab, or the anti-HER2/neu antibody, may be conjugated to the linker RK-Val-Cit-MMAE. In certain embodiments, Trastuzumab, or the anti-HER2/neu antibody, may be conjugated to the linker RK-Val-Cit-PABC-PNP-MMAE. In certain embodiments, Trastuzumab, or the anti-HER2/neu antibody, may be conjugated to the linker RK-Val-Cit-(NH)—(CH$_3$)—O—B, wherein O is the oxygen atom of an ether bond and B is a hydroxyl-comprising toxin. In certain embodiments, Trastuzumab, or the anti-HER2/neu antibody, may be conjugated to the linker RK-Val-Cit-(NH)—(CH$_3$)—O-camptothecin. In certain embodiments, Trastuzumab, or the anti-HER2/neu antibody, may be conjugated to the linker RK-Val-Cit-(NH)—(CH$_3$)—S—B, wherein S is the sulfur atom of an thioether bond and B is a thiol-comprising toxin. In certain embodiments, Trastuzumab, or the anti-HER2/neu antibody, may be conjugated to the linker RK-Val-Cit-(NH)—(CH$_3$)—S-DM1.

In a particular embodiment, the invention relates to an antibody-linker conjugate or an antibody drug-conjugate comprising the antibody Enfortumab or, alternatively, an anti-Nectin-4 antibody.

That is, in a particular embodiment, the invention relates to an antibody-linker conjugate comprising:
  a) Enfortumab or an anti-Nectin-4 antibody; and
  b) a linker comprising the structure:

(Sp$_1$)-RK-(Sp$_2$)-B-(Sp$_3$) or (Sp$_1$)-B-(Sp$_2$)-RK-(Sp$_3$); wherein (Sp$_1$) is a chemical spacer or is absent;
  (Sp$_2$) is a chemical spacer or is absent;
  (Sp$_3$) is a chemical spacer or is absent;
  R is arginine or an arginine derivative or an arginine mimetic;
  K is lysine or a lysine derivative or a lysine mimetic;
  B is a linking moiety or a payload;
  wherein the linker is conjugated to Enfortumab, or the anti-Nectin-4 antibody, via an isopeptide bond formed between a γ-carboxamide group of a glutamine residue comprised in Enfortumab, or the anti-Nectin-4 antibody, and a primary amine comprised in the side chain of the lysine residue, the lysine derivative or the lysine mimetic comprised in the RK motif comprised in the linker.

In a particular embodiment, the invention relates to the antibody-payload conjugate comprising Enfortumab or the anti-Nectin-4 antibody, wherein the linker is any one of the linkers shown in FIG. 1, FIG. 2, FIG. 3, FIG. 8, FIG. 9, FIG. 14, FIG. 15, FIG. 17, FIG. 18, FIG. 19, FIG. 20, FIG. 21, FIG. 22, FIG. 23, FIG. 24, FIG. 25, FIG. 26, FIG. 27, FIG. 28, FIG. 29, FIG. 30, FIG. 31, FIG. 32, FIG. 33 or FIG. 34.

Enfortumab is commercially available as the antibody-drug conjugate Enfortumab vedotin and marketed under the name Padcev. Enfortumab vedotin comprises the anti-Nectin-4 antibody Enfortumab and the linker maleimidocaproyl-L-valine-L-citrulline-PABC-MMAE (mc-vc-PABC-MMAE), which is commonly known as vedotin. The mc-vc-PABC-MMAE linker of Enfortumab vedotin is conjugated to free cysteine residues comprised in the antibody. The antibody Enfortumab has been disclosed in WO 2012/047724, which is incorporated herein by reference in its entirety.

In certain embodiments, the antibody is Enfortumab comprising a heavy chain as set forth in SEQ ID NO:9 and a light chain as set forth in SEQ ID NO:10. However, the invention also encompasses variants of Enfortumab wherein the heavy and/or light chain comprise at least 80%, at least 85%, at least 90%, at least 95% sequence identity with SEQ ID NO:9 and/or SEQ ID NO:10, respectively. In particular, the antibody may comprise any of the sequence variations that have been disclosed in WO 2012/047724. In certain embodiments, the light chain of Enfortumab may comprise a mutation in residue Q55 of SEQ ID NO:10. In particular, the mutation is Q55N (SEQ ID NO:11).

It is preferred herein that Enfortumab, or an anti-Nectin-4 antibody, is present in the antibody-linker conjugate in glycosylated form. That is, Enfortumab, or the anti-Nectin-4 antibody, is preferably glycosylated at residue N297 (EU numbering). However, Enfortumab, or the anti-Nectin-4 antibody, may also be de-glycosylated as described herein.

Enfortumab, or an anti-Nectin-4 antibody, may be conjugated to any one of the linkers that have been disclosed herein, in particular for the method according to the invention. Preferably, the linker is conjugated in an MTG-catalyzed manner to the glutamine residue Q295 (EU numbering) of the antibody. However, the linker may also be conjugated to an engineered glutamine residue, such as N297Q (EU numbering) and/or to any one of the glutamine-comprising tags that have been disclosed herein.

The linker that is conjugated to Enfortumab, or the anti-Nectin-4 antibody, may comprise a single linking moiety or payload B or may comprise multiple linking moieties and/or payloads B$_1$, B$_2$ and so forth.

That is, in certain embodiments, the linker comprised in an Enfortumab-linker conjugate may comprise one or more linking moieties B. Such Enfortumab-linker conjugates may be subsequently functionalized with a suitable payload in a two-step process as disclosed herein.

In certain embodiments, the linker comprised in an Enfortumab-payload conjugate may comprise one or more payloads B. Such Enfortumab-payload conjugates may have been obtained in a two-step process, wherein a linker comprising a linking moiety has been conjugated to Enfortumab in a first step and a payload has been linked to the linking moiety in a second step. Alternatively, Enfortumab-payload conjugates may have been obtained in a one-step process, wherein a linker comprising a payload is directly conjugated to Enfortumab.

In certain embodiments, the invention relates to an antibody-drug conjugate comprising Enfortumab, or an anti-Nectin-4 antibody. That is, the linker comprised in the antibody-drug conjugate may comprise one or more toxins as described herein.

In certain embodiments, an antibody-drug conjugate comprising Enfortumab, or an anti-Nectin-4 antibody, may comprises a linker comprising the amino acid sequence RKAA (SEQ ID NO:1), RKA (SEQ ID NO:2), ARK (SEQ ID NO:3), RKR (SEQ ID NO:4) or RK-Val-Cit (SEQ ID NO:54).

That is, in a particular embodiment, the invention relates to an antibody-drug conjugate comprising:
  a) Enfortumab, or an anti-Nectin-4 antibody; and
  b) a linker comprising a drug moiety B, wherein the drug moiety B is covalently linked to an amino acid sequence selected from the group consisting of: RKAA (SEQ ID NO:1), RKA (SEQ ID NO:2), ARK (SEQ ID NO:3), RKR (SEQ ID NO:4) or RK-Val-Cit (SEQ ID NO:54);
    wherein the linker is conjugated to Enfortumab, or the anti-Nectin-4 antibody via an isopeptide bond formed between the γ-carboxamide group of glutamine residue Q295 (EU numbering) of the C$_H$2 domain of the antibody and the primary amine comprised in the side chain of the lysine residue comprised in the linker.

Preferably, the antibody is Enfortumab comprising a heavy chain as set forth in SEQ ID NO:9 and a light chain as set forth in SEQ ID NO:10. Thus, in a particular embodiment, the invention relates to the antibody-drug conjugate according to the invention, wherein the IgG antibody is Enfortumab or an antibody comprising a heavy chain as set forth in SEQ ID NO:9 and a light chain as set forth in SEQ ID NO:10.

In certain embodiments, the linker that is conjugated to Enfortumab, or an anti-Nectin-4 antibody, may comprise the structure RKAA (SEQ ID NO:1), RKA (SEQ ID NO:2), ARK (SEQ ID NO:3), RKR (SEQ ID NO:4) or RK-Val-Cit (SEQ ID NO:54). In certain embodiments, a linker comprising the structure RKAA (SEQ ID NO:1), RKA (SEQ ID NO:2), ARK (SEQ ID NO:3), RKR (SEQ ID NO:4) or RK-Val-Cit (SEQ ID NO:54) may be conjugated to residue Q295 of Enfortumab, or of an anti-Nectin-4 antibody, via a primary amine comprised in the residue K.

In certain embodiments, Enfortumab, or the anti-Nectin-4 antibody, may be conjugated to the linker RKAA-B as disclosed herein, wherein B is preferably a toxin. In certain embodiments, Enfortumab, or the anti-Nectin-4 antibody, may be conjugated to the linker RKAA-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Enfortumab, or the anti-Nectin-4 antibody, may be conjugated to the linker RKAA-PABC-B. In certain embodiments, Enfortumab, or the anti-Nectin-4 antibody, may be conjugated to the linker RKAA-PABC-MMAE (see FIG. 1). In certain embodiments, Enfortumab, or the anti-Nectin-4 antibody, may be conjugated to the linker RKAA-PABC-maytansine (see FIG. 8). In certain embodiments, Enfortumab, or the anti-Nectin-4 antibody, may be conjugated to the linker RKAA-MMAE. In certain embodiments, Enfortumab, or the anti-Nectin-4 antibody, may be conjugated to the linker RKAA-PABC-PNP-MMAE. In certain embodiments, Enfortumab, or the anti-Nectin-4 antibody, may be conjugated to the linker RKAA-(NH)—(CH$_3$)—O—B, wherein O is the oxygen atom of an ether bond and B is a hydroxyl-comprising toxin. In certain embodiments, Enfortumab, or the anti-Nectin-4 antibody, may be conjugated to the linker RKAA-(NH)—(CH$_3$)—O-camptothecin. In certain embodiments, Enfortumab, or the anti-Nectin-4 antibody, may be conjugated to the linker RKAA-(NH)—(CH$_3$)—S—B, wherein S is the sulfur atom of an thioether bond and B is a thiol-comprising toxin. In certain embodiments, Enfortumab, or the anti-Nectin-4 antibody, may be conjugated to the linker RKAA-(NH)—(CH$_3$)—S-DM1.

In certain embodiments, Enfortumab, or the anti-Nectin-4 antibody, may be conjugated to the linker B-RKAA as disclosed herein, wherein B is preferably a toxin. In certain embodiments, Enfortumab, or the anti-Nectin-4 antibody, may be conjugated to the linker B-(self-immolative moiety)-RKAA as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety. In certain embodiments, an amine comprising payload B may be coupled to the N-terminal arginine moiety via a dicarboxylic acid linker, analogous to FIG. 9.

In certain embodiments, Enfortumab, or the anti-Nectin-4 antibody, may be conjugated to the linker RKA-B as disclosed herein, wherein B is preferably a toxin. In certain embodiments, Enfortumab, or the anti-Nectin-4 antibody, may be conjugated to the linker RKA-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self immolative moiety may be PABC or a methyl-amine comprising group.

In certain embodiments, Enfortumab, or the anti-Nectin-4 antibody, may be conjugated to the linker RKA-PABC-B. In certain embodiments, Enfortumab, or the anti-Nectin-4 antibody, may be conjugated to the linker RKA-PABC-MMAE (see FIG. 2). In certain embodiments, Enfortumab, or the anti-Nectin-4 antibody, may be conjugated to the linker RKA-PABC-maytansine. In certain embodiments, Enfortumab, or the anti-Nectin-4 antibody, may be conjugated to the linker RKA-MMAE. In certain embodiments, Enfortumab, or the anti-Nectin-4 antibody, may be conjugated to the linker RKA-PABC-PNP-MMAE. In certain embodiments, Enfortumab, or the anti-Nectin-4 antibody, may be conjugated to the linker RKA-(NH)—(CH$_3$)—O—B, wherein O is the oxygen atom of an ether bond and B is a hydroxyl-comprising toxin. In certain embodiments, Enfortumab, or the anti-Nectin-4 antibody, may be conjugated to the linker RKA-(NH)—(CH$_3$)—O-camptothecin. In certain embodiments, Enfortumab, or the anti-Nectin-4 antibody, may be conjugated to the linker RKA-(NH)—(CH$_3$)—S—B, wherein S is the sulfur atom of an thioether bond and B is a thiol-comprising toxin. In certain embodiments, Enfortumab, or the anti-Nectin-4 antibody, may be conjugated to the linker RKA-(NH)—(CH$_3$)—S-DM1.

In certain embodiments, Enfortumab, or the anti-Nectin-4 antibody, may be conjugated to the linker B-RKA as disclosed herein, wherein B is preferably a toxin. In certain embodiments, Enfortumab, or the anti-Nectin-4 antibody, may be conjugated to the linker B-(self-immolative moiety)-RKA as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety. In certain embodiments, an amine comprising payload B may be coupled to the N-terminal arginine moiety via a dicarboxylic acid linker, analogous to FIG. 9.

In certain embodiments, Enfortumab, or the anti-Nectin-4 antibody, may be conjugated to the linker ARK-B as disclosed herein, wherein B is preferably a toxin. In certain embodiments, Enfortumab, or the anti-Nectin-4 antibody, may be conjugated to the linker ARK-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Enfortumab, or the anti-Nectin-4 antibody, may be conjugated to the linker ARK-PABC-B. In certain embodiments, Enfortumab, or the anti-Nectin-4 antibody, may be conjugated to the linker ARK-PABC-MMAE (see FIG. 3). In certain embodiments, Enfortumab, or the anti-Nectin-4 antibody, may be conjugated to the linker ARK-PABC-maytansine. In certain embodiments, Enfortumab, or the anti-Nectin-4 antibody, may be conjugated to the linker ARK-MMAE. In certain embodiments, Enfortumab, or the anti-Nectin-4 antibody, may be conjugated to the linker ARK-PABC-PNP-MMAE. In certain embodiments, Enfortumab, or the anti-Nectin-4 antibody, may be conjugated to the linker ARK-(NH)—(CH$_3$)—O—B, wherein O is the oxygen atom of an ether bond and B is a hydroxyl-comprising toxin. In certain embodiments, Enfortumab, or the anti-Nectin-4 antibody, may be conjugated to the linker ARK-(NH)—(CH$_3$)—O-camptothecin. In certain embodiments, Enfortumab, or the anti-Nectin-4 antibody, may be conjugated to the linker ARK-(NH)—(CH$_3$)—S—B, wherein S is the sulfur atom of an thioether bond and B is a thiol-comprising toxin. In certain embodiments, Enfortumab, or the anti-Nectin-4 antibody, may be conjugated to the linker ARK-(NH)—(CH$_3$)—S-DM1.

In certain embodiments, Enfortumab, or the anti-Nectin-4 antibody, may be conjugated to the linker B-ARK as disclosed herein, wherein B is preferably a toxin. In certain embodiments, Enfortumab, or the anti-Nectin-4 antibody, may be conjugated to the linker B-(self-immolative moiety)-ARK as disclosed herein, wherein B is preferably a toxin. The self-immolative moiety may be any self-immolative moiety known in the art and/or disclosed herein that is suitable for coupling a payload to the N-terminus of a peptide. In certain embodiments, the self-immolative moiety may be a self-immolative moiety comprising an ortho-hydroxy-protected aryl sulfate (OHPAS) moiety.

In certain embodiments, Enfortumab, or the anti-Nectin-4 antibody, may be conjugated to the linker RKR-B as disclosed herein, wherein B is preferably a toxin. In certain embodiments, Enfortumab, or the anti-Nectin-4 antibody, may be conjugated to the linker RKR-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self immolative moiety may be PABC or a methyl-amine comprising group.

In certain embodiments, Enfortumab, or the anti-Nectin-4 antibody, may be conjugated to the linker RKR-PABC-B. In certain embodiments, Enfortumab, or the anti-Nectin-4 antibody, may be conjugated to the linker RKR-PABC-MMAE. In certain embodiments, Enfortumab, or the anti-Nectin-4 antibody, may be conjugated to the linker RKR-PABC-maytansine. In certain embodiments, Enfortumab, or the anti-Nectin-4 antibody, may be conjugated to the linker RKR-MMAE. In certain embodiments, Enfortumab, or the anti-Nectin-4 antibody, may be conjugated to the linker RKR-PABC-PNP-MMAE. In certain embodiments, Enfortumab, or the anti-Nectin-4 antibody, may be conjugated to the linker RKR-(NH)—(CH$_3$)—O—B, wherein O is the oxygen atom of an ether bond and B is a hydroxyl-comprising toxin. In certain embodiments, Enfortumab, or the anti-Nectin-4 antibody, may be conjugated to the linker RKR-(NH)—(CH$_3$)—O-camptothecin. In certain embodiments, Enfortumab, or the anti-Nectin-4 antibody, may be conjugated to the linker RKR-(NH)—(CH$_3$)—S—B, wherein S is the sulfur atom of an thioether bond and S is a thiol-comprising toxin. In certain embodiments, Enfortumab, or the anti-Nectin-4 antibody, may be conjugated to the linker RKR-(NH)—(CH$_3$)—S-DM1.

In certain embodiments, Enfortumab, or the anti-Nectin-4 antibody, may be conjugated to the linker B—RKR as disclosed herein, wherein B is preferably a toxin. In certain embodiments, Enfortumab, or the anti-Nectin-4 antibody, may be conjugated to the linker B-(self-immolative moiety)-RKR as disclosed herein, wherein B is preferably a toxin. The self-immolative moiety may be any self-immolative moiety known in the art and/or disclosed herein that is suitable for coupling a payload to the N-terminus of a peptide. In certain embodiments, the self immolative moiety may be a self-immolative moiety comprising an ortho-hydroxy-protected aryl sulfate (OHPAS) moiety. In certain embodiments, an amine comprising payload B may be coupled to the N-terminal arginine moiety via a dicarboxylic acid linker, as exemplified in FIG. 9.

In certain embodiments, Enfortumab, or the anti-Nectin-4 antibody, may be conjugated to the linker RK-Val-Cit-B as disclosed herein, wherein B is preferably a toxin. In certain embodiments, Enfortumab, or the anti-Nectin-4 antibody, may be conjugated to the linker RK-Val-Cit-(self-immolative moiety)-B as disclosed herein, wherein B is preferably a toxin. The self-immolative moiety may be any self-immolative moiety known in the art and/or disclosed herein that is suitable for coupling a payload to the C-terminus of a peptide. In certain embodiments, the self-immolative moiety may be PABC or a methyl-amine comprising group.

In certain embodiments, Enfortumab, or the anti-Nectin-4 antibody, may be conjugated to the linker RK-Val-Cit-PABC-B. In certain embodiments, Enfortumab, or the anti-Nectin-4 antibody, may be conjugated to the linker RK-Val-Cit-PABC-MMAE. In certain embodiments, Enfortumab, or the anti-Nectin-4 antibody, may be conjugated to the linker RK-Val-Cit-PABC-maytansine. In certain embodiments, Enfortumab, or the anti-Nectin-4 antibody, may be conjugated to the linker RK-Val-Cit-MMAE. In certain embodiments, Enfortumab, or the anti-Nectin-4 antibody, may be conjugated to the linker RK-Val-Cit-PABC-PNP-MMAE. In certain embodiments, Enfortumab, or the anti-Nectin-4 antibody, may be conjugated to the linker RK-Val-Cit-(NH)—(CH$_3$)—O—B, wherein O is the oxygen atom of an ether bond and B is a hydroxyl-comprising toxin. In certain embodiments, Enfortumab, or the anti-Nectin-4 antibody, may be conjugated to the linker RK-Val-Cit-(NH)—(CH$_3$)—O-camptothecin. In certain embodiments, Enfortumab, or the anti-Nectin-4 antibody, may be conjugated to the linker RK-Val-Cit-(NH)—(CH$_3$)—S—B, wherein S is the sulfur atom of an thioether bond and B is a thiol-comprising toxin. In certain embodiments, Enfortumab, or the anti-Nectin-4 antibody, may be conjugated to the linker RK-Val-Cit-(NH)—(CH$_3$)—S-DM1.

Further, the invention relates to linker constructs comprising the motif RK. Linker constructs according to the invention may be used for the conjugation of a wide range of antibodies. Due to the highly conserved conjugation site Q295, the linker conjugates according to the invention may be used "off the shelf" to produce antibody-payload conjugates of basically any IgG type antibody. In comparison to linkers known from the prior art, the RK linkers of the present invention can be used for highly efficient conjugation of glycosylated antibodies and even resulted in high conjugation efficiencies when comprising bulky payloads, such as toxins.

Thus, in a particular embodiment, the invention relates to a linker construct comprising the structure:

(Sp$_1$)-RK-(Sp$_2$)-B-(Sp$_3$) or (Sp$_1$)-B-(Sp$_2$)-RK-(Sp$_3$); wherein (Sp$_1$) is a chemical spacer or is absent;
(Sp$_2$) is a chemical spacer or is absent;
(Sp$_3$) is a chemical spacer or is absent;
R is arginine or an arginine derivative or an arginine mimetic;
K is lysine or a lysine derivative or a lysine mimetic;
B is a linking moiety or a payload.

It is to be understood that the linker construct may have the same structure and/or characteristics as the linkers disclosed above for the method according to the invention, for the antibody-linker conjugate according to the invention and/or for the antibody-drug conjugates according to the invention.

In a particular embodiment, the invention relates to the linker construct according to the invention, wherein the chemical spacers (Sp$_1$), (Sp$_2$) and (Sp$_3$) each independently comprise between 0 and 12 amino acid residues.

In a particular embodiment, the invention relates to the linker construct according to the invention, wherein the linker comprises not more than 25, 20, 15, 14, 13, 12, 11, 10, 9, 8, 7, 6, 5, 4 amino acid residues.

In a particular embodiment, the invention relates to the linker construct according to the invention, wherein the net charge of the linker is neutral or positive.

In a particular embodiment, the invention relates to the linker construct according to the invention, wherein the linker comprises no negatively-charged amino acid residues.

In a particular embodiment, the invention relates to the linker construct according to the invention, wherein the linker comprises the amino acid sequence RKAA (SEQ ID NO:1), RKA (SEQ ID NO:2), ARK (SEQ ID NO:3), RKR (SEQ ID NO:4) or RK-Val-Cit (SEQ ID NO:54).

In a particular embodiment, the invention relates to the linker construct according to the invention, wherein B is a linking moiety.

In a particular embodiment, the invention relates to the linker construct according to the invention, wherein the linking moiety B comprises
   a bioorthogonal marker group, or
   a non-bio-orthogonal entity for crosslinking.

In a particular embodiment, the invention relates to the linker construct according to the invention, wherein the bioorthogonal marker group or the non-bio-orthogonal entity for crosslinking consists of or comprises at least one molecule or moiety selected from the group consisting of:
   —N—N≡N, or —N$_3$;
   Lys(N$_3$);
   a tetrazine;
   an alkyne;
   a strained cyclooctyne;
   BCN;
   a strained alkene;
   a photoreactive group;
   an aldehyde;
   an acyltrifluoroborate;
   a protein degradation agent ('PROTAC');
   a cyclopentadiene/spirolocyclopentadiene;
   a thio-selective electrophile;
   —SH; and
   cysteine.

In a particular embodiment, the invention relates to the linker construct according to the invention, wherein the linker construct consists of or comprises the structure RKAA-B or B-RKAA, in particular wherein B is Lys(N$_3$) or cysteine.

That is, in a particular embodiment, the invention relates to a linker comprising the structure RKAA-B or B-RKAA, wherein B is a linking moiety. It is to be understood that B may be any linking moiety known in the art and/or disclosed herein. In certain embodiments, B may be a thiol-comprising linking moiety, such as cysteine, an azide comprising linking moiety, such as Lys(N$_3$), or a tetrazine comprising linking moiety. It is to be understood that a linker comprising the structure RKAA-B or B-RKAA may comprise additional amino acid residues, linking moieties, payloads and/or other chemical groups, such as, without limitation PEG moieties. In certain embodiments, the linker construct consists of the structure RKAA-B or B-RKAA.

In a particular embodiment, the invention relates to the linker construct according to the invention, wherein the linker construct consists of or comprises the structure RKA-B or B-RKA, in particular wherein B is Lys(N$_3$) or cysteine.

That is, in a particular embodiment, the invention relates to a linker comprising the structure RKA-B or B-RKA, wherein B is a linking moiety. It is to be understood that B may be any linking moiety known in the art and/or disclosed herein. In certain embodiments, B may be a thiol-comprising linking moiety, such as cysteine, an azide comprising linking moiety, such as Lys(N$_3$), or a tetrazine comprising linking moiety. It is to be understood that a linker comprising the structure RKA-B or B-RKA may comprise additional amino acid residues, linking moieties, payloads and/or other chemical groups, such as, without limitation PEG moieties. In certain embodiments, the linker construct consists of the structure RKA-B or B-RKA.

In a particular embodiment, the invention relates to the linker construct according to the invention, wherein the linker construct consists of or comprises the structure ARK-B or B-ARK, in particular wherein B is Lys(N$_3$) or cysteine.

That is, in a particular embodiment, the invention relates to a linker comprising the structure ARK-B or B-ARK, wherein B is a linking moiety. It is to be understood that B may be any linking moiety known in the art and/or disclosed herein. In certain embodiments, B may be a thiol-comprising linking moiety, such as cysteine, an azide comprising linking moiety, such as Lys(N$_3$), or a tetrazine comprising linking moiety. It is to be understood that a linker comprising the structure ARK-B or B-ARK may comprise additional amino acid residues, linking moieties, payloads and/or other chemical groups, such as, without limitation PEG moieties. In certain embodiments, the linker construct consists of the structure ARK-B or B-ARK.

In a particular embodiment, the invention relates to the linker construct according to the invention, wherein the linker construct consists of or comprises the structure RKR—B or B—RKR, in particular wherein B is Lys(N$_3$) or cysteine.

That is, in a particular embodiment, the invention relates to a linker comprising the structure RKR—B or B—RKR, wherein B is a linking moiety. It is to be understood that B may be any linking moiety known in the art and/or disclosed herein. In certain embodiments, B may be a thiol-comprising linking moiety, such as cysteine, an azide comprising linking moiety, such as Lys(N$_3$), or a tetrazine comprising linking moiety. It is to be understood that a linker comprising the structure RKR—B or B—RKR may comprise additional amino acid residues, linking moieties, payloads and/or other chemical groups, such as, without limitation PEG moieties. In certain embodiments, the linker construct consists of the structure RKR—B or B—RKR.

In a particular embodiment, the invention relates to the linker construct according to the invention, wherein B is a payload.

In a particular embodiment, the invention relates to the linker construct according to the invention, wherein the payload comprises at least one of:
   a toxin;
   a cytokine;
   a growth factor;
   a radionuclide;
   a hormone;
   an anti-viral agent;
   an anti-bacterial agent;
   a fluorescent dye;
   an immunoregulatory/immunostimulatory agent;

a half-life increasing moiety;

a solubility increasing moiety;

a polymer-toxin conjugate;

a nucleic acid;

a biotin or streptavidin moiety;

a vitamin;

a protein degradation agent ('PROTAC');

a target binding moiety; and/or an anti-inflammatory agent.

In a particular embodiment, the invention relates to the linker construct according to the invention, wherein the toxin is at least one selected from the group consisting of a pyrrolobenzodiazepine (e.g., PBD);

an auristatin (e.g., MMAE, MMAF);

a maytansinoid (e.g., maytansine, DM1, DM4, DM21);

a duocarmycin;

a nicotinamide phosphoribosyltransferase (NAMPT) inhibitor;

a tubulysin;

an enediyne (e.g. calicheamicin);

an anthracycline derivative (PNU) (e.g., doxorubicin);

a pyrrole-based kinesin spindle protein (KSP) inhibitor;

a cryptophycin;

a drug efflux pump inhibitor;

a sandramycin;

an amanitin (e.g., α-amanitin); and a camptothecin (e.g., exatecans, deruxtecans).

In a particular embodiment, the invention relates to the linker construct according to the invention, wherein chemical spacer ($Sp_2$) comprises a self-immolative moiety.

In a particular embodiment, the invention relates to the linker construct according to the invention, wherein the self-immolative moiety is directly attached to the payload B.

In a particular embodiment, the invention relates to the linker construct according to the invention, wherein the self-immolative moiety comprises a p-aminobenzyl carbamoyl (PABC) moiety.

In a particular embodiment, the invention relates to the linker construct according to the invention, wherein the linker construct consists of or comprises the structure RKAA-(self-immolative moiety)-B. That is, the linker construct may comprise any self-immolative moiety known in the art and/or disclosed herein that is suitable for coupling a payload B to the C-terminus of a peptide. In certain embodiments, the payload B may be a toxin. The skilled person is aware toxins that can be coupled to the C-terminus of a peptide via a suitable self-immolative moiety. Preferably, the self-immolative moiety is any one of the self-immolative moieties disclosed herein, such as, without limitation, a PABC-based self-immolative linker, a PABE-based self-immolative linker or a methyl amine comprising self-immolative moiety.

In a particular embodiment, the invention relates to the linker construct according to the invention, wherein the linker construct consists of or comprises the structure B-(self-immolative moiety)-RKAA. That is, the linker construct may comprise any self-immolative moiety that is known in the art and/or disclosed herein that is suitable for coupling a payload B to the N-terminus of a peptide. In certain embodiments, the payload B may be a toxin. The skilled person is aware toxins that can be coupled to the N-terminus of a peptide via a suitable self-immolative moiety. Preferably, the self-immolative moiety is any one of the self-immolative moieties disclosed herein, such as, without limitation, a self-immolative moiety comprising an OHPAS moiety.

In a particular embodiment, the invention relates to the linker construct according to the invention, wherein the linker construct consists of or comprises the structure B-RKAA or RKAA-B. That is, the payload B may be coupled directly to the N- or C-terminus of a peptide. In cases where the functional groups comprised in the payload are not compatible with the N- and/or C-terminus of a peptide, a linker molecule may be used to couple the payload to the N- and/or C-terminus of the peptide, respectively. Suitable linker molecules for coupling a payload to the N- or C-terminus of a peptide have been disclosed herein.

In a particular embodiment, the invention relates to the linker construct according to the invention, wherein the linker construct consists of or comprises the structure RKAA-PABC-B, in particular wherein B is an auristatin or a maytansinoid, in particular wherein the auristatin is MMAE and wherein the maytansinoid is maytansine.

That is, in a particular embodiment, the invention relates to a linker comprising the structure RKAA-B, wherein B is a payload. It is to be understood that B may be any payload known in the art and/or disclosed herein. In certain embodiments, B may be a toxin. In certain embodiments, the payload B may be separated from the peptide RKAA by a self-immolative moiety. Thus, the linker may comprise or consist of the structure RKAA-(self-immolative moiety)-B, wherein B is a payload. In certain embodiments, the self-immolative moiety may be PABC or a methyl amine group. Thus, in certain embodiments, the linker may comprise or consist of the structure RKAA-PABC-B. In certain embodiments, the linker may comprise or consist of the structure RKAA-(NH)—(CH$_3$)—O—B, wherein O is the oxygen atom comprised in an ether bond and B is a hydroxyl-comprising payload. In certain embodiments, the linker may comprise or consist of the structure RKAA-(NH)—(CH$_3$)—S—B, wherein S is the sulfur atom comprised in a thioether bond and B is a thiol-comprising payload. In certain embodiments, the payload may be an auristatin or a maytansinoid. In certain embodiments, the auristatin may be MMAE. In such embodiments, the linker may comprise or consist of the structure RKAA-PABC-MMAE or RKAA-MMAE. In certain embodiments, the maytansinoid may be maytansine. In such embodiments, the linker may comprise or consist of the structure RKAA-PABC-maytansine or RKAA-maytansine. In certain embodiments, the maytansinoid may be DM1 or a DM1 derivative. In such embodiments, the linker may comprise or consist of the structure RKAA-(NH)—(CH$_3$)—S-DM1. In certain embodiments, the payload may be a camptothecin. In such embodiments, the linker may comprise or consist of the structure RKAA-(NH)—(CH$_3$)—O-camptothecin.

In a particular embodiment, the invention relates to the linker construct according to the invention, wherein the linker construct consists of or comprises the structure RKA-(self-immolative moiety)-B. That is, the linker construct may comprise any self-immolative moiety known in the art and/or disclosed herein that is suitable for coupling a payload B to the C-terminus of a peptide. In certain embodiments, the payload B may be a toxin. The skilled person is aware toxins that can be coupled to the C-terminus of a peptide via a suitable self-immolative moiety. Preferably, the self-immolative moiety is any one of the self-immolative moieties disclosed herein, such as, without limitation, a PABC-based self-immolative linker, a PABE-based self-immolative linker or a methyl amine comprising self-immolative moiety.

In a particular embodiment, the invention relates to the linker construct according to the invention, wherein the linker construct consists of or comprises the structure B-(self-immolative moiety)-RKA. That is, the linker construct may comprise any self-immolative moiety that is known in the art and/or disclosed herein that is suitable for coupling a payload B to the N-terminus of a peptide. In certain embodiments, the payload B may be a toxin. The skilled person is aware toxins that can be coupled to the N-terminus of a peptide via a suitable self-immolative moiety. Preferably, the self-immolative moiety is any one of the self-immolative moieties disclosed herein, such as, without limitation, a self-immolative moiety comprising an OHPAS moiety.

In a particular embodiment, the invention relates to the linker construct according to the invention, wherein the linker construct consists of or comprises the structure B-RKA or RKA-B. That is, the payload B may be coupled directly to the N- or C-terminus of a peptide. In cases where the functional groups comprised in the payload are not compatible with the N- and/or C-terminus of a peptide, a linker molecule may be used to couple the payload to the N- and/or C-terminus of the peptide, respectively. Suitable linker molecules for coupling a payload to the N- or C-terminus of a peptide have been disclosed herein.

In a particular embodiment, the invention relates to the linker construct according to the invention, wherein the linker construct consists of or comprises the structure RKA-PABC-B, in particular wherein B is an auristatin or a maytansinoid, in particular wherein the auristatin is MMAE and wherein the maytansinoid is maytansine.

That is, in a particular embodiment, the invention relates to a linker comprising the structure RKA-B, wherein B is a payload. It is to be understood that B may be any payload known in the art and/or disclosed herein. In certain embodiments, B may be a toxin. In certain embodiments, the payload B may be separated from the peptide RKA by a self-immolative moiety. Thus, the linker may comprise or consist of the structure RKA-(self-immolative moiety)-B, wherein B is a payload. In certain embodiments, the self-immolative moiety may be PABC or a methyl amine group. Thus, in certain embodiments, the linker may comprise or consist of the structure RKA-PABC-B. In certain embodiments, the linker may comprise or consist of the structure RKA-(NH)—(CH$_3$)—O—B, wherein O is the oxygen atom comprised in an ether bond and B is a hydroxyl-comprising payload. In certain embodiments, the linker may comprise or consist of the structure RKA-(NH)—(CH$_3$)—S—B, wherein S is the sulfur atom comprised in a thioether bond and B is a thiol-comprising payload. In certain embodiments, the payload may be an auristatin or a maytansinoid. In certain embodiments, the auristatin may be MMAE. In such embodiments, the linker may comprise or consist of the structure RKA-PABC-MMAE or RKA-MMAE. In certain embodiments, the maytansinoid may be maytansine. In such embodiments, the linker may comprise or consist of the structure RKA-PABC-maytansine or RKA-maytansine. In certain embodiments, the maytansinoid may be DM1 or a DM1 derivative. In such embodiments, the linker may comprise or consist of the structure RKA-(NH)—CH$_3$)—S-DM1. In certain embodiments, the payload may be a camptothecin. In such embodiments, the linker may comprise or consist of the structure RKA-(NH)—CH$_3$)—O-camptothecin.

In a particular embodiment, the invention relates to the linker construct according to the invention, wherein the linker construct consists of or comprises the structure ARK-(self-immolative moiety)-B. That is, the linker construct may comprise any self-immolative moiety known in the art and/or disclosed herein that is suitable for coupling a payload B to the C-terminus of a peptide. In certain embodiments, the payload B may be a toxin. The skilled person is aware toxins that can be coupled to the C-terminus of a peptide via a suitable self-immolative moiety. Preferably, the self-immolative moiety is any one of the self-immolative moieties disclosed herein, such as, without limitation, a PABC-based self-immolative linker, a PABE-based self-immolative linker or a methyl amine comprising self-immolative moiety.

In a particular embodiment, the invention relates to the linker construct according to the invention, wherein the linker construct consists of or comprises the structure B-(self-immolative moiety)-ARK. That is, the linker construct may comprise any self-immolative moiety that is known in the art and/or disclosed herein that is suitable for coupling a payload B to the N-terminus of a peptide. In certain embodiments, the payload B may be a toxin. The skilled person is aware toxins that can be coupled to the N-terminus of a peptide via a suitable self-immolative moiety. Preferably, the self-immolative moiety is any one of the self-immolative moieties disclosed herein, such as, without limitation, a self-immolative moiety comprising an OHPAS moiety.

In a particular embodiment, the invention relates to the linker construct according to the invention, wherein the linker construct consists of or comprises the structure B-ARK or ARK-B. That is, the payload B may be coupled directly to the N- or C-terminus of a peptide. In cases where the functional groups comprised in the payload are not compatible with the N- and/or C-terminus of a peptide, a linker molecule may be used to couple the payload to the N- and/or C-terminus of the peptide, respectively. Suitable linker molecules for coupling a payload to the N- or C-terminus of a peptide have been disclosed herein.

In a particular embodiment, the invention relates to the linker construct according to the invention, wherein the linker construct consists of or comprises the structure ARK-PABC-B, in particular wherein B is an auristatin or a maytansinoid, in particular wherein the auristatin is MMAE and wherein the maytansinoid is maytansine.

That is, in a particular embodiment, the invention relates to a linker comprising the structure ARK-B, wherein B is a payload. It is to be understood that B may be any payload known in the art and/or disclosed herein. In certain embodiments, B may be a toxin. In certain embodiments, the payload B may be separated from the peptide ARK by a self-immolative moiety. Thus, the linker may comprise or consist of the structure ARK-(self-immolative moiety)-B, wherein B is a payload. In certain embodiments, the self-immolative moiety may be PABC or a methyl amine group. Thus, in certain embodiments, the linker may comprise or consist of the structure ARK-PABC-B. In certain embodiments, the linker may comprise or consist of the structure ARK-(NH)—(CH$_3$)—O—B, wherein O is the oxygen atom comprised in an ether bond and B is a hydroxyl-comprising payload. In certain embodiments, the linker may comprise or consist of the structure ARK-(NH)—(CH$_3$)—S—B, wherein S is the sulfur atom comprised in a thioether bond and B is a thiol-comprising payload. In certain embodiments, the payload may be an auristatin or a maytansinoid. In certain embodiments, the auristatin may be MMAE. In such embodiments, the linker may comprise or consist of the structure ARK-PABC-MMAE or ARK-MMAE. In certain embodiments, the maytansinoid may be maytansine. In such embodiments, the linker may comprise or consist of the structure ARK-PABC-maytansine or ARK-maytansine. In certain embodiments, the maytansinoid may be DM1 or a DM1 derivative. In such embodiments, the linker may comprise or consist of the structure ARK-(NH)—CH$_3$)—S-DM1. In certain embodiments, the payload may be a camptothecin. In such embodiments, the linker may comprise or consist of the structure ARK-(NH)—CH$_3$)—O-camptothecin.

In a particular embodiment, the invention relates to the linker construct according to the invention, wherein the linker construct consists of or comprises the structure RKR-(self-immolative moiety)-B. That is, the linker construct may comprise any self-immolative moiety known in the art and/or disclosed herein that is suitable for coupling a payload B to the C-terminus of a peptide. In certain embodiments, the payload B may be a toxin. The skilled person is aware toxins that can be coupled to the C-terminus of a peptide via a suitable self-immolative moiety. Preferably, the self-immolative moiety is any one of the self-immolative moieties disclosed herein, such as, without limitation, a PABC-based self-immolative linker, a PABE-based self-immolative linker or a methyl amine comprising self-immolative moiety.

In a particular embodiment, the invention relates to the linker construct according to the invention, wherein the linker construct consists of or comprises the structure B-(self-immolative moiety)-RKR. That is, the linker construct may comprise any self-immolative moiety that is known in the art and/or disclosed herein that is suitable for coupling a payload B to the N-terminus of a peptide. In certain embodiments, the payload B may be a toxin. The skilled person is aware toxins that can be coupled to the N-terminus of a peptide via a suitable self-immolative moiety. Preferably, the self-immolative moiety is any one of the self-immolative moieties disclosed herein, such as, without limitation, a self-immolative moiety comprising an OHPAS moiety.

In a particular embodiment, the invention relates to the linker construct according to the invention, wherein the linker construct consists of or comprises the structure B—RKR or RKR-B. That is, the payload B may be coupled directly to the N- or C-terminus of a peptide. In cases where the functional groups comprised in the payload are not compatible with the N- and/or C-terminus of a peptide, a linker molecule may be used to couple the payload to the N- and/or C-terminus of the peptide, respectively. Suitable linker molecules for coupling a payload to the N- or C-terminus of a peptide have been disclosed herein.

In a particular embodiment, the invention relates to the linker construct according to the invention, wherein the linker construct consists of or comprises the structure RKR-PABC-B, in particular wherein B is an auristatin or a maytansinoid, in particular wherein the auristatin is MMAE and wherein the maytansinoid is maytansine.

That is, in a particular embodiment, the invention relates to a linker comprising the structure RKR-B, wherein B is a payload. It is to be understood that B may be any payload known in the art and/or disclosed herein. In certain embodiments, B may be a toxin. In certain embodiments, the payload B may be separated from the peptide RKR by a self-immolative moiety. Thus, the linker may comprise or consist of the structure RKR-(self-immolative moiety)-B, wherein B is a payload. In certain embodiments, the self-immolative moiety may be PABC or a methyl amine group. Thus, in certain embodiments, the linker may comprise or consist of the structure RKR-PABC-B. In certain embodiments, the linker may comprise or consist of the structure RKR-(NH)—(CH$_3$)—O—B, wherein O is the oxygen atom comprised in an ether bond and B is a hydroxyl-comprising payload. In certain embodiments, the linker may comprise or consist of the structure RKR-(NH)—(CH$_3$)—S—B, wherein S is the sulfur atom comprised in a thioether bond and B is a thiol-comprising payload. In certain embodiments, the payload may be an auristatin or a maytansinoid. In certain embodiments, the auristatin may be MMAE. In such embodiments, the linker may comprise or consist of the structure RKR-PABC-MMAE or RKR-MMAE. In certain embodiments, the maytansinoid may be maytansine. In such embodiments, the linker may comprise or consist of the structure RKR-PABC-maytansine or RKR-maytansine. In certain embodiments, the maytansinoid may be DM1 or a DM1 derivative. In such embodiments, the linker may comprise or consist of the structure RKR-(NH)—CH$_3$)—S-DM1. In certain embodiments, the payload may be a camptothecin. In such embodiments, the linker may comprise or consist of the structure RKR-(NH)—CH$_3$)—O-camptothecin.

In a particular embodiment, the invention relates to the linker construct according to the invention, wherein the linker construct consists of or comprises the structure RK-Val-Cit-(self-immolative moiety)-B. That is, the linker construct may comprise any self-immolative moiety known in the art and/or disclosed herein that is suitable for coupling a payload B to the C-terminus of a peptide. In certain embodiments, the payload B may be a toxin. The skilled person is aware toxins that can be coupled to the C-terminus of a peptide via a suitable self-immolative moiety. Preferably, the self-immolative moiety is any one of the self-immolative moieties disclosed herein, such as, without limitation, a PABC-based self-immolative linker, a PABE-based self-immolative linker or a methyl amine comprising self-immolative moiety.

In a particular embodiment, the invention relates to the linker construct according to the invention, wherein the linker construct consists of or comprises the structure RK-Val-Cit-B. That is, the payload B may be coupled directly to the C-terminus of a peptide. In cases where the functional groups comprised in the payload are not compatible with the C-terminus of a peptide, a linker molecule may be used to couple the payload to the C-terminus of the peptide. Suitable linker molecules for coupling a payload to the C-terminus of a peptide have been disclosed herein.

In a particular embodiment, the invention relates to the linker construct according to the invention, wherein the linker construct consists of or comprises the structure RK-Val-Cit-PABC-B, in particular wherein B is an auristatin or a maytansinoid, in particular wherein the auristatin is MMAE and wherein the maytansinoid is maytansine.

That is, in a particular embodiment, the invention relates to a linker comprising the structure RK-Val-Cit-B, wherein B is a payload. It is to be understood that B may be any payload known in the art and/or disclosed herein. In certain embodiments, B may be a toxin. In certain embodiments, the payload B may be separated from the peptide RK-Val-Cit by a self-immolative moiety. Thus, the linker may comprise or consist of the structure RK-Val-Cit-(self-immolative moiety)-B, wherein B is a payload. In certain embodiments, the self-immolative moiety may be PABC or a methyl amine group. Thus, in certain embodiments, the linker may comprise or consist of the structure RK-Val-Cit-PABC-B. In certain embodiments, the linker may comprise or consist of the structure RK-Val-Cit-(NH)—(CH$_3$)—O—B, wherein O is the oxygen atom comprised in an ether bond and B is a hydroxyl-comprising payload. In certain embodiments, the linker may comprise or consist of the structure RK-Val-Cit- (NH)—(CH$_3$)—S—B, wherein S is the sulfur atom comprised in a thioether bond and B is a thiol-comprising payload. In certain embodiments, the payload may be an auristatin or a maytansinoid. In certain embodiments, the auristatin may be MMAE. In such embodiments, the linker may comprise or consist of the structure RK-Val-Cit-PABC-MMAE or RK-Val-Cit-MMAE. In certain embodiments, the maytansinoid may be maytansine. In such embodiments, the linker may comprise or consist of the structure RK-Val-Cit-PABC-maytansine or RK-Val-Cit-maytansine. In certain embodiments, the maytansinoid may be DM1 or a DM1 derivative. In such embodiments, the linker may comprise or consist of the structure RK-Val-Cit-(NH)—(CH$_3$)—S-DM1. In certain embodiments, the payload may be a camptothecin. In such embodiments, the linker may comprise or consist of the structure RK-Val-Cit-(NH)—(CH$_3$)—O-camptothecin.

In a particular embodiment, the invention relates to the antibody-linker conjugate or the antibody-drug conjugate according to the invention, wherein the antibody-linker conjugate or the antibody-drug conjugate comprises at least one toxin.

That is, the antibody-linker conjugate or the antibody-drug conjugate according to the invention comprises an antibody that is conjugated to at least one linker, wherein the one linker comprises at least one toxin. In certain embodiments, the antibody-linker conjugate or the antibody-drug conjugate comprises two linkers, wherein each heavy chain of the antibody is conjugated to one linker. In certain embodiments, the antibody-linker conjugate or the antibody-drug-conjugate comprises four linkers, wherein each heavy chain of the antibody is conjugated to two linkers. In such cases, each linker may contain one or more payloads, such as toxins.

In certain embodiments, the antibody-linker conjugate or the antibody-drug-conjugate according to the invention comprises two linkers, wherein each linker comprises one payload, for example a toxin. In other embodiments, the antibody-linker conjugate or the antibody-drug-conjugate according to the invention comprises two linkers, wherein each linker comprises two payloads, for example one toxin and one other payload or two identical or different toxins. In embodiments where the antibody-linker conjugate or the antibody-drug-conjugate comprises two linkers, it is preferred that the linkers are conjugated to residue Q295 of the two heavy chains of an IgG antibody. Even more preferably, the antibody is an IgG antibody that is glycosylated at residue N297.

In certain embodiments, the antibody-linker conjugate or the antibody-drug conjugate according to the invention comprises four linkers, wherein each linker comprises one payload, for example a toxin. In other embodiments, the antibody-linker conjugate or the antibody-drug-conjugate according to the invention comprises four linkers, wherein each linker comprises two payloads, for example one toxin and one other payload or two identical or different toxins. In embodiments where the antibody-linker conjugate or the antibody-drug-conjugate comprises four linkers, it is preferred that the linkers are conjugated to residues Q295 and N297Q of the two heavy chains of an IgG antibody.

In a particular embodiment, the invention relates to the antibody-linker conjugate or the antibody-drug-conjugate according to the invention, wherein the antibody-linker conjugate or the antibody-drug-conjugate comprises two different toxins.

In certain embodiments, the antibody-linker conjugate or the antibody-drug-conjugate according to the invention may comprise two different toxins. That is, in certain embodiments, the antibody-linker conjugate or the antibody-drug-conjugate may comprise two linkers, wherein each linker comprises two different toxins. Antibody-linker conjugates or the antibody-drug conjugates comprising two different toxins have the advantage that they may have increased cytotoxic activity. Such increased cytotoxic activity may be achieved by combining two toxins that target two different cellular mechanisms. For example, the antibody-linker conjugates or the antibody-drug-conjugates according to the invention may comprise a first toxin that inhibits cell division and a second toxin is a toxin that interferes with replication and/or transcription of DNA.

Accordingly, in a particular embodiment, the invention relates to the antibody-linker conjugate or the antibody-drug-conjugate according to the invention, wherein a first toxin is a toxin that inhibits cell division and a second toxin is a toxin that interferes with replication and/or transcription of DNA.

A toxin that inhibits cell division, such as an anti-mitotic agent or a spindle poison, is an agent that has the potential to inhibit or prevent mitotic division of a cell. A spindle poison is a poison that disrupts cell division by affecting the protein threads that connect the centromere regions of chromosomes, known as spindles. Spindle poisons effectively cease the production of new cells by interrupting the mitosis phase of cell division at the spindle assembly checkpoint (SAC). The mitotic spindle is composed of microtubules (polymerized tubulin) that aid, along with regulatory proteins; each other in the activity of appropriately segregating replicated chromosomes. Certain compounds affecting the mitotic spindle have proven highly effective against solid tumors and hematological malignancies.

Two specific families of antimitotic agents—vinca alkaloids and taxanes—interrupt the cell's division by the agitation of microtubule dynamics. The vinca alkaloids work by causing the inhibition of the polymerization of tubulin into microtubules, resulting in the G2/M arrest within the cell cycle and eventually cell death. In contrast, the taxanes arrest the mitotic cell cycle by stabilizing microtubules against depolymerization. Even though numerous other spindle proteins exist that could be the target of novel chemotherapeutics, tubulin-binding agents are the only types in clinical use. Agents that affect the motor protein kinesin are beginning to enter clinical trials. Another type, paclitaxel, acts by attaching to tubulin within existing microtubules. Preferred toxins that inhibit cell division within the present invention are auristatins, such as MMAE and MMAF, and maytansinoids, such as DM1, DM3, DM4 and/or DM21.

In a particular embodiment, the invention relates to the antibody-linker conjugate or the antibody-drug conjugate according to the invention, wherein at least one of the toxins is an auristatin or a maytansinoid.

Several agents that prevent the correct replication and/or transcription of DNA molecules and have been shown to be suitable in cancer treatment are known to the person skilled in the art. For example, antimetabolites such as nucleotide or nucleoside analogs which are misincorporated into newly formed DNA and/or RNA molecules are known in the art and have been summarized by Tsesmetzis et al, Cancers (Basel), 2018, 10(7): 240. Other toxins that are known to interfere with the replication and/or transcription of DNA are duoromycins.

Accordingly, in certain embodiments, the antibody-linker conjugate or the antibody-drug-conjugate according to the invention comprises two different toxins, wherein the first toxin is a duoromycin and wherein the second payload is an auristatin or a maytansinoid.

In certain embodiments, the invention relates to the antibody-linker conjugate or the antibody-drug-conjugate according to the invention, wherein the antibody-linker conjugate comprises two different auristatins.

One main advantage of antibody-linker conjugates or antibody-drug conjugates comprising two different toxins is that the antibody-linker conjugates or the antibody-drug conjugates may still act against target cells that have escaped the mechanism of action of one of the toxins and/or that the antibody-payload conjugate may have a higher efficacy against heterogenous tumors.

In a particular embodiment, the invention relates to the antibody-linker conjugate or the antibody-drug-conjugate according to the invention, wherein the antibody-linker conjugate comprises a toxin and an inhibitor of a drug efflux transporter.

In a particular embodiment, the invention relates to the antibody-linker conjugate or the antibody-drug conjugate according to the invention, wherein the antibody-linker conjugate or the antibody-drug conjugate comprises a toxin and a solubility increasing moiety.

That is, the antibody-linker conjugate or the antibody-drug conjugate may comprise two payloads, wherein the first payload is a toxin and the second payload is a solubility increasing moiety. Alternatively, an antibody-linker conjugate or an antibody-drug-conjugate may be obtained by clicking a toxin to an azide-comprising linking moiety of a linker and by clicking a maleimide-comprising solubility increasing moiety to a cysteine side chain of the same linker. Alternatively, the toxin and/or the solubility increasing moiety may be attached to the linker by chemical synthesis.

In a particular embodiment, the invention relates to the antibody-linker conjugate or the antibody-drug-conjugate according to the invention, wherein the antibody-linker conjugate comprises a toxin and an immunostimulatory agent.

As used herein and depending on context, the term "immunostimulatory agent" includes compounds that increase a subject's immune response to an antigen. Examples of immunostimulatory agents include immune stimulants and immune cell activating compounds. antibody-linker conjugates of the present invention may contain immunostimulatory agents that help program the immune cells to recognize ligands and enhance antigen presentation. Immune cell activating compounds include Toll-like receptor (TLR) agonists. Such agonists include pathogen associated molecular patterns (PAMPs), e.g., an infection-mimicking composition such as a bacterially-derived immunomodulator (a.k.a., danger signal) and damage associated molecular pattern (DAMPs), e.g. a composition mimicking a stressed or damaged cell. TLR agonists include nucleic acid or lipid compositions (e.g., monophosphoryl lipid A (MPLA)). In one example, the TLR agonist comprises a TLR9 agonist such as a cytosine-guanosine oligonucleotide (CpG-ODN), a poly(ethylenimine) (PEI)-condensed oligonucleotide (ODN) such as PEI-CpG-ODN, or double stranded deoxyribonucleic acid (DNA). In another example, the TLR agonist comprises a TLR3 agonist such as polyinosine-polycytidylic acid (poly (I:C)), PEI-poly (I:C), polyadenylic-polyuridylic acid (poly (A:U)), PEI-poly (A:U), or double stranded ribonucleic acid (RNA). Other exemplary vaccine immunostimulatory compounds include lipopolysaccharide (LPS), chemokines/cytokines, fungal beta-glucans (such as lentinan), imiquimod, CRX-527, and OM-174.

In a particular embodiment, the invention relates to the antibody-linker conjugate or the antibody-drug-conjugate according to the invention, wherein the antibody-linker conjugate or the antibody-drug-conjugate comprises two different immunostimulatory agents.

In a particular embodiment, the invention relates to the antibody-linker conjugate or the antibody-drug-conjugate according to the invention, wherein the at least one immunostimulatory agent is a TLR agonist.

The term "TLR agonist", as used herein, refers to a molecule which is capable of causing a signaling response through a TLR signaling pathway, either as a direct ligand or indirectly through generation of endogenous or exogenous. Agonistic ligands of TLR receptors are (i) natural ligands of the actual TLR receptor, or functionally equivalent variants thereof which conserve the capacity to bind to the TLR receptor and induce co-stimulation signals thereon, or (ii) an agonist antibody against the TLR receptor, or a functionally equivalent variant thereof capable of specifically binding to the TLR receptor and, more particularly, to the extracellular domain of said receptor, and inducing some of the immune signals controlled by this receptor and associated proteins. The binding specificity can be for the human TLR receptor or for a TLR receptor homologous to the human one of a different species.

In certain embodiments, the antibody-linker conjugate according to the invention may comprise one or more imaging agents. Thus, in a particular embodiment, the invention relates to the antibody-linker conjugate according to the invention, wherein the antibody-linker conjugate comprises a radionuclide and a fluorescent dye.

In a particular embodiment, the invention relates to the antibody-linker conjugate according to the invention, wherein the radionuclide is a radionuclide that is suitable for use in tomography, in particular single-photon emission computed tomography (SPECT) or positron emission tomography (PET), and wherein the fluorescent dye is a near-infrared fluorescent dye.

The term "radionuclide" as used herein has the same meaning as radioactive nuclide, radioisotope or radioactive isotope.

The radionuclide is preferably detectable by nuclear medicine molecular imaging technique(s), such as, Positron Emission Tomography (PET), Single Photon Emission Computed Tomography (SPECT), an hybrid of SPECT and/or PET or their combinations. Single Photon Emission Computed Tomography (SPECT) herein includes planar scintigraphy (PS).

An hybrid of SPECT and/or PET is for example SPECT/CT, PET/CT, PET/IRM or SPECT/IRM.

SPECT and PET acquire information on the concentration (or uptake) of radionuclides introduced into a subject's body. PET generates images by detecting pairs of gamma rays emitted indirectly by a positron-emitting radionuclide. A PET analysis results in a series of thin slice images of the body over the region of interest (e.g., brain, breast, liver, etc.). These thin slice images can be assembled into a three dimensional representation of the examined area. SPECT is similar to PET, but the radioactive substances used in SPECT have longer decay times than those used in PET and emit single instead of double gamma rays. Although SPECT images exhibit less sensitivity and are less detailed than PET images, the SPECT technique is much less expensive than PET and offers the advantage of not requiring the proximity of a particle accelerator. Actual clinical PET presents higher sensitivity and better spatial resolution than SPECT, and presents the advantage of an accurate attenuation correction due to the high energy of photons; so PET provides more accurate quantitative data than SPECT. Planar scintigraphy (PS) is similar to SPECT in that it uses the same radionuclides. However, PS only generates 2D-information.

SPECT produces computer-generated images of local radiotracer uptake, while CT produces 3-D anatomic images of X ray density of the human body. Combined SPECT/CT imaging provides sequentially functional information from SPECT and the anatomic information from CT, obtained during a single examination. CT data are also used for rapid and optimal attenuation correction of the single photon emission data. By precisely localizing areas of abnormal and/or physiological tracer uptake, SPECT/CT improves sensitivity and specificity, but can also aid in achieving accurate dosimetric estimates as well as in guiding interventional procedures or in better defining the target volume for external beam radiation therapy. Gamma camera imaging with single photon emitting radiotracers represents the majority of procedures.

The radionuclide may be selected in the group consisting of technetium-99m ($^{99m}$Tc), gallium-67 ($^{67}$Ga), gallium-68 ($^{68}$Ga) yttrium-90 ($^{90}$Y), indium-111 ($^{111}$In), rhenium-186 ($^{186}$Re), fluorine-18 ($^{18}$F), copper-64 ($^{64}$Cu), terbium-149 ($^{149}$Tb) or thallium-201 ($^{201}$Tl). The radionuclide may be comprised in a molecule or bound to a chelating agent.

In a particular embodiment, the invention relates to the use of a linker construct according to the invention in the production of an antibody-linker conjugate by means of a microbial transglutaminase.

That is, the linker construct described above may be used for the production of antibody-linker conjugates as described herein. Preferably, the antibody is an IgG antibody comprising the endogenous glutamine residue Q295 (EU numbering). In certain embodiments, the linker according to the invention is used for the production of antibody-linker conjugates by applying any of the reaction conditions disclosed herein.

Thus, in a particular embodiment, the invention relates to the use according to the invention, wherein the antibody is an IgG antibody, in particular an IgG1 antibody.

In a particular embodiment, the invention relates to the use according to the invention, wherein the antibody is Polatuzumab or Trastuzumab or Enfortumab.

Further, the invention relates to pharmaceutical compositions comprising the antibody-linker conjugate or the antibody-drug conjugate according to the invention.

Thus, in a particular embodiment, the invention relates to a pharmaceutical composition comprising
  a) the antibody-linker conjugate according to the invention, in particular wherein the antibody-linker conjugate comprises at least one payload;
  or
  b) the antibody drug-conjugate according to the invention; and
  the pharmaceutical composition comprising at least one pharmaceutically acceptable ingredient.

It is to be understood that the pharmaceutical composition may comprises an antibody-payload conjugate that has been produced with the one-step or two-step process disclosed herein.

The type of payload that is comprised in the antibody-payload construct comprised in the pharmaceutical composition depends on the use of the pharmaceutical composition. In embodiments where the pharmaceutical composition is used for the treatment of a disease, the payload is preferably a drug. If the disease is a neoplastic disease, the payload is preferably a toxin. In embodiments where the pharmaceutical composition is used in diagnostics, the payload is preferably an imaging agent.

Alternatively, the pharmaceutical may comprise an antibody-drug conjugate as disclosed herein. Pharmaceutical compositions comprising an antibody-drug conjugate are preferably used for the treatment of diseases.

In a particular embodiment, the invention relates to a pharmaceutical composition according to the invention comprising at least one additional therapeutically active agent.

The pharmaceutical composition according to the invention may comprise at least one pharmaceutically acceptable ingredient.

A pharmaceutically acceptable ingredient refers to an ingredient in a pharmaceutical formulation, other than an active ingredient, which is nontoxic to a subject. A pharmaceutically acceptable ingredient includes, but is not limited to, a buffer, excipient, stabilizer, or preservative.

Pharmaceutical formulations of the antibody-linker conjugates described herein are prepared by mixing such conjugates having the desired degree of purity with one or more optional pharmaceutically acceptable ingredients (Flemington's Pharmaceutical Sciences 16th edition, Oslo, A. Ed. (1980)), in the form of lyophilized formulations or aqueous solutions. Pharmaceutically acceptable ingredients are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn protein complexes); and/or non-ionic surfactants such as polyethylene glycol (PEG). Exemplary pharmaceutically acceptable ingredients herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. For example, a sHASEGP may be combined with one or more additional glycosaminoglycanases such as chondroitinases.

In a particular embodiment, the invention relates to the antibody-linker conjugate according to the invention, in particular wherein the antibody-linker conjugate comprises at least one payload, the antibody-drug conjugate according to the invention, or the pharmaceutical composition according to the invention for use in therapy and/or diagnostics.

That is, the antibody-linker conjugate, the antibody-drug conjugate or the pharmaceutical composition according to the invention may be used in the treatment of a subject or in diagnosing a disease or condition in a subject. An individual or subject is preferably a mammal. Mammals include, but are not limited to, domesticated animals (e.g., cows, sheep, cats, dogs, and horses), primates (e.g., humans and non human primates such as macaques), rabbits, and rodents (e.g., mice and rats). In certain embodiments, the individual or subject is a human. When an antibody-linker conjugate or a pharmaceutical composition comprising an antibody-linker conjugate according to the invention is used in therapy, it is preferred that the linker comprises a drug. When an antibody-linker conjugate or a pharmaceutical composition comprising an antibody-linker conjugate according to the invention is used in diagnostics, it is preferred that the linker comprises at least one imaging agent.

In a particular embodiment, the invention relates to the antibody-linker conjugate according to the invention, in particular wherein the antibody-linker conjugate comprises at least one payload, the antibody-drug conjugate according to the invention, or the pharmaceutical composition according to the invention for use in the treatment of a patient
    suffering from,
    being at risk of developing, and/or
    being diagnosed for
a neoplastic disease, a neurological disease, an autoimmune disease, an inflammatory disease or an infectious disease.

In a particular embodiment, the invention relates to the antibody-linker conjugate according to the invention, in particular wherein the antibody-linker conjugate comprises at least one payload, the antibody-drug conjugate according to the invention, or the pharmaceutical composition according to the invention for use in treatment of a patient suffering from a neoplastic disease.

The term "neoplastic disease" as used herein refers to a condition characterized by uncontrolled, abnormal growth of cells. Neoplastic diseases include cancer. Examples of cancer include but are not limited to, carcinoma, lymphoma, blastoma, sarcoma, and leukemia. More particular examples of such cancers include breast cancer, prostate cancer, colon cancer, squamous cell cancer, small-cell lung cancer, non-small cell lung cancer, ovarian cancer, cervical cancer, gastrointestinal cancer, pancreatic cancer, glioblastoma, liver cancer, bladder cancer, hepatoma, colorectal cancer, uterine cervical cancer, endometrial carcinoma, salivary gland carcinoma, kidney cancer, vulval cancer, thyroid cancer, hepatic carcinoma, skin cancer, melanoma, brain cancer, ovarian cancer, neuroblastoma, myeloma, various types of head and neck cancer, acute lymphoblastic leukemia, acute myeloid leukemia, Ewing sarcoma and peripheral neuroepithelioma. Preferred cancers include liver cancer, lymphoma, acute lymphoblastic leukemia, acute myeloid leukemia, Ewing sarcoma and peripheral neuroepithelioma.

That is, the antibody-linker conjugates or the antibody-drug conjugates according to the invention are preferably used for the treatment of cancer. As such, in certain embodiments, the antibody-linker conjugates or the antibody-drug conjugates according to invention comprise an antibody that specifically binds to an antigen that is present on a tumor cell. In certain embodiments, the antigen may be an antigen on the surface of a tumor cell. In certain embodiments, the antigen on the surface of the tumor cell may be internalized into the cell together with the antibody-linker conjugate upon binding of the antibody-linker conjugate to the antigen.

If the antibody-linker conjugate or the antibody-drug conjugate according to the invention is used in the treatment of cancer, it is preferred that the antibody-linker conjugate or the antibody-drug conjugate comprises at least one payload that has the potential to kill or inhibit the proliferation of the tumor cell to which the antibody-linker conjugate or the antibody-drug conjugate binds to. In certain embodiments, the at least one payload exhibits its cytotoxic activity after the antibody-linker conjugate or the antibody-drug conjugate has been internalized into the tumor cell. In certain embodiments, the at least one payload is a toxin.

The inflammatory disease may be an autoimmune disease. The infectious disease may be a bacterial infection or a viral infection.

In certain embodiments, the antibody-linker conjugate, the antibody-drug-conjugate and/or the pharmaceutical composition according to the invention may be used in the treatment of B-cell-associated cancer.

Thus, in a particular embodiment, the invention relates to the antibody-linker conjugate, the antibody-drug conjugate or the pharmaceutical composition for use according to the invention, wherein the antibody-linker conjugate or the antibody-drug conjugate comprised in the pharmaceutical composition comprises Polatuzumab and wherein the neoplastic disease is a B-cell associated cancer.

For this, it is preferred that the antibody-linker conjugate or the antibody-drug-conjugate comprises an anti-CD79b antibody as disclosed herein, preferably wherein the anti-CD79b antibody is internalized into a target cell upon binding to CD79b. In certain embodiments, the anti-CD79b antibody is Polatuzumab with a heavy chain as set forth in SEQ ID NO:5 and a light chain as set forth in SEQ ID NO:6. Further, it is preferred that the antibody-linker conjugate or the antibody-drug-conjugate comprises at least one toxin.

In certain embodiments, the anti-CD79b antibody comprised in the antibody-linker conjugate, the antibody-drug conjugate or the pharmaceutical composition may be conjugated to any one of the linkers shown in FIG. 1, 2, 3, 8, 9, 14 or 15 or any one of the linkers disclosed herein.

A B-cell associated cancer may be any one selected from a group consisting of: high, intermediate and low grade lymphomas (including B cell lymphoma such as, for example, mucosa-associated lymphoid tissue B cell lymphoma and non-Hodgkin's lymphoma(NHL), mantle cell lymphoma, Burkitt's lymphoma, small lymphocytic lymphoma, marginal Zone lymphoma, diffuse large B cell lymphoma, follicular lymphoma, and Hodgkin's lymphoma and T cell lymphomas) and leukemias (including secondary leukemia, chronic lymphocytic leukemia(CLL), such as B cell leukemia (CD5+ B lymphocytes), myeloid leukemia, such as acute myeloid leukemia, chronic myeloid leukemia, lymphoid leukemia, such as acute lymphoblastic leukemia (ALL) and myelodysplasia), and other hematological and/or B cell- or T-cell-associated cancers, including cancers of additional hematopoietic cells, including polymorphonuclear leukocytes, such as basophils, eosinophils, neutrophils and monocytes, dendritic cells, platelets, erythrocytes and natural killer cells. Also included are cancerous B cell proliferative disorders selected from the following: lymphoma, non-Hodgkins lymphoma(NHL) aggressive NHL, relapsed aggressive NHL, relapsed indolent NHL, refractory NHL, refractory indolent NHL, chronic lymphocytic leukemia (CLL), Small lymphocytic lymphoma, leukemia, hairy cell leukemia(HCL), acute lymphocytic leukemia (ALL), and mantle cell lymphoma.

In a particular embodiment, the invention relates to the antibody-linker conjugate, the antibody-drug conjugate or the pharmaceutical composition for use according to the invention, wherein the B-cell associated cancer is non-Hodgkin lymphoma, in particular wherein the B-cell associated cancer is diffuse large B-cell lymphoma.

Further, the anti-CD79b antibody-linker conjugate, the anti-CD79b antibody-drug conjugate and/or the pharmaceutical composition comprising an anti-CD79b antibody-linker conjugate or an anti-CD79b antibody-drug conjugate may be used in conjunction with other therapies that are suitable for the treatment of B-cell-associated cancer.

Thus, in a particular embodiment, the invention relates to the antibody-linker conjugate, the antibody-drug conjugate or the pharmaceutical composition for use according to the invention, wherein the antibody-linker conjugate, the antibody-drug conjugate or the pharmaceutical composition is administered in combination with bendamustine and/or rituximab.

It is to be understood that the antibody-linker conjugate, the antibody-drug conjugate or the pharmaceutical composition does not necessarily have to be administered at the same time as the additional therapeutic agent, such as bendamustine and/or rituximab. Instead the antibody-linker conjugate, the antibody-drug conjugate or the pharmaceutical composition may be administered with a different administration schedule and, consequently, on different days as other therapeutic agents that are used for the treatment of the same disease.

In certain embodiments, the antibody-linker conjugate, the antibody-drug-conjugate and/or the pharmaceutical composition according to the invention may be used in the treatment of HER2-positive cancers.

Thus, in a particular embodiment, the invention relates to the antibody-linker conjugate, the antibody-drug conjugate or the pharmaceutical composition for use according to the invention, wherein the antibody-linker conjugate or the antibody-drug conjugate comprised in the pharmaceutical composition comprises Trastuzumab and wherein the neoplastic disease is a HER2-positive cancer, in particular HER2-positive breast, gastric, ovarian or lung cancer.

For this, it is preferred that the antibody-linker conjugate or the antibody-drug-conjugate comprises an anti-HER2/neu antibody as disclosed herein, preferably wherein the anti-HER2/neu antibody is internalized into a target cell upon binding to HER2/neu. In certain embodiments, the anti-HER2/neu antibody is Trastuzumab with a heavy chain as set forth in SEQ ID NO:7 and a light chain as set forth in SEQ ID NO:8. Further, it is preferred that the antibody-linker conjugate or the antibody-drug-conjugate comprises at least one toxin.

In certain embodiments, the anti-HER2/neu antibody comprised in the antibody-linker conjugate, the antibody-drug conjugate or the pharmaceutical composition may be conjugated to any one of the linkers shown in FIG. 1, 2, 3, 8, 9, 14 or 15 or any one of the linkers disclosed herein.

A HER2-positive cancer, as used herein, may be, without limitation HER2-positive breast, gastric, ovarian or lung cancer. The skilled person is able do determine whether a cancer is a HER2-positive cancer. For example, tumor cells may be isolated in a biopsy and the presence of HER2/neu may be determined with any method known in the art.

Further, the anti-HER2/neu antibody-linker conjugate, the anti-HER2/neu antibody-drug conjugate and/or the pharmaceutical composition comprising an anti-HER2/neu antibody-linker conjugate or an anti-HER2/neu antibody-drug conjugate may be used in conjunction with other therapies that are suitable for the treatment of HER2-positive cancers.

Thus, in a particular embodiment, the invention relates to the antibody-linker conjugate, the antibody-drug conjugate or the pharmaceutical composition for use according to the invention, wherein the antibody-linker conjugate, the antibody-drug conjugate or the pharmaceutical composition is administered in combination with lapatinib, capecitabine and/or a taxane.

It is to be understood that the antibody-linker conjugate, the antibody-drug conjugate or the pharmaceutical composition does not necessarily have to be administered at the same time as the additional therapeutic agent, such as lapatinib, capecitabine and/or a taxane. Instead the antibody-linker conjugate, the antibody-drug conjugate or the pharmaceutical composition may be administered with a different administration schedule and, consequently, on different days as other therapeutic agents that are used for the treatment of the same disease.

In certain embodiments, the antibody-linker conjugate, the antibody-drug-conjugate and/or the pharmaceutical composition according to the invention may be used in the treatment of Nectin-4-positive cancers.

Thus, in a particular embodiment, the invention relates to the antibody-linker conjugate, the antibody-drug conjugate or the pharmaceutical composition for use according to the invention, wherein the antibody-linker conjugate or the antibody-drug conjugate comprised in the pharmaceutical composition comprises Enfortumab or an Enfortumab variant and wherein the neoplastic disease is a Nectin-4 positive cancer, in particular Nectin-4 positive pancreatic cancer, lung cancer, bladder cancer or breast cancer.

For this, it is preferred that the antibody-linker conjugate or the antibody-drug-conjugate comprises an anti-Nectin-4 antibody as disclosed herein, preferably wherein the anti-Nectin-4 antibody is internalized into a target cell upon binding to Nectin-4. In certain embodiments, the anti-Nectin-4 antibody is Enfortumab with a heavy chain as set forth in SEQ ID NO:9 and a light chain as set forth in SEQ ID NO:10. Further, it is preferred that the antibody-linker conjugate or the antibody-drug-conjugate comprises at least one toxin.

In certain embodiments, the anti-Nectin-4 antibody comprised in the antibody-linker conjugate, the antibody-drug conjugate or the pharmaceutical composition may be conjugated to any one of the linkers shown in FIG. 1, 2, 3, 8, 9, 14 or 15 or any one of the linkers disclosed herein.

A Nectin-4-positive cancer, as used herein, may be, without limitation Nectin-4-positive pancreatic cancer, lung cancer, bladder cancer or breast cancer. The skilled person is able do determine whether a cancer is a Nectin-4-positive cancer. For example, tumor cells may be isolated in a biopsy and the presence of Nectin-4 may be determined with any method known in the art.

Further, the anti-Nectin-4 antibody-linker conjugate, the anti-Nectin-4 antibody-drug conjugate and/or the pharmaceutical composition comprising an anti-Nectin-4 antibody-linker conjugate or an anti-Nectin-4 antibody-drug conjugate may be used in conjunction with other therapies that are suitable for the treatment of Nectin-4-positive cancers.

Thus, in a particular embodiment, the invention relates to the antibody-linker conjugate, the antibody-drug conjugate or the pharmaceutical composition for use according to the invention, wherein the antibody-linker conjugate, the antibody-drug conjugate or the pharmaceutical composition is administered in combination with a cisplatin-based chemotherapeutic agent and/or Pembrolizumab.

It is to be understood that the antibody-linker conjugate, the antibody-drug conjugate or the pharmaceutical composition does not necessarily have to be administered at the same time as the additional therapeutic agent, such as the cisplatin-based chemotherapeutic agent and/or Pembrolizumab. Instead the antibody-linker conjugate, the antibody-drug conjugate or the pharmaceutical composition may be administered with a different schedule and, consequently, on different days as other therapeutic agents that are used for the treatment of the same disease.

In a particular embodiment, the invention relates to the use of the antibody-linker conjugate according to the invention, in particular wherein the antibody-linker conjugate comprises at least one payload, the antibody-drug conjugate according to the invention, or the pharmaceutical composition according to the invention for the manufacture of a medicament for the treatment of a patient suffering from, being at risk of developing, and/or being diagnosed for a neoplastic disease, neurological disease, an autoimmune disease, an inflammatory disease or an infectious disease.

In a particular embodiment, the invention relates to a method of treating or preventing a neoplastic disease, said method comprising administering to a patient in need thereof the antibody-linker conjugate according to the invention, in particular wherein the antibody-linker conjugate comprises at least one payload, the antibody-drug conjugate according to the invention, or the pharmaceutical composition according to the invention.

In a particular embodiment, the invention relates to the antibody-linker conjugate according to the invention, in particular wherein the antibody-linker conjugate comprises at least one payload, the antibody-drug conjugate according to the invention, or the pharmaceutical composition according to the invention for use in pre-, intra- or post-operative imaging.

That is, the antibody-linker conjugate according to the invention may be used in medical imaging. For that, the antibody-linker conjugate may be visualized while binding to a specific target molecule, cell or tissue. Different techniques are known in the art to visualize particular payloads. For example, if the payload is a radionuclide, the molecules, cells, or tissues to which the antibody-linker conjugate binds may be visualized by PET or SPECT. If the payload is a fluorescent dye, the molecules, cells, or tissues to which the antibody-linker conjugate binds may be visualized by fluorescence imaging. In certain embodiments, the antibody-linker conjugate according to the invention comprises two different payloads, for example a radionuclide and a fluorescent dye. In this case, the molecule, cell or tissue to which the antibody-linker conjugate binds may be visualized using two different and/or complementary imaging techniques, for example PET/SPECT and fluorescence imaging.

The antibody-linker conjugate may be used for pre- intra- and/or post-operative imaging.

Pre-operative imaging encompasses all imaging techniques that may be performed before a surgery to make specific target molecules, cells or tissues visible when diagnosing a certain disease or condition and, optionally, to provide guidance for a surgery. Preoperative imaging may comprise a step of making a tumor visible by PET or SPECT before a surgery is performed by using an antibody-linker conjugate that comprises an antibody that specifically binds to an antigen on the tumor and is conjugated to a payload that comprises a radionuclide.

Intra-operative imaging encompasses all imaging techniques that may be performed during a surgery to make specific target molecules, cells or tissues visible and thus provide guidance for the surgery. In certain embodiments, an antibody-linker conjugate comprising a near-infrared fluorescent dye may be used to visualize a tumor during surgery by near-infrared fluorescent imaging. Intraoperative imaging allows the surgeon to identify specific tissues, for example tumor tissue, during surgery and thus may allow complete removal of tumor tissue.

Post-operative imaging encompasses all imaging techniques that may be performed after a surgery to make specific target molecules, cells or tissues visible and to evaluate the result of the surgery. Post-operative imaging may be performed similarly as pre-operative surgery.

In certain embodiments, the invention relates to antibody-linker conjugates comprising two or more different payloads. For example, the antibody-linker conjugate may comprise a radionuclide and a near-infrared fluorescent dye. Such an antibody-payload conjugate may be used for imaging by PET/SPECT and near-infrared fluorescent imaging. The advantage of such an antibody is that it may be used to visualize the target tissue, for example a tumor before and after a surgery by PET or SPECT. At the same time, the tumor may be visualized during the surgery by near-fluorescent infrared imaging.

In a particular embodiment, the invention relates to the antibody-linker conjugate according to the invention, in particular wherein the antibody-linker conjugate comprises at least one payload, the antibody-drug conjugate according to the invention, or the pharmaceutical composition according to the invention for use in intraoperative imaging-guided cancer surgery.

As mentioned above, the antibody-linker conjugate of the invention may be used to visualize a target molecule, cell or tissue and to guide a surgeon or robot during a surgery. That is, the antibody-linker conjugate may be used to visualize tumor tissue during a surgery, for example by near-infrared imaging and to allow complete removal of the tumor tissue.

The antibody-linker conjugate, the antibody-drug conjugate or the pharmaceutical composition according to the invention may be administered to the human or animal subject in an amount or dosage that efficiently treats a disease or is sufficient for diagnostic purposes.

The antibody-linker conjugate, the antibody-drug conjugate or the pharmaceutical composition according to the invention may be administered by any suitable means, including parenteral, intrapulmonary, and intranasal, and, if desired for local treatment, intralesional, intrauterine or intravesical administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

The antibody-linker conjugate, the antibody-drug conjugate or the pharmaceutical composition according to the invention may be formulated, dosed, and administered in a fashion consistent of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody-linker conjugate, the antibody-drug conjugate or the pharmaceutical composition according to the invention need not be, but is optionally formulated with one or more agents currently used to prevent or treat the disorder in question. The effective amount of such other agents depends on the amount of antibody-linker conjugate present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of the antibody-linker conjugate, the antibody-drug conjugate or the pharmaceutical composition according to the invention (when used alone or in combination with one or more other additional therapeutic agents) will depend on the type of disease to be treated, the type of antibody-payload conjugate, the severity and course of the disease, whether the antibody-linker conjugate is administered for preventive or therapeutic purposes, previous therapy, the patient's clinical history and response to the antibody-linker conjugate, and the discretion of the attending physician. The antibody-linker conjugate, the antibody-drug conjugate or the pharmaceutical composition according to the invention is suitably administered to the patient at one time or over a series of treatments.

EXAMPLES

Example 1: Conjugation of Peptide-MMAE Linkers to Two Different Antibodies

Methods

The antibody trastuzumab was commercially available (Herceptin®, Roche, bought from a pharmacy), as well as all linker-payload constructs (custom synthesized by Levena Biopharma). Polatuzumab with heavy and light chain consisting of the sequences of SEQ ID NOs: 5 and 6 were transiently transfected into suspension-adapted CHO-K1 cells and expressed in serum-free/animal component-free media. The proteins were purified from the supernatants by Protein A affinity chromatography (Mab Select Sure column; GE Healthcare).

Figure 13:
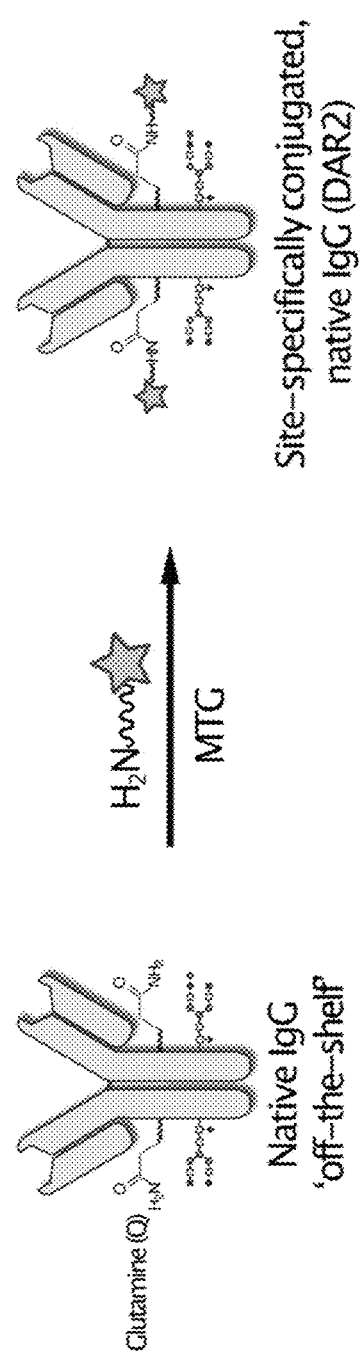
FIG. 13 shows schematically the one-step conjugation process.

For the 1-step conjugation (see FIG. 13), 5 mg/ml of native, glycosylated monoclonal antibody in 50 mM Tris pH 7.6, microbial transglutaminase (MTG, Zedira) at a concentration of 5 U/mg in 50 mM Tris pH 7.6 or water, and 5 molar equivalents of the indicated linker-payload were used and incubated for 24 hours at 37° C. in a rotating thermomixer. Conjugation efficiency was assessed by LC-MS under DTT reduced conditions. Reduction of samples was achieved by incubation of antibody-drug-conjugates (ADCs) for 10 min at 37° C. in in 50 mM DTT/50 mM Tris buffer. Probes were analyzed in a Xevo G2-XS QTOF (Waters) coupled to an Acquity UPLC H-Class System (Waters) and a ACQUITY UPLC BEH C18 Column. Conjugation efficiency was calculated from deconvoluted spectra and presented in % linker-payload conjugated antibody (=ADC). Intensities resulting from both glycoforms (G1F and G0F) were taken into account for the calculation of total conjugation efficiency, i.e., Total Conjugation efficiency (%)=total intensity−% intensity of unconjugated antibody, leading to the following formula:

Conjugation efficiency (%)=100*(1−(intensity(G1F)+intensity(G0F))/total intensity))

Results

The conjugation efficiency varied depending on the linker structure and antibody used, however, it could be observed that conjugation efficiency was highest when the lysine containing peptide linkers comprised an RK motif (Tables 3 and 4).

TABLE 3

Conjugation efficiency of linker-payload complexes (according to this invention) are shown

Figure 1:
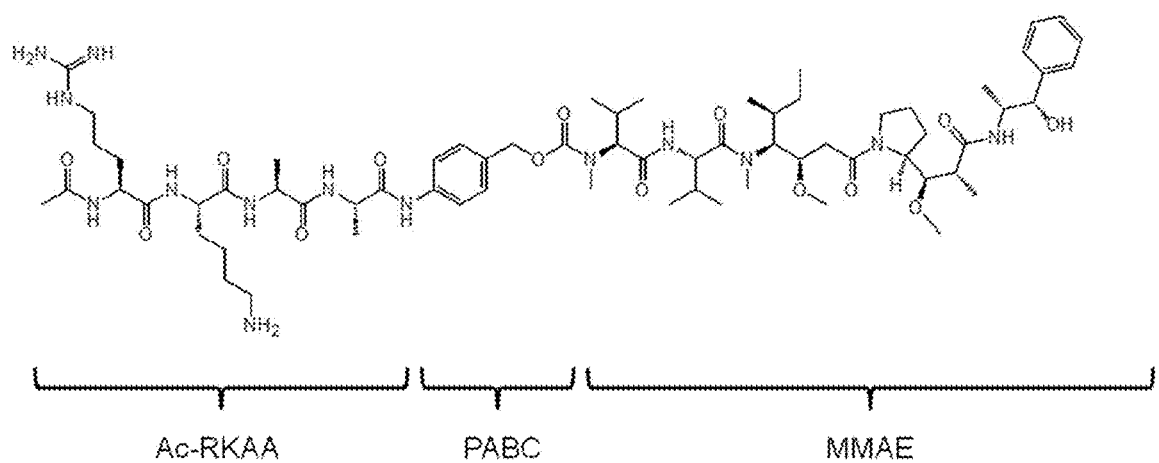
FIG. 1 shows the chemical structure of RKAA-MMAE linker-payload complex according to this invention, wherein the N-terminally protected Ac-RKAA peptide is covalently linked to PABC and MMAE.
Figure 2:
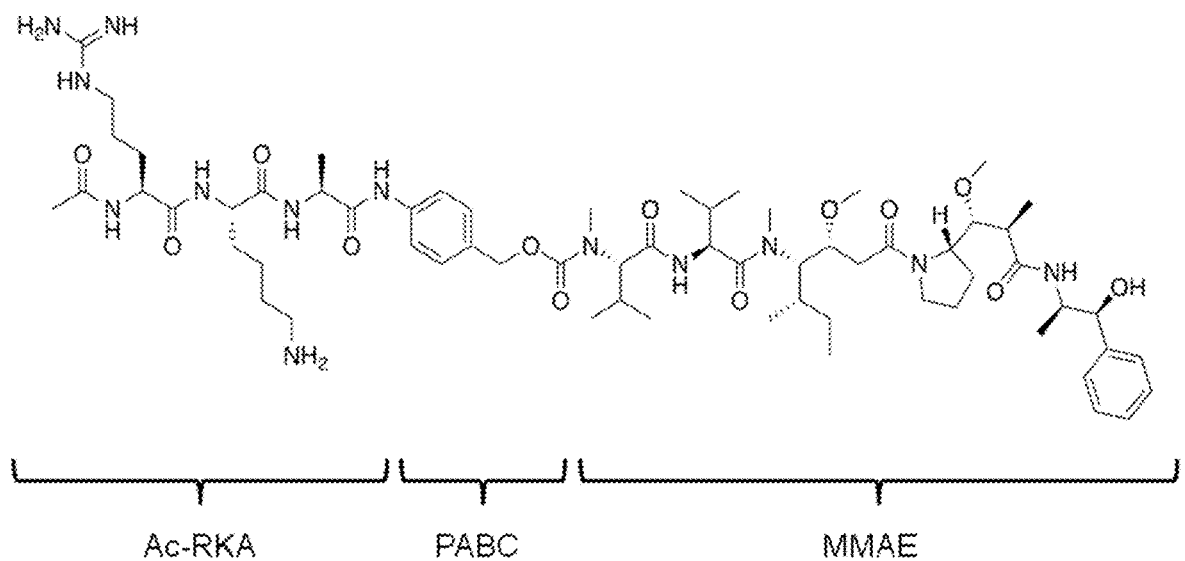
FIG. 2 shows the chemical structure of RKA-MMAE linker-payload complex according to this invention, wherein the N-terminally protected Ac-RKA peptide is covalently linked to PABC and MMAE.
Figure 3:
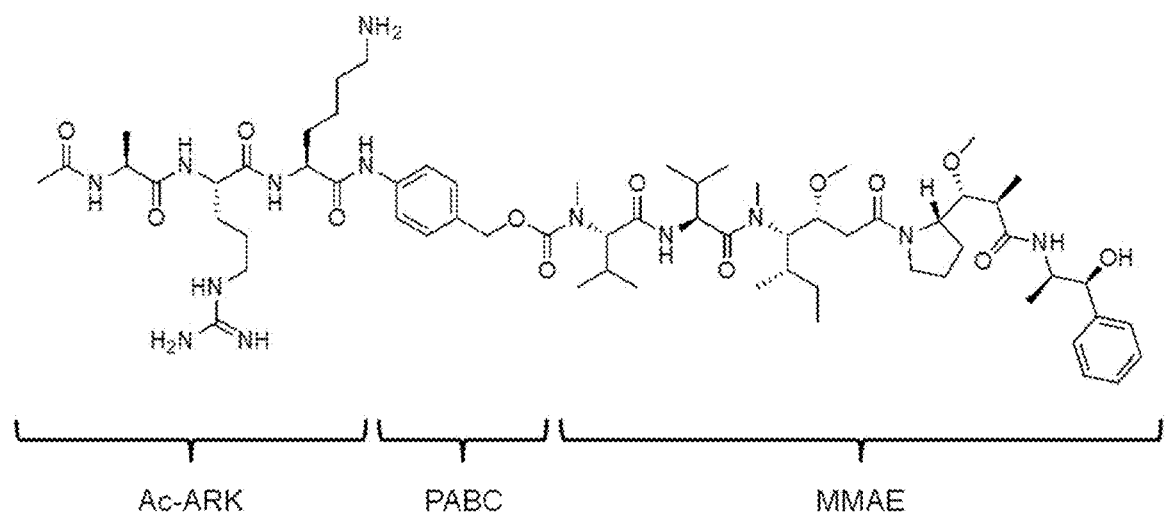
FIG. 3 shows the chemical structure of ARK-MMAE linker-payload complex according to this invention, wherein the N-terminally protected Ac-ARK peptide is covalently linked to PABC and MMAE.

| Linker-payload (according to this invention) | Conjugation efficiency (%) to antibody trastuzumab | Conjugation efficiency (%) to antibody polatuzumab |
|---|---|---|
| RKAA-MMAE (FIG. 1) | 100% | 89% |
| RKA-MMAE (FIG. 2) | 100% | 93% |
| ARK-MMAE (FIG. 3) | 100% | 94% |

TABLE 4

Conjugation efficiency of linker-payload (NOT according to this invention) complexes are shown

Figure 4:
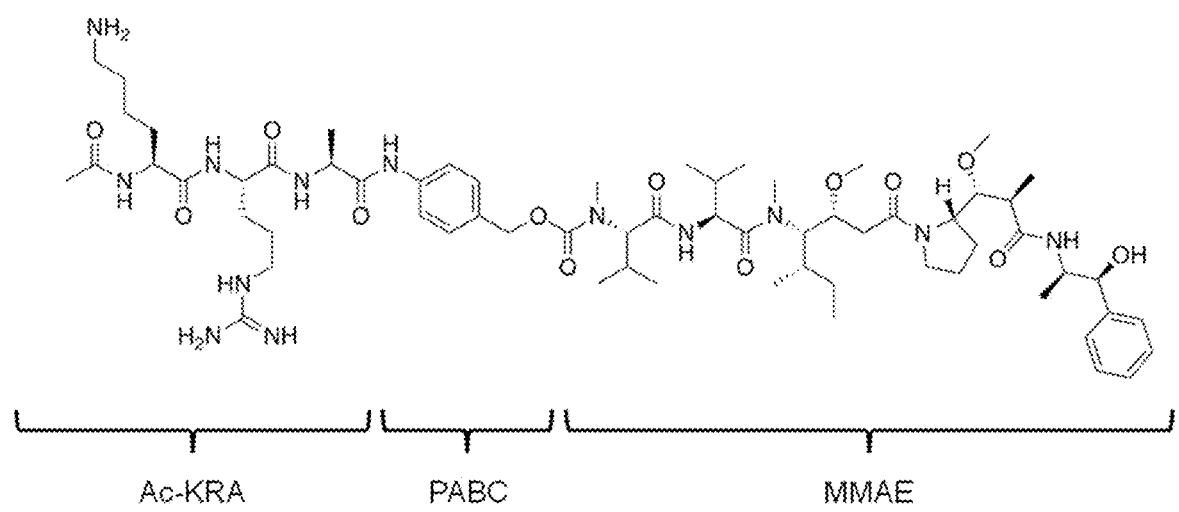
FIG. 4 shows the chemical structure of KRA-MMAE linker-payload complex (not according to this invention), wherein the N-terminally protected Ac-KRA peptide is covalently linked to PABC and MMAE.
Figure 5:
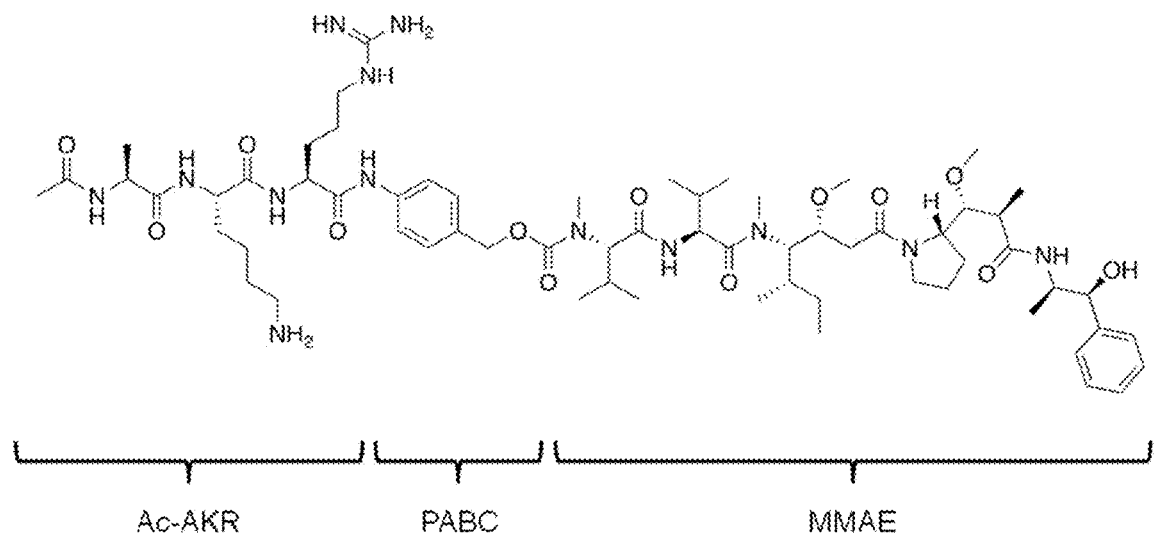
FIG. 5 shows the chemical structure of AKR-MMAE linker-payload complex (not according to this invention), wherein the N-terminally protected Ac-AKR peptide is covalently linked to PABC and MMAE.
Figure 6:
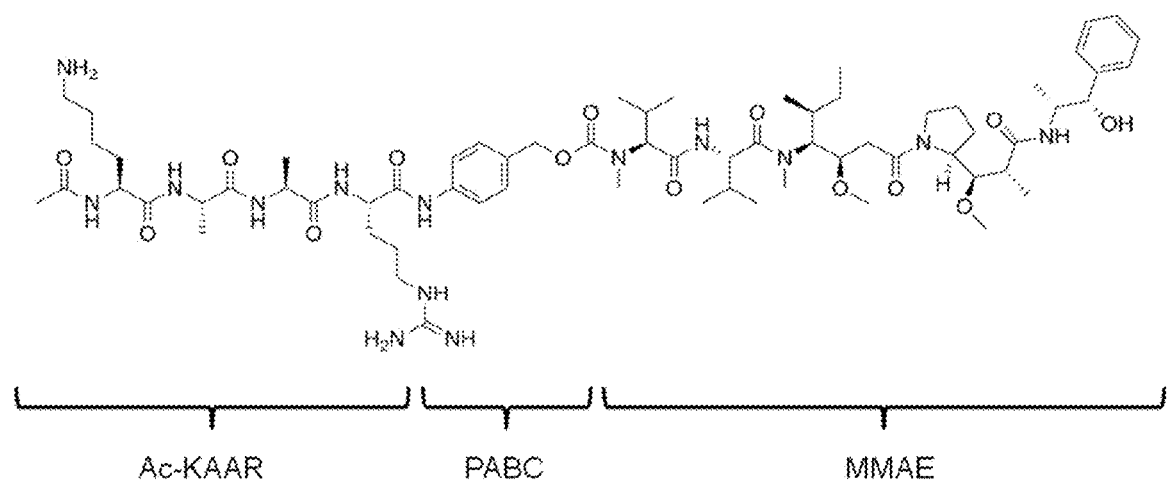
FIG. 6 shows the chemical structure of KAAR-MMAE linker-payload complex (not according to this invention), wherein the N-terminally protected Ac-KAAR peptide is covalently linked to PABC and MMAE.
Figure 7:
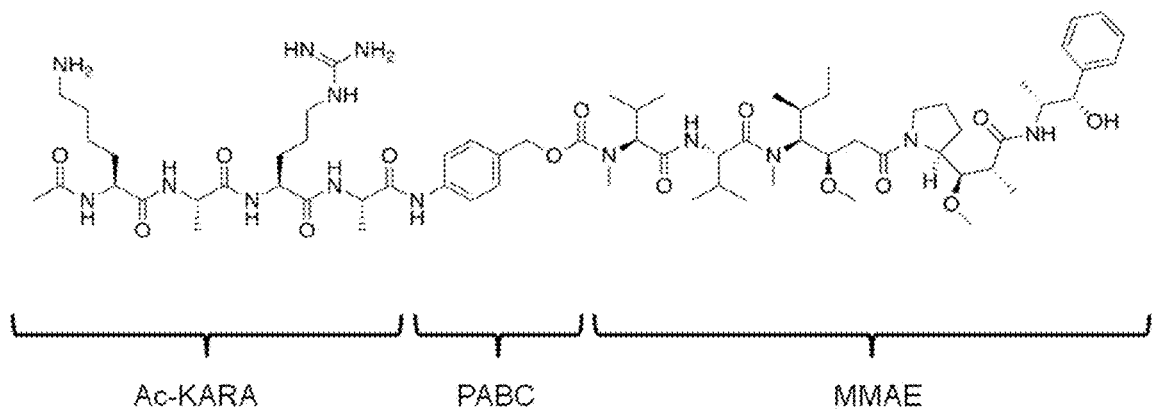
FIG. 7 shows the chemical structure of KARA-MMAE linker-payload complex (not according to this invention), wherein the N-terminally protected Ac-KARA peptide is covalently linked to PABC and MMAE.

| Linker-payload (NOT according to this invention) | Conjugation efficiency (%) to antibody trastuzumab | Conjugation efficiency (%) to antibody polatuzumab |
|---|---|---|
| KRA-MMAE (FIG. 4) (SEQ ID NO: 50) | 43% | 49% |
| AKR-MMAE (FIG. 5) (SEQ ID NO: 51) | 68% | 27% |
| KAAR-MMAE (FIG. 6) (SEQ ID NO: 52) | 64% | 28% |
| KARA-MMAE (FIG. 7) (SEQ ID NO: 53) | 77% | 65% |

Example 2: Conjugation of Peptide-Maytansine to Two Different Antibodies

In order to demonstrate that high conjugation efficiencies could be achieved also with another payload, ie, other than MMAE, maytansine containing linker-payload constructs were used for conjugation to two different antibodies.

Methods

The conjugations were performed exactly the same way as described in Example 1. The corresponding maytansine-linker constructs were custom synthesized by Levena Biopharm.

Results

When using a different payload than MMAE, in this example maytansine, the conjugation efficiency was also very high when the lysine containing peptide linkers comprised an RK motif (table 4). This example shows that irrespective of the payload the conjugation efficiency is high when the lysine containing peptide linkers comprises an RK motif.

TABLE 5

Figure 8:
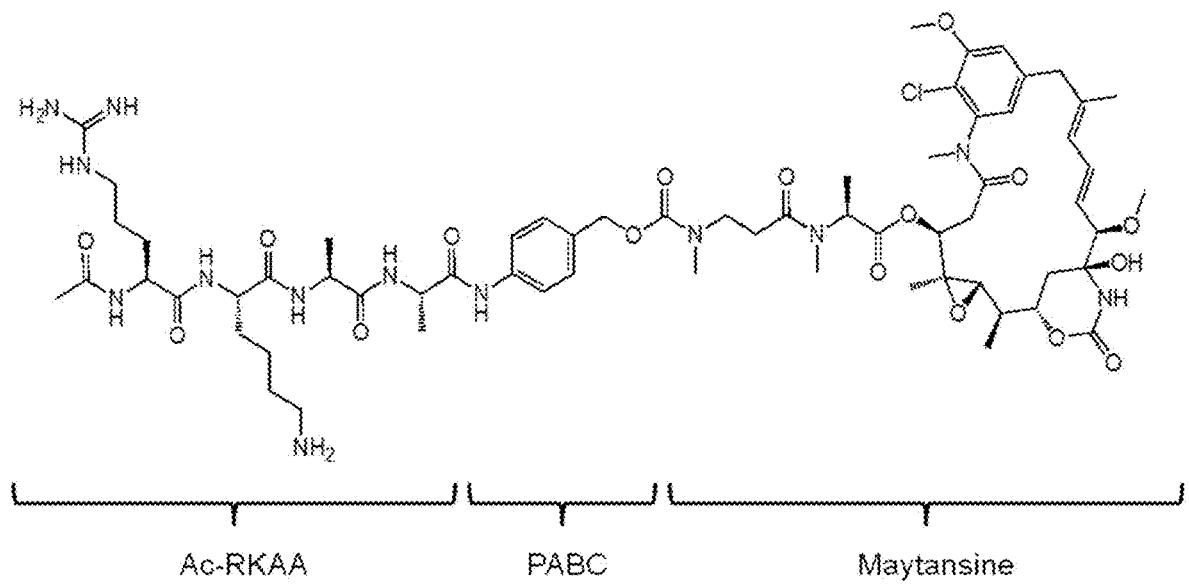
FIG. 8 shows the chemical structure of RKAA-maytansine linker-payload complex according to this invention, wherein the N-terminally protected Ac-RKAA peptide is covalently linked to PABC and maytansine.
Figure 9:
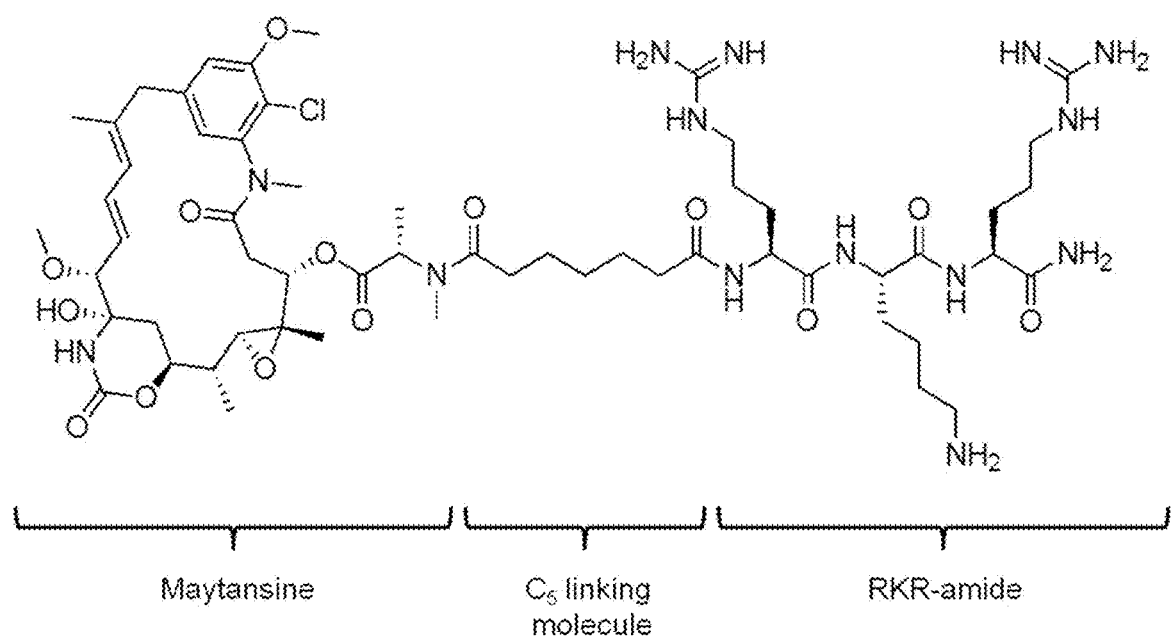
FIG. 9 shows the chemical structure of maytansine-RKR linker-payload complex according to this invention, wherein maytansine is covalently linked to a C4-alkyl-amide spacer connected to RKR peptide (having a C-terminal amide protecting group).

| Conjugation efficiency of linker-payload complexes (according to this invention) are shown | | |
|---|---|---|
| Linker-payload (according to this invention) | Conjugation efficiency (%) to antibody trastuzumab | Conjugation efficiency (%) to antibody polatuzumab |
| RKAA-maytansine (FIG. 8) | 92% | 82% |
| Maytansine-RKR (FIG. 9) | 96% | 95% |

Example 3: Conjugation of Linker-Payloads (According to this Invention) to a Third Antibody In order to further demonstrate the high conjugation efficiency obtained with linker-payload constructs (according to this invention) a third antibody was chosen and successfully conjugated with high efficiency (for two different payloads, further demonstrating the universal applicability).

Methods

The conjugations were performed exactly the same way as described in Example 1. The antibody Enfortumab with heavy chain consisting of the sequence of SEQ ID NO: 9 and light chain variant consisting of the sequence of SEQ ID NO: 10 were transiently transfected into suspension-adapted CHO-K1 cells and expressed in serum-free/animal component-free media. The proteins were purified from the supernatants by Protein A affinity chromatography (Mab Select Sure column; GE Healthcare).

Results

High conjugation efficiencies were obtained with the antibody Enfortumab using two different linker-payload constructs according to this invention.

TABLE 6

| Conjugation efficiency of linker-payload complexes (according to this invention) are shown | |
|---|---|
| Linker-payload (according to this invention) | Conjugation efficiency (%) to antibody Enfortumab |
| RKAA-MMAE (FIG. 1) | 91% |
| RKAA-maytansine (FIG. 8) | 97% |

Example 4: Conjugation of Linker-Payloads (According to this Invention) Comprising Non-Amino Acid Spacers In order to further demonstrate the high conjugation efficiency obtained with linker-payload constructs (according to this invention), linkers having polyethelene glycol (PEG) spacers were used and conjugated to two different antibodies with high efficiency.

Methods

The conjugations were performed exactly the same way as described in Example 1. All linker-payload constructs were custom synthesized by Levena Biopharma.

Results

High conjugation efficiencies to two different antibodies were obtained with linker-payloads (according to this invention) comprising PEG spacers.

TABLE 7

Figure 14:
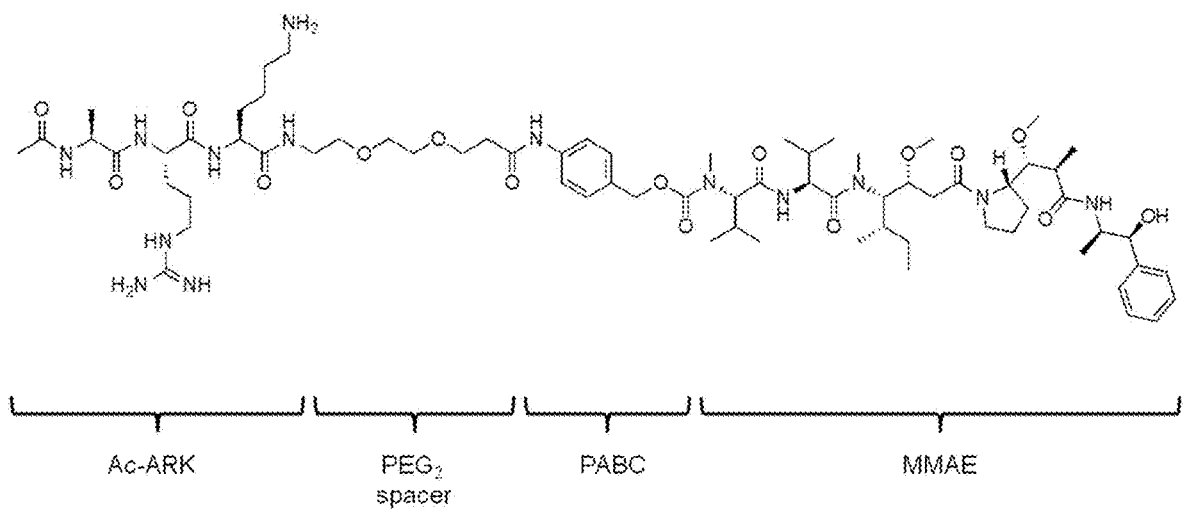
FIG. 14 shows the chemical structure of ARK-PEG2-PABC-MMAE linker-payload complex according to this invention, wherein the N-terminally protected Ac-ARK peptide is covalently linked to a PEG2 spacer and PABC-MMAE payload.
Figure 15:
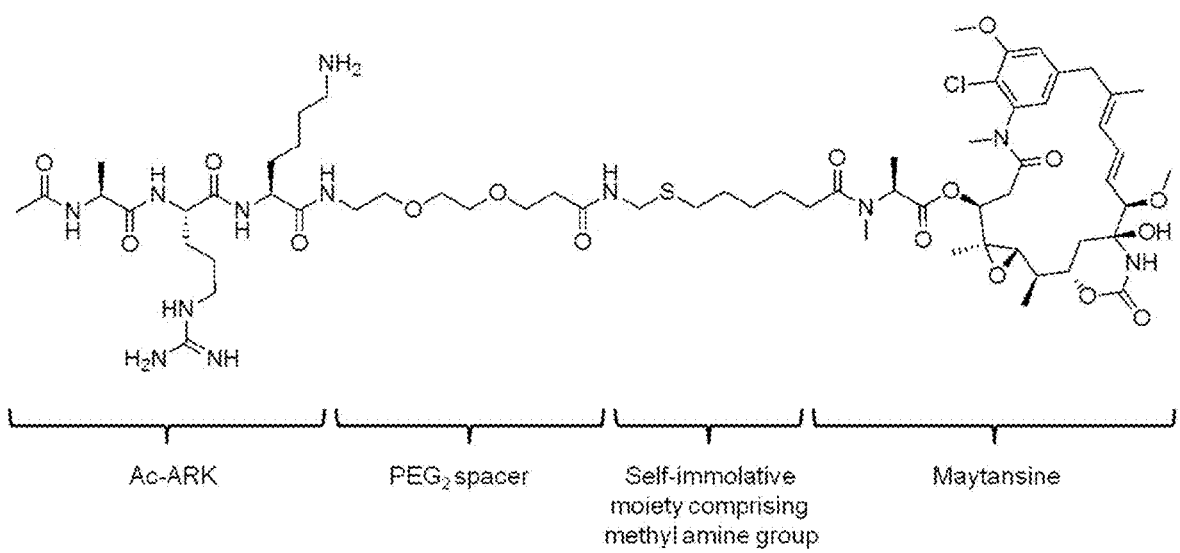
FIG. 15 shows the chemical structure of ARK-PEG2-(NH)—(CH$_3$)—S—C4-maytansine linker-payload complex according to this invention, wherein the N-terminally protected Ac-ARK peptide is covalently linked to a PEG2-(NH)—(CH$_3$)—S—C4 alkyl spacer and the maytansine payload.

| Conjugation efficiency of linker-payload complexes (according to this invention) are shown | | |
|---|---|---|
| Linker-payload (according to this invention) | Conjugation efficiency (%) to antibody trastuzumab | Conjugation efficiency (%) to antibody polatuzumab |
| ARK-PEG2-PABC-MMAE (FIG. 14) | 99% | 92% |
| ARK-PEG2-S-C4-maytansine (FIG. 15) | 99% | 90% |

Example 5: ADCs of the Invention are Monomeric and do not Aggregate

The linker-payload RKAA-PABC-MMAE (FIG. 1) was conjugated to the antibody Polatuzumab (SEQ ID NOs: 5 and 6) as described in Example 1 above. The resulting ADC termed ARA-01-RKAA-PABC-MMAE had a drug-to-antibody ratio (DAR) of 1.9 (determined using standard mass spectrometry methodologies essentially as described in Richard Y. C. Huang and Guodong Chen (2016) Characterization of antibody-drug conjugates by mass spectrometry: advances and future trends, Drug Discover Today Volume 21, Number 5) was analyzed by size exclusion chromatography.

Methods

Size exclusion chromatography (SEC) was performed using an ÄKTA FPLC (Amersham Pharmacia Biotech) with a Superdex™ 200 Increase 10/300 (Amersham Pharmacia Biotech) column. Proteins were detected with UV/VIS at a wavelength of 280 nm. Samples were analyzed at a flow rate of 1 mL/min in a 50 mM phosphate, 100 mM NaCl, pH 7.4 running buffer.

Results

Figure 10:
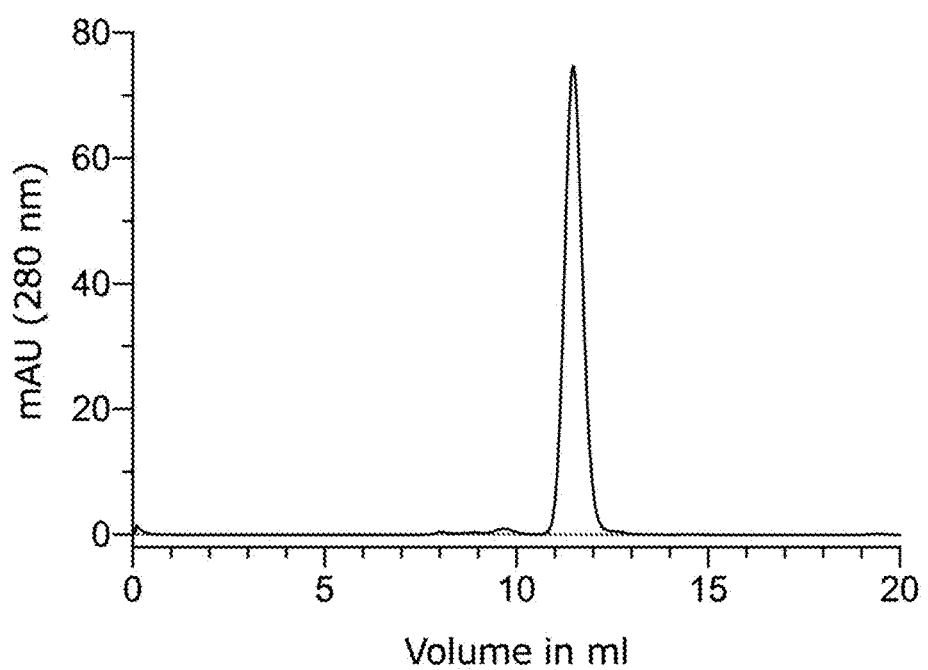
FIG. 10 shows the size exclusion chromatogram (SEC) of the antibody-drug conjugate ARA-01-RKAA-PABC-MMAE of the invention.

Size exclusion chromatography (SEC) profiles after purification demonstrated that ARA-01-RKAA-MMAE eluted as single, monomeric peak showing that the ADC has excellent biophysical properties (FIG. 10).

Example 6: ADCs of the Invention Show Potent Anti-Tumor Effects In Vitro

Methods

The growth inhibitory effect of ARA01-RKAA-PABC-MMAE was investigated in vitro on the following three CD79b over-expressing cell lines: Granta-519 (DSMZ, Acc No: 342), BJAB (CLS) and WSU-DLCL2 (DSMZ, ACC 575). As a negative control the CD79 negative cell line HT (ATCC, Ref: CRL-2260) was used. 4000 cells were seeded into 96-well culture plates and incubated with ARA-01-RKAA-PABC-MMAE for 72 hours at 37° C. in a humidified chamber and 5% $CO_2$.

The viability of the treated cultures was determined by ATP-quantification in a CellTiterGloLuminescence Assay as described by the supplier (Promega). The % viability relative to untreated cells was calculated according to the formula:

$$\% \text{ viability} = \left( \frac{OD_{experimental} - OD_{blank}}{OD_{untreated} - OD_{blank}} \right) \times 100$$

The average % viability was plotted against $\log_{10}$(concentration), and the resulting dose-response curves were analyzed by nonlinear regression with the software Prism8, using a four parameter dose-response curve equation.

Results

Figure 11:
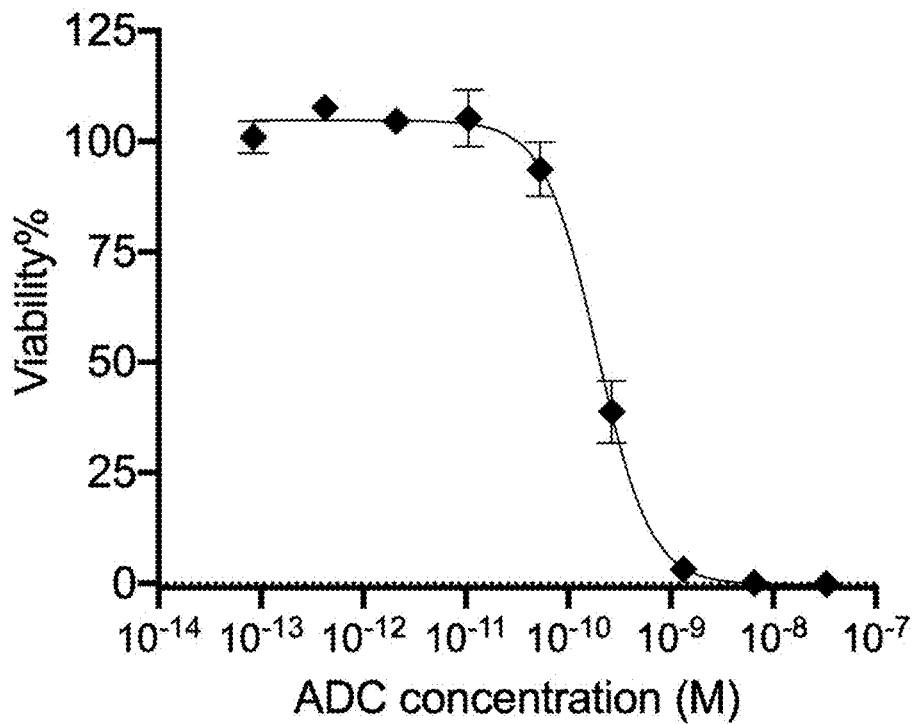
FIG. 11 depicts the results of the dose-dependent in vitro cytotoxic effects of the antibody-drug conjugate ARA-01-RKAA-PABC-MMAE of the invention against three different CD79b overexpressing cell lines (a-c) and a CD79b non-expressing cell line (d).
Figure 11:
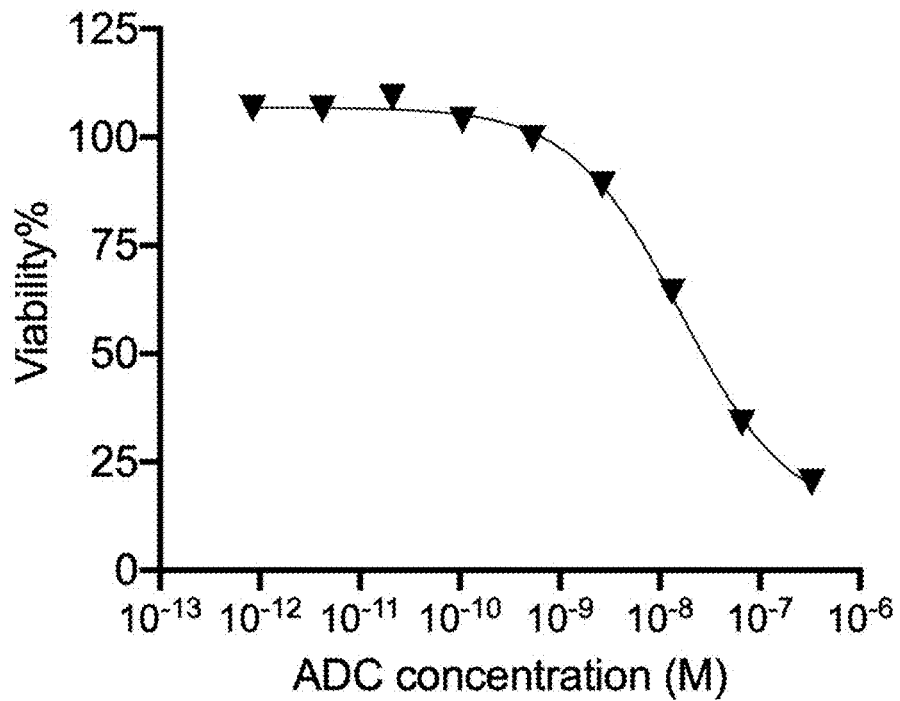
Figure 11:
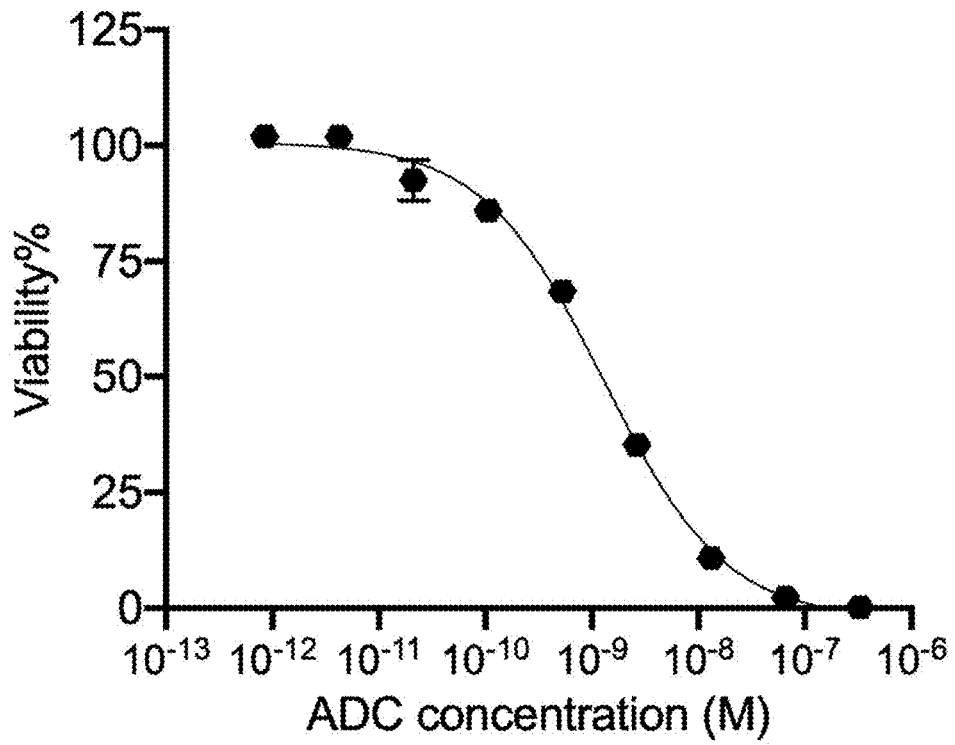
Figure 11:
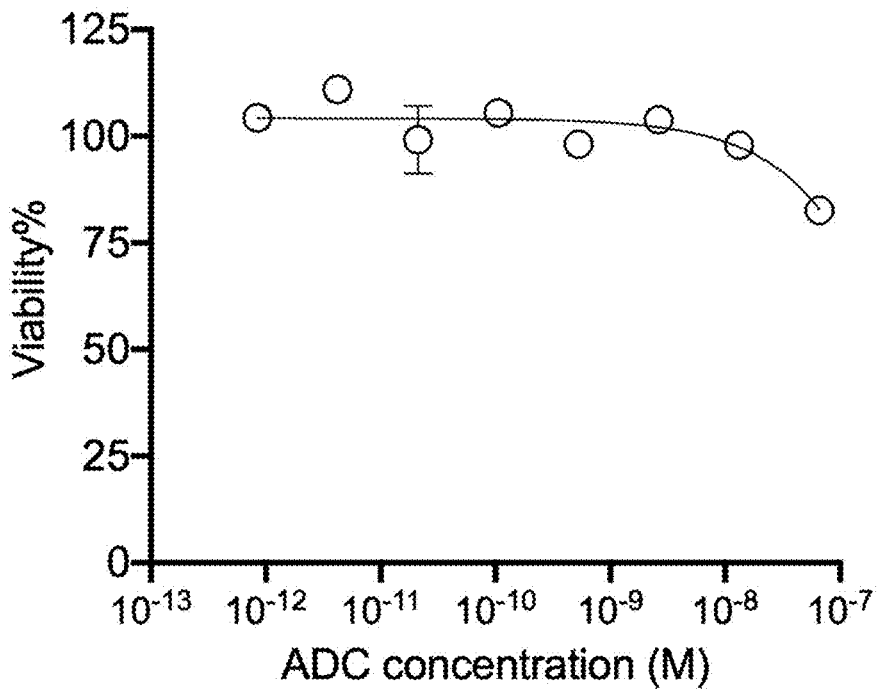

FIG. 11 shows that ARA01-RKAA-PABC-MMAE had a very high cytotoxic activity against CD79b over-expressing cells with $EC_{50}$ values comparable to conventional ADCs. The cytotoxic activity was highly selective towards CD79b over-expressing cells, as there was essentially no decrease of cell viability in the HT cell line, as expected. In summary, ARA01-RKAA-PABC-MMAE showed an antigen-specific, significant anti-proliferative activity in vitro.

Example 7: ADCs of the Invention Show Favorable Pharmacokinetic Parameters In Vivo The pharmacokinetic profile of the anti-CD79b ADC according to this invention ARA01-RKAA-MMAE was investigated in mice and compared to the commercially available anti-CD79b ADC polatuzumab-vedotin (Polivy®). Polatuzumab-vedotin is an ADC consisting of the anti-CD79b antibody polatuzumab wherein MMAE was conjugated to cysteines of the antibody, leading to an average of 3.5 linked MMAE moieties per antibody (European Medicines Agency, Assessment Report on Polivy®, Procedure number: EMEA/H/C/004879/0000, see https://www.ema.europa.eu/en/medicines/human/EPAR/polivy).

Methods

ARA01-RKAA-PABC-MMAE (produced in-house as described in Example 5 above), Polivy® (Roche, bought from a pharmacy) and the naked anti-CD79b antibody polatuzumab (SEQ ID NOs: 5 and 6; expressed and purified as described above) were injected intravenously into 5 female mice (CD1 Swiss, Janvier) at a dose of 5 mg/kg of ADC or antibody respectively. After 10 minutes, 5.5, 24, 48, 96, 144, 168 and 360 hours, approximately 20 µl of blood was drawn from the vena saphena into EDTA-coated Microvettes CB 300 (Sarstedt). Blood samples were centrifuged for 10 min at 9500×g and the plasma was stored at −80° until the ELISA analysis was performed. Using dilution series with known concentrations of the corresponding sample, concentration in plasma was determined by ELISA using His-tagged human CD79b as capturing agent: 125 ng of HisCD79b (SinoBiological, Ref.: 29750-H08H) diluted in PBS was added to Nickel plates (Ni-NTA HisSorb, Qiagen) and after blocking with 200 µl PBS, 4% milk (Rapilait, Migros, Switzerland), 50 µl of diluted plasma samples (in PBS, 4% milk) was added. After incubation for 1 h and washing with PBS, either total antibody was detected by addition of donkey-anti-human IgG-HRP (Biolegend, Poly24109) to the wells, or, for total ADC detection, a rabbit anti-MMAE antibody (Levena, Ref: LEV-PAE1) was added for another hour at room temperature, washed and detected via anti-rabbit IgG-HRP. Peroxidase activity was detected by addition of 3,3',5,5'-Tetramethylbenzidine (Sigma) and stopped by the addition of acid. The readout was measured after 1 to 5 min at 450 nm. From the concentrations of the samples determined by ELISA in plasma at different time points after injection and the resulting slope k of the elimination phase (time-points 24 h-360 h) (plotted in a semi-logarithmic scale), the half-lives ($t_{1/2}$) of the samples were calculated using the formula $t_{1/2}=\ln2/-k$.

Results

Figure 12:
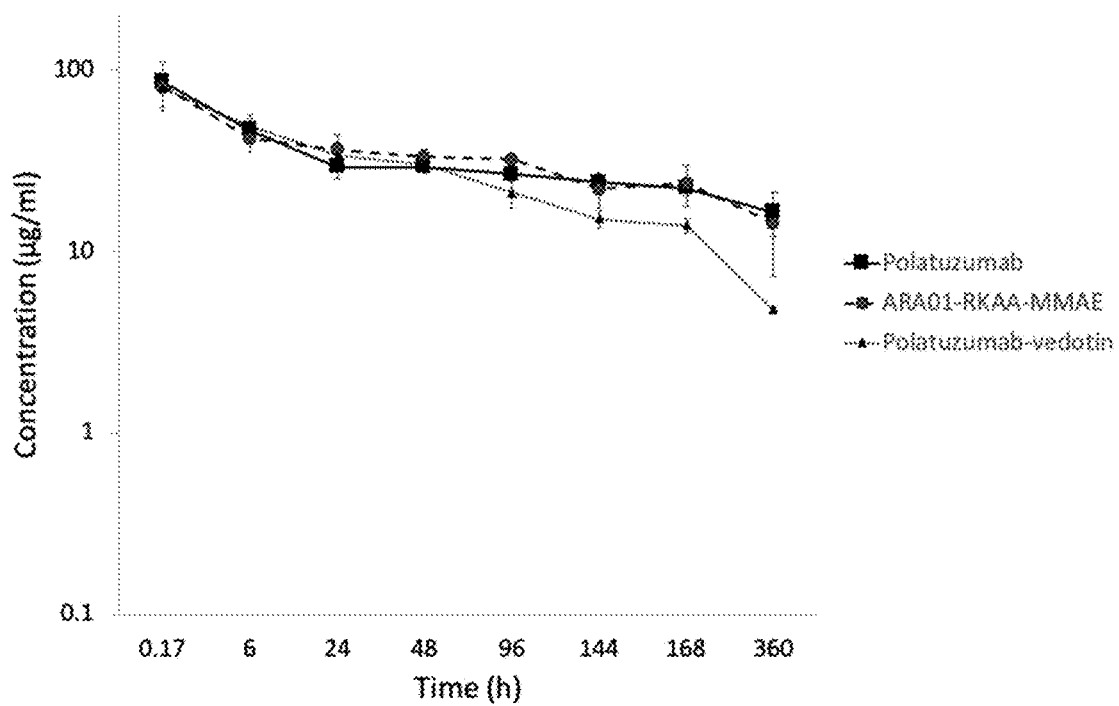
FIG. 12 shows the plasma concentrations of polatuzumab (SEQ ID NOs: 5 and 6), antibody-drug conjugate of the invention (ARA01-RKAA-PABC-MMAE) and polatuzumab-vedotin (Polivy®) at different time-points after a single i.v. injection of 5 mg/kg into CD1 Swiss mice. The concentration in plasma was determined by ELISA. Mean plasma concentrations of 5 mice are plotted versus time, error bars represent standard error of mean (SEM). It is to be understood that the abbreviation ARA01-RKAA-MMAE in FIG. 12 refers to the antibody-drug conjugate ARA01-RKAA-PABC-MMAE.

The plasma concentrations measured in the samples taken at different time points after injection are shown in FIG. 12. The half-lives of the ARA01-RKAA-PABC-MMAE and Polivy® are given below in the table 4. It can be seen that the ADC according to this invention, ARA01-RKAA-PABC-MMAE, had at least a 2 times longer half-life than the approved ADC Polivy® in vivo. The improved stability in plasma may lead to a better safety profile as the payload seems not to be released prematurely.

TABLE 8

| Plasma half-lives | |
|---|---|
| Construct | Half-life ($t_{1/2}$), hours |
| Polatuzumab (SEQ ID NOs: 5 and 6), naked antibody | 385 |
| ARA01-RKAA-MMAE, intact ADC | 248 |
| polatuzumab-vedotin (Polivy ®), intact ADC | 120 |

Example 8: Anti-CD79b ADC of the Invention Inhibits Tumor Growth In Vivo More Efficiently than the Approved Anti-CD79b ADC Polatuzumab-Vedotin The anti-CD79b ADC ARA01-RKAA-PABC-MMAE was investigated in vivo for tumor growth inhibition and was compared to the commercially available polatuzumab-vedotin.

Figure 16A:
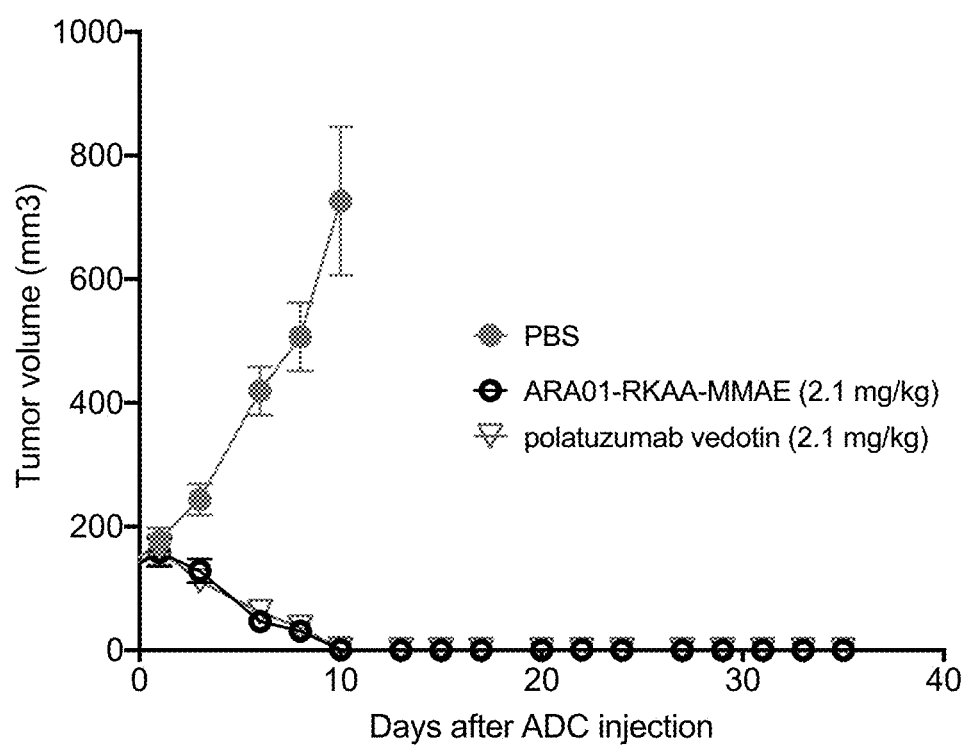
FIGS. 16A-16B depict the Granta 519 mouse tumor model. Human B-cell lymphoma-tumor cells (Granta 519) were inoculated subcutaneously in CB17 SCID mice (n=8 per treatment group). When tumors reached a size of about 200 mm$^3$, the animals received a single injection of 0.53 mg/kg or 2.1 mg/kg polatuzumab-vedotin (Polivy®) and either 0.53 mg/kg, 1 mg/kg or 2.1 mg/kg of ARA01-RKAA-PABC-MMAE. ARA01-RKAA-PABC-MMAE provided equal tumor growth inhibition and survival at about half the payload dose relative to polatuzumab-vedotin (FIG. 16A, and 0.53 mg/kg doses in FIG. 16B). At an approximately equal payload dose relative to polatuzumab-vedotin, ARA01-RKAA-PABC-MMAE treatment led to a greater antitumor efficacy and a considerable survival advantage with 6/8 complete tumor remissions over polatuzumab-vedotin with 0/8 complete tumor remission (comparison of the 0.53 mg/kg dose of polatuzumab-vedotin and 1 mg/kg dose of ARA01-RKAA-PABC-MMAE in FIG. 16B). Mean tumor volumes are shown ±standard error of the mean (SEM).
Figure 16B:
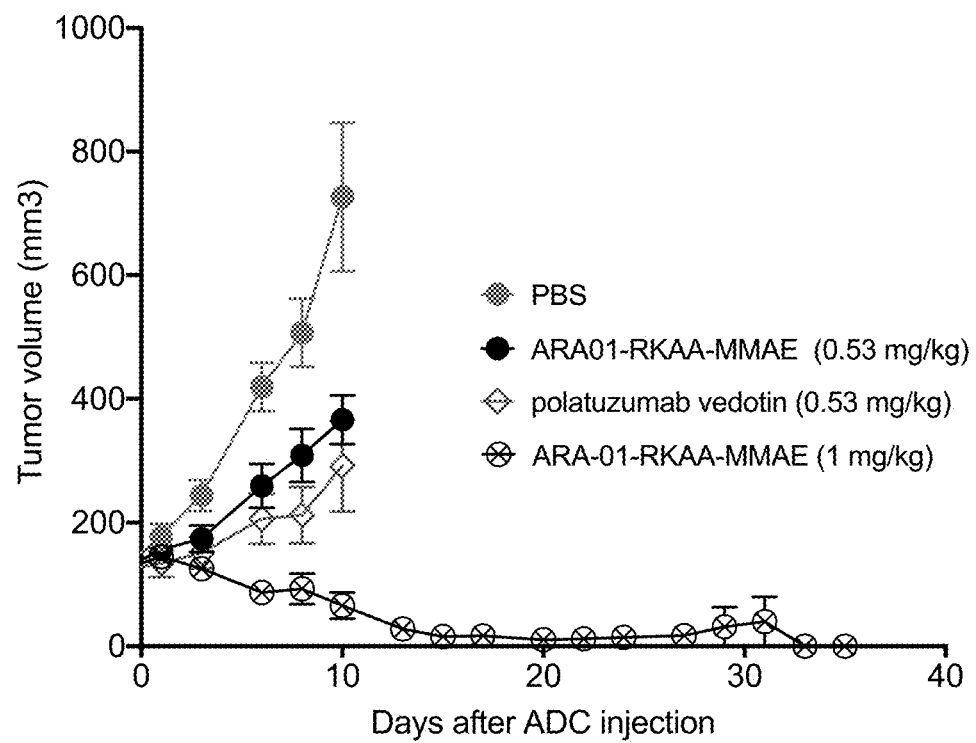
Figure 17:
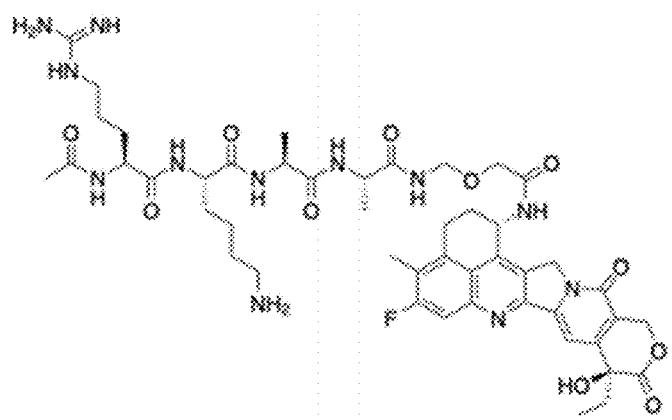
FIG. 17 shows the chemical structure of an RKAA-payload complex according to this invention, wherein the N-terminally protected Ac-RKAA peptide is covalently linked to the exatecan derivative Dxd via a self-immolative methyl amine linker.
Figure 18:
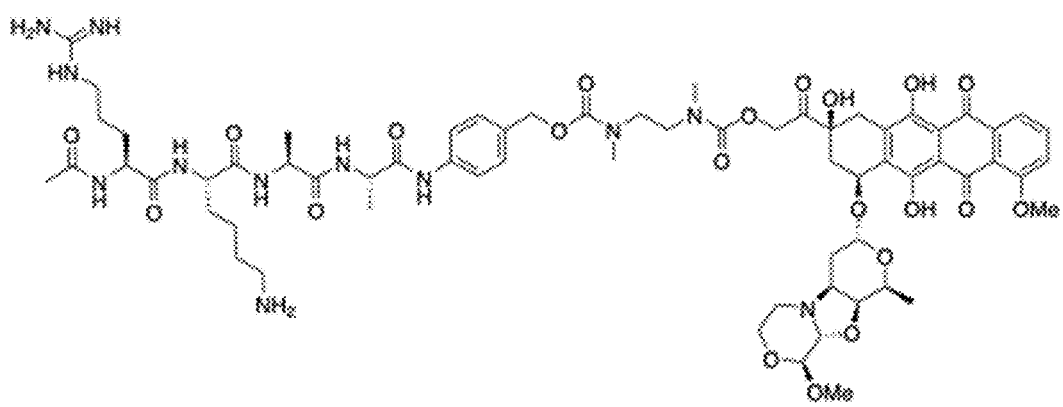
FIG. 18 shows the chemical structure of an RKAA-payload complex according to this invention, wherein the N-terminally protected Ac-RKAA peptide is covalently linked to the payload PNU-159682 via the self-immolative moiety PABC-EDA.
Figure 19:
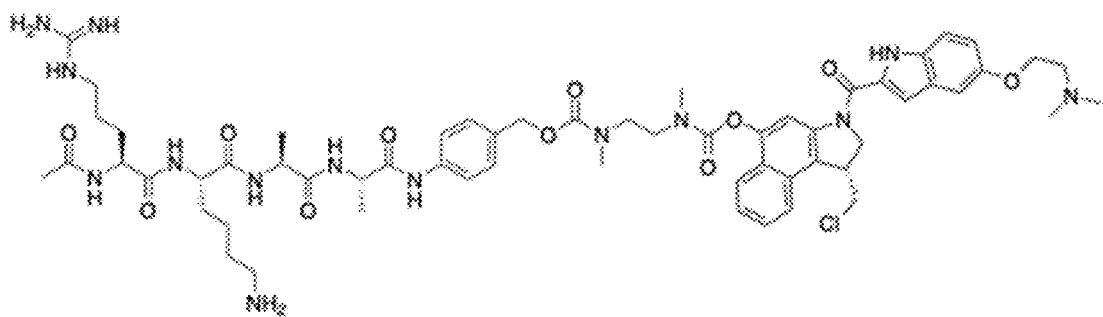
FIG. 19 shows the chemical structure of an RKAA-payload complex according to this invention, wherein the N-terminally protected Ac-RKAA peptide is covalently linked to the payload Duocarmycin GA via the self-immolative moiety PABC-EDA.
Figure 20:
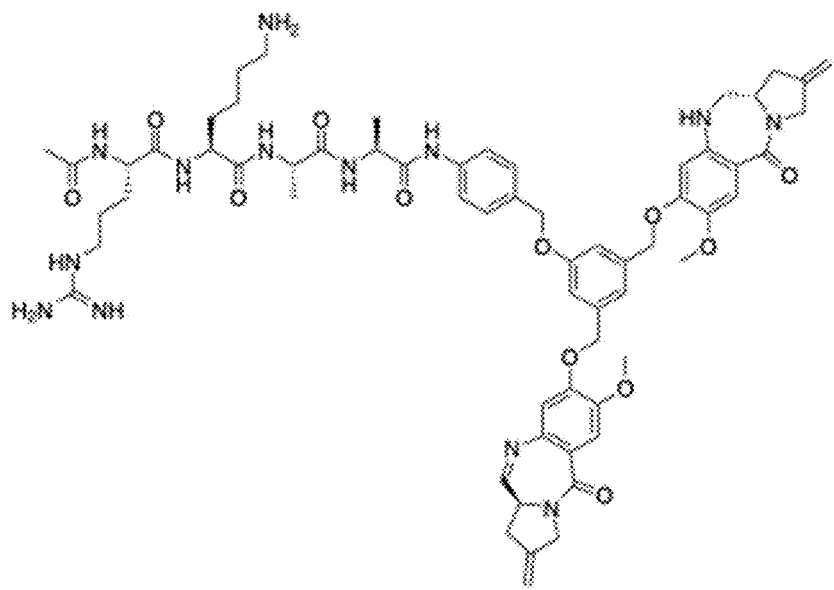
FIG. 20 shows the chemical structure of an RKAA-payload complex according to this invention, wherein the N-terminally protected Ac-RKAA peptide is covalently linked to the payload PBD via the self-immolative moiety PABE.
Figure 21:
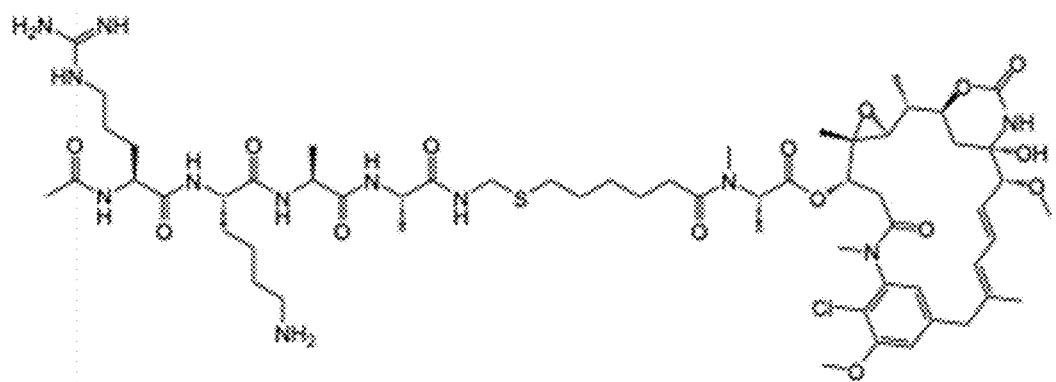
FIG. 21 shows the chemical structure of an RKAA-payload complex according to this invention, wherein the N-terminally protected Ac-RKAA peptide is covalently linked to the payload maytansine via a self-immolative methyl amine linker and an additional alkyl linker molecule.
Figure 22:
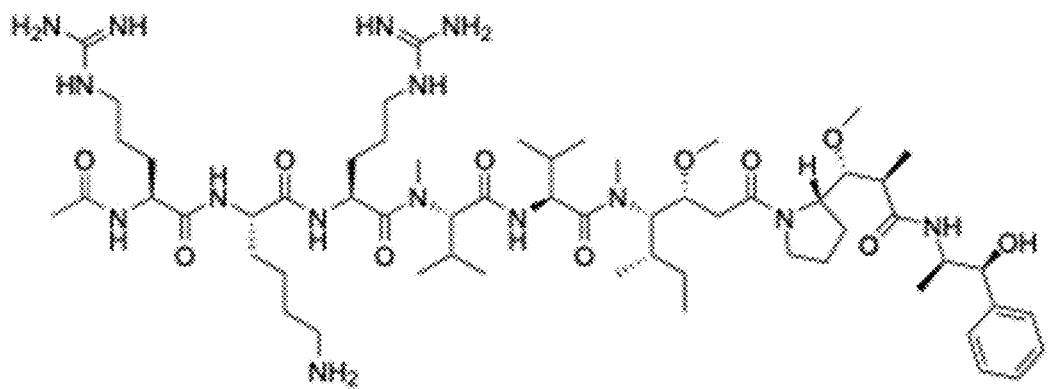
FIG. 22 shows the chemical structure of an RKR-payload complex according to this invention, wherein the N-terminally protected Ac-RKR peptide is directly coupled to the payload MMAE.
Figure 23:
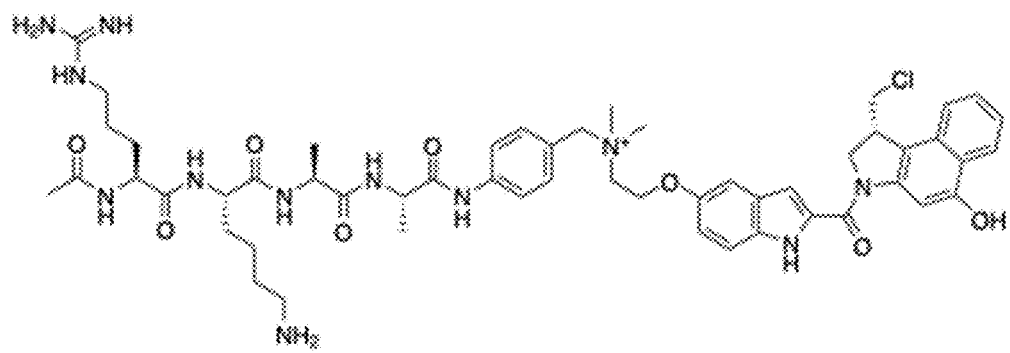
FIG. 23 shows the chemical structure of an RKAA-payload complex according to this invention, wherein the N-terminally protected Ac-RKAA peptide is covalently linked to the payload Duocarmycin GA via a self-immolative para-methyl aniline (PMA) moiety.
Figure 24:
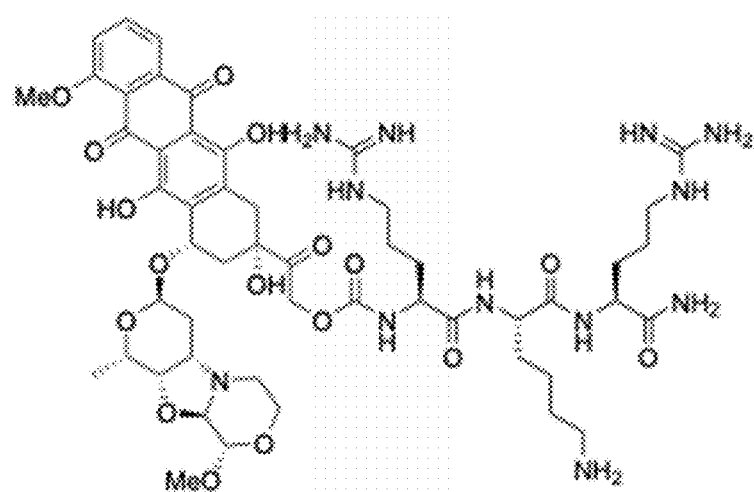
FIG. 24 shows the chemical structure of an RKR-payload complex according to this invention, wherein the C-terminally protected RKR-amide peptide is covalently linked to the payload PNU-159682 via a carbamate.
Figure 25:
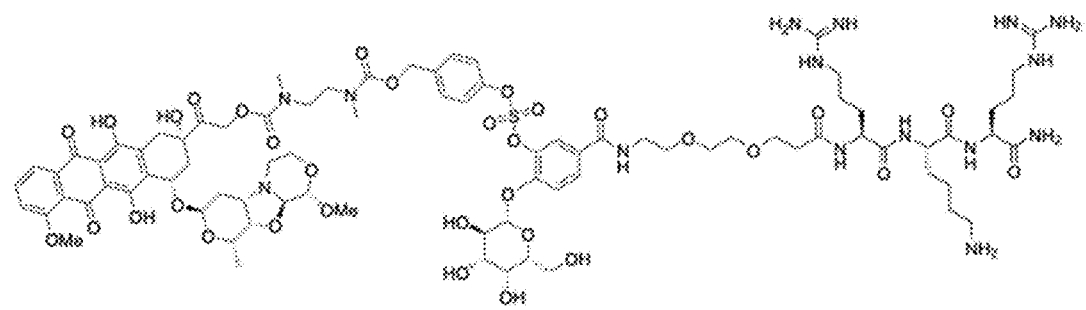
FIG. 25 shows the chemical structure of an RKR-payload complex according to this invention, wherein the C-terminally protected RKR-amide peptide is covalently linked to the payload PNU-159682 via a the self-immolative moiety OHPAS-PHB-EDA and an additional (PEG)$_2$ moiety.
Figure 26:
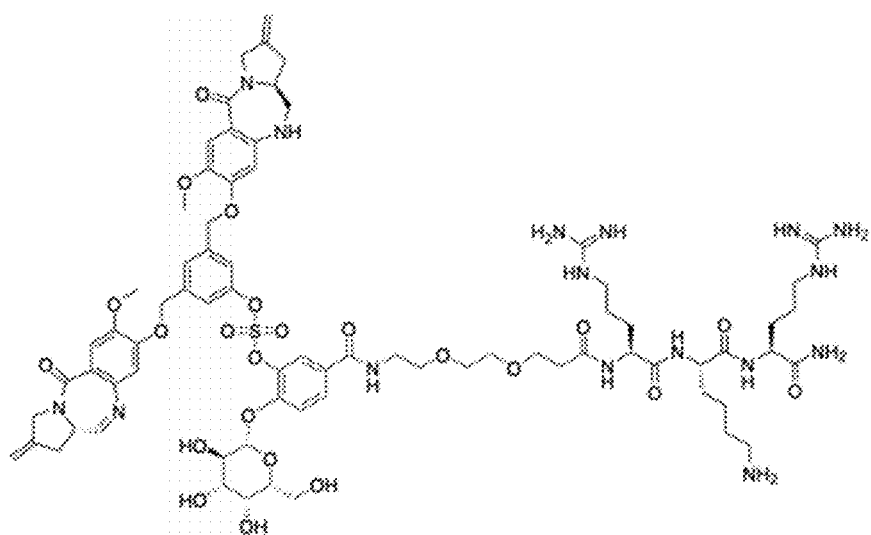
FIG. 26 shows the chemical structure of an RKR-payload complex according to this invention, wherein the C-terminally protected RKR-amide peptide is covalently linked to the payload PBD via a the self-immolative moiety OHPAS and an additional (PEG)$_2$ moiety.
Figure 27:
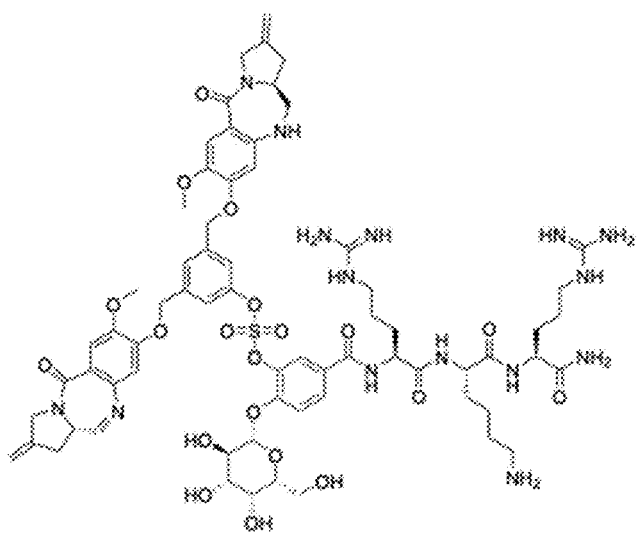
FIG. 27 shows the chemical structure of an RKR-payload complex according to this invention, wherein the C-terminally protected RKR-amide peptide is covalently linked to the payload PBD via a the self-immolative moiety OHPAS.
Figure 28:
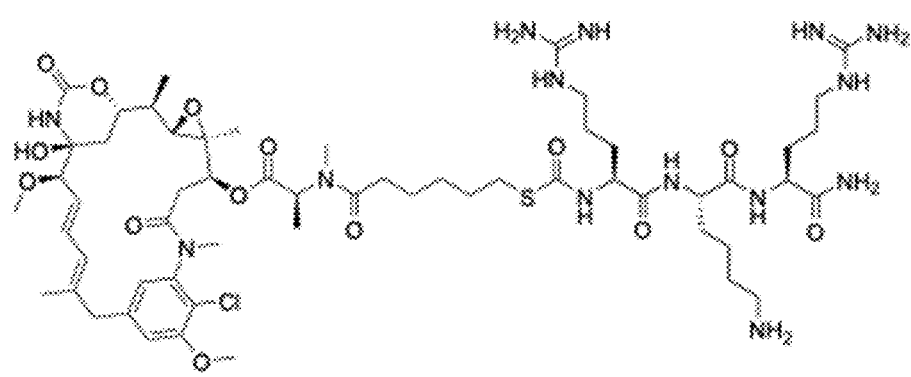
FIG. 28 shows the chemical structure of an RKR-payload complex according to this invention, wherein the C-terminally protected RKR-amide peptide is directly coupled to the payload DM21.
Figure 29:
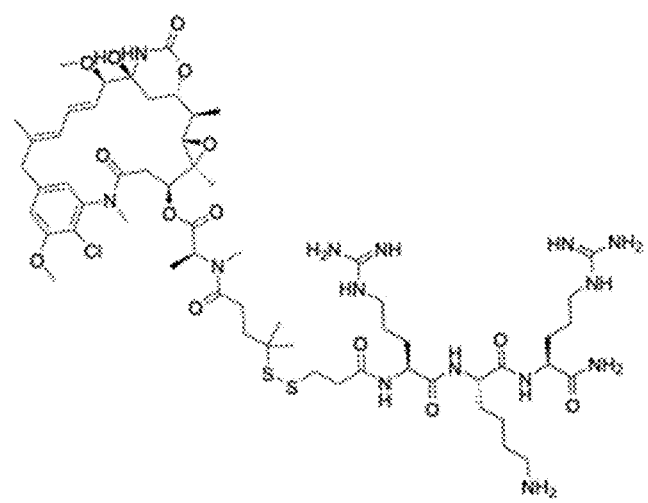
FIG. 29 shows the chemical structure of an RKR-payload complex according to this invention, wherein the C-terminally protected RKR-amide peptide is covalently linked to the payload DM4 via an alkyl linker molecule comprising a carboxyl group and a thiol group.
Figure 30:
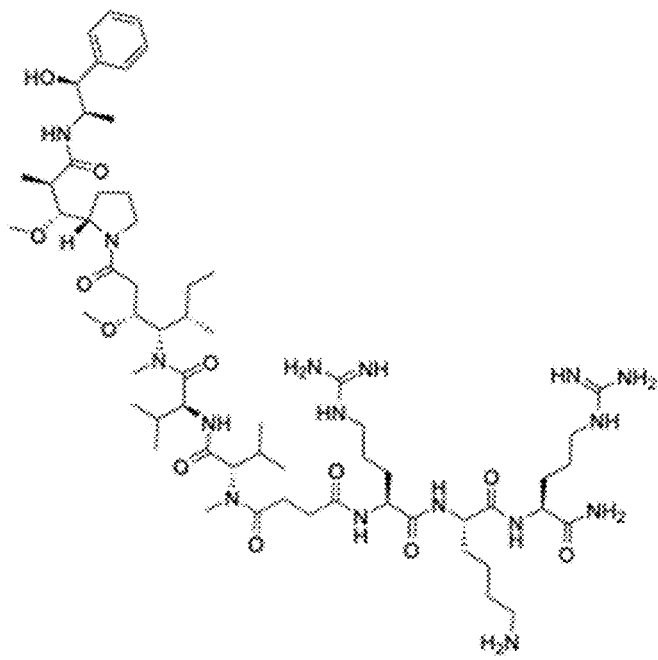
FIG. 30 shows the chemical structure of an RKR-payload complex according to this invention, wherein the C-terminally protected RKR-amide peptide is covalently linked to the payload MMAE via a dicarboxylic acid linker molecule.
Figure 31:
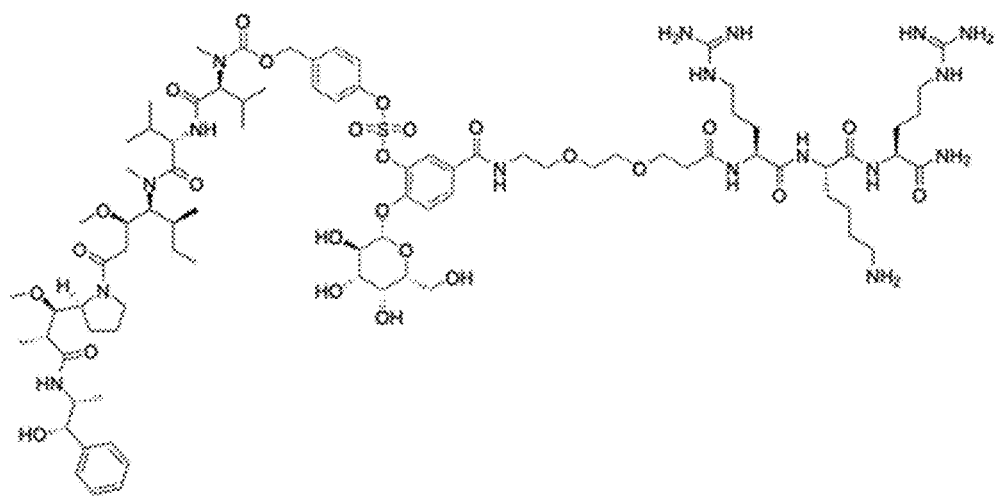
FIG. 31 shows the chemical structure of an RKR-payload complex according to this invention, wherein the C-terminally protected RKR-amide peptide is covalently linked to the payload MMAE via a the self-immolative moiety OHPAS-PHB and an additional (PEG)$_2$ moiety.
Figure 32:
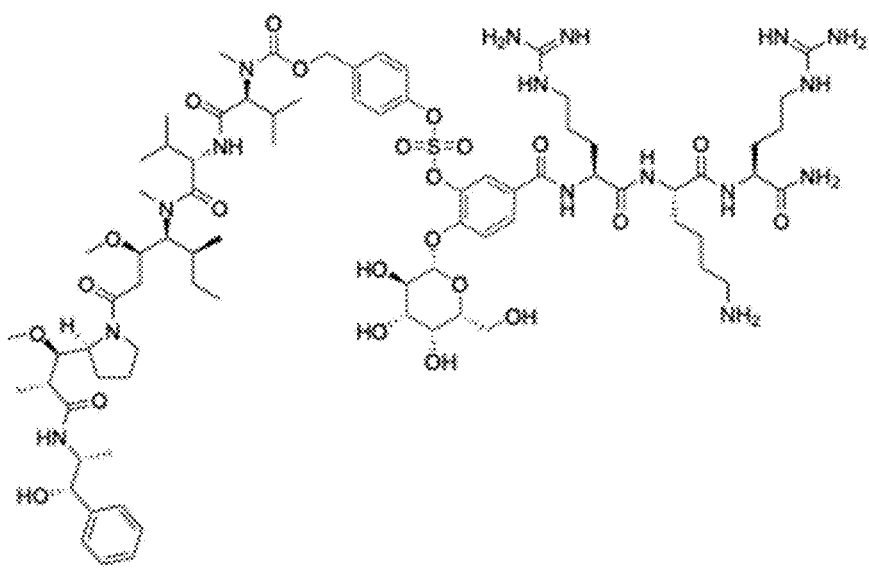
FIG. 32 shows the chemical structure of an RKR-payload complex according to this invention, wherein the C-terminally protected RKR-amide peptide is covalently linked to the payload MMAE via a the self-immolative moiety OHPAS-PHB.
Figure 33:
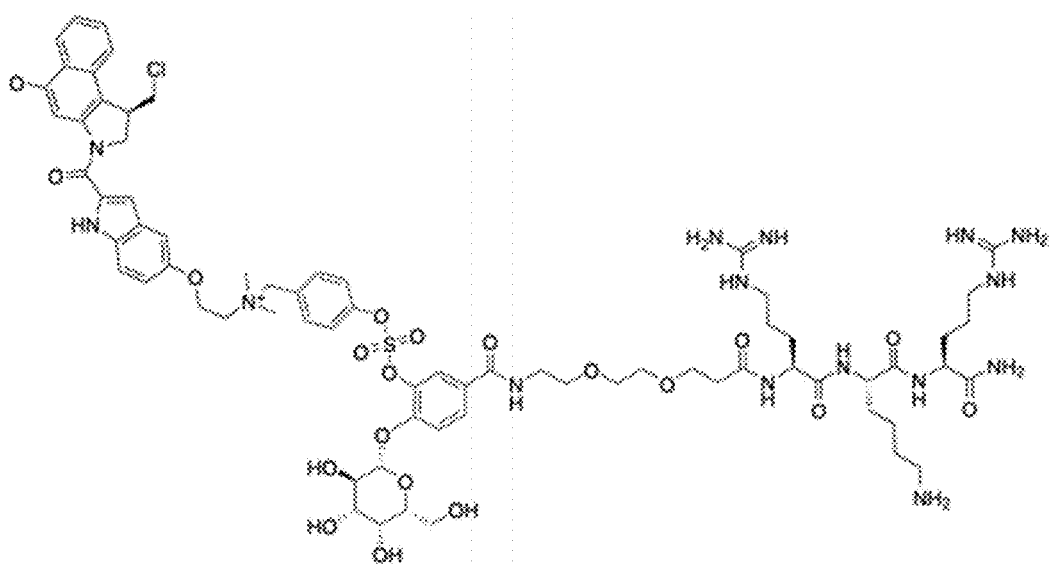
FIG. 33 shows the chemical structure of an RKR-payload complex according to this invention, wherein the C-terminally protected RKR-amide peptide is covalently linked to the payload Duocarmycin GA via a the self-immolative moiety OHPAS-quaternary ammonium and an additional (PEG)$_2$ moiety.
Figure 34:
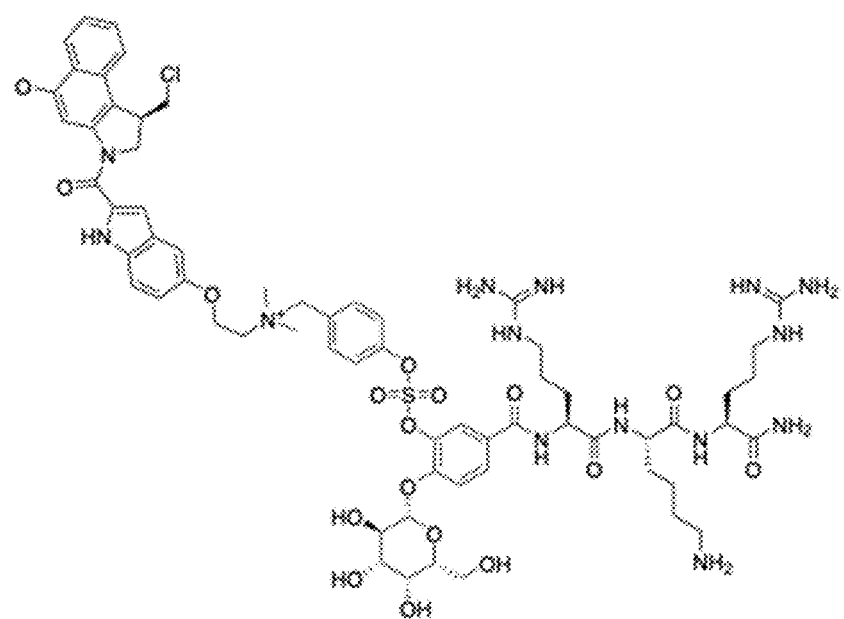
FIG. 34 shows the chemical structure of an RKR-payload complex according to this invention, wherein the C-terminally protected RKR-amide peptide is covalently linked to the payload Duocarmycin GA via a the self-immolative moiety OHPAS-quaternary ammonium.

Methods $20 \times 10^6$ human B-cell lymphoma tumor cells Granta 519 (DSMZ, Acc No: 342) were implanted s.c. into CB17 SCID mice (Janvier). Tumor dimensions and body weights were recorded three times weekly. The tumor volume was calculated according to the formula volume=(width)$^2$×length× 0.5. When the average tumor size reached about 200 mm$^3$, mice were allocated using a non-random stratification protocol into the treatment groups comprising eight mice each. ARA01-RKAA-PABC-MMAE (produced in-house as described in Example 5 above) at doses of 0.53 mg/kg, 1 mg/kg and 2.1 mg/kg and polatuzumab vedotin at doses of 0.53 mg/kg and 2.1 mg/kg were administered in a single i.v. injection on day 0 (day of randomization). Mice in the control group were injected with PBS. All mouse experiments were performed in accordance with Swiss guidelines and were approved by the Veterinarian Office of Zürich, Switzerland. Following these guidelines, mice had to be sacrificed at day 10 for the PBS group and all 0.53 mg/kg doses, and 2 mice in the 1 mg/kg group at day 6 and 30 (ulcerations of the tumor).
Results:

The in vivo efficacy of ARA01-RKAA-PABC-MMAE (DAR 1.9) as compared with polatuzumab-vedotin (DAR 3.5) was assessed against the Granta 519 tumor model. Specifically, the animals received a single injection of 0.53 mg/kg or 2.1 mg/kg polatuzumab-vedotin (Polivy®) and either 0.53 mg/kg, 1 mg/kg or 2.1 mg/kg of ARA01-RKAA-PABC-MMAE. Importantly, ARA01-RKAA-PABC-MMAE provided equal tumor growth inhibition and survival at about half the payload dose relative to polatuzumab-vedotin (comparison of the 2 mg/kg doses, see FIG. 16A, and 0.53 mg/kg doses in FIG. 16B). At an approximately equal payload dose relative to polatuzumab-vedotin, ARA01-RKAA-PABC-MMAE treatment led to a greater antitumor efficacy and a considerable survival advantage with 6/8 complete tumor remissions over polatuzumab-vedotin with 0/8 complete tumor remission (comparison of the 0.53 mg/kg dose of polatuzumab-vedotin and 1 mg/kg dose of ARA01-RKAA-PABC-MMAE in FIG. 16B). In summary, at approximately equal payload doses, ARA01-RKAA-PABC-MMAE treatment resulted in greater antitumor efficacy and a considerable survival advantage over polatuzumab vedotin.

Example 9: Conjugation of Various RK-Motif-Peptides to Antibody Trastuzumab

All tested RK-containing peptides conjugated with high efficiency.
Methods

Conjugation reactions were adapted from conditions described in Example 1. In brief, mixing 5 mg/ml of native, glycosylated Trastuzumab antibody, MTG at a concentration of 1.5 U/mg, and 20 molar equivalents of the indicated peptide-linker containing a RK-motif, in Tris 50 mM pH 7.6 for 24 hours at 37° C. in a rotating thermomixer. Conjugation efficiency was assessed by LCMS as follows: Conjugation efficiency (CE) was calculated from deconvoluted spectra and presented in %. Intensities resulting from both glycoforms (G1F and G0F) were taken into account for the calculation, according to the formula:

$$CE\% = \frac{\sum((\text{Int}(G0F+G1F))_{cj})}{\sum(\text{Int}(G0F+G1F))_{cj,ncj}} \text{ with } cj = \text{conjugated and } ncj = \text{non-conjugated}$$

Results

All tested RK-motif-linkers conjugated with well with efficiencies >50% to native, fully glycosylated Trastuzumab as shown in Table 9.

TABLE 9

Conjugation efficiency of peptide linkers containing the RK-motif to Trastuzumab

| RK-motif peptide linker | Conjugation efficiency (%) |
|---|---|
| HRKHA (SEQ ID NO: 55) | 98% |
| HRKAH (SEQ ID NO: 56) | 91% |

TABLE 9-continued

Conjugation efficiency of peptide linkers containing the RK-motif to Trastuzumab

| RK-motif peptide linker | Conjugation efficiency (%) |
|---|---|
| RKAH (SEQ ID NO: 57) | 91% |
| RKH (SEQ ID NO: 58) | 87% |
| RKAA (SEQ ID NO: 1) | 86% |
| RKA (SEQ ID NO: 2) | 86% |
| RKHA (SEQ ID NO: 59) | 86% |
| RKHH (SEQ ID NO: 60) | 85% |
| ARKAH (SEQ ID NO: 61) | 82% |
| ARKHA (SEQ ID NO: 62) | 82% |
| HRK (SEQ ID NO: 63) | 81% |
| RKAAH (SEQ ID NO: 64) | 81% |
| ARKHH (SEQ ID NO: 65) | 80% |
| RKAAA (SEQ ID NO: 66) | 80% |

Example 10: Conjugation of RK-Motif-Peptides

Method

Reaction conditions: 5 mg/ml of native, glycosylated Trastuzumab antibody, MTG at a concentration of 5 U/mg, and 5 molar equivalents of the indicated peptide-linker, in Tris 50 mM pH 7.6 for 24 hours at 37° C. in a rotating thermomixer. Conjugation efficiency was assessed by LCMS as described in Example 9.

Results

The peptides containing the RK-motif conjugated with significant conjugation efficiency as shown in Table 10.

TABLE 10

Conjugation efficiency of peptide linkers containing the RK-motif to Trastuzumab

| RK-motif peptide linker | Conjugation efficiency (%) |
|---|---|
| RKAAR (SEQ ID NO: 67) | 95% |
| RRKAY (SEQ ID NO: 68) | 100% |
| RRK (SEQ ID NO: 69) | 99% |
| ARKRA (SEQ ID NO: 70) | 98% |

Example 11: Conjugation of RK-Motif-Linker-Payloads with MMAE

In order to show that RK-motif-linker-payloads are also suitable for antibody conjugation in one-step, additional linker-payloads containing the RK-motif, using MMAE as a payload, were used for conjugation to Trastuzumab.

Method

Conjugation reactions were performed by mixing 5 mg/ml of native, glycosylated Trastuzumab antibody, MTG at a concentration of 5 U/mg, and 5 molar equivalents of the indicated linker-payload, in Tris 50 mM pH 7.6 for 24 hours at 37° C. in a rotating thermomixer. Conjugation efficiency was assessed by LCMS as described in Example 9.

Results

Surprisingly, excellent conjugation efficiencies (above 85%) were obtained using various RK-motif-linker-payloads containing MMAE for conjugation to native, glycosylated Trastuzumab antibody as shown in Table 11A. Surprisingly, it was observed that conjugation efficiency was significantly lower when the linker-payloads did NOT comprise an RK motif as shown in Tables 11A and 11B.

TABLE 11A

Conjugation efficiencies of RK-motif linker-payloads containing MMAE to Trastuzumab (according to this invention)

| RK-linker-payload with MMAE | Conjugation efficiency (%) |
|---|---|
| RKAA-PABC-MMAE (SEQ ID NO: 1) | 100% |
| RKA-PABC-MMAE (SEQ ID NO: 2) | 100% |
| ARK-PABC-MMAE (SEQ ID NO: 3) | 100% |
| RKAAR-PABC-MMAE (SEQ ID NO: 67) | 99% |
| RRKAY-PABC-MMAE (SEQ ID NO: 68) | 100% |
| RRK-PABC-MMAE (SEQ ID NO: 69) | 96% |
| ARKRA-PABC-MMAE (SEQ ID NO: 70) | 89% |
| RKValCit-PABC-MMAE (SEQ ID NO: 54) | 91% |
| ARK-PEG2-PABC-MMAE (SEQ ID NO: 3) | 99% |

TABLE 11B

Conjugation efficiencies of NON-RK-motif-linker-payloads with MMAE (NOT according to this invention).

| Non-RK-Linker-payload with MMAE | Conjugation efficiency (%) |
|---|---|
| KRA-PABC-MMAE (SEQ ID NO: 50) | 43% |
| AKR-PABC-MMAE (SEQ ID NO: 51) | 68% |
| KR-PABC-MMAE (SEQ ID NO: 71) | 46% |
| KAAR-PABC-MMAE (SEQ ID NO: 52) | 64% |
| KARA-PABC-MMAE (SEQ ID NO: 53) | 77% |
| KAA-PABC-MMAE (SEQ ID NO: 72) | 57% |

Example 12: Conjugation of RK-Motif Linker-Payloads Using Alternative Payload Classes In order to demonstrate the versatility of the linker technology of this invention, various RK-motif linker-payloads were used for conjugation to Trastuzumab. Payloads were selected from the following payload classes: cytotoxins, steroids (Cortisol=CS) and immunomodulators (i.e. STING agonists) were evaluated.

Method

Conjugation reactions were performed by mixing 5 mg/ml of native, glycosylated Trastuzumab antibody, MTG at a concentration of 5-10 U/mg, and 5-10 molar equivalents of the indicated linker-payload, in Tris 50 mM pH 7.6 for 24 hours at 37° C. in a rotating thermomixer. Conjugation efficiency was assessed by LCMS as described in Example 9.

Results

Surprisingly, excellent conjugation efficiencies (above 80%) were obtained using various RK-motif linker versions and payload classes as shown in Table 4. It was also surprising to observe that the payload located at the N-terminal position was very well tolerated (as demonstrated by May-C5-RKR).

TABLE 12

Conjugation efficiency of linker-payloads containing the RK-motif linkers with 3 various payload classes.

| RK-linker-payload with diverse toxins and drugs | Conjugation efficiency (%) |
|---|---|
| RKAA-PABC-May (SEQ ID NO: 1) | 92% |
| RKAA-PABC-Exa (SEQ ID NO: 1) | 98% |
| RKAA-PABC-EDA-PNU (SEQ ID NO: 1) | 99% |
| RKAA-PABE-Amanitin (SEQ ID NO: 1) | 90% |
| RKAA-EDA-Cortisol (SEQ ID NO: 1) | 88% |
| RKAA-PABC-EDA-STING (SEQ ID NO: 1) | 96% |
| RKAAR-PABC-Exa (SEQ ID NO: 67) | 99% |
| RKAAR-EDA-CS (SEQ ID NO: 67) | 98% |
| ARK-S-C5-May (SEQ ID NO: 3) | 98% |
| ARK-PABC-Exa (SEQ ID NO: 3) | 94% |
| ARK-PEG2-S-C5-May (SEQ ID NO: 3) | 99% |
| May-C5-RKR (SEQ ID NO: 4) | 96% |
| RRK-PABC-Exa (SEQ ID NO: 69) | 83% |

Maytansine; Exa: Exatecan-derivative; STING (stimulator of interferon genes; class of immunestimulators); PNU (anthracycline analog).

Example 13: Conjugation of RK-Motif Linker-Payloads to Three Different Antibodies To demonstrate the universal applicability of the reaction, a selection of RK-motif-linker-payloads containing MMAE or Maytansine (May) were conjugated to three different antibodies: Trastuzumab, Polatuzumab and Enfortumab variant (heavy chain SEQ ID NO: 9 and light chain SEQ ID: 11).

Method

Conjugation reactions were performed by mixing 5 mg/ml of the indicated native, glycosylated antibody, MTG at a concentration of 5-10 U/mg, and 5-10 molar equivalents of the indicated linker-payload, in Tris 50 mM pH 7.6 for 24 hours at 37° C. in a rotating thermomixer. Conjugation efficiency was assessed by LCMS as described in Example 9.

Results

Surprisingly, high conjugation efficiencies were obtained to all three tested antibodies with all tested RK-motif-MMAE or May linker payloads as shown in Table 13.

TABLE 13

Conjugation efficiency of linker-
payloads to three different antibodies

| RK-linker-payload | Conjugation efficiency (%) with Trastuzumab | Conjugation efficiency (%) with Polatuzumab | Conjugation efficiency (%) with Enfortumab |
|---|---|---|---|
| RKAA-PABC-MMAE (SEQ ID NO: 1) | 100% | 98% | 96% |
| ARK-PABC-MMAE (SEQ ID NO: 3) | 100% | 94% | 97% |
| RKA-PABC-MMAE (SEQ ID NO: 2) | 100% | 93% | 95% |
| RKValCit-PABC-MMAE (SEQ ID NO: 54) | 91% | 97% | 87% |
| RKAA-PABC-May (SEQ ID NO: 1) | 92% | 82% | 94% |
| May-C5-RKR (SEQ ID NO: 4) | 96% | 95% | NT |

NT: not tested

Example 14: Conjugation of RK-Motif Linker-Payload with Different Reaction Conditions To demonstrate that conjugation with RK-linker-payloads tolerate a wide variety of the reaction conditions, linker-payload conjugation to Polatuzumab was performed using a range of reaction conditions with varying parameters.

Method

As standard condition, the following parameters were used: 5 mg/ml of native, glycosylated polatuzumab antibody, MTG at a concentration of 5 U/mg, and 5 molar equivalents of RKAA-PABC-MMAE, in Tris 50 mM, pH 7.6, for 24 hours at 37° C. in a rotating thermomixer. Conjugation efficiency was assessed by LCMS as described above in Example 9.

The variable parameters are shown in Table 14.

Results

The RKAA-PABC-MMAE linker-payload conjugated with very high conjugation efficiency over a very large range of reaction conditions: Conjugation efficiencies of >80% were achieved using antibody concentration between 5 to 17 mg/ml, MTG concentration relative to antibody concentration (U/mg) between 2 and 10 U/mg. Further, high conjugation efficiencies were also obtained with molar concentrations of linker versus antibody (2 to 8 equivalents) as well as a very wide range of pH (from pH 6.0 with conjugation efficiency of 67% and pH 8 of 86%).

Surprisingly, higher conjugation efficiency was obtained with less linker-payload excess vs antibody, ie, 2-20 equivalent of linker payload yielded higher conjugation efficiencies than using 80 equivalents, which is contrary to what can be expected. (Table 14).

TABLE 14

Conjugation efficiency of RK-linker-payload to Polatuzumab under different reaction conditions
Effects on reaction parameters on conjugation efficiency

| Antibody final concentration (mg/mL) | | | | | | |
|---|---|---|---|---|---|---|
| Parameters | 5 | 6 | 8 | 10 | 15 | 17 |
| CE (%) | 98% | 95% | 95% | 96% | 86% | 95% |

| MTG loading (U/mg) | | | | | | | |
|---|---|---|---|---|---|---|---|
| Parameters | 2 | 3 | 3.5 | 4.5 | 5 | 6 | 9 | 10 |
| CE (%) | 94% | 92% | 95% | 97% | 98% | 100% | 96% | 88% |

| Molar equivalent of RK-linker-payload vs antibody | | | | | | | | |
|---|---|---|---|---|---|---|---|---|
| Parameters | 2 | 2.5 | 3 | 4 | 5 | 6 | 8 | 20 | 80 |
| CE (%) | 70% | 81% | 80% | 92% | 98% | 94% | 93% | 71% | 50% |

| pH | | | | | | |
|---|---|---|---|---|---|---|
| Parameters | 6.0 | 6.5 | 7.0 | 7.5 | 7.6 | 8.0 |
| CE (%) | 67% | 86% | 91% | 90% | 98% | 86% |

Example 15: ADCs Containing RK-Motif-PABC-Payload Linker Payloads are Efficient In Vitro Using Three Different Antibodies To demonstrate ADCs according to this invention, ie, generated with RK-motif-MMAE/Maytansine linker payloads lead to efficient release and target-specific toxicity on cancer cell lines, Trastuzumab-, Polatzumab- (ARA01), and Enfortumab- (SEQ ID 9 and SEQ ID 11; ARA04)-based ADCs were tested on target-expressing cells using linkers RKAA-PABC-MMAE, RKAA-PABC-Maytansine, ARK-PABC-MMAE, RKA-PABC-MMAE and RKValCit-MMAE.

Method

The growth inhibitory effect of Trastuzumab-RKAA-PABC-MMAE and Trastuzumab-RKAA-PABC-Maytansine was investigated on HER-2 positive SKBR-3 (ATCC HTB-30) cells, the inhibitory effects of ARA01-ARK-PABC-MMAE, ARA01-RKA-PABC-MMAE and ARA01-RKVal-Cit-PABC-MMAE were tested on CD79b-positive Granta-519 lymphoma cells and the cytotoxic effects of ARA04-RKAA-PABC-MMAE, ARA04-ARK-PABC-MMAE, ARA04-RKA-PABC-MMAE and ARA04-RKValCit-PABC-MMAE was investigated on Nectin-4 positive breast cancer cells, SUM190PT (BIOIVT, 28068A16284) cells. Target dependency and specificity was tested on Nectin-4-negative lung carcinoma cells A549 (ATCC CCL-185). For all conditions, 4000 cells were seeded into 96-well culture plates and incubated with the respective ADCs for 72 hours at 37° C. in a humidified chamber and 5% $CO_2$.

Results

Figure 35:
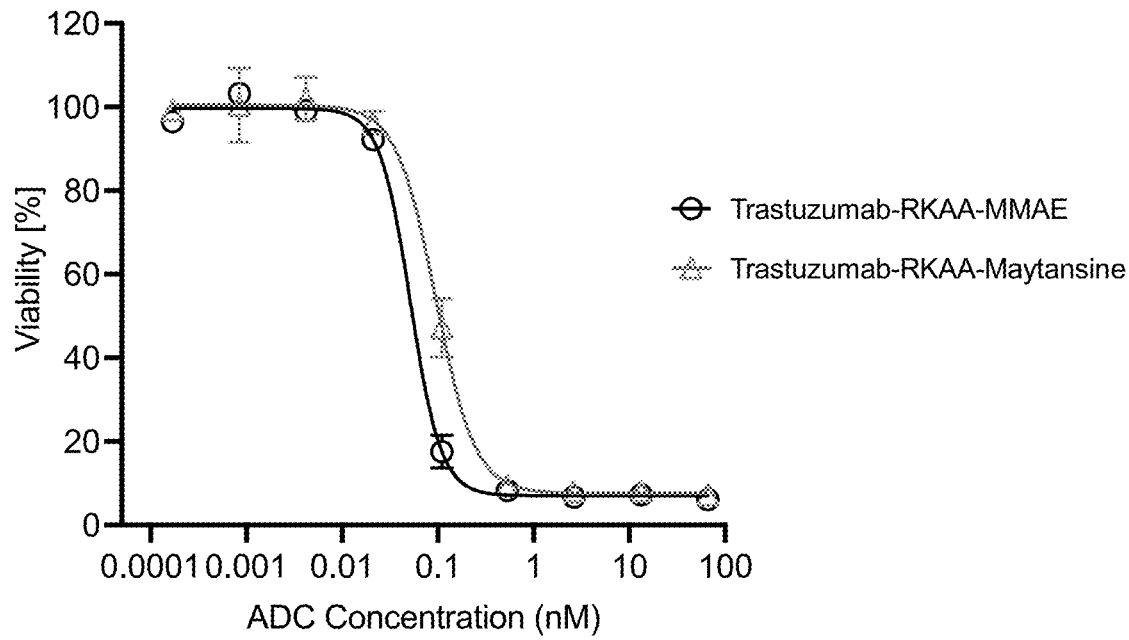
FIG. 35 depicts the results of the dose-dependent in vitro cytotoxic effects of the antibody-drug conjugate Trastuzumab-RKAA-PABC-MMAE or Trastuzumab-RKAA-PABC-Maytansine of the invention against the HER2-positive cell line SKBR-3.

FIG. 35 shows that Trastuzumab-RKAA-PABC-MMAE and Trastuzumab-RKAA-PABC-Maytansine of this invention both exert a very high cytotoxic activity against HER-2 over-expressing cells with $EC_{50}$ values comparable to conventional ADCs.

Figure 36:
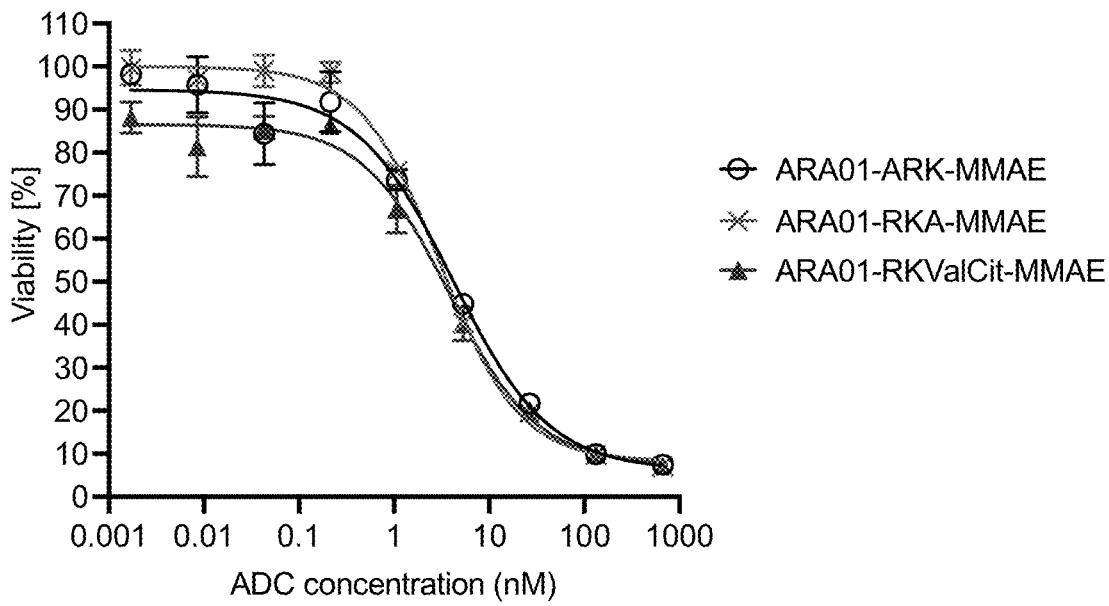
FIG. 36 depicts the results of the dose-dependent in vitro cytotoxic effects of the anti-CD79b antibody-drug conjugates ARA01-ARK-PABC-MMAE, ARA01-RKA-PABC-MMAE and ARA01-RKValCit-PABC-MMAE of the invention against the CD79b-positive cell line Granta-519.
Figure 37:
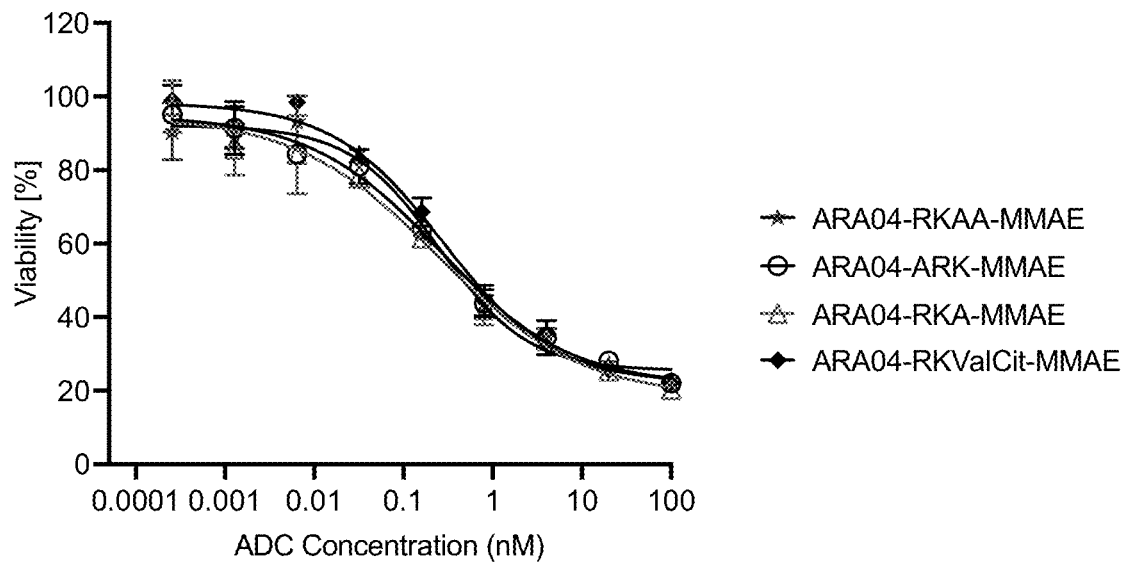
FIG. 37 depicts the results of the dose-dependent in vitro cytotoxic effects of the anti-Nectin-4 antibody-drug conjugates ARA04-RKAA-PABC-MMAE, ARA04-ARK-PABC-MMAE, ARA04-RKA-PABC-MMAE and ARA04-RKValCit-PABC-MMAE of the invention against the Nectin-4-positive cell line SUM190PT.
Figure 38:
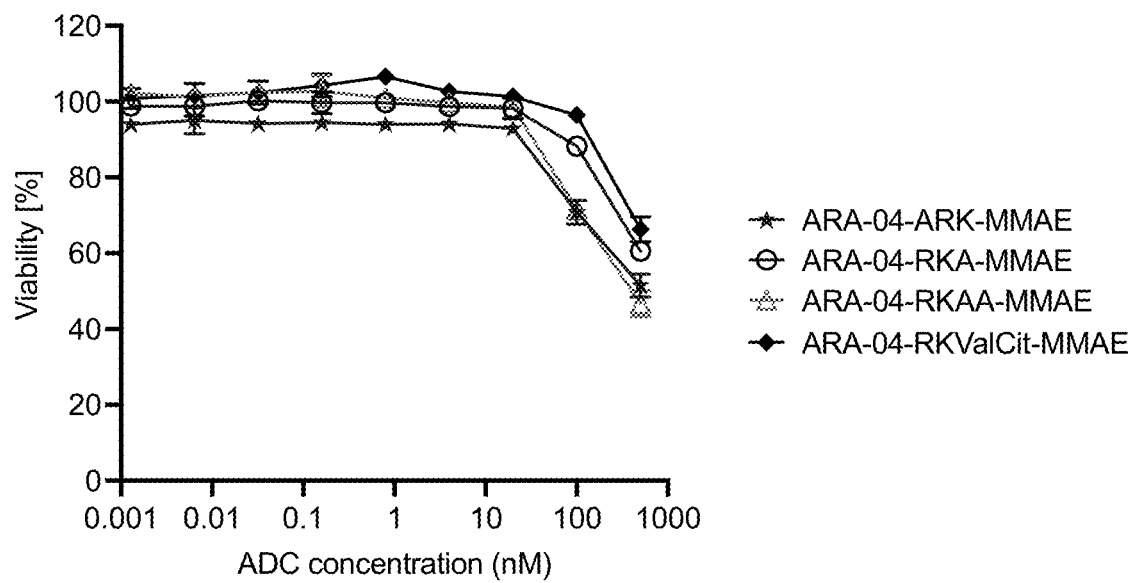
FIG. 38 depicts the results of the dose-dependent in vitro cytotoxic effects of the anti-Nectin-4 antibody-drug conjugates ARA04-RKAA-PABC-MMAE, ARA04-ARK-PABC-MMAE, ARA04-RKA-PABC-MMAE and ARA04-RKValCit-PABC-MMAE of the invention against the Nectin-4-negative cell line A549.

Of the CD79b and Nectin-4 targeting ADCs, ARA01 and ARA04 ADCs containing different linkers of this invention show very high and target-specific cytotoxic activity on target-positive Granta-519 (FIG. 36) and SUM190PT (FIG. 37) cells, respectively. The $EC_{50}$ values are in the range of conventional ADCs. In contrast, the same ADCs do not affect target-negative A549 cells (FIG. 38) and show comparable effects as conventional ADCs.

In summary, all ADCs using RK-motif linker-payloads according to this invention either conjugated to Trastuzumab, Polatuzumab or Enfortumab as parent antibodies showed target-specific and significant anti-proliferative activity in vitro.

Example 16: ADCs Containing RK-Motif-PABC-MMAE Linker Payloads Show Favorable Pharmacokinetic Properties In Vivo To assess the in vivo stability of the RK-motif MMAE ADCs, mouse pharmacokinetic studies were performed using different RK-motif linker payloads conjugated to Polatuzumab and Enfortumab.

The pharmacokinetic profile of the anti-CD79b ADCs ARA01-ARK-PABC-MMAE, ARA01-RKA-PABC-MMAE and ARA01-RKValCit-PABC-MMAE generated with linker-payloads according to this invention and anti-Nectin-4 ADCs generated with different linkers ARA04-ARK-PABC-MMAE, ARA04-RKA-PABC-MMAE and ARA04-RKValCit-PABC-MMAE were investigated in mice and compared to the commercially available anti-CD79b ADC polatuzumab-vedotin (Polivy®) and commercially available anti-Nectin-4 ADC enfortumab-vedotin (Padcev®).

Method

The pharmacokinetic study was performed as described in Example 7, with adaptations of sampling timepoints: blood samples were drawn after 10 minutes, 4, 48, 96, 168, 264, 336 and 504 hours from the vena saphena. For anti-CD79b ADC detection, the method described in Example 7 was adapted. Anti-Nectin-4 ADC detection was performed in brief as follows: ADC concentration in plasma was determined by ELISA using His-tagged human Nectin-4 as capturing agent: 125 ng of His-Nectin-4 (SinoBiological, Ref.: 19771-H08H) was diluted in PBS and added to Nickel plates (Ni-NTA HisSorb, Qiagen). After blocking with 200 µl PBS, 4% milk (Rapilait, Migros, Switzerland), 50 µl of diluted plasma sample (in PBS, 4% milk) was added. After incubation for 1 h and washing with PBS, total ADC was detected using a rabbit anti-MMAE antibody (Levena, Ref: LEV-PAE1) that was added for another hour at room temperature, washed and detected via anti-rabbit IgG-HRP. Peroxidase activity was detected by addition of 3,3',5,5'-Tetramethylbenzidine (Sigma) and stopped by the addition of acid. The readout was measured after 1 to 5 min at 450 nm. Half-lives were calculated using the ADC concentrations of the samples in plasma plotted against time (semi-logarithmic scale). The resulting slope k of the elimination phase using time-points 48-504 h was used to determine the halve life ($t_{1/2}$) with the following formula: $t_{1/2} = \ln 2/-k$.

Results

Figure 39:
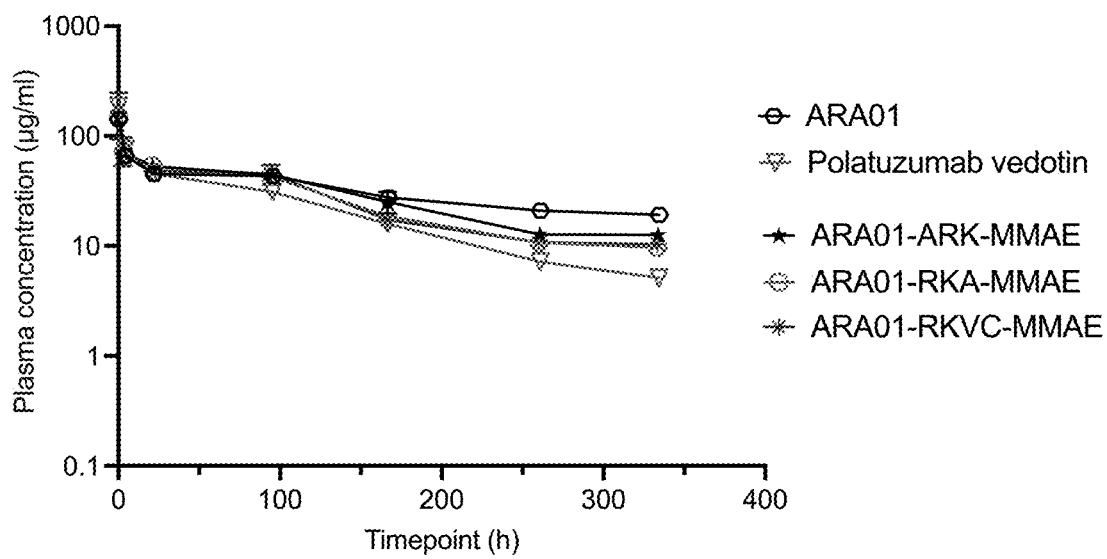
FIG. 39 shows the plasma concentrations of polatuzumab/ARA01 (SEQ ID NOs: 5 and 6) antibody-drug conjugates of the invention (ARA01-ARK-PABC-MMAE, ARA01-RKA-PABC-MMAE, ARA01-RKValCit-PABC-MMAE,) and polatuzumab-vedotin (Polivy®) at different time-points after a single i.v. injection of 5 mg/kg into CD1 Swiss mice. The ADC concentration in plasma was determined by ELISA. Mean plasma concentrations of 5 mice are plotted versus time, error bars represent standard error of mean (SEM). It is to be understood that the abbreviation ARA01-ARK/RKA/RKValCit-PABC-MMAE in FIG. 39 refers to the antibody-drug conjugates ARA01-ARK/RKA/RKValCit-PABC-MMAE.
Figure 40:
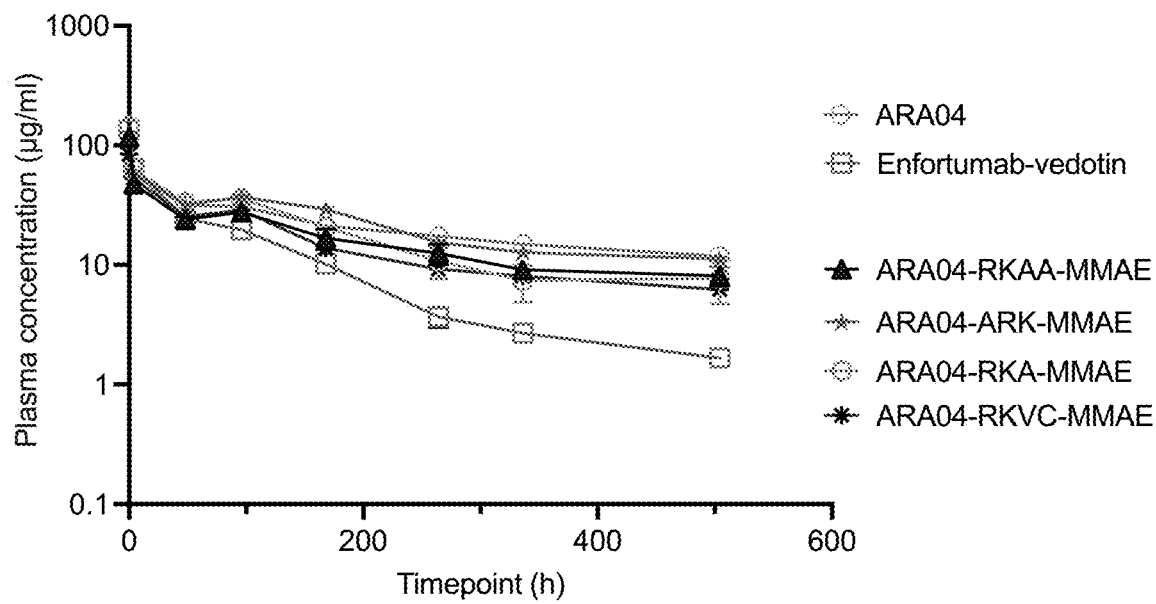
FIG. 40 shows the plasma concentrations of enfortumab/ARA04 (SEQ ID NOs: 9 and 11) antibody-drug conjugates of the invention (ARA04-RKAA-PABC-MMAE, ARA04-ARK-PABC-MMAE, ARA04-RKA-PABC-MMAE, ARA04-RKValCit-PABC-MMAE,) and enfortumab-vedotin (Padcev®9) at different time-points after a single i.v. injection of 5 mg/kg into CD1 Swiss mice. The ADC concentration in plasma was determined by ELISA. Mean plasma concentrations of 5 mice are plotted versus time, error bars represent standard error of mean (SEM). It is to be understood that the abbreviation ARA04-ARK/RKA/RKValCit-PABC-MMAE in FIG. 39 refers to the antibody-drug conjugates ARA04-ARK/RKA/RKValCit-PABC-MMAE.

The plasma concentrations of intact ADCs measured in the samples taken at different time points after injection are shown for anti-CD79b ADCs (FIG. 39) and for Nectin-4 ADCs (FIG. 40).

The half-lives for ARA01-ARK-PABC-MMAE, ARA01-RKA-PABC-MMAE and ARA01-RKValCit-PABC-MMAE are given below in Table 15. Surprisingly, an approximately 2-fold longer half-life of all ADCs according to this invention was observed compared to the polatuzumab-vedotin was calculated.

The half-lives for ARA04-RKAA-MMAE, ARA04-ARK-MMAE, ARA04-RKA-MMAE, ARA04-RKValCit-MMAE and Padcev® are given below in the table 16 showing an average 2 to 2.5-fold longer half-lives of these ADCs compared to the the approved enfortumab-vedotin.

In summary, all ADCs generated according to this invention, using either Polatuzumab or Enfortumab as parent antibody, show 2-2.5-fold improved half-lives as compared to the vedotin benchmarks. This indicates that the ADCs generated with linker-payloads according to this invention result in improved ADC stability in vivo which may lead to an overall better safety profile and therapeutic index (TI) as the payload does not get released prematurely.

TABLE 15

| Plasma half-lives for anti-CD79b ADCs | |
|---|---|
| Construct | Half-life ($t_{1/2}$), hours |
| Polatuzumab/ARA01 (SEQ ID NOs: 5 and 6), naked antibody | 393 |
| ARA01-ARK-MMAE, intact ADC | 237 |
| ARA01-RKA-MMAE, intact ADC | 197 |
| ARA01-RKValCit-MMAE, intact ADC | 220 |
| Polatuzumab-vedotin (Polivy ®), intact ADC | 118 |

TABLE 16

Plasma half-lives for anti-Nectin-4 ADCs

| Construct | Half-life ($t_{1/2}$), hours |
|---|---|
| ARA04 (SEQ ID NOs: 9 and 11), naked antibody | 303 |
| ARA04-RKAA-MMAE, intact ADC | 245 |
| ARA04-ARK-MMAE, intact ADC | 242 |
| ARA04-RKA-MMAE, intact ADC | 179 |
| ARA04-RKValCit-MMAE, intact ADC | 199 |
| Enfortumab-vedotin (Padcev ®), intact ADC | 109 |

Example 17: ADCs Containing RK-Motif-PABC-MMAE Linker Payloads Show More Efficient Tumor Growth Inhibition In Vivo Compared to Benchmarks in CD79b-Positive Liquid and Nectin-4 Positive Solid Tumor Models The anti-CD79b ADCs according to this invention, ARA01-RKAA-PABC-MMAE and ARA01-ARK-PABC-MMAE were investigated in vivo for tumor growth inhibition in a Ramos (CD79b-positive, liquid tumor) model. The anti-tumor properties of anti-Nectin-4 ADCs according to this invention ARA04-RKAA-PABC-MMAE and AR04-ARK-PAPBC-MMAE were tested in a SUM190PT (Nectin-4 positive, solid tumor) xenograft model. A non-binding mAb-RKAA-PABC-MMAE control ADC was included to exclude unspecific ADC activity.

Method

For SUM190PT xenografts, $2 \times 10^6$ cells were injected into the mammary fatpad; for Ramos, $20 \times 10^6$ cells were injected s.c. into CB17 SCID mice (Janvier). Tumor dimensions and body weights were recorded three times weekly. The tumor volume was calculated according to the formula volume= (width)$^2 \times$length$\times 0.5$. When the average tumor size reached about 200 mm$^3$, mice were allocated using a non-random stratification protocol into the treatment groups comprising six mice each. ADCs were intravenously injected once on the day of randomization.

All ADCs were produced in-house as described in Example 5.

ARA01-RKAA-PABC-MMAE and ARA01-RKAA-PABC-MMAE (both DAR1.9) were injected at a dose of 1.25 mg/kg (corresponding to 25 ug of payload per kg body weight).

Polatuzumab vedotin (PV, DAR 3.6) was injected at 1.43 mg/kg corresponding to 50 ug/kg payload or double the payload dose of ARA01-ADCs.

ARA04-RKAA-PABC-MMAE and ARA04-RKAA-PABC-MMAE (both DAR 1.9) were injected at ADC doses of 1 and 3 mg/kg (corresponding to 10 and 30 ug payload per kg body weight) and were compared to enfortumab vedotin (EV, DAR 3.8) at doses of 0.5 mg/kg and 1.5 mg/kg. A non-binding mAb-RKAA-PABC-MMAE ADC (harboring the same linker-payload and DAR as ARA04 ADCs) was injected at 3 mg/kg. Mice in the control group were injected with PBS. All mouse experiments were performed in accordance with Swiss guidelines and were approved by the Veterinarian Office of Zürich, Switzerland.

Figure 41:
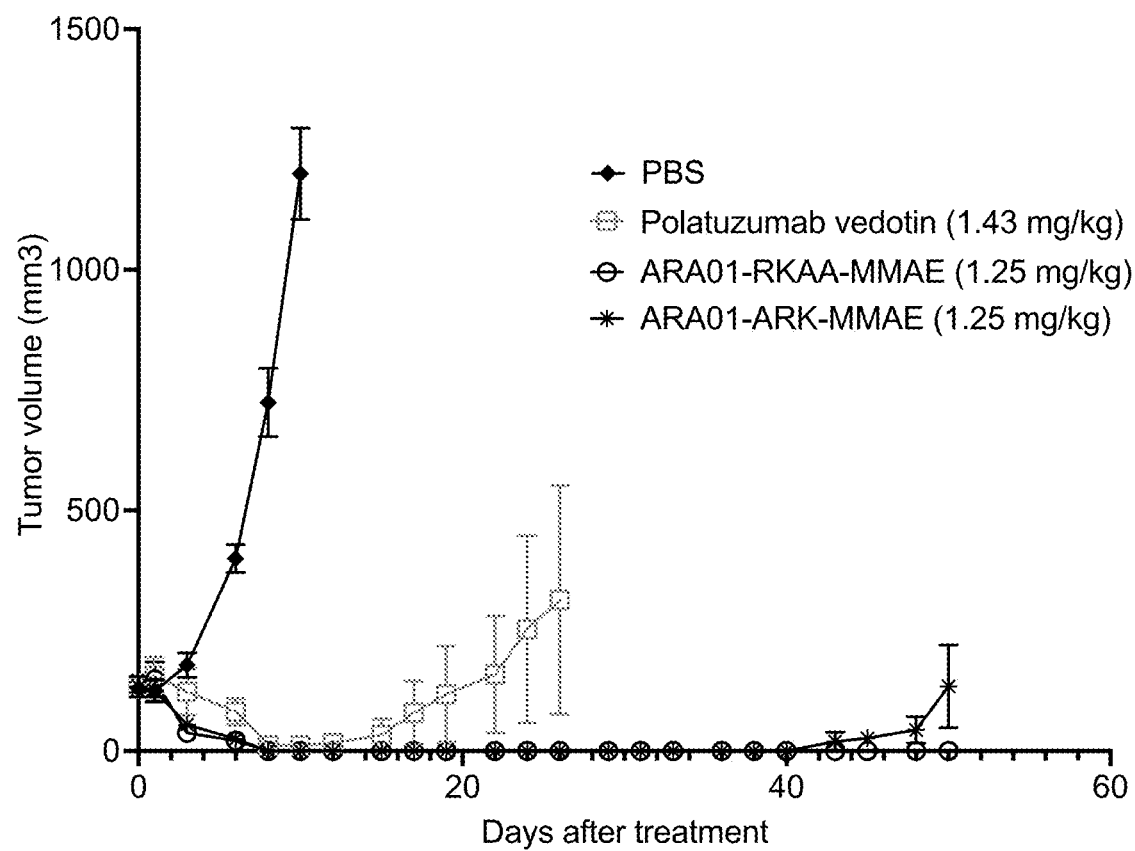
FIG. 41 depicts the Ramos mouse tumor model. Human Burkitt's lymphoma-tumor cells (Ramos) were inoculated subcutaneously in CB17 SCID mice (n=6 per treatment group). When tumors reached a size of about 200 mm$^3$, the animals received a single injection of 1.43 mg/kg polatuzumab-vedotin (Polivy®) or 1.25 mg/kg (payload adjusted dose to polatuzumab vedotin) ARA01-RKAA-PABC-MMAE or ARA01-ARK-PABC-MMAE. Both ADCs of this invention provided equal tumor growth inhibition and survival and long-lasting anti-tumor response at about half the payload dose relative to polatuzumab-vedotin. In contrast, polatuzumab vedotin dosed at the same payload dose, only showed a transient tumor elimination. Mean tumor volumes are shown ±standard error of the mean (SEM).

Results:

ADCs of this invention ARA01-RKAA-PABC-MMAE and ARA01-ARK-PABC-MMAE were compared to polatuzumab vedotin (PV) in a in a fast-growing Ramos xenograft model. FIG. 41 shows that one i.v. injection of 1.25 mg/kg (or 25 ug payload per kg mouse weight) resulted in highly efficient anti-tumor response in all mice. In contrast, PV dosed at 1.43 mg/kg or 50 ug payload per kg body weight, only showed a short and transient tumor elimination with no tumor-free individuals at 20 days after treatment. In contrast and very surprisingly, ARA01-RKAA-PABC-MMAE and ARA01-ARK-PABC-MMAE showed a durable complete anti-tumor response at half the payload dose.

In a solid tumor model, ARA04-RKAA-PABC-MMAE and ARA04-ARK-PABC-MMAE were compared to enfortumab-vedotin (EV) in the SUM190PT breast cancer tumor model. Importantly, both ADCs of this invention, ARA04-RKAA-PABC-MMAE and ARA04-ARK-PABC-MMAE were highly efficacious at 1 and 3 mg/kg and resulted in complete tumor eradication and long-lasting response during the whole course of the study (103 days after injection) as shown in FIGS. 42 and 43.

Figure 42:
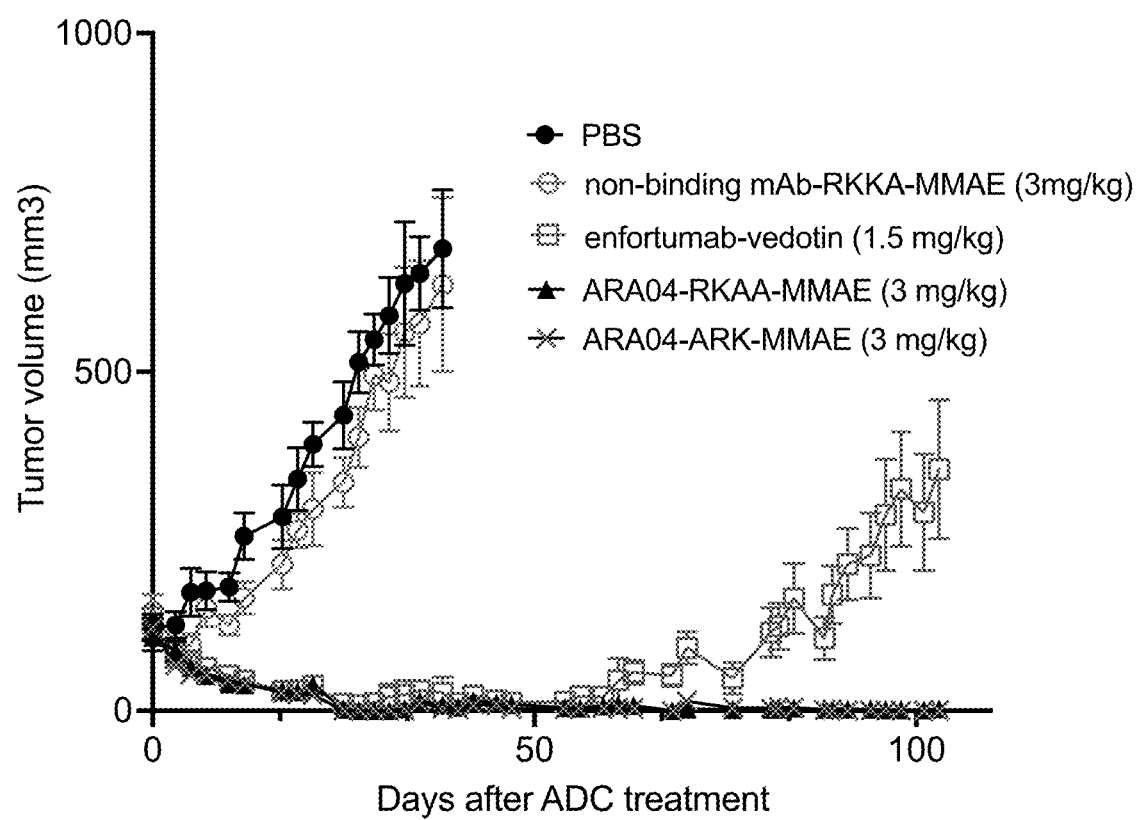
FIG. 42 depicts the SUM190PT mouse tumor model. Breast cancer-tumor cells (SUM190PT) were inoculated into the mammary fatpat of CB17 SCID mice (n=6 per treatment group). When tumors reached a size of about 200 mm$^3$, the animals received a single injection of 1.5 mg/kg enfortumab-vedotin (Padcev®9) or 3 mg/kg (payload adjusted dose to enfortumab vedotin) ARA04-RKAA-PABC-MMAE or ARA04-ARK-PABC-MMAE, respectively. Both ADCs of this invention provided complete and long-lasting anti-tumor responses lasting over 103 days at same payload doses as enfortumab-vedotin. In contrast, enfortumab vedotin dosed at the same payload dose, showed a transient anti-tumor response. When looking at FIGS. 42 and 43 it is evident, that the ADCs of this invention, ARA04-RKAA-PABC-MMAE or ARA04-ARK-PABC-MMAE, showed superior efficacy even when only ¼$^{th}$ of the payload dose (=4-fold less) was adminstered. The non-binding mAb-RKAA-PABC-MMAE did not show any effect on tumor growth. Mean tumor volumes are shown ±standard error of the mean (SEM).
Figure 43:
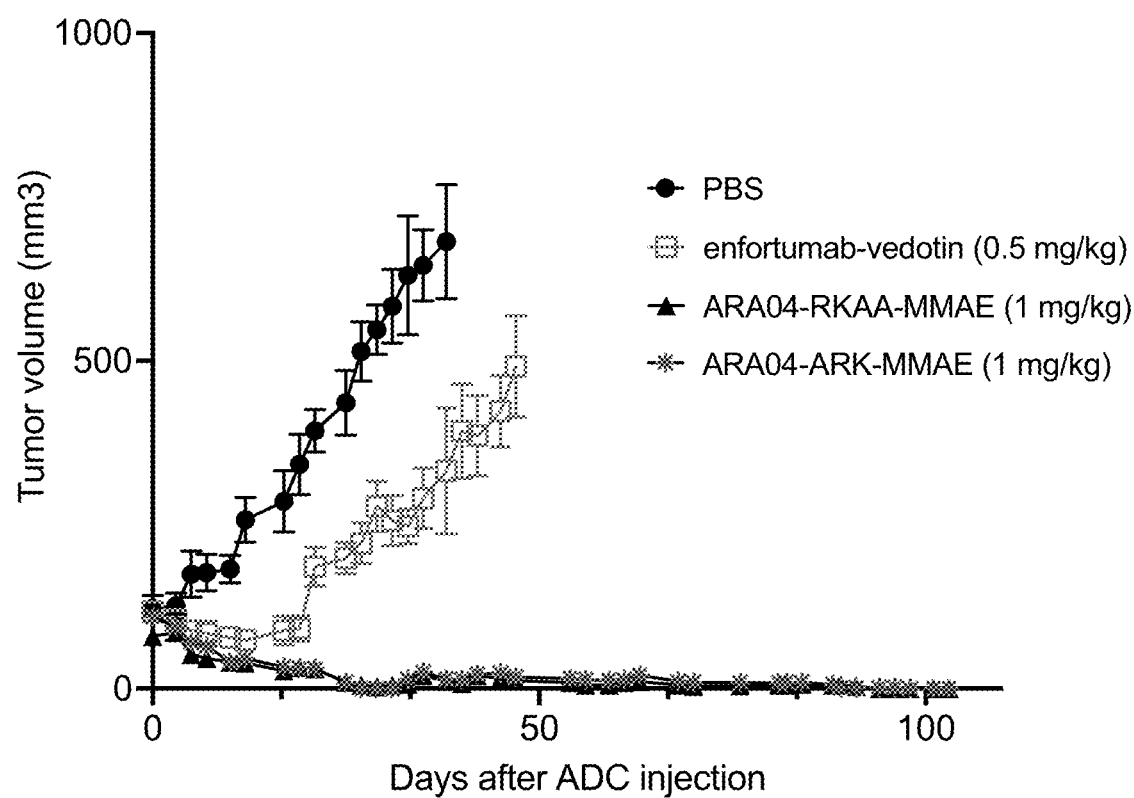
FIG. 43 depicts the SUM190PT mouse tumor model. Breast cancer-tumor cells (SUM190PT) were inoculated into the mammary fatpat of CB17 SCID mice (n=6 per treatment group). When tumors reached a size of about 200 mm$^3$, the animals received a single injection of 0.5 mg/kg enfortumab-vedotin (Padcev®9) or 1 mg/kg (payload adjusted dose to enfortumab vedotin) ARA04-RKAA-PABC-MMAE or ARA04-ARK-PABC-MMAE. Both ADCs of this invention provided complete and long-lasting anti-tumor responses lasting over 103 days at same payload doses as enfortumab-vedotin. In contrast, enfortumab-vedotin dosed at the same payload dose resulted only in a mild tumor-growth retardation. Mean tumor volumes are shown ±standard error of the mean (SEM).

At approximately equal payload doses relative to enfortumab-vedotin, both, ARA04-RKAA-PABC-MMAE and ARA04-ARK-PABC-MMAE (3 mg/kg) treatments led to a greater and longer lasting antitumor efficacy and a considerable survival advantage with 4/6 complete tumor remissions over EV with 0/6 complete tumor remission (comparison of the 1.5 mg/kg dose of EV and 3 mg/kg dose of ARA04-RKAA-PABC-MMAE in FIG. 42). The non-binding mAb-RKAA-PABC-MMAE did not have any effect on tumor growth and suggest high target-specificity of the targeting ADCs. Strikingly, both ARA04-RKAA-PABC-MMAE and ARA04-ARK-PABC-MMAE ADCs provided equal tumor growth inhibition and survival at about one-third of dose relative to enfortumab-vedotin (comparison of the 1.5 mg/kg=30 ug/kg payload dose) and 1 mg/kg (=10 ug/kg payload dose) ARA04-RKAA/ARK-MMAE doses, see FIGS. 42 and 43. Taken together, at approximately one third of payload doses, ARA04-RKAA-PABC-MMAE and ARA04-ARK-PABC-MMAE treatments resulted in greater and durable antitumor efficacy and a considerable survival advantage over enfortumab vedotin.

Overall we summarize that anti-CD79b and anti-Nectin-4 ADCs generated with RK-motif linker-payloads according to this invention, consisting of the same antibody and payload as their respective benchmark ADCs, are highly active in vivo and show 2-3-fold superior efficacy providing considerable survival advantage over vedotin-based ADCs, which is highly surprising.

The invention claimed is:

1. An antibody-drug conjugate comprising:
   a) an IgG antibody; and
   b) a linker comprising a drug moiety B, wherein the drug moiety B is a toxin covalently linked to a peptide selected from the group consisting of: RKAA (SEQ ID NO:1), RKA (SEQ ID NO:2), ARK (SEQ ID NO:3), or RK-Val-Cit (SEQ ID NO:54);
   wherein the linker is conjugated to the IgG antibody via an isopeptide bond formed between the γ-carboxamide group of glutamine residue Q295 (EU numbering) of the $C_H2$ domain of the antibody and the primary amine comprised in the side chain of the lysine residue comprised in the peptide.

2. The antibody-drug conjugate according to claim 1, wherein the toxin is linked to the N- or C-terminus of the peptide via a self-immolative moiety.

3. The antibody-drug conjugate according to claim 1, wherein the IgG antibody is glycosylated at residue N297 (EU numbering) of the $C_H2$ domain.

4. The antibody-drug conjugate according to claim 1, wherein the IgG antibody is an IgG1 antibody.

5. The antibody-drug conjugate according to claim 1, wherein the IgG antibody is Polatuzumab or an antibody comprising a heavy chain as set forth in SEQ ID NO:5 and a light chain as set forth in SEQ ID NO:6.

6. The antibody-drug conjugate according to claim 1, wherein the IgG antibody is Trastuzumab or an antibody comprising a heavy chain as set forth in SEQ ID NO:7 and a light chain as set forth in SEQ ID NO:8.

7. The antibody-drug conjugate according to claim 1, wherein the IgG antibody is Enfortumab or an antibody comprising a heavy chain as set forth in SEQ ID NO:9 and a light chain as set forth in SEQ ID NO:10 or 11.

8. The antibody-drug conjugate according to claim 1, wherein the toxin is selected from the group consisting of:
   a pyrrolobenzodiazepine;
   an auristatin;
   a maytansinoid;
   a duocarmycin;
   a nicotinamide phosphoribosyltransferase (NAMPT) inhibitor;
   a tubulysin;
   an enediyne;
   an anthracycline derivative (PNU);
   a pyrrole-based kinesin spindle protein (KSP) inhibitor;
   a cryptophycin;
   a drug efflux pump inhibitor;
   a sandramycin;
   an amanitin; and
   a camptothecin.

9. The antibody-drug conjugate according to claim 1, wherein the linker has the structure RKAA-PABC-B.

10. The antibody-drug conjugate according to claim 1, wherein the linker has the structure RKA-PABC-B.

11. The antibody-drug conjugate according to claim 1, wherein the linker has the structure ARK-PABC-B.

12. The antibody-drug conjugate according to claim 1, wherein the linker has the structure RK-Val-Cit-PABC-B.

13. A pharmaceutical composition comprising the antibody-drug conjugate according to claim 1 and at least one pharmaceutically acceptable ingredient.

14. The antibody-drug conjugate according to claim 11, wherein B is an auristatin or a maytansinoid.

15. The antibody-drug conjugate according to claim 14, wherein the auristatin is MMAE and wherein the maytansinoid is DM1 or maytansine.

16. The antibody-drug conjugate according to claim 1, wherein the linker has the following structure:

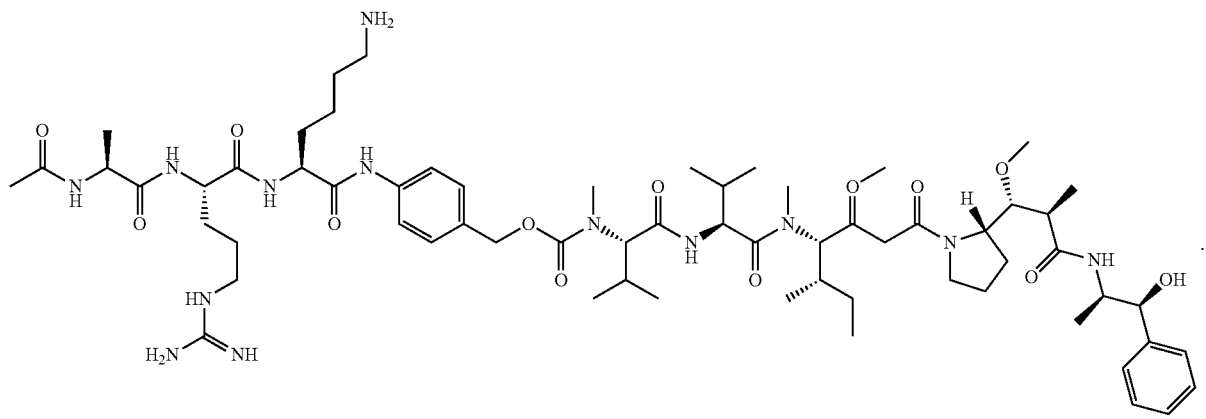

17. The antibody-drug conjugate according to claim 2, wherein the self-immolative moiety comprises a p-aminobenzyl carbamoyl (PABC) moiety.

18. The antibody-drug conjugate according to claim 9, wherein B is an auristatin or a maytansinoid.

19. The antibody-drug conjugate according to claim 18, wherein the auristatin is MMAE and wherein the maytansinoid is DM1 or maytansine.

20. The antibody-drug conjugate according to claim 10, wherein B is an auristatin or a maytansinoid.

21. The antibody-drug conjugate according to claim 20, wherein the auristatin is MMAE and wherein the maytansinoid is DM1 or maytansine.

22. The antibody-drug conjugate according to claim 12, wherein B is an auristatin or a maytansinoid.

23. The antibody-drug conjugate according to claim 22, wherein the auristatin is MMAE and wherein the maytansinoid is DM1 or maytansine.

24. An antibody-drug conjugate comprising:
   a) an IgG antibody wherein the IgG antibody is Polatuzumab or an antibody comprising a heavy chain as set forth in SEQ ID NO:5 and a light chain as set forth in SEQ ID NO:6; and b) a linker having the structure

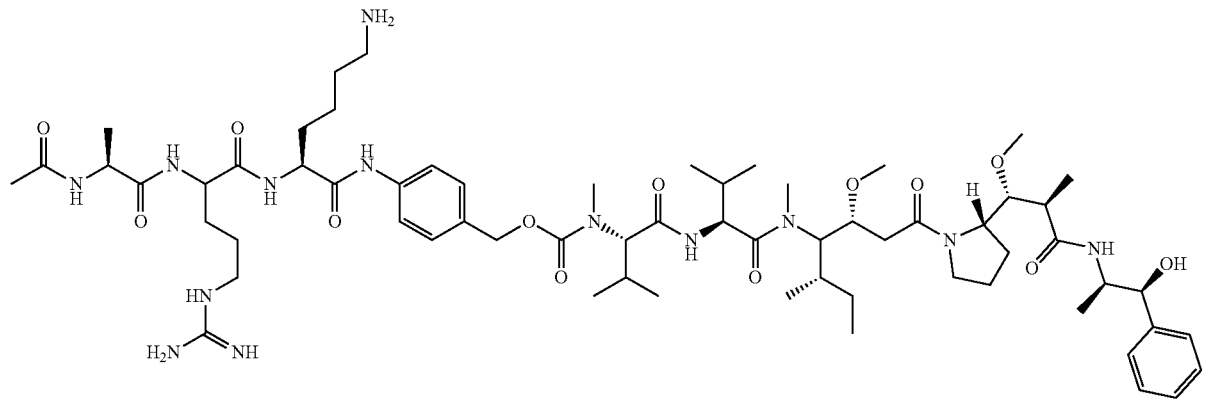 [SMILES: CC[C@H](C)[C@@H](C(CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCCN)NC(=O)C(CCCNC(=N)N)NC(=O)[C@H](C)NC(C)=O)cc1)C(C)C]

wherein the linker is conjugated to the IgG antibody via an isopeptide bond formed between the γ-carboxamide group of glutamine residue Q295 (EU numbering) of the $C_H2$ domain of the antibody and the primary amine comprised in the side chain of the lysine residue comprised in the linker.

25. An antibody-drug conjugate comprising:
a) an IgG antibody, wherein the IgG antibody, is Trastuzumab or an antibody comprising a heavy chain as set forth in SEQ ID NO:7 and a light chain as set forth in SEQ ID NO:8; and
b) a linker having the structure

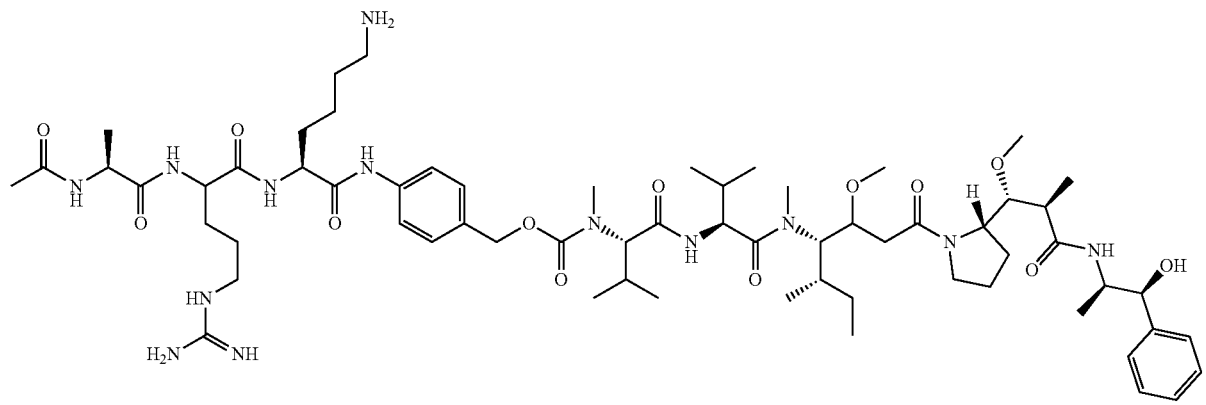

wherein the linker is conjugated to the IgG antibody via an isopeptide bond formed between the γ-carboxamide group of glutamine residue Q295 (EU numbering) of the $C_H2$ domain of the antibody and the primary amine comprised in the side chain of the lysine residue comprised in the linker.

26. An antibody-drug conjugate comprising:
a) an IgG antibody, wherein the IgG antibody is Enfortumab or an antibody comprising a heavy chain as set forth in SEQ ID NO:9 and a light chain as set forth in SEQ ID NO:10 or 11; and b) a linker having the structure
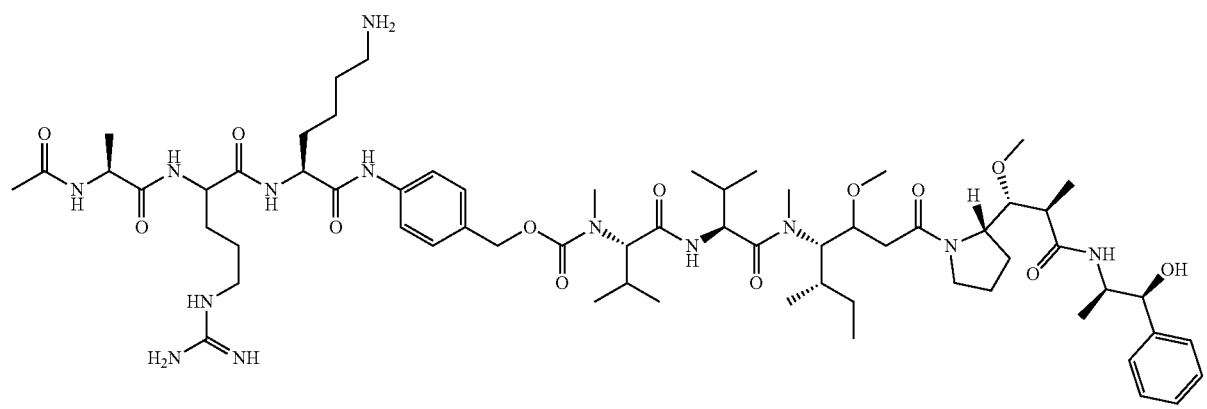 [SMILES: CC[C@H](C)[C@@H](C(CC(=O)N1CCC[C@H]1[C@H](OC)[C@@H](C)C(=O)N[C@H](C)[C@@H](O)c1ccccc1)OC)N(C)C(=O)[C@@H](NC(=O)[C@H](C(C)C)N(C)C(=O)OCc1ccc(NC(=O)[C@H](CCCCN)NC(=O)C(CCCNC(=N)N)NC(=O)[C@H](C)NC(C)=O)cc1)C(C)C]
wherein the linker is conjugated to the IgG antibody via an isopeptide bond formed between the γ-carboxamide group of glutamine residue Q295 (EU numbering) of the $C_H2$ domain of the antibody and the primary amine comprised in the side chain of the lysine residue comprised in the linker.
* * * * *

SEQUENCE LISTING

```
Sequence total quantity: 72
SEQ ID NO: 1            moltype = AA  length = 4
FEATURE                 Location/Qualifiers
REGION                  1..4
                        note = Linker 1
source                  1..4
                        mol_type = protein
                        organism = synthetic construct
SEQUENCE: 1
```

```
RKAA                                                                    4

SEQ ID NO: 2            moltype =    length =
SEQUENCE: 2
000

SEQ ID NO: 3            moltype =    length =
SEQUENCE: 3
000

SEQ ID NO: 4            moltype =    length =
SEQUENCE: 4
000

SEQ ID NO: 5            moltype = AA   length = 446
FEATURE                 Location/Qualifiers
REGION                  1..446
                        note = Polatuzumab heavy chain
source                  1..446
                        mol_type = protein
                        organism = synthetic construct
SEQUENCE: 5
EVQLVESGGG LVQPGGSLRL SCAASGYTFS SYWIEWVRQA PGKGLEWIGE ILPGGGDTNY   60
NEIFKGRATF SADTSKNTAY LQMNSLRAED TAVYYCTRRV PIRLDYWGQG TLVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APELLGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALPA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPG                                      446

SEQ ID NO: 6            moltype = AA   length = 218
FEATURE                 Location/Qualifiers
REGION                  1..218
                        note = Polatuzumab light chain
source                  1..218
                        mol_type = protein
                        organism = synthetic construct
SEQUENCE: 6
DIQLTQSPSS LSASVGDRVT ITCKASQSVD YEGDSFLNWY QQKPGKAPKL LIYAASNLES   60
GVPSRFSGSG SGTDFTLTIS SLQPEDFATY YCQQSNEDPL TFGQGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

SEQ ID NO: 7            moltype = AA   length = 450
FEATURE                 Location/Qualifiers
REGION                  1..450
                        note = Trastuzumab heavy chain
source                  1..450
                        mol_type = protein
                        organism = synthetic construct
SEQUENCE: 7
EVQLVESGGG LVQPGGSLRL SCAASGFNIK DTYIHWVRQA PGKGLEWVAR IYPTNGYTRY   60
ADSVKGRFTI SADTSKNTAY LQMNSLRAED TAVYYCSRWG GDGFYAMDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKKVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                  450

SEQ ID NO: 8            moltype = AA   length = 214
FEATURE                 Location/Qualifiers
REGION                  1..214
                        note = Trastuzumab light chain
source                  1..214
                        mol_type = protein
                        organism = synthetic construct
SEQUENCE: 8
DIQMTQSPSS LSASVGDRVT ITCRASQDVN TAVAWYQQKP GKAPKLLIYS ASFLYSGVPS   60
RFSGSRSGTD FTLTISSLQP EDFATYYCQQ HYTTPPTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

SEQ ID NO: 9            moltype = AA   length = 447
FEATURE                 Location/Qualifiers
REGION                  1..447
                        note = Enfortumab heavy chain
source                  1..447
```

```
                        mol_type = protein
                        organism = synthetic construct
SEQUENCE: 9
EVQLVESGGG  LVQPGGSLRL  SCAASGFTFS  SYNMNWVRQA  PGKGLEWVSY  ISSSSSTIYY   60
ADSVKGRFTI  SRDNAKNSLS  LQMNSLRDED  TAVYYCARAY  YYGMDVWGQG  TTVTVSSAST  120
KGPSVFPLAP  SSKSTSGGTA  ALGCLVKDYF  PEPVTVSWNS  GALTSGVHTF  PAVLQSSGLY  180
SLSSVVTVPS  SSLGTQTYIC  NVNHKPSNTK  VDKRVEPKSC  DKTHTCPPCP  APELLGGPSV  240
FLFPPKPKDT  LMISRTPEVT  CVVVDVSHED  PEVKFNWYVD  GVEVHNAKTK  PREEQYNSTY  300
RVVSVLTVLH  QDWLNGKEYK  CKVSNKALPA  PIEKTISKAK  GQPREPQVYT  LPPSREEMTK  360
NQVSLTCLVK  GFYPSDIAVE  WESNGQPENN  YKTTPPVLDS  DGSFFLYSKL  TVDKSRWQQG  420
NVFSCSVMHE  ALHNHYTQKS  LSLSPGK                                         447

SEQ ID NO: 10           moltype = AA  length = 214
FEATURE                 Location/Qualifiers
REGION                  1..214
                        note = Enfortumab light chain
source                  1..214
                        mol_type = protein
                        organism = synthetic construct
SEQUENCE: 10
DIQMTQSPSS  VSASVGDRVT  ITCRASQGIS  GWLAWYQQKP  GKAPKFLIYA  ASTLQSGVPS   60
RFSGSGSGTD  FTLTISSLQP  EDFATYYCQQ  ANSFPPTFGG  GTKVEIKRTV  AAPSVFIFPP  120
SDEQLKSGTA  SVVCLLNNFY  PREAKVQWKV  DNALQSGNSQ  ESVTEQDSKD  STYSLSSTLT  180
LSKADYEKHK  VYACEVTHQG  LSSPVTKSFN  RGEC                                214

SEQ ID NO: 11           moltype = AA  length = 447
FEATURE                 Location/Qualifiers
REGION                  1..447
                        note = Enfortumab heavy chain
source                  1..447
                        mol_type = protein
                        organism = synthetic construct
SEQUENCE: 11
EVQLVESGGG  LVQPGGSLRL  SCAASGFTFS  SYNMNWVRQA  PGKGLEWVSY  ISSSSSTIYY   60
ADSVKGRFTI  SRDNAKNSLS  LQMNSLRDED  TAVYYCARAY  YYGMDVWGQG  TTVTVSSAST  120
KGPSVFPLAP  SSKSTSGGTA  ALGCLVKDYF  PEPVTVSWNS  GALTSGVHTF  PAVLQSSGLY  180
SLSSVVTVPS  SSLGTQTYIC  NVNHKPSNTK  VDKRVEPKSC  DKTHTCPPCP  APELLGGPSV  240
FLFPPKPKDT  LMISRTPEVT  CVVVDVSHED  PEVKFNWYVD  GVEVHNAKTK  PREEQYNSTY  300
RVVSVLTVLH  QDWLNGKEYK  CKVSNKALPA  PIEKTISKAK  GQPREPQVYT  LPPSREEMTK  360
NQVSLTCLVK  GFYPSDIAVE  WESNGQPENN  YKTTPPVLDS  DGSFFLYSKL  TVDKSRWQQG  420
NVFSCSVMHE  ALHNHYTQKS  LSLSPGK                                         447

SEQ ID NO: 12           moltype = AA  length = 335
FEATURE                 Location/Qualifiers
REGION                  1..335
                        note = Streptomyces mobaraensis MTG Zedira
source                  1..335
                        mol_type = protein
                        organism = synthetic construct
SEQUENCE: 12
FRAPDSDDRV  TPPAEPLDRM  PDPYRPSYGR  AETVVNNYIR  KWQQVYSHRD  GRKQQMTEEQ   60
REWLSYGCVG  VTWVNSGQYP  TNRLAFASFD  EDRFKNELKN  GRPRSGETRA  EFEGRVAKES  120
FDEEKGFQRA  REVASVMNRA  LENAHDESAY  LDNLKKELAN  GNDALRNEDA  RSPFYSALRN  180
TPSFKERNGG  NHDPSRMKAV  IYSKHFWSGQ  DRSSSADKRK  YGDPDAFRPA  PGTGLVDMSR  240
DRNIPRSPTS  PGEGFVNFDY  GWFGAQTEAD  ADKTVWTHGN  HYHAPNGSLG  AMHVYESKFR  300
NWSEGYSDFD  RGAYVITFIP  KSWNTAPDKV  KQGWP                               335

SEQ ID NO: 13           moltype = AA  length = 335
FEATURE                 Location/Qualifiers
REGION                  1..335
                        note = Streptomyces mobaraensis MTG
source                  1..335
                        mol_type = protein
                        organism = synthetic construct
SEQUENCE: 13
FRAPDSDERV  TPPAEPLDRM  PDPYRPSYGR  AETIVNNYIR  KWQQVYSHRD  GRKQQMTEEQ   60
REWLSYGCVG  VTWVNSGQYP  TNRLAFAFFD  EDKYKNELKN  GRPRSGETRA  EFEGRVAKDS  120
FDEAKGFQRA  RDVASVMNKA  LENAHDEGAY  LDNLKKELAN  GNDALRNEDA  RSPFYSALRN  180
TPSFKDRNGG  NHDPSKMKAV  IYSKHFWSGQ  DRSGSSDKRK  YGDPEAFRPD  RGTGLVDMSR  240
DRNIPRSPTS  PGESFVNFDY  GWFGAQTEAD  ADKTVWTHGN  HYHAPNGSLG  AMHVYESKFR  300
NWSDGYSDFD  RGAYVVTFVP  KSWNTAPDKV  TQGWP                               335

SEQ ID NO: 14           moltype = AA  length = 407
FEATURE                 Location/Qualifiers
REGION                  1..407
                        note = Streptomyces mobaraensis MTG P81453
source                  1..407
                        mol_type = protein
                        organism = synthetic construct
```

```
SEQUENCE: 14
MRIRRRALVF ATMSAVLCTA GFMPSAGEAA ADNGAGEETK SYAETYRLTA DDVANINALN    60
ESAPAASSAG PSFRAPDSDD RVTPPAEPLD RMPDPYRPSY GRAETVVNNY IRKWQQVYSH   120
RDGRKQQMTE EQREWLSYGC VGVTWVNSGQ YPTNRLAFAS FDEDRFKNEL KNGRPRSGET   180
RAEFEGRVAK ESFDEEKGFQ RAREVASVMN RALENAHDES AYLDNLKKEL ANGNDALRNE   240
DARSPFYSAL RNTPSFKERN GGNHDPSRMK AVIYSKHFWS GQDRSSSADK RKYGDPDAFR   300
PAPGTGLVDM SRDRNIPRSP TSPGEGFVNF DYGWFGAQTE ADADKTVWTH GNHYHAPNGS   360
LGAMHVYESK FRNWSEGYSD FDRGAYVITF IPKSWNTAPD KVKQGWP                 407

SEQ ID NO: 15           moltype = AA   length = 395
FEATURE                 Location/Qualifiers
REGION                  1..395
                        note = Streptoverticillium ladakanum MTG
source                  1..395
                        mol_type = protein
                        organism = synthetic construct
SEQUENCE: 15
MHRRIHAVGQ ARPPPTMARG KETKSYAETY RLTADDVANI NALNESAPAA SSAGPSFRAP    60
DSDDRVTPPA EPLDRMPDPY RPSYGRAETV VNNYIRKWQQ VYSHRDGRKQ QMTEEQREWL   120
SYGCVGVTWV NSGQYPTNRL AFASFDEDRF KNELKNGRPR SGETRAEFEG RVAKESFDEE   180
KGFQRAREVA SVMNRALENA HDESAYLDNL KKELANGNDA LRNEDARSPF YSALRNTPSF   240
KERNGGNHDP SRMKAVIYSK HFWSGQDRSS SADKRKYGDP DAFRSAPGTG LVDMSRDRNI   300
PRSPTSPGEG FVNFDYGWFG AQTEADADKT VWTHGNHYHA PNGSLGCHAC LTRASSATGS   360
EGYSDFDRGE PYVVSPSPSP RMLEHRPRQG KAGLA                              395

SEQ ID NO: 16           moltype = AA   length = 5
FEATURE                 Location/Qualifiers
REGION                  1..5
                        note = Q-Tag 1
source                  1..5
                        mol_type = protein
                        organism = synthetic construct
SEQUENCE: 16
LLQGG                                                                 5

SEQ ID NO: 17           moltype = AA   length = 4
FEATURE                 Location/Qualifiers
REGION                  1..4
                        note = Q-Tag 2
source                  1..4
                        mol_type = protein
                        organism = synthetic construct
SEQUENCE: 17
LLQG                                                                  4

SEQ ID NO: 18           moltype = AA   length = 6
FEATURE                 Location/Qualifiers
REGION                  1..6
                        note = Q-Tag 3
source                  1..6
                        mol_type = protein
                        organism = synthetic construct
SEQUENCE: 18
LSLSQG                                                                6

SEQ ID NO: 19           moltype = AA   length = 8
FEATURE                 Location/Qualifiers
REGION                  1..8
                        note = Q-Tag 4
source                  1..8
                        mol_type = protein
                        organism = synthetic construct
SEQUENCE: 19
GGGLLQGG                                                              8

SEQ ID NO: 20           moltype = AA   length = 5
FEATURE                 Location/Qualifiers
REGION                  1..5
                        note = Q-Tag 5
source                  1..5
                        mol_type = protein
                        organism = synthetic construct
SEQUENCE: 20
GLLQG                                                                 5

SEQ ID NO: 21           moltype =     length =
SEQUENCE: 21
000
```

```
SEQ ID NO: 22              moltype = AA  length = 10
FEATURE                    Location/Qualifiers
REGION                     1..10
                           note = Q-Tag 7
source                     1..10
                           mol_type = protein
                           organism = synthetic construct
SEQUENCE: 22
GSPLAQSHGG                                                              10

SEQ ID NO: 23              moltype = AA  length = 7
FEATURE                    Location/Qualifiers
REGION                     1..7
                           note = Q-Tag 8
source                     1..7
                           mol_type = protein
                           organism = synthetic construct
SEQUENCE: 23
GLLQGGG                                                                 7

SEQ ID NO: 24              moltype = AA  length = 6
FEATURE                    Location/Qualifiers
REGION                     1..6
                           note = Q-Tag 9
source                     1..6
                           mol_type = protein
                           organism = synthetic construct
SEQUENCE: 24
GLLQGG                                                                  6

SEQ ID NO: 25              moltype = AA  length = 4
FEATURE                    Location/Qualifiers
REGION                     1..4
                           note = Q-Tag 10
source                     1..4
                           mol_type = protein
                           organism = synthetic construct
SEQUENCE: 25
GLLQ                                                                    4

SEQ ID NO: 26              moltype = AA  length = 8
FEATURE                    Location/Qualifiers
REGION                     1..8
                           note = Q-Tag 11
source                     1..8
                           mol_type = protein
                           organism = synthetic construct
SEQUENCE: 26
LLQLLQGA                                                                8

SEQ ID NO: 27              moltype = AA  length = 5
FEATURE                    Location/Qualifiers
REGION                     1..5
                           note = Q-Tag 12
source                     1..5
                           mol_type = protein
                           organism = synthetic construct
SEQUENCE: 27
LLQGA                                                                   5

SEQ ID NO: 28              moltype = AA  length = 7
FEATURE                    Location/Qualifiers
REGION                     1..7
                           note = Q-Tag 13
source                     1..7
                           mol_type = protein
                           organism = synthetic construct
SEQUENCE: 28
LLQYQGA                                                                 7

SEQ ID NO: 29              moltype = AA  length = 6
FEATURE                    Location/Qualifiers
REGION                     1..6
                           note = Q-Tag 14
source                     1..6
                           mol_type = protein
                           organism = synthetic construct
SEQUENCE: 29
LLQGSG                                                                  6
```

```
SEQ ID NO: 30           moltype = AA   length = 6
FEATURE                 Location/Qualifiers
REGION                  1..6
                        note = Q-Tag 15
source                  1..6
                        mol_type = protein
                        organism = synthetic construct
SEQUENCE: 30
LLQYQG                                                                   6

SEQ ID NO: 31           moltype = AA   length = 7
FEATURE                 Location/Qualifiers
REGION                  1..7
                        note = Q-Tag 16
source                  1..7
                        mol_type = protein
                        organism = synthetic construct
SEQUENCE: 31
LLQLLQG                                                                  7

SEQ ID NO: 32           moltype = AA   length = 5
FEATURE                 Location/Qualifiers
REGION                  1..5
                        note = Q-Tag 17
source                  1..5
                        mol_type = protein
                        organism = synthetic construct
SEQUENCE: 32
SLLQG                                                                    5

SEQ ID NO: 33           moltype = AA   length = 5
FEATURE                 Location/Qualifiers
REGION                  1..5
                        note = Q-Tag 18
source                  1..5
                        mol_type = protein
                        organism = synthetic construct
SEQUENCE: 33
LLQLQ                                                                    5

SEQ ID NO: 34           moltype = AA   length = 6
FEATURE                 Location/Qualifiers
REGION                  1..6
                        note = Q-Tag 19
source                  1..6
                        mol_type = protein
                        organism = synthetic construct
SEQUENCE: 34
LLQLLQ                                                                   6

SEQ ID NO: 35           moltype = AA   length = 5
FEATURE                 Location/Qualifiers
REGION                  1..5
                        note = Q-Tag 20
source                  1..5
                        mol_type = protein
                        organism = synthetic construct
SEQUENCE: 35
LLQGR                                                                    5

SEQ ID NO: 36           moltype = AA   length = 8
FEATURE                 Location/Qualifiers
REGION                  1..8
                        note = Q-Tag 21
source                  1..8
                        mol_type = protein
                        organism = synthetic construct
SEQUENCE: 36
EEQYASTY                                                                 8

SEQ ID NO: 37           moltype = AA   length = 8
FEATURE                 Location/Qualifiers
REGION                  1..8
                        note = Q-Tag 22
source                  1..8
                        mol_type = protein
                        organism = synthetic construct
SEQUENCE: 37
```

```
EEQYQSTY                                                                  8

SEQ ID NO: 38            moltype = AA  length = 8
FEATURE                  Location/Qualifiers
REGION                   1..8
                         note = Q-Tag 23
source                   1..8
                         mol_type = protein
                         organism = synthetic construct
SEQUENCE: 38
EEQYNSTY                                                                  8

SEQ ID NO: 39            moltype = AA  length = 6
FEATURE                  Location/Qualifiers
REGION                   1..6
                         note = Q-Tag 24
source                   1..6
                         mol_type = protein
                         organism = synthetic construct
SEQUENCE: 39
EEQYQS                                                                    6

SEQ ID NO: 40            moltype = AA  length = 7
FEATURE                  Location/Qualifiers
REGION                   1..7
                         note = Q-Tag 25
source                   1..7
                         mol_type = protein
                         organism = synthetic construct
SEQUENCE: 40
EEQYQST                                                                   7

SEQ ID NO: 41            moltype = AA  length = 7
FEATURE                  Location/Qualifiers
REGION                   1..7
                         note = Q-Tag 26
source                   1..7
                         mol_type = protein
                         organism = synthetic construct
SEQUENCE: 41
EQYQSTY                                                                   7

SEQ ID NO: 42            moltype = AA  length = 4
FEATURE                  Location/Qualifiers
REGION                   1..4
                         note = Q-Tag 27
source                   1..4
                         mol_type = protein
                         organism = synthetic construct
SEQUENCE: 42
QYQS                                                                      4

SEQ ID NO: 43            moltype = AA  length = 6
FEATURE                  Location/Qualifiers
REGION                   1..6
                         note = Q-Tag 28
source                   1..6
                         mol_type = protein
                         organism = synthetic construct
SEQUENCE: 43
QYQSTY                                                                    6

SEQ ID NO: 44            moltype = AA  length = 5
FEATURE                  Location/Qualifiers
REGION                   1..5
                         note = Q-Tag 29
source                   1..5
                         mol_type = protein
                         organism = synthetic construct
SEQUENCE: 44
YRYRQ                                                                     5

SEQ ID NO: 45            moltype = AA  length = 5
FEATURE                  Location/Qualifiers
REGION                   1..5
                         note = Q-Tag 30
source                   1..5
                         mol_type = protein
                         organism = synthetic construct
```

-continued

```
SEQUENCE: 45
DYALQ                                                                       5

SEQ ID NO: 46           moltype = AA  length = 7
FEATURE                 Location/Qualifiers
REGION                  1..7
                        note = Q-Tag 31
source                  1..7
                        mol_type = protein
                        organism = synthetic construct
SEQUENCE: 46
FGLQRPY                                                                     7

SEQ ID NO: 47           moltype = AA  length = 10
FEATURE                 Location/Qualifiers
REGION                  1..10
                        note = Q-Tag 32
source                  1..10
                        mol_type = protein
                        organism = synthetic construct
SEQUENCE: 47
EQKLISEEDL                                                                 10

SEQ ID NO: 48           moltype =   length =
SEQUENCE: 48
000

SEQ ID NO: 49           moltype =   length =
SEQUENCE: 49
000

SEQ ID NO: 50           moltype =   length =
SEQUENCE: 50
000

SEQ ID NO: 51           moltype =   length =
SEQUENCE: 51
000

SEQ ID NO: 52           moltype = AA  length = 4
FEATURE                 Location/Qualifiers
REGION                  1..4
                        note = Linker 7
source                  1..4
                        mol_type = protein
                        organism = synthetic construct
SEQUENCE: 52
KAAR                                                                        4

SEQ ID NO: 53           moltype = AA  length = 4
FEATURE                 Location/Qualifiers
REGION                  1..4
                        note = Linker 8
source                  1..4
                        mol_type = protein
                        organism = synthetic construct
SEQUENCE: 53
KARA                                                                        4

SEQ ID NO: 54           moltype =   length =
SEQUENCE: 54
000

SEQ ID NO: 55           moltype = AA  length = 5
FEATURE                 Location/Qualifiers
REGION                  1..5
                        note = Linker 10
source                  1..5
                        mol_type = protein
                        organism = synthetic construct
SEQUENCE: 55
HRKHA                                                                       5

SEQ ID NO: 56           moltype = AA  length = 5
FEATURE                 Location/Qualifiers
REGION                  1..5
                        note = Linker 11
source                  1..5
                        mol_type = protein
```

```
                       organism = synthetic construct
SEQUENCE: 56
HRKAH                                                                            5

SEQ ID NO: 57          moltype = AA  length = 4
FEATURE                Location/Qualifiers
REGION                 1..4
                       note = Linker 12
source                 1..4
                       mol_type = protein
                       organism = synthetic construct
SEQUENCE: 57
RKAH                                                                             4

SEQ ID NO: 58          moltype =     length =
SEQUENCE: 58
000

SEQ ID NO: 59          moltype = AA  length = 4
FEATURE                Location/Qualifiers
REGION                 1..4
                       note = Linker 14
source                 1..4
                       mol_type = protein
                       organism = synthetic construct
SEQUENCE: 59
RKHA                                                                             4

SEQ ID NO: 60          moltype = AA  length = 4
FEATURE                Location/Qualifiers
REGION                 1..4
                       note = Linker 15
source                 1..4
                       mol_type = protein
                       organism = synthetic construct
SEQUENCE: 60
RKHH                                                                             4

SEQ ID NO: 61          moltype = AA  length = 5
FEATURE                Location/Qualifiers
REGION                 1..5
                       note = Linker 16
source                 1..5
                       mol_type = protein
                       organism = synthetic construct
SEQUENCE: 61
ARKAH                                                                            5

SEQ ID NO: 62          moltype = AA  length = 5
FEATURE                Location/Qualifiers
REGION                 1..5
                       note = Linker 17
source                 1..5
                       mol_type = protein
                       organism = synthetic construct
SEQUENCE: 62
ARKHA                                                                            5

SEQ ID NO: 63          moltype =     length =
SEQUENCE: 63
000

SEQ ID NO: 64          moltype = AA  length = 5
FEATURE                Location/Qualifiers
REGION                 1..5
                       note = Linker 19
source                 1..5
                       mol_type = protein
                       organism = synthetic construct
```

```
SEQUENCE: 64
RKAAH                                                                   5

SEQ ID NO: 65          moltype = AA  length = 5
FEATURE                Location/Qualifiers
REGION                 1..5
                       note = Linker 20
source                 1..5
                       mol_type = protein
                       organism = synthetic construct
SEQUENCE: 65
ARKHH                                                                   5

SEQ ID NO: 66          moltype = AA  length = 5
FEATURE                Location/Qualifiers
REGION                 1..5
                       note = Linker 21
source                 1..5
                       mol_type = protein
                       organism = synthetic construct
SEQUENCE: 66
RKAAA                                                                   5

SEQ ID NO: 67          moltype = AA  length = 5
FEATURE                Location/Qualifiers
REGION                 1..5
                       note = Linker 22
source                 1..5
                       mol_type = protein
                       organism = synthetic construct
SEQUENCE: 67
RKAAR                                                                   5

SEQ ID NO: 68          moltype = AA  length = 5
FEATURE                Location/Qualifiers
REGION                 1..5
                       note = Linker 23
source                 1..5
                       mol_type = protein
                       organism = synthetic construct
SEQUENCE: 68
RRKAY                                                                   5

SEQ ID NO: 69          moltype =    length =
SEQUENCE: 69
000

SEQ ID NO: 70          moltype = AA  length = 5
FEATURE                Location/Qualifiers
REGION                 1..5
                       note = Linker 25
source                 1..5
                       mol_type = protein
                       organism = synthetic construct
SEQUENCE: 70
ARKRA                                                                   5

SEQ ID NO: 71          moltype =    length =
SEQUENCE: 71
000

SEQ ID NO: 72          moltype =    length =
SEQUENCE: 72
000
```